US011364131B2

(12) United States Patent
LaChappelle et al.

(10) Patent No.: US 11,364,131 B2
(45) Date of Patent: Jun. 21, 2022

(54) SOCKET FOR UPPER EXTREMITY PROSTHESIS

(71) Applicant: Unlimited Tomorrow, Inc., Rhinebeck, NY (US)

(72) Inventors: Easton J. LaChappelle, Rhinebeck, NY (US); Alexandru Stefan Malcoci, Rhinebeck, NY (US)

(73) Assignee: Unlimited Tomorrow, Inc., Rhinebeck, NY (US)

( * ) Notice: Subject to any disclaimer, the term of this patent is extended or adjusted under 35 U.S.C. 154(b) by 0 days.

(21) Appl. No.: 16/992,253

(22) Filed: Aug. 13, 2020

(65) Prior Publication Data
US 2021/0045896 A1 Feb. 18, 2021

Related U.S. Application Data

(60) Provisional application No. 62/887,797, filed on Aug. 16, 2019.

(51) Int. Cl.
*A61F 2/80* (2006.01)
*A61F 2/78* (2006.01)
*A61F 2/58* (2006.01)
*A61F 2/72* (2006.01)
(Continued)

(52) U.S. Cl.
CPC ............... *A61F 2/80* (2013.01); *A61F 2/582* (2013.01); *A61F 2/72* (2013.01); *A61F 2002/503* (2013.01); *A61F 2002/543* (2013.01)

(58) Field of Classification Search
CPC .... A61F 2/80; A61F 2/582; A61F 2/72; A61F 2/78; A61F 2/58; A61F 2/54; A61F 2002/503; A61F 2002/543; A61F 2002/7862
See application file for complete search history.

(56) References Cited

U.S. PATENT DOCUMENTS

| 1,408,157 | A | * | 2/1922 | Armstrong ............... A61F 2/80 623/59 |
| 2,853,711 | A |   | 9/1958 | Becker |
| 4,732,143 | A |   | 3/1988 | Kausek et al. |
| 2005/0043822 | A1 |   | 2/2005 | Didrick |
| 2006/0129248 | A1 |   | 6/2006 | Stark |

(Continued)

FOREIGN PATENT DOCUMENTS

| WO | 2008030419 A2 | 3/2008 |
| WO | 2015060793 A1 | 4/2015 |

OTHER PUBLICATIONS

International Search Report and Written Opinion for PCT/US19/12603, dated Apr. 9, 2019.
International Search Report and Written Opinion for PCT/US20/46054, dated Oct. 29, 2020.

*Primary Examiner* — Bruce E Snow
(74) *Attorney, Agent, or Firm* — Lerner, David, Littenberg, Krumholz & Mentlik, LLP

(57) ABSTRACT

A socket may be for coupling a prosthetic upper extremity to a residual limb of a user. The socket may include a proximal socket portion and a distal socket portion coupled to the proximal socket portion by a polycentric joint. The polycentric joint may include a plate having a first end coupled to the proximal socket portion via a first fastener, and a second end coupled to the distal socket portion via a second fastener. The proximal socket portion may be rotatable relative to the distal socket portion about a first axis passing through the first fastener and about a second axis passing through the second fastener.

17 Claims, 96 Drawing Sheets

(51) Int. Cl.
    *A61F 2/50*      (2006.01)
    *A61F 2/54*      (2006.01)

(56) References Cited

U.S. PATENT DOCUMENTS

| | | |
|---|---|---|
| 2006/0167564 A1 | 7/2006 | Flaherty et al. |
| 2007/0032884 A1* | 2/2007 | Veatch ................... A61F 5/01 |
| | | 623/64 |
| 2012/0101597 A1 | 4/2012 | Bache |
| 2012/0150322 A1 | 6/2012 | Goldfarb et al. |
| 2013/0053984 A1 | 2/2013 | Hunter et al. |
| 2014/0094351 A1* | 4/2014 | Cersonsky ............ A63B 21/15 |
| | | 482/115 |
| 2014/0277589 A1 | 9/2014 | Veatch |
| 2015/0230945 A1 | 8/2015 | Bache et al. |
| 2015/0351935 A1 | 12/2015 | Donati et al. |
| 2017/0049583 A1 | 2/2017 | Belter et al. |
| 2017/0266020 A1 | 9/2017 | Glasgow |
| 2018/0296372 A1* | 10/2018 | Johnson .................... A61F 2/78 |
| 2018/0296373 A1 | 10/2018 | Granz |
| 2019/0209345 A1 | 7/2019 | LaChappelle |
| 2021/0113356 A1* | 4/2021 | Laszczak ................. A61F 2/80 |

* cited by examiner

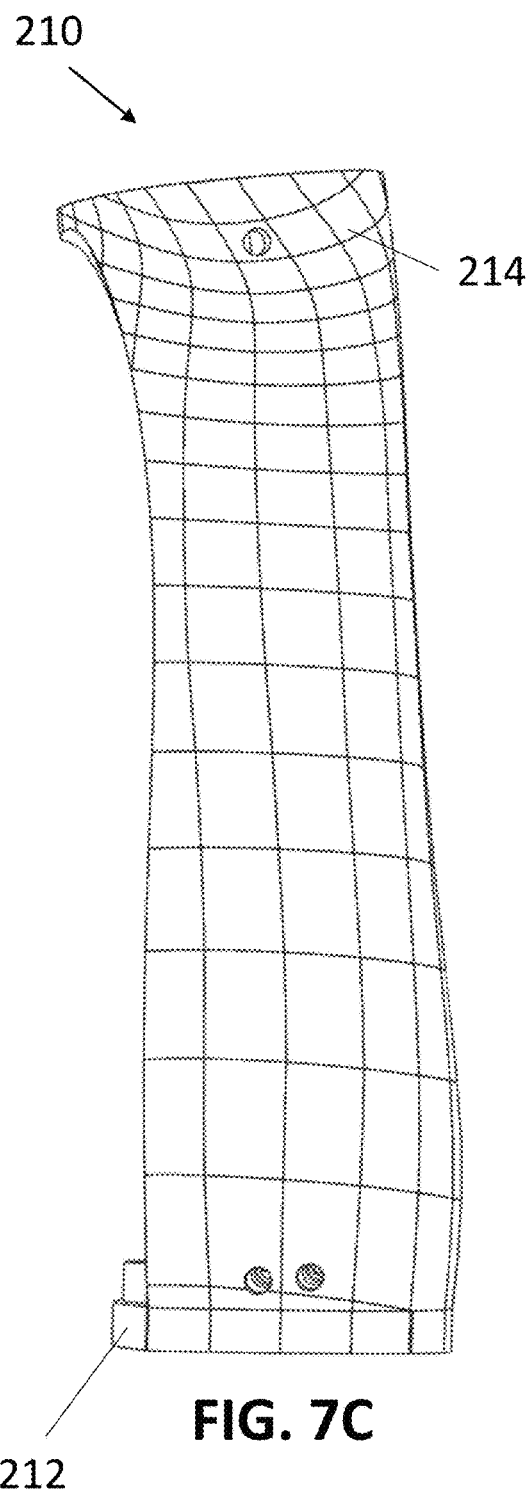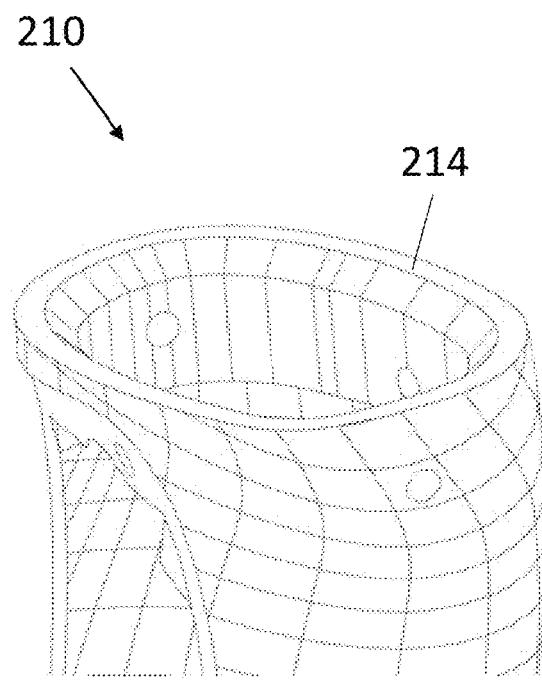
FIG. 7C
FIG. 7D

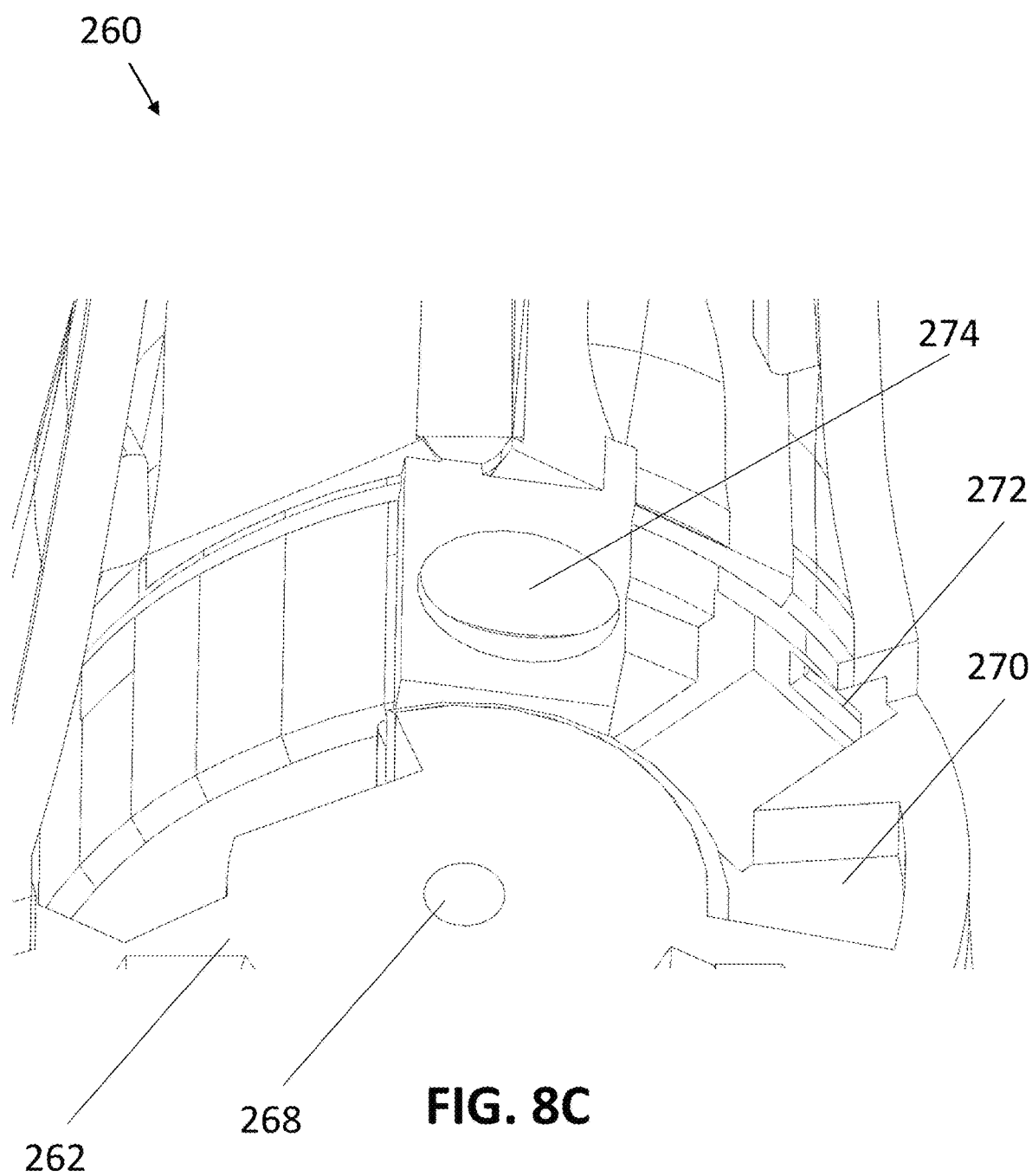

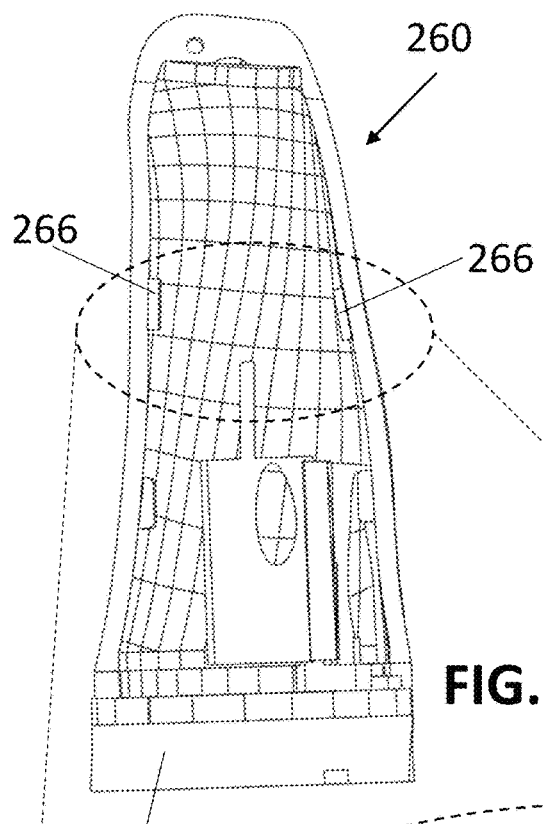
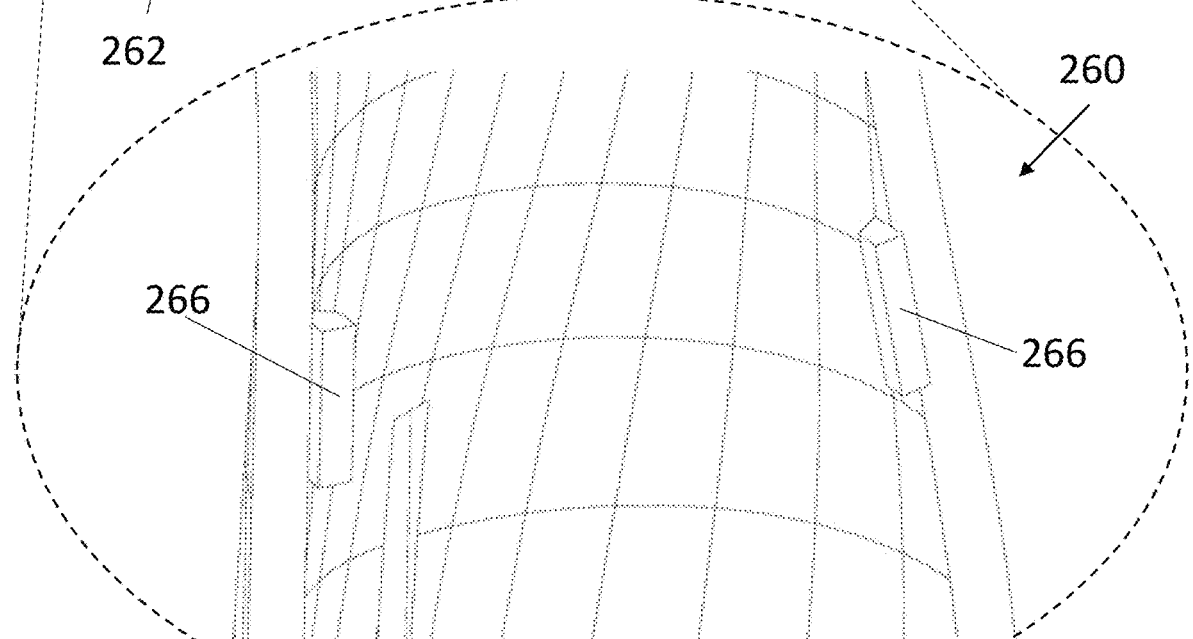

FIG. 16A  FIG. 16B

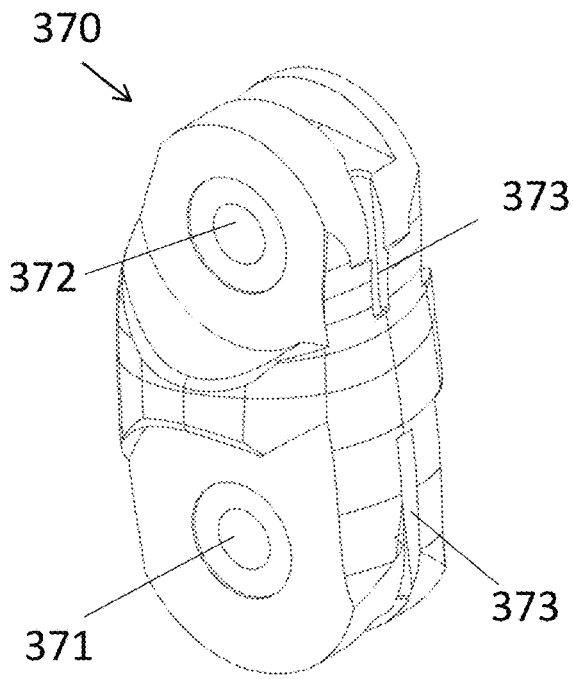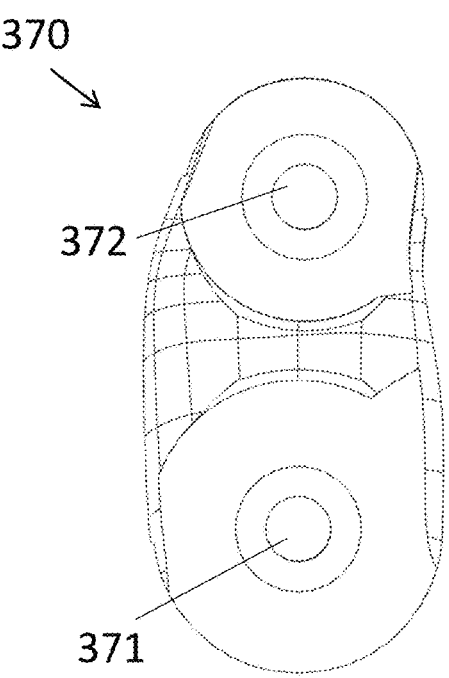
FIG. 18A  FIG. 18B
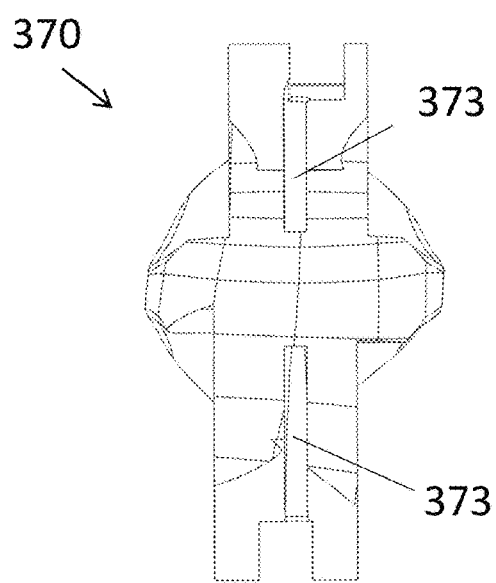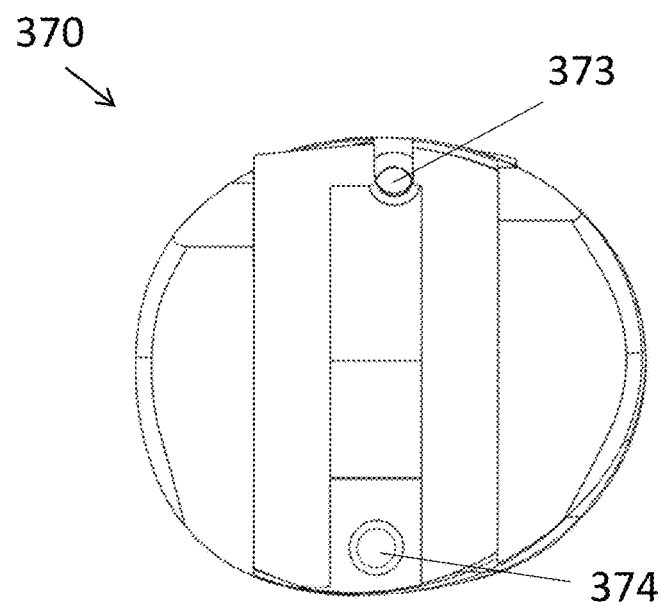
FIG. 18C  FIG. 18D

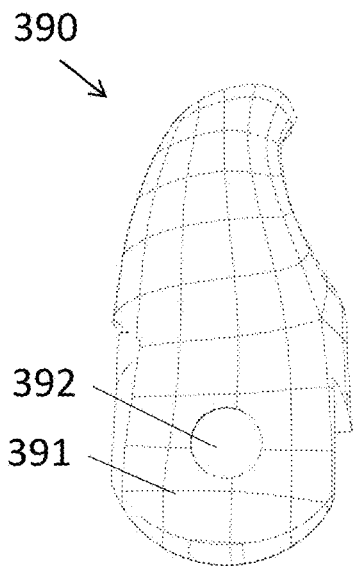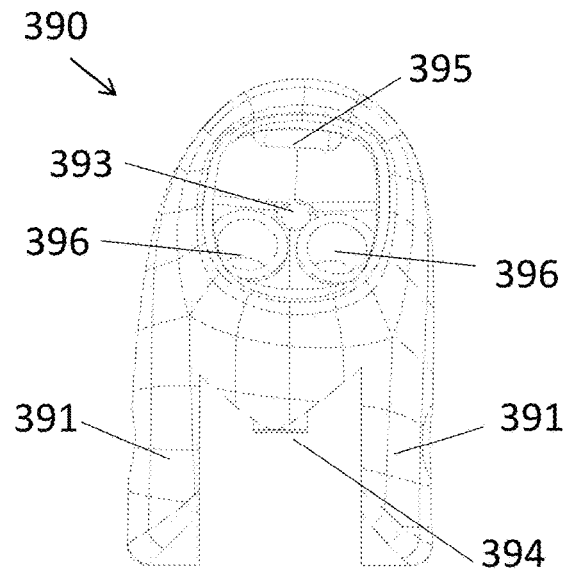
FIG. 20A    FIG. 20B
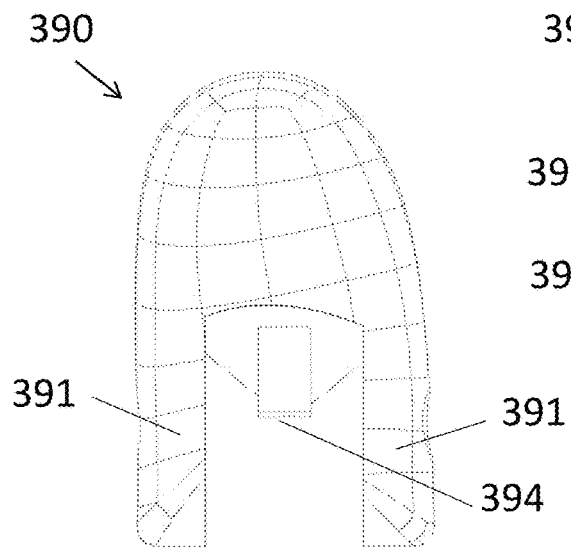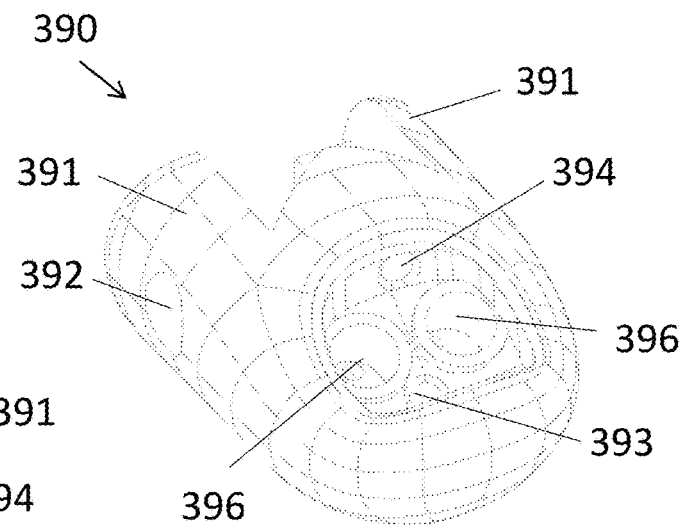
FIG. 20C    FIG. 20D

4100

SOCKET FOR UPPER EXTREMITY PROSTHESIS

CROSS-REFERENCE TO RELATED APPLICATIONS

This application claims the benefit of the filing date of U.S. Provisional Patent Application No. 62/887,797, filed Aug. 16, 2019, the disclosure of which is hereby incorporated by reference herein.

BACKGROUND OF THE DISCLOSURE

The present disclosure is directed to sockets for use with prostheses, including upper extremity prostheses.

Prosthetic arms have been available for use, for example by amputees, for many years. More recently, mechanical and robotic components have been introduced into prosthetic arms to provide a wide range of functionality to the prosthetic arm, for example, with individual finger joints with various mechanisms of control, including based on the user's muscle control.

Conventional upper extremity prosthetic devices can be expensive and can take a long time to produce, which may make them unsuitable or undesirable for many uses. Some advanced electric hands on the market use a linkage mechanism to move the fingers to grab objects and perform tasks. This generally means that the fingers have a predetermined motion path and are unable to conform to objects. These hands may cost between $10,000 and $30,000, not including the cost to create the socket which couples to the residual limb of the user. The socket creation may result in even more time and even more cost to the prosthesis. As a result, many child amputees do not use these existing market devices. The conventional socket system is generally created by hand and is manual labor intensive. This may include making a plaster negative mold of the user's residual limb, then casting a positive, and molding a thermal plastic around this positive. From there, the socket may be tested and the process repeated until the socket fits properly and is comfortable. Muscle sensors may be molded into the socket to sense specific muscles that are used to control the hand. These sensors may use surface electrodes to sense the electrical activity of the user's muscle. The result of all of this is a generic and heavy robotic-looking device. In order to provide a more natural appearance of the prosthesis, custom silicon gloves have been created to match the user's skin tone, but this can dramatically increase costs and the glove often wears and breaks down rapidly. Thus, there is much room for improvement in robotic upper extremity prosthetic devices.

BRIEF SUMMARY

According to one aspect of the disclosure, a socket is for coupling a prosthetic upper extremity to a residual limb of a user. The socket may include a proximal socket portion and a distal socket portion coupled to the proximal socket portion by a joint. The joint may include a biasing element connecting the proximal socket portion to the distal socket portion so that, in the absence of applied force, the biasing element tends to move the distal socket portion from an extended condition relative to the proximal socket portion to a flexed condition relative to the distal socket portion. The joint can include two joints. Each of the two joints may include a corresponding one of the biasing elements. The biasing element may be a torsion spring that includes a first leg and a second leg, the first leg received within the proximal socket portion and the second leg received within the distal socket portion. In the absence of applied force, the first leg may extend at an angle of about 90 degrees relative to the second leg. The distal socket portion may include a proximal coupling portion for receiving the residual limb of the user, and a distal linking portion for coupling to the prosthetic upper extremity. The prosthetic upper extremity may be included with the socket, and the prosthetic upper extremity may include a prosthetic forearm having a weight. When the prosthetic forearm is coupled to the linking portion, the weight of the prosthetic forearm may tend to overcome force of the biasing element to maintain the distal socket portion in the extended condition relative to the proximal socket portion. The proximal coupling portion of the distal socket may be sized and shaped to correspond to a size and shape of the residual limb of the user, and the linking portion may be sized and shaped to correspond to a proximal end of the prosthetic forearm.

The proximal coupling portion of the socket may include a plurality of axially extending ribs being spaced apart from one another, the axially extending ribs being flexible. The socket may include a tensioning system to tension the proximal coupling portion. The tensioning system may include a tensioner and a lace that circumscribes an outer surface of the socket. First and second ends of the lace may be coupled to the tensioner, and rotation of the tensioner may tension the lace to cause at least some of the plurality of axially extending ribs to flex inwardly. The proximal coupling portion may include a posterior side that includes a first group of the plurality of axially extending ribs, an anterior side that includes a second group of the plurality of axially extending ribs, and two lateral portions that each include at least one of the plurality of axially extending ribs. The at least one of the plurality of axially extending ribs of the two lateral portions may each be more rigid than the first and second groups of the plurality of axially extending ribs, such that tensioning the tensioning system flexes the first and second groups of the plurality of axially extending ribs to a greater degree than the at least one of the plurality of axially extending ribs of the two lateral portions. At least one axially extending rib in each of the posterior side, anterior side, and two lateral portions may include a thickened portion. Each thickened portion may include at least one passageway, and at least a portion of the lace passes through each passageway. The distal linking portion may include a distal face, and the distal face may have an arcuate recess formed therein. The arcuate recess may be adapted to receive therein a corresponding protrusion of the prosthetic upper extremity so that the prosthetic upper extremity may be manually rotated with respect to the linking portion. The proximal socket may include a substantially C-shaped support member coupled to two extension members, each extension member coupled to the distal socket portion to form the joint.

According to another embodiment of the disclosure, a socket for coupling a prosthetic upper extremity to a residual limb of a user may include a proximal socket portion and a distal socket portion coupled to the proximal socket portion by a polycentric joint. The polycentric joint may include a plate having a first end coupled to the proximal socket portion via a first fastener, and a second end coupled to the distal socket portion via a second fastener, so that the proximal socket portion is rotatable relative to the distal socket portion about a first axis passing through the first fastener and about a second axis passing through the second fastener. The polycentric joint may include two polycentric joints. The distal socket portion may include a proximal coupling portion for receiving the residual limb of the user, and a distal linking portion for coupling to the prosthetic upper extremity. The distal linking portion may include a distal-facing recess therein, an electronics control board being received in the distal-facing recess. The proximal coupling portion may include a plurality of muscle sensors therein. The plurality of muscle sensors may be coupled to the electronics control board via one or more cables. The one or more cables may extend through one or more apertures in the distal-facing recess of the distal linking portion. A first connecting cable may connect the electronics control board to a slip ring. The slip ring may include a second connecting cable connecting the slip ring to another component distal to the slip ring, the slip ring being configured to be received within a prosthetic forearm of the prosthetic upper extremity so that the prosthetic forearm is rotatable relative to the distal linking portion with an unlimited range of rotation. The proximal socket portion may include at least one adjustable strap, the adjustable strap configured to secure the proximal socket portion to a biceps or triceps area of the user.

According to a further embodiment of the disclosure, a socket for coupling a prosthetic upper extremity to a residual limb of a user may include a first socket portion adapted to receive the residual limb of the user therein, and a tensioning system. The first socket portion may have an anterior panel for contacting an anterior surface of the residual limb, a posterior panel for contacting a posterior surface of the residual limb, and at least two side panels for contacting at least two side surfaces of the residual limb. The tensioning system may be coupled to the first socket portion. The tensioning system may include a tensioner and a lace coupled to the tensioner, the lace passing through the anterior panel, the posterior panel, and the at least two side panels, so that upon rotation of the tensioner, the lace is drawn into the tensioner so that the anterior panel, the posterior panel, and the at least two side panels are drawn radially inwardly. The socket may include a second socket portion, the first socket portion being a distal socket portion, the second socket portion being a proximal socket portion, the proximal socket portion being coupled to the distal socket portion by a polycentric hinge. An outer panel may be on a posterior side of the first socket portion, the outer panel surrounding the posterior panel, the outer panel configured to contact both the user's residual limb and a biceps or triceps region of the user. A gap may be formed between the outer panel and the posterior panel, the gap configured to align and receive a portion of an elbow joint of the user. The residual limb may be a residual forearm, and the first socket portion may be configured to receive the residual forearm without any other portion of the socket being supported by a biceps or triceps region of the user. The tensioning system may include a first tensioning system and a second tensioning system, the first tensioning system being coupled to a proximal portion of the first socket portion, the second tensioning system being coupled to a distal portion of the first socket portion, the first and second tensioning systems being independently controllable. The anterior panel may include a thickened area that is thickened relative to a remainder of the anterior panel, the thickened area including a passageway therethrough, the lace received through the passageway. The posterior panel may include a thickened area that is thickened relative to a remainder of the posterior panel, the thickened area including a passageway therethrough, the lace received through the passageway. The posterior panel may not be directly coupled to the anterior panel and may not be directly coupled to the at least two side panels, so that the posterior panel is suspended via the lace of the tensioning system. The first socket may include a distal linking portion configured to couple to the prosthetic upper extremity, and the anterior panel, the posterior panel, and the at least two side panels may be collectively directly coupled to the distal linking portion at no more than three locations.

BRIEF DESCRIPTION OF THE DRAWINGS

FIGS. 7A-E are views of a main forearm component of the prosthetic forearm of FIGS. 6A-E.

FIGS. 8A-E are views of a forearm cover component of the prosthetic forearm of FIGS. 6A-E.

FIGS. 16A-C are enlarged views of a representative finger coupling of the palm of FIGS. 12A-D.

FIGS. 18A-F are views of a base of the finger of FIGS. 17A-D.

FIGS. 20A-H are views of a tip of the finger of FIGS. 17A-D.

DETAILED DESCRIPTION

Figure 1A:
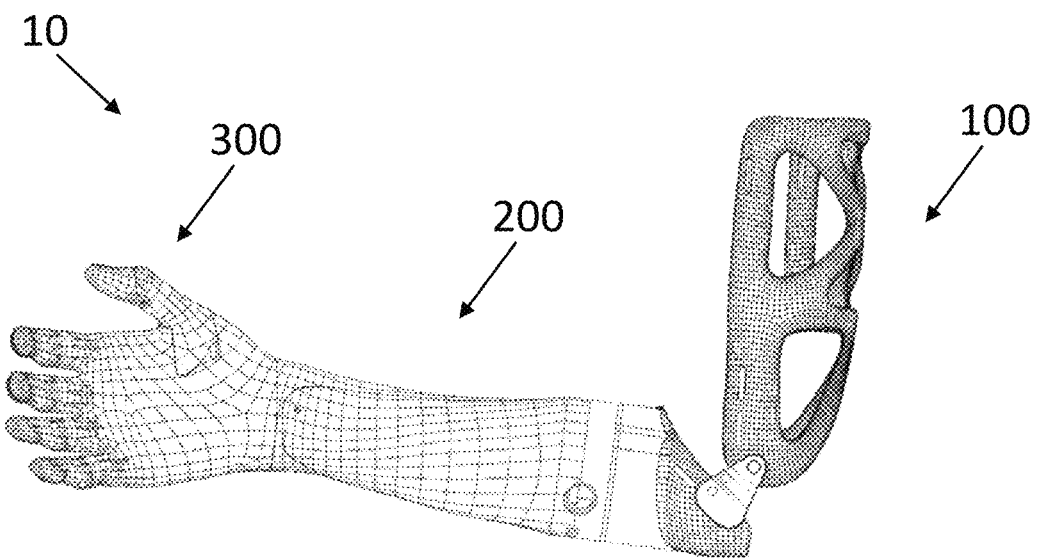
FIGS. 1A-C are views of a prosthetic upper extremity according to an aspect of the disclosure.
Figure 1B:
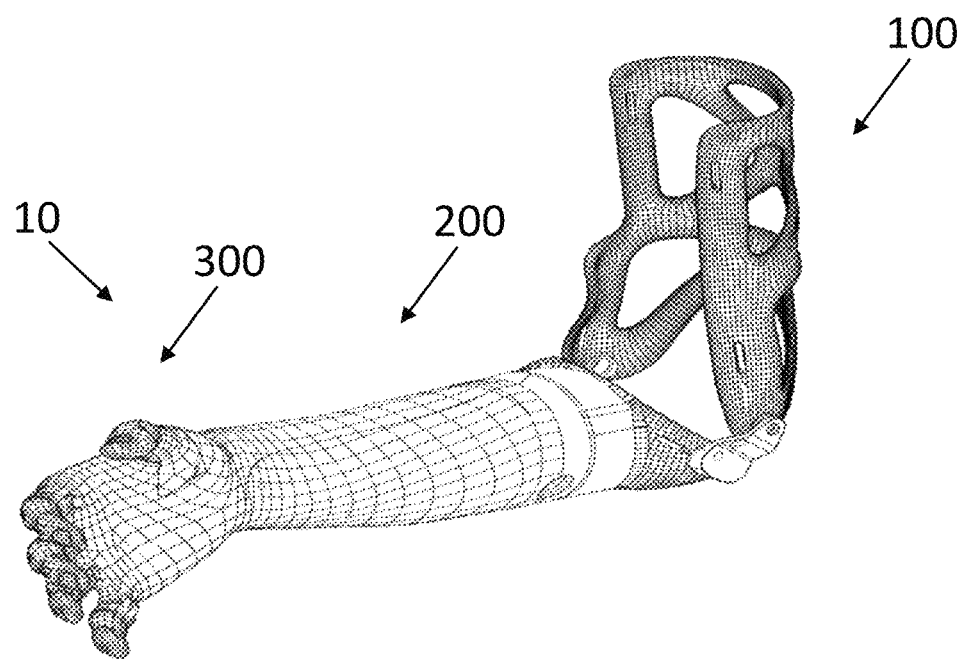
Figure 1C:
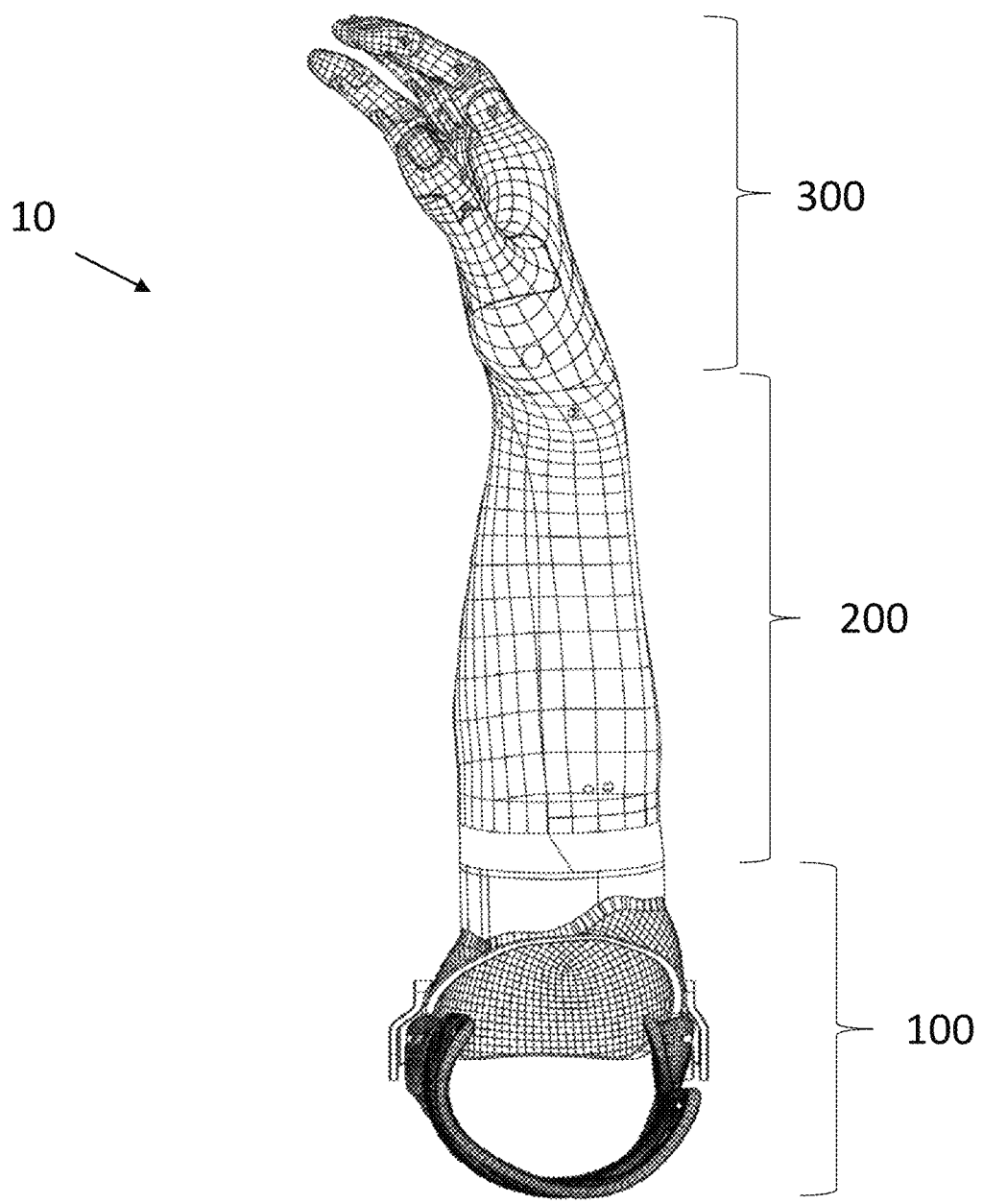

FIGS. 1A-C show an embodiment of a prosthetic upper extremity 10 for use in humans. Generally, prosthetic upper extremity 10 may include a socket 100, a prosthetic forearm 200, and a prosthetic hand 300, each of which is described in greater detail below. It should be understood that the illustrated prosthetic upper extremity 10 is for a right side of a user, but a substantially identical prosthetic upper extremity could be used for the left side of a user, with the features of the left side prosthetic extremity being substantially a mirror image of the illustrated right side prosthetic upper extremity 10.

Figure 2A:
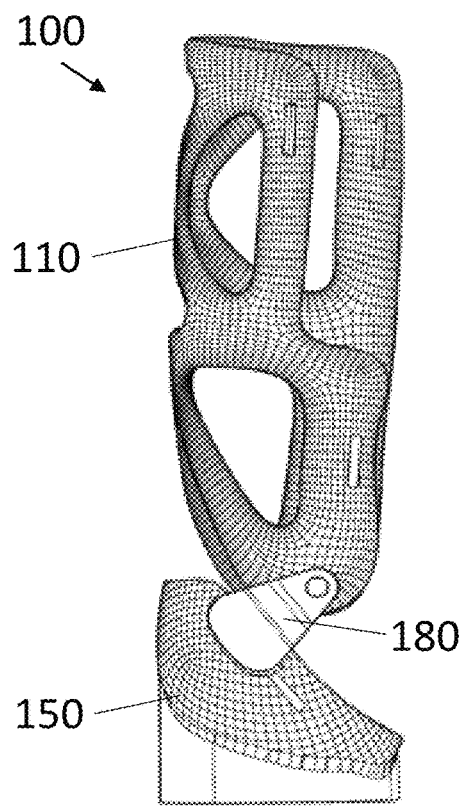
FIGS. 2A-C are views of a socket of the prosthetic of FIGS. 1A-C.
Figure 2B:
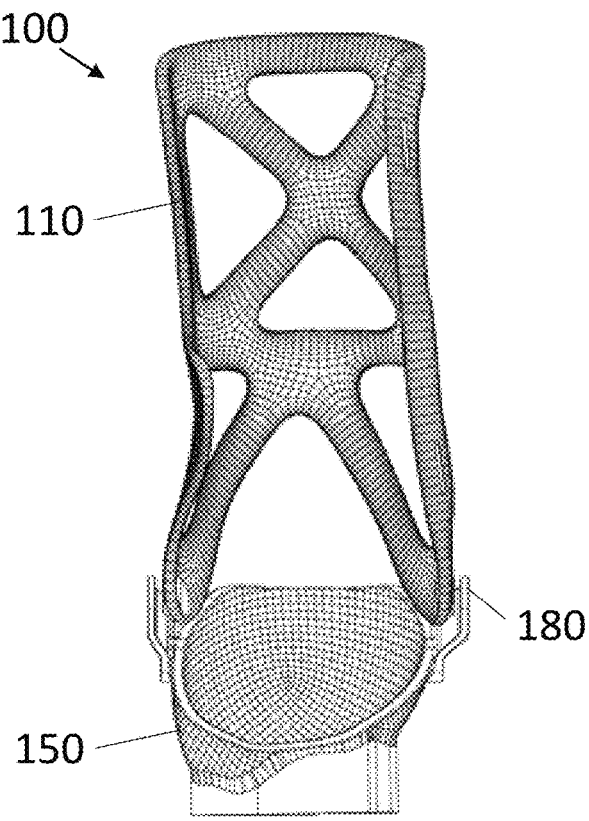
Figure 2C:
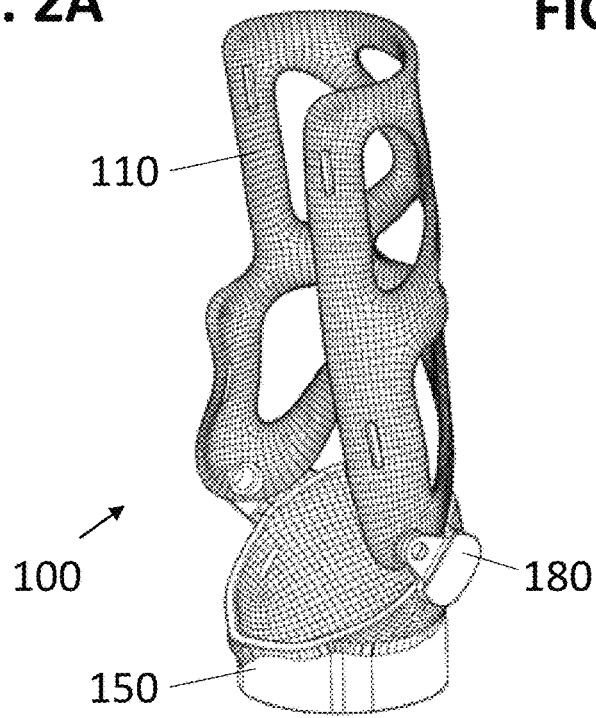

FIGS. 2A-C show an embodiment of socket 100, which may generally function to couple the user's residual limb to the prosthetic forearm 200. Generally, socket 100 is a rigid member that matches the shape and contours of the user's residual limb, and may be attached to the residual by a compression fit or other suitable mechanism. In the illustrated embodiment, socket 100 includes a proximal socket 110 and a distal socket 150, the proximal socket 110 and distal socket 150 being coupled by a joint 180. As used herein, the term "proximal" refers to a portion of the prosthetic upper extremity 10 that is relatively close to the user's heart when being used as intended, while the term "distal" refers to a portion of the prosthetic upper extremity 10 that is relatively far from the user's heart when being used as intended.

Figure 3A:
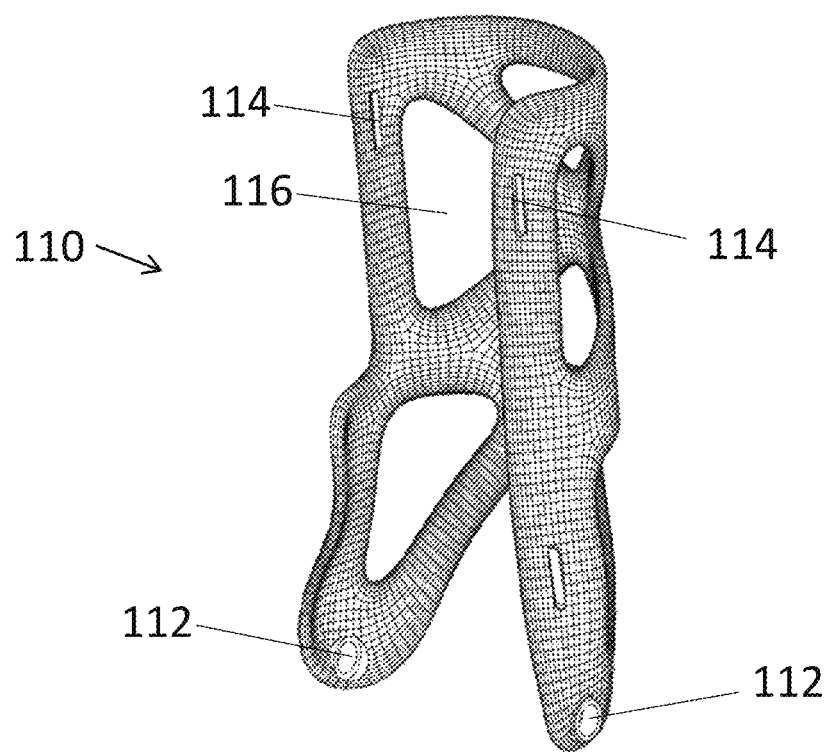
FIGS. 3A-B are views of a proximal socket of the socket of FIGS. 2A-C.
Figure 3B:
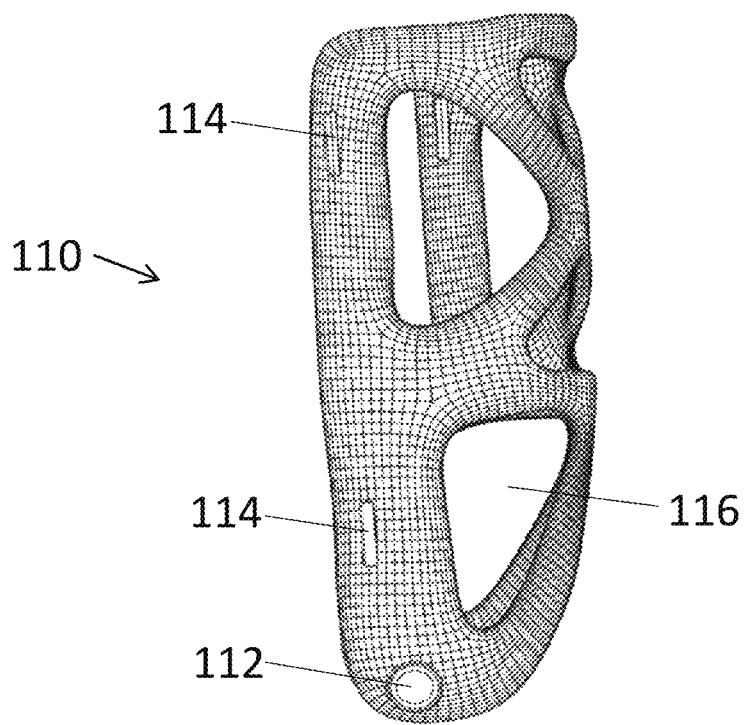

FIGS. 3A-B show two views of one embodiment of the proximal socket 110. Proximal socket 110 is preferably formed of a single integral member. Proximal socket 110 may be intended to fit over or otherwise couple to a user's upper arm, such as the bicep area proximal to the user's elbow joint. A proximal portion of proximal socket 110 is preferably generally "C"- or "U"-shaped in transverse cross-section. A distal portion of proximal socket 110 may also be generally "C"- or "U"-shaped in transverse cross-section, and may include one or more apertures 112. The distal end of proximal socket 110 preferably includes two apertures 112 that function to couple the proximal socket 110 to the distal socket 150 via joint 180. A plurality of slots 114 may also be provided on proximal socket 110. As illustrated, the proximal portion of proximal socket 110 includes a pair of slots 114 oriented substantially longitudinally near the ends of the "C"- or "U"-shape. The distal portion of proximal socket 110 is also illustrated as including a second pair of slots 114 with similar positioning. Slots 114 may be shaped and positioned to receive a strap or other coupling member. For example, a strap with a hook-and-loop fastener such as VELCRO® brand straps may be used with each pair of slots 114, with the straps helping attach and secure the proximal socket 110 to the bicep area of the user's residual limb. One or more voids 116 may be provided in proximal socket 110, regardless of whether proximal socket 110 is formed as a single integral member. Voids 116 may be areas where material has been actively removed during a stage of manufacture, or the voids 116 may be formed passively by forming proximal socket 110 to define voids 116. Regardless, voids 116 may provide one or more benefits, including reducing the weight of proximal socket 110, increasing air flow to the user and/or increasing comfort of the proximal socket 110, and/or increasing the duration of use of proximal socket 110. It should be understood that, although voids 116 are illustrated as having certain positions and shapes and being provided in certain numbers, other numbers and/or positions and/or shapes of voids 116 may be suitable.

Proximal socket 110 includes an interior surface adapted to directly or indirectly couple to the user's upper arm. Preferably, the interior surface is user-specific in the sense that it is shaped and contoured to match the shape of the portions of the user's upper arm that will contact the interior surface of the proximal socket 110. A pre-determined offset may be introduced into proximal socket 110. In other words, rather than produce proximal socket 110 to include an interior surface that exactly matches the contours of the user's upper arm, the surface may be offset a fixed distance to allow for foam or other compressible or moldable material to be positioned as an interface between the user's upper arm and the interior surface of the proximal socket 110. The thickness of the foam or other interference material may be equal or substantially equal to the amount of fixed distance offset.

FIGS. 4A-D show various views of one embodiment of the distal socket 150. Distal socket 150 may generally include a coupling portion 160 for directly or indirectly attaching to the residual limb of a user, and a linking portion 170 for coupling to prosthetic forearm 200. Coupling portion 160 preferably has user-specific shape and/or contours so that the coupling portion closely matches the portion of the user's residual limb that it will contact. Similar to above, an offset may be introduced into the contact surface of the coupling portion 160 in order to account for one or more additional interface layers, such as foam or another compressible or moldable material, which will be positioned between the user's residual limb and the interior surface of coupling portion 160. Coupling portion 160 may include one or more slots 164. Preferably, a pair of slots 164 are included on substantially opposite sides of the coupling portion 160 to receive a strap or other device to help better secure distal socket 150 to the user's residual limb.

Figure 5:
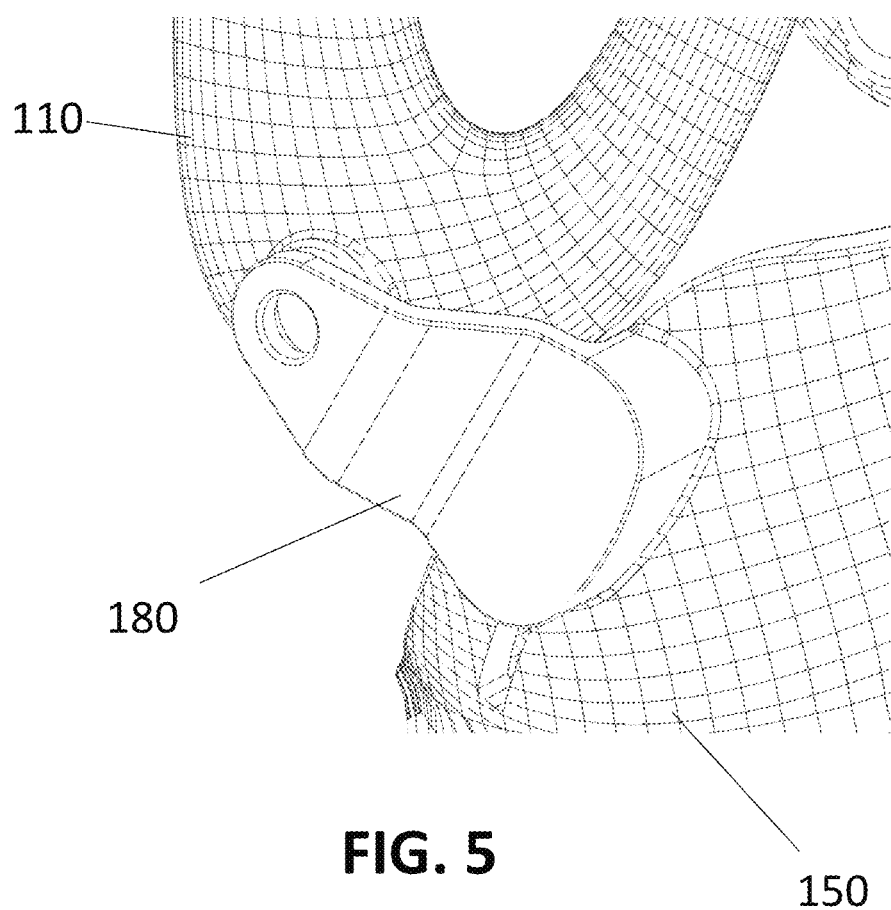
FIG. 5 is an enlarged view of a hinge of the socket of FIGS. 2A-C.

A joint 180 may be coupled to distal socket 150, preferably to coupling portion 160. Joint 180 may include two bracket members on substantially opposite sides of the coupling portion. The bracket members of joint 180 may include apertures or other structures to couple the brackets to the apertures 112 in proximal socket 110, for example via pins so that joint 180 may rotate about an axis extending through apertures 112 of proximal socket 110. FIG. 5 illustrates proximal 110 coupled to distal socket 150 via joint 180. The joint 180 preferably substantially aligns with the elbow joint of the user so that, as the user rotates his or her residual forearm relative to the upper arm via the elbow, the proximal socket 110 correspondingly rotates relative to the distal socket 150.

Figure 4A:
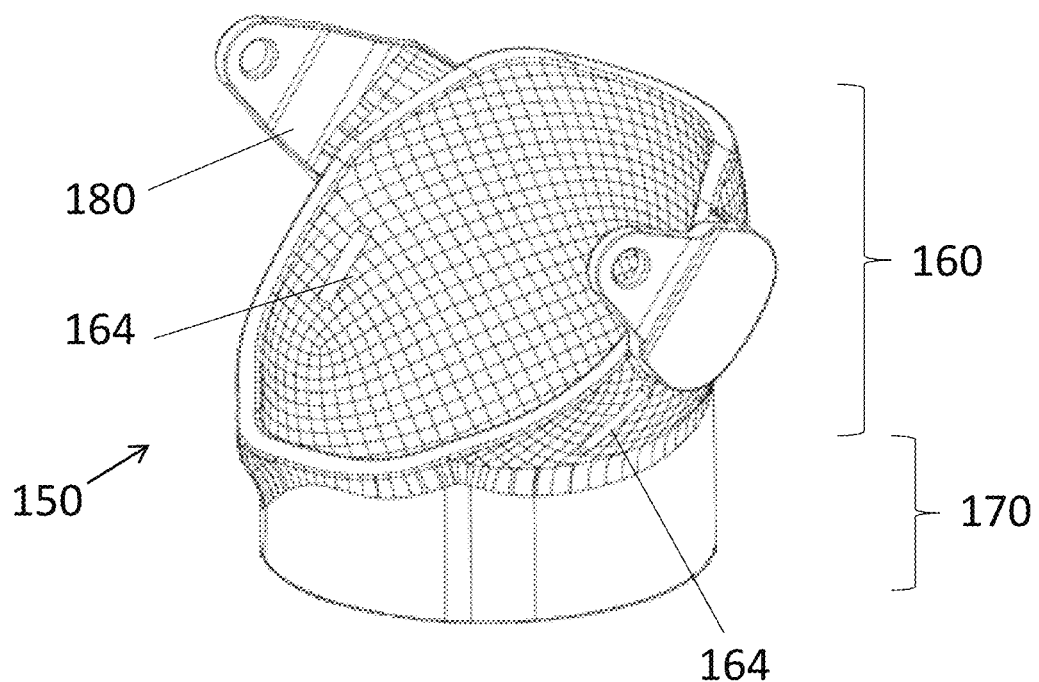
FIGS. 4A-D are views of a distal socket of the socket of FIGS. 2A-C.
Figure 4B:
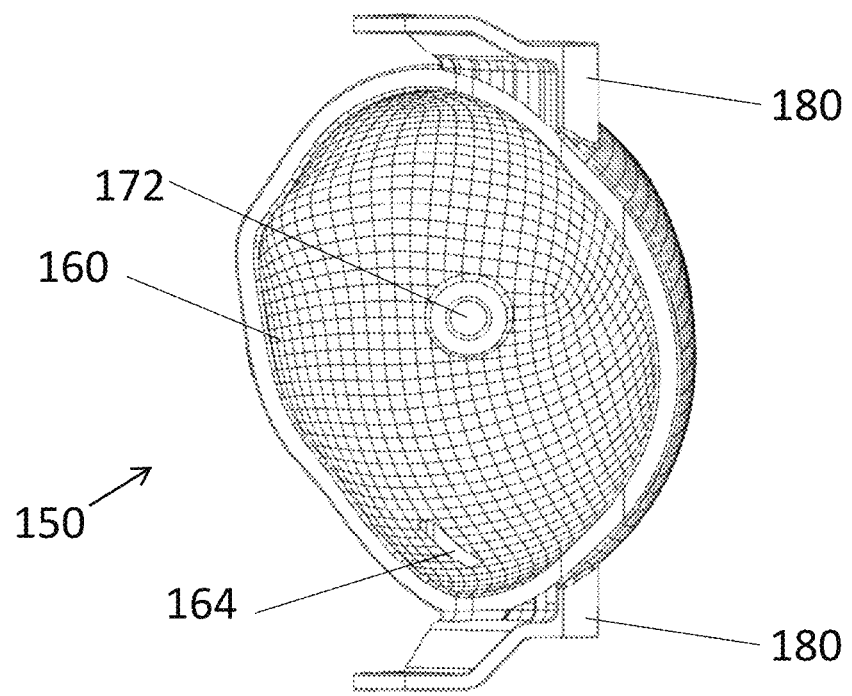
Figure 4C:
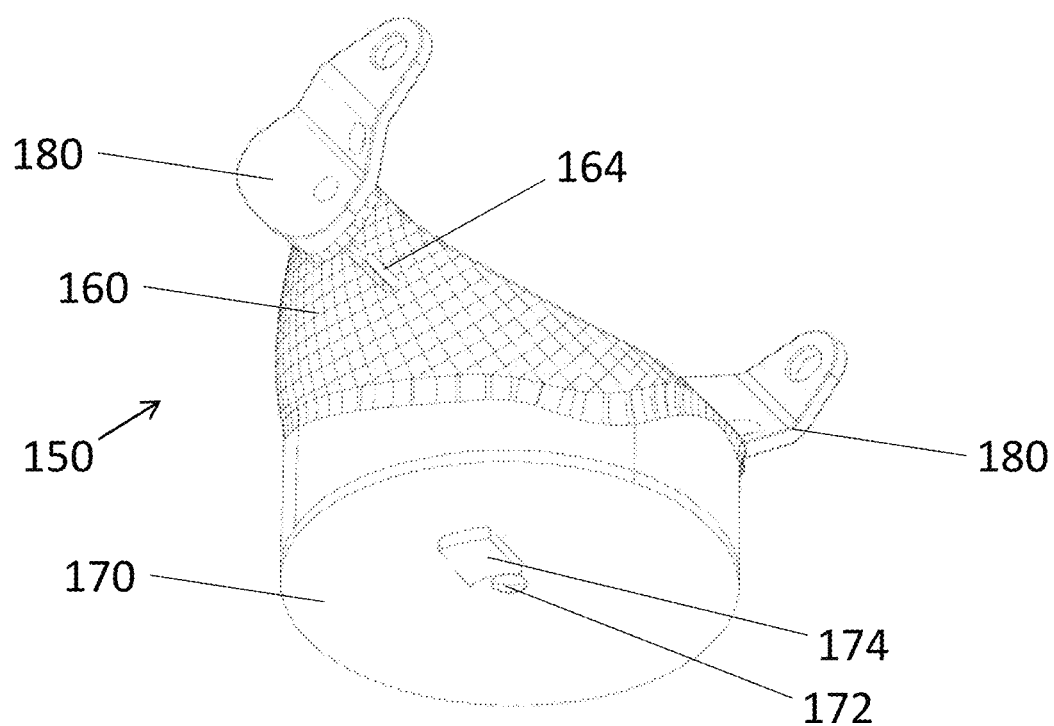
Figure 4D:
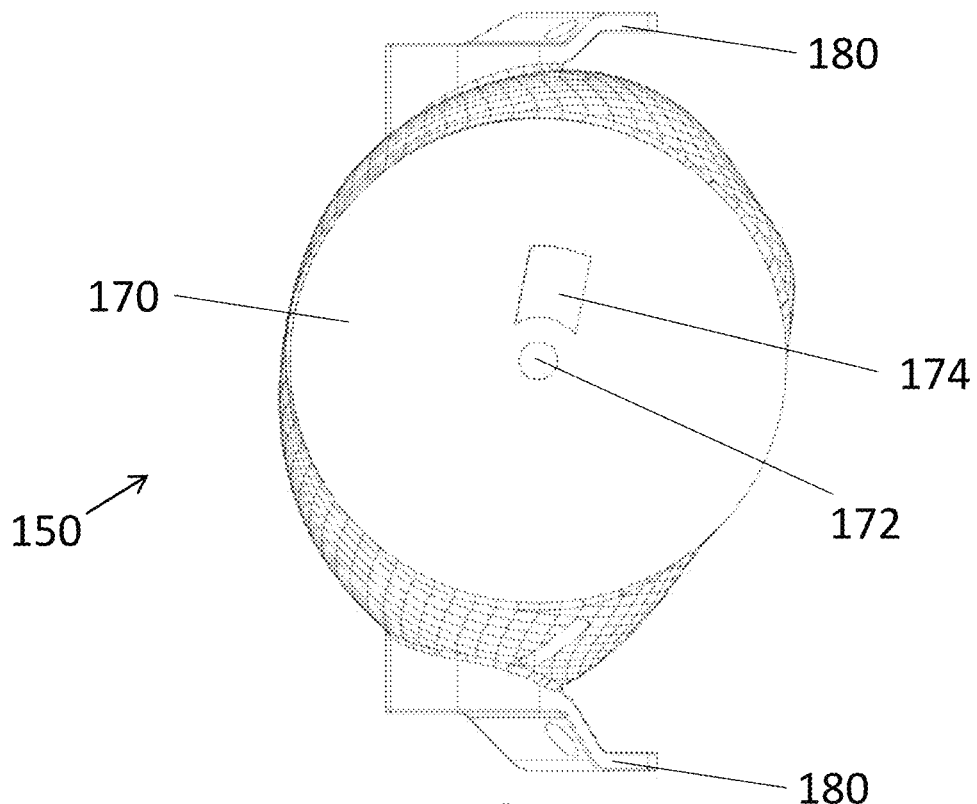

Linking portion 170 may extend distally from coupling portion 160, the linking portion being substantially cylindrical. As best shown in FIGS. 4C-D, a distal surface of linking portion 170 may include an aperture 172, preferably at a longitudinal center of the cylinder, and a protrusion 174 extending from the distal surface. Aperture 172 and protrusion 174 may help link distal socket 150 to prosthetic forearm 200, as described in greater detail below.

FIGS. 6A-E show various views of prosthetic forearm 200 in an assembled condition. Generally, prosthetic forearm may include a main forearm 210 and a forearm cover 260. In the assembled condition, prosthetic forearm 200 may have a shape, size, contour, color, and/or texture that substantially is a mirror image of the user's remaining forearm, if such a forearm exists. Methods for creating prosthetic forearm 200 are described in greater detail below after the remaining structures and functions of upper prosthetic extremity 10 are described. In the illustrated embodiment, main forearm 210 houses most or all of the mechanical components that cause movement of the prosthetic hand 300, while cover 260 houses most or all of the electronic components that control the mechanical components, as described in greater detail below. However, in other embodiments, prosthetic forearm 200 may serve mostly or solely as a structural member that couples the prosthetic hand 300 to the socket 100, with most or all of the electronic and/or mechanical components being housed within prosthetic hand 300.

Figure 7A:
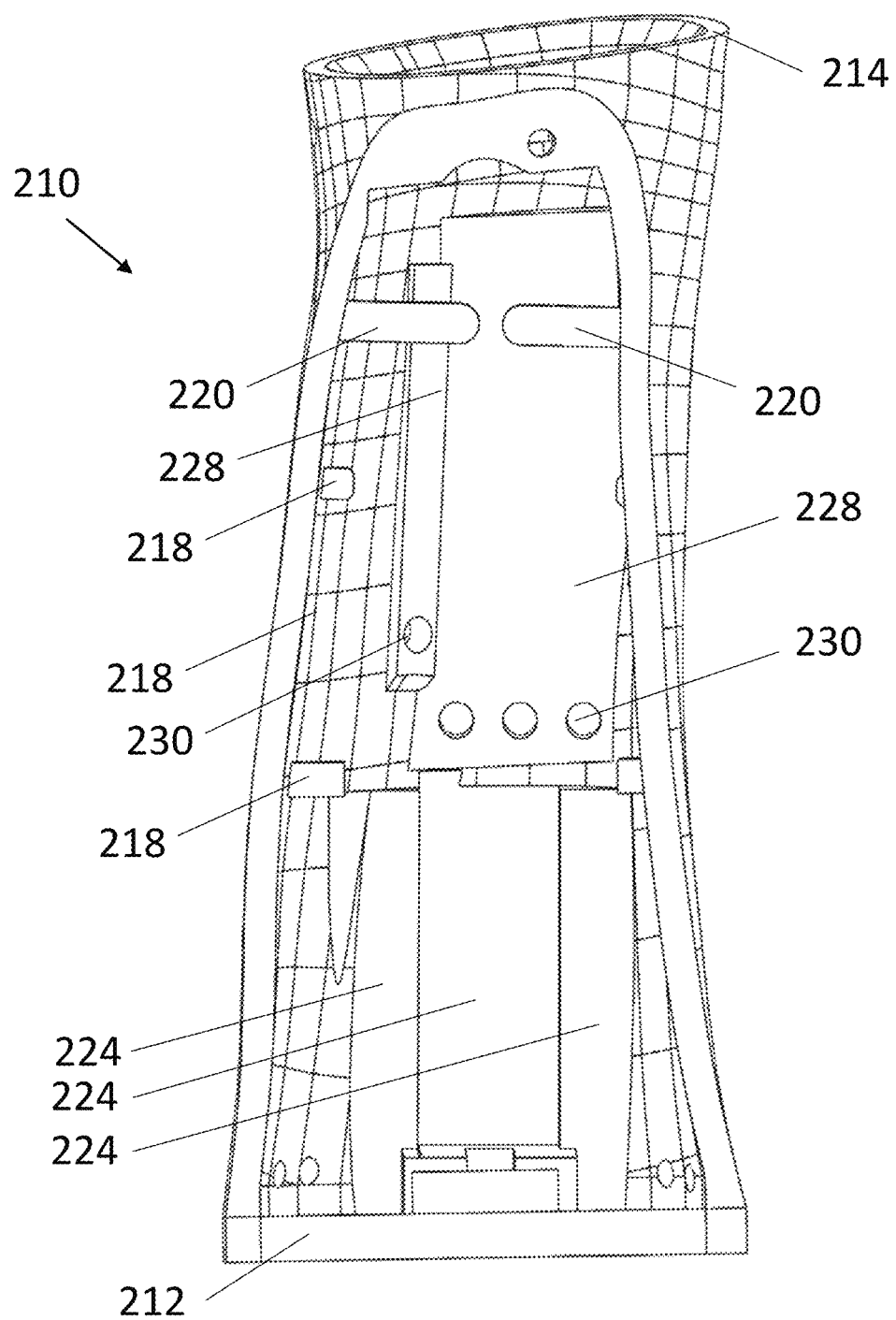

FIGS. 7A-E illustrate various views of the main forearm 210 of prosthetic forearm 200. Main forearm 210 may extend from a proximal base 212 to a distal wrist 214. As noted above and explained in greater detail below, main forearm 210 may include a substantially closed outer portion that preferably is substantially a mirror image of the user's remaining forearm. Main forearm 210 may be substantially hollow with an interior compartment to receive components, such as mechanical components to allow for movement of the prosthetic hand 300. Distal wrist 214, an illustrative shape of which is illustrated in FIGS. 7C-D, may include apertures or other features to facilitate coupling the prosthetic hand 300, described in greater detail below, to the main forearm 210. However, in other embodiments, the palm of the prosthetic hand 300 may be integral with the main forearm 210.

Figure 7B:
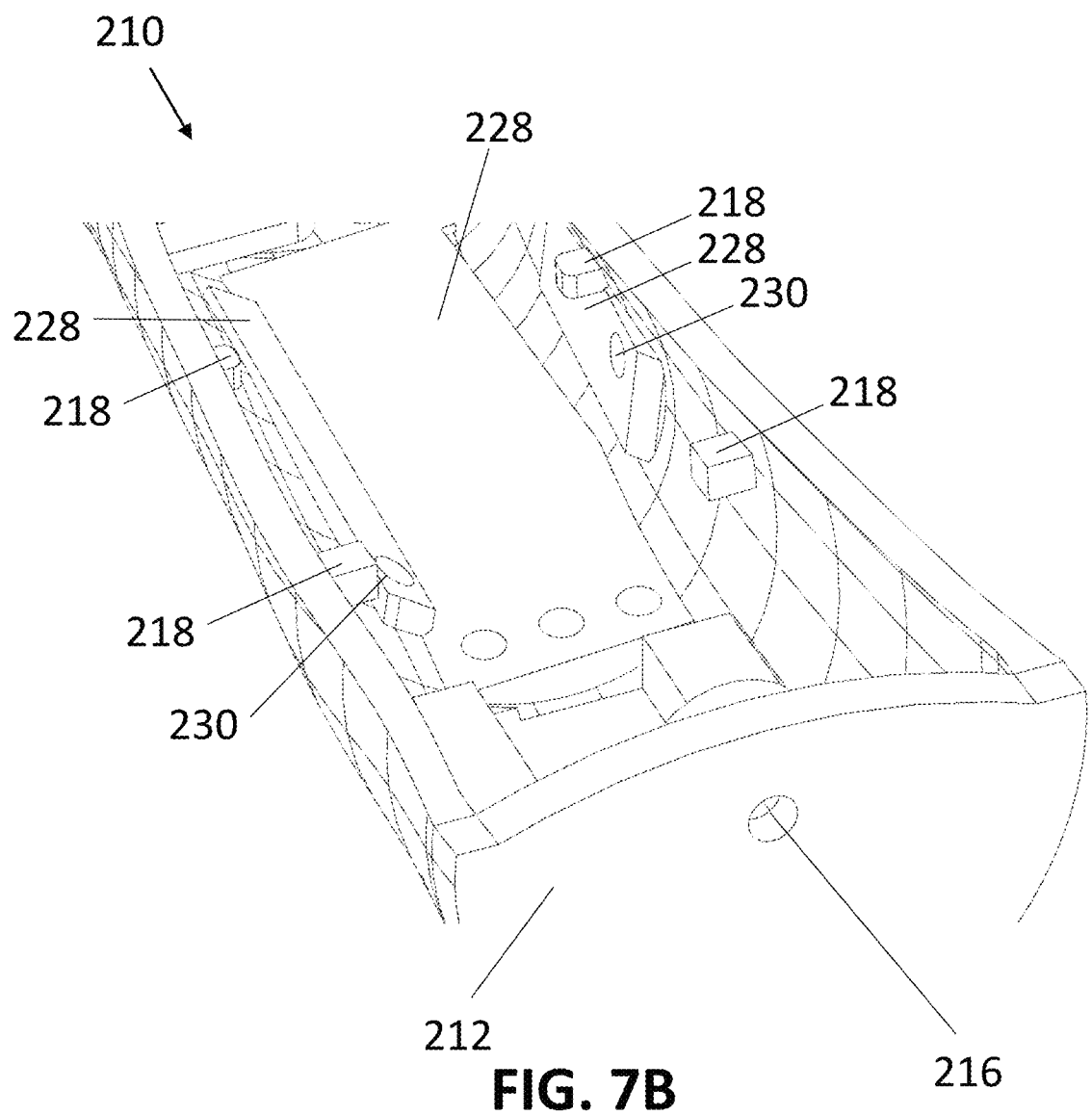
Figure 7E:
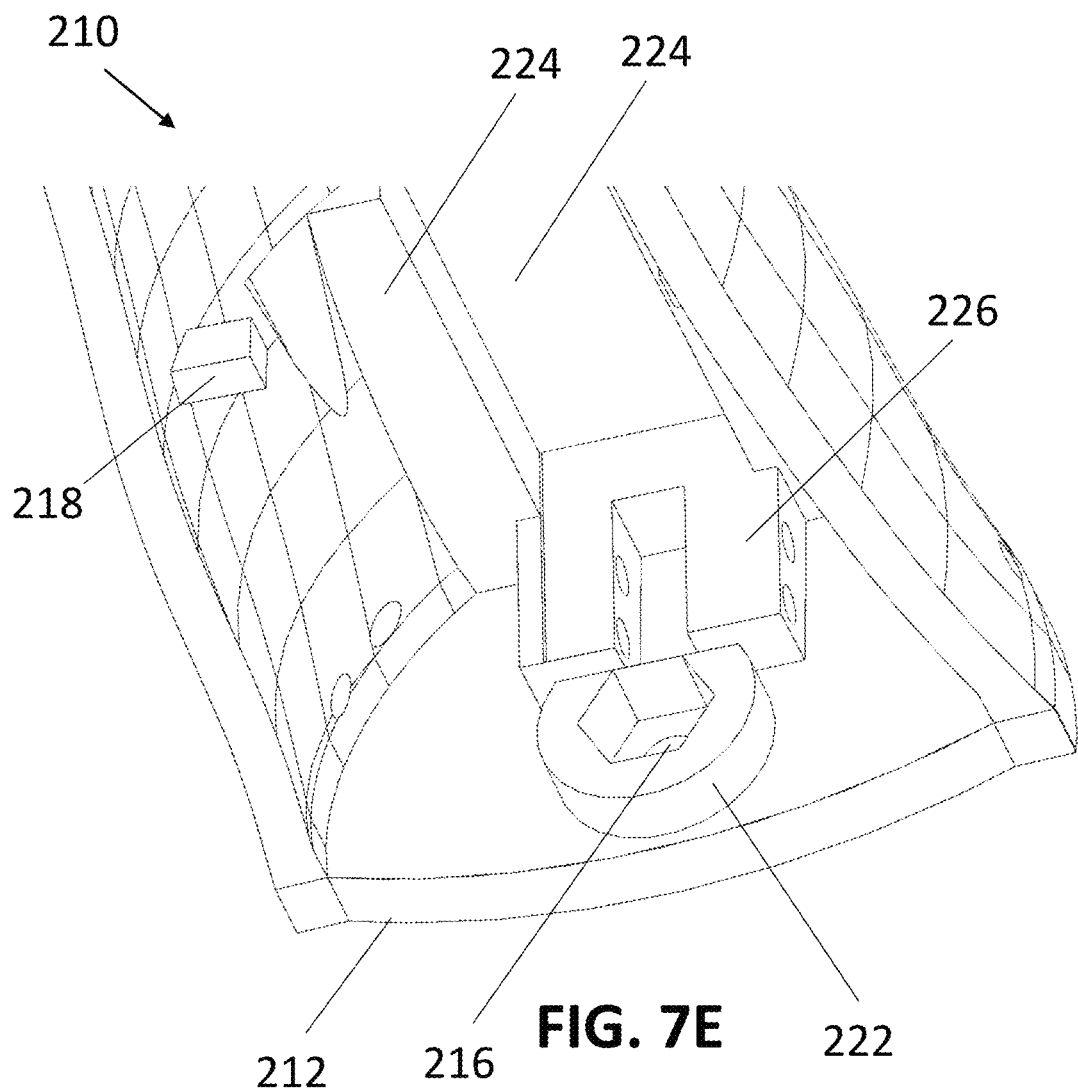

The proximal base 212 of main forearm 210, which is best shown in FIGS. 7A-B and 7E, may help couple the main forearm 210 to the cover 260 and the distal socket 150, for example via an aperture 216. Base 212 may form a portion of a cylinder, with aperture 216 preferably positioned near the center of that cylinder. In the illustrated embodiment, a nut housing 222 may be positioned around aperture 216 to receive a nut therein, so that a bolt passing through aperture 216 passes through the nut in in nut housing 222, with the nut housing 222 preventing the nut from rotating. A plurality of tabs 218 may project from an interior surface of main forearm 210 and may assist in keeping electronic components within cover 260 separated from mechanical components within main forearm 210. In some embodiments, a plate or other cover may sit on or attach to tabs 218 to cover the springs and prosthetic tendons (described in greater detail below) to help ensure the prosthetic tendons do not become ensnared on other components of the system. As shown in FIG. 7A, a pair of tabs 220 may extend toward one another substantially the entire distance of the opening near distal wrist portion 214. As will become evident in the description below, tabs 220 may help guide and retain prosthetic tendons extending toward and through distal wrist portion 214, as well as help separate electronic components within cover 260 from the mechanical components of main forearm 210.

The interior surface of main forearm 210 may include a number of structures to facilitate positioning and fixation of mechanical components therein. For example, as best shown in FIG. 7A, a plurality of flat surfaces 224 may be provided on the interior surface of main forearm 210 to provide a surface for positioning a flat surface of an actuator. In one example, three flat surfaces 224 may be provided for contacting the flat surfaces of three corresponding linear actuators. As best shown in FIG. 7E, a support member 226 may be provided to help secure the actuators to the main forearm 210. In the illustrated embodiment, the support member may include two prongs with apertures, and one actuator may be positioned between the two prongs, and an actuator may be positioned on the outside of each prong. In this embodiment, the actuators may include apertures so that one or more pins may pass through the bodies of the actuators and the apertures of the support member 226 to fix the actuators to the support member 226 of the main forearm 210. Additional apertures or other structures may be included in the wall of the main forearm 210 in order to further secure the actuators to the main forearm 210. As is described in greater detail below, each actuator may be a linear actuator coupled to a prosthetic tendon routed to one or more of the prosthetic fingers, the linear actuators adapted to cause flexion of the prosthetic fingers.

Referring to FIGS. 7A-B, additional flat surfaces 228 may be provided distal to surface 224, with a plurality of apertures 230 provided therein. In the illustrated embodiment, five total apertures 230 are provided on three flat surfaces 228. Each aperture 230 may facilitate coupling a spring or other tension member to the main forearm 210, for example by screwing the tension member into the aperture 230. As is described in greater detail below, prosthetic tendons may be coupled to each tension member, with one prosthetic tendon extending from each tension member to a corresponding finger or thumb in order to cause the fingers to extend in the absence of applied forces other than the tension member. It should be understood that the tension members may be coupled to main forearm 210 with structures and configurations other than the three flat surface 228 and five corresponding apertures 230.

Figure 8A:
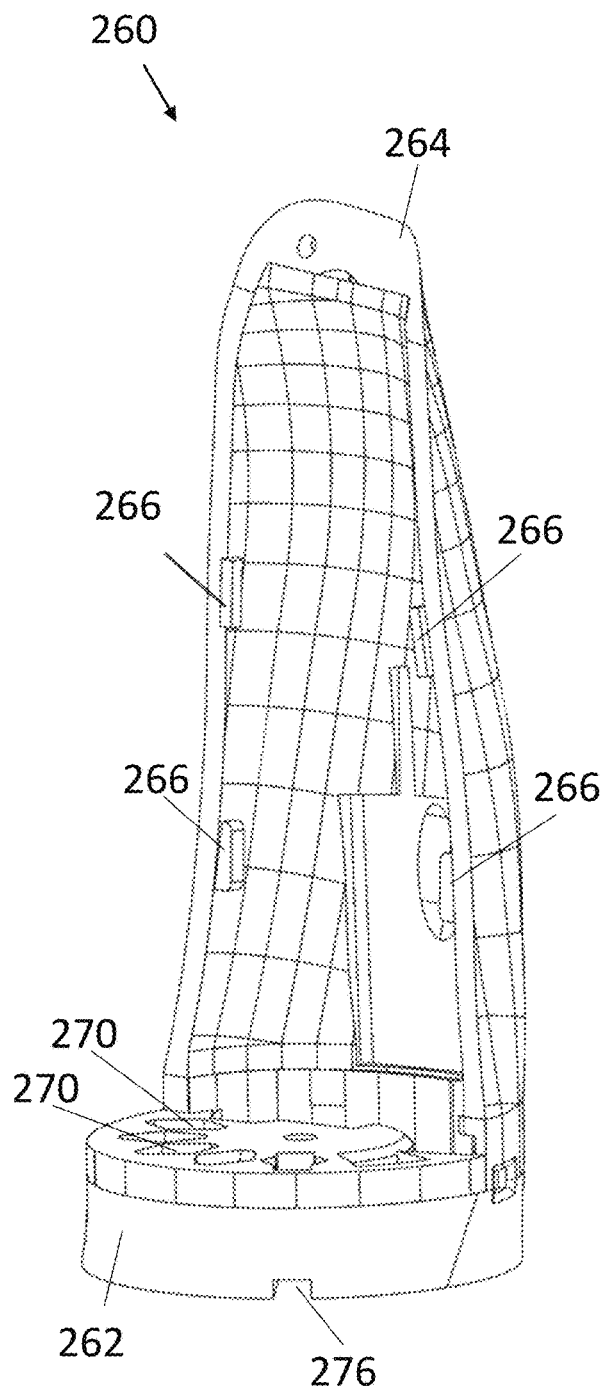

FIGS. 8A-E illustrate various views of cover 260. Cover 260 may extend from a proximal base 262 to a distal end 264. Cover 260 may include an exterior surface that, when coupled to main forearm 210, substantially replicates a mirror image of the user's remaining forearm. Cover 260 may be shaped and contoured so that it can only interface with main forearm 210 in one or substantially one orientation. One or more tabs 266 may protrude from an interior surface of cover 260. Tabs 266 are best illustrated in FIG. 8E. In the assembled condition of prosthetic forearm 200, each tab 266 of cover 260 may be in contact with a corresponding tab 218 of main forearm 210. Tabs 266 may also help separate mechanical components within main forearm 210 from electronic components within cover 260. Distal end 264 of cover 260 may include an aperture that aligns with a corresponding aperture near distal wrist 214 (best seen in FIG. 7A) in the assembled condition of the prosthetic forearm 200, the apertures adapted to receive a fastener therethrough to further secure the cover 260 to the main forearm 210.

The base 262 of cover 260 may function to couple prosthetic forearm 200 to distal socket 150, and the help secure main forearm 210 to both cover 260 and distal socket 150. In the illustrated embodiment, base 262 is substantially cylindrical and includes a central aperture 268 that substantially aligns with central aperture 216 of the base 212 of main forearm 210, as well as aperture 172 of the linking portion 170 if distal socket 150. Prior to describing the coupling of prosthetic forearm 200 to distal socket 150, additional structures of cover 260 are described.

Figure 8B:
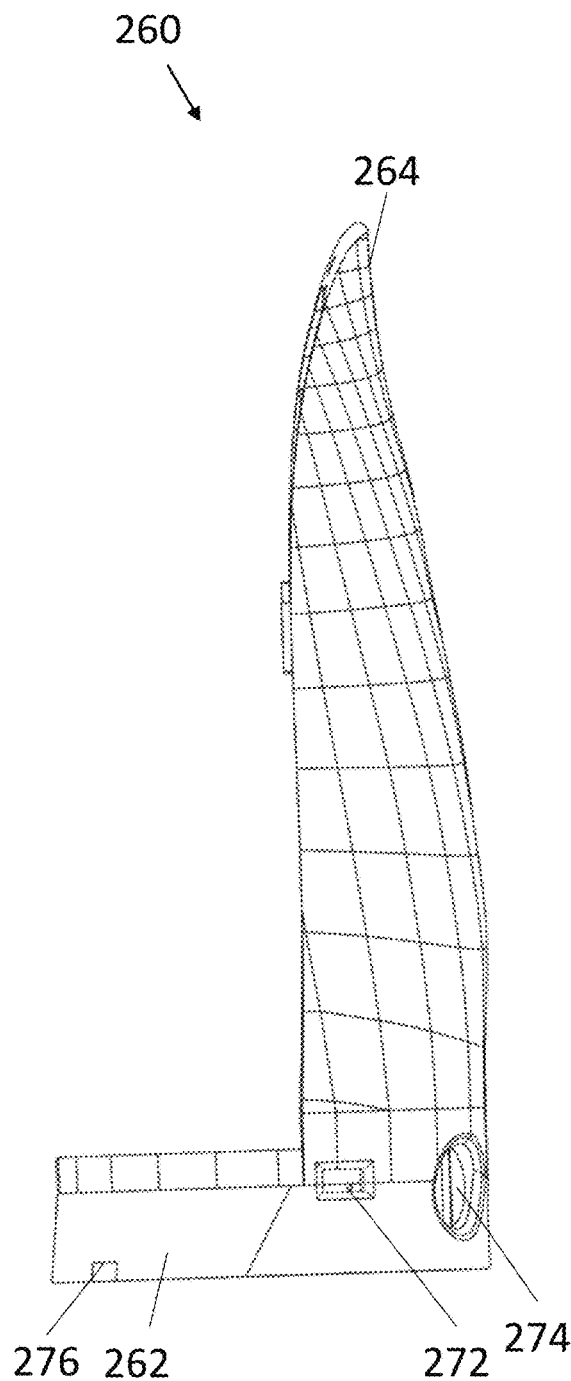

As best shown in FIGS. 8A and 8C, base 262 of cover 260 may include a plurality of cut-outs or other recesses 270 in order to reduce the material used in creating cover 260. As best shown in FIG. 8B, a first recess 272 may be provided in an exterior surface of cover 260. Recess 272 may be sized to receive a button that connects to electronic components housed in cover 260. The button in recess 272 may act as a power button or switch to turn the power to the prosthetic upper extremity on or off. A second recess 274 may be provided in an exterior surface of cover 260. Recess 274 may be sized to receive another button that connects to electronic components housed in cover 260. The button in recess 274 may provide any one or more of various functions described in greater detail below. Additional ports may be provided as desired, including for example ports to charge one or more batteries within prosthetic forearm 200.

Referring to FIGS. 8A-B, base 262 may include an indentation 276 in a bottom surface thereof. When base 262 is coupled to distal socket 150, indentation 276 may provide an area through which one or more cables may extend in order to couple electronic components within cover 260 to sensors within socket 100 or any other components as desired. Indentation 276 may provide a continuous pathway to the interior of prosthetic forearm 200 in the assembled condition, for example via one of the recesses 270 in base 262. In the assembled condition of prosthetic forearm 200, as described in greater detail below, base 262 of cover 260 may be positioned proximal to base 212 of main forearm 210, so that the base 262 of the cover 260 serve as the base for the assembled prosthetic forearm 200. This is shown best in FIG. 6D which illustrates a bottom view of assembled prosthetic forearm 200. In this view, indentation 262 is shown leading to recess 270 to allow for cables or other wires to pass from within prosthetic forearm 200 to a position external to the prosthetic forearm.

Figure 6A:
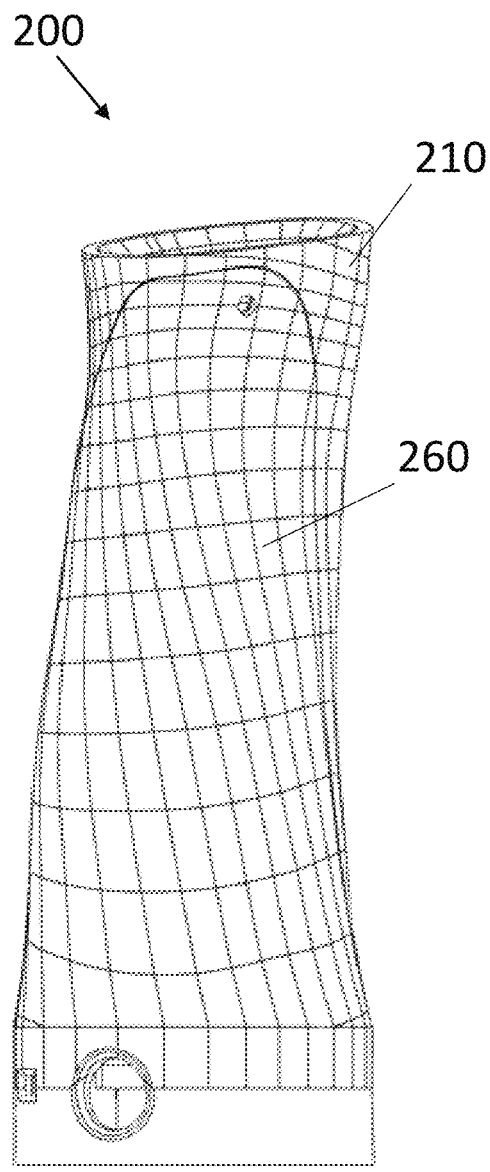
FIGS. 6A-E are views of a prosthetic forearm of the prosthetic extremity of FIGS. 1A-C in an assembled condition.
Figure 6B:
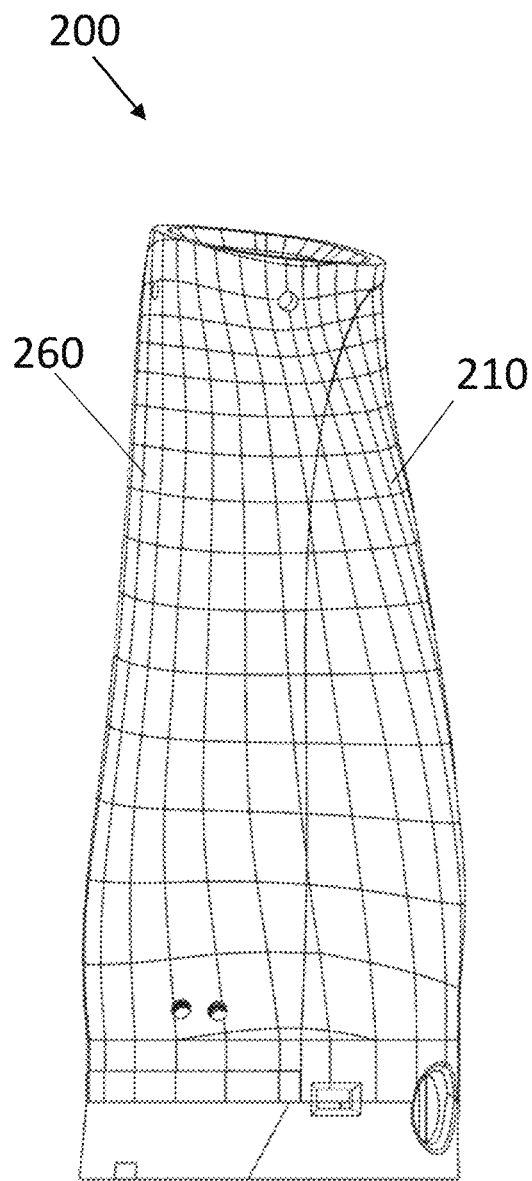
Figure 6C:
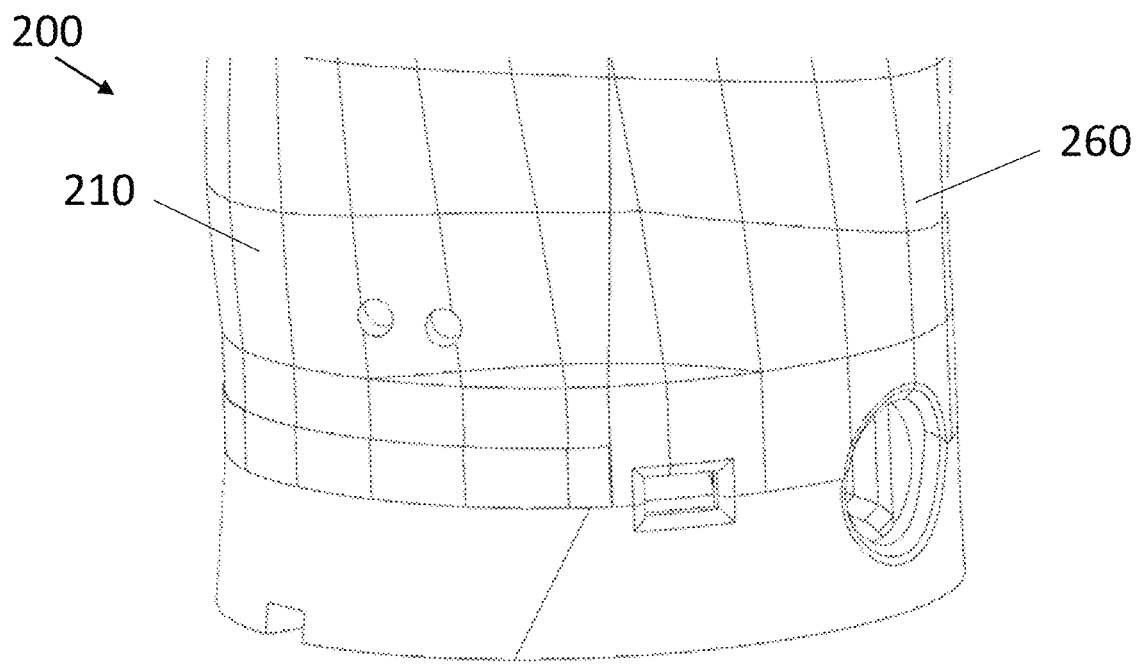
Figure 6D:
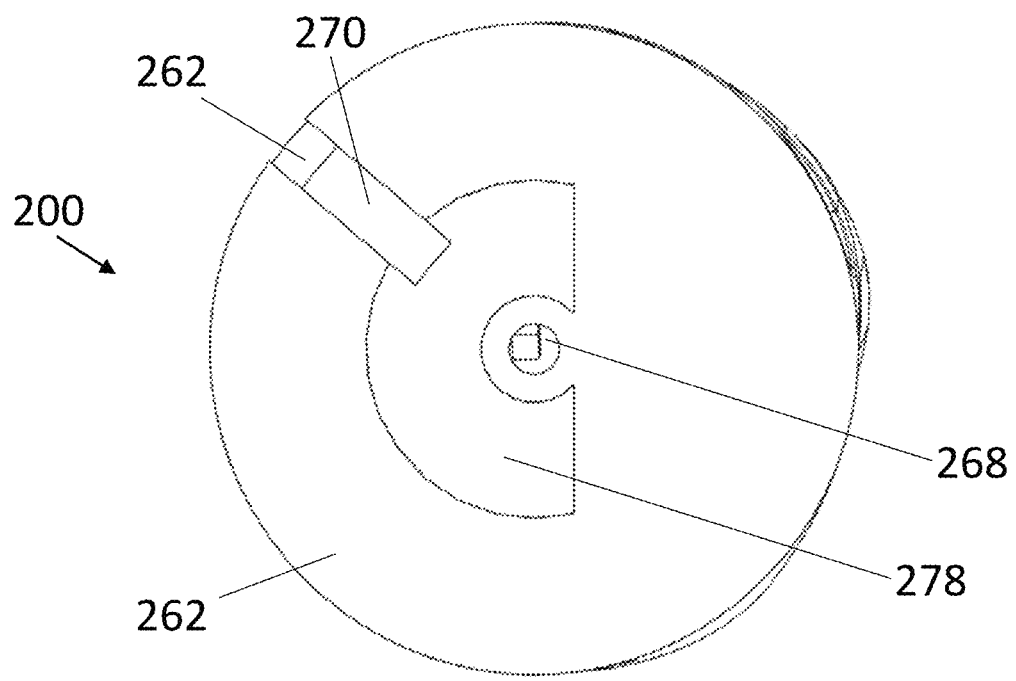
Figure 6E:
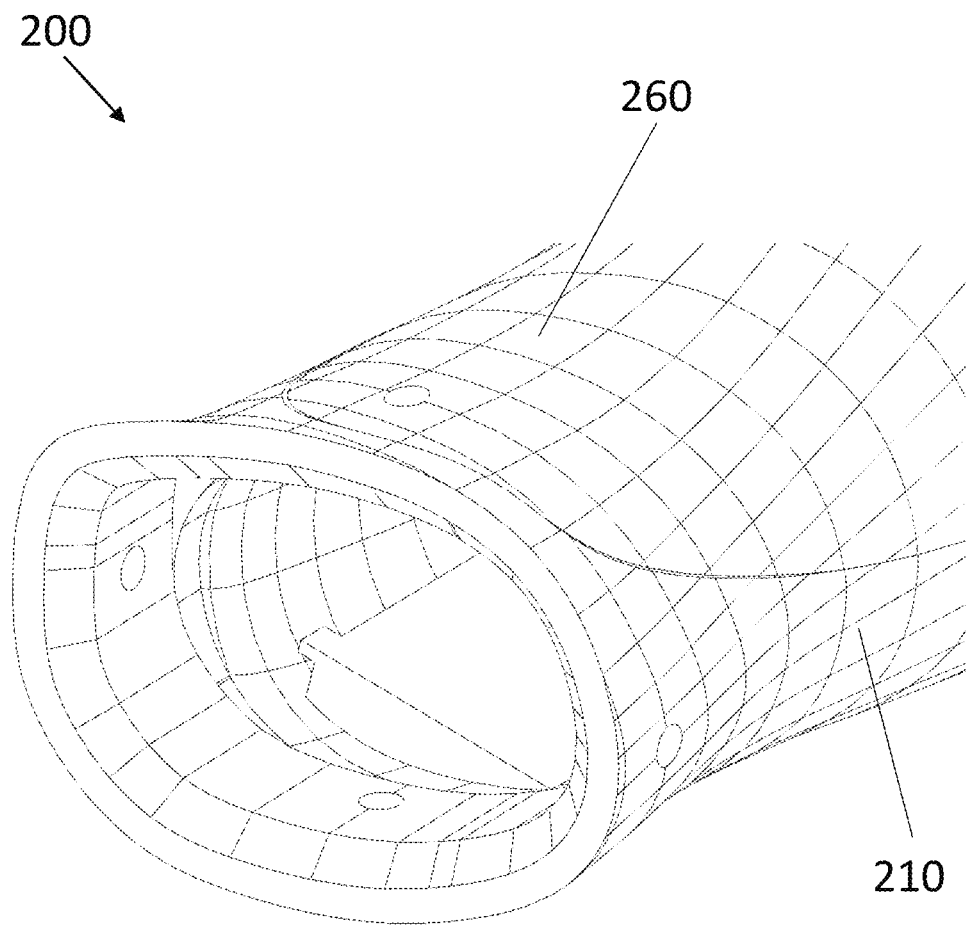

Still referring to FIG. 6D, a bottom surface of base 262 of cover 260 may include an semi-circular or semi-annular recess 278 shaped and positioned to receive the protrusion 174 of linking portion 170 therein. Thus, when the prosthetic forearm 200 is coupled to the socket 100, prosthetic forearm 200 may rotate with respect to distal socket 150. In the illustrated embodiment, semi-annular recess 278 may provide for about 180 degrees of rotation, although it should be understood that the recess 278 may be shaped to provide a greater or smaller amount of rotation. In some embodiments, the recess 278 and/or protrusion 174 may be omitted. In the illustrated embodiment, rotation between prosthetic forearm 200 and distal socket 150 may be performed manually, although in other embodiments automated or semi-automated rotation may be provided.

Figure 9:
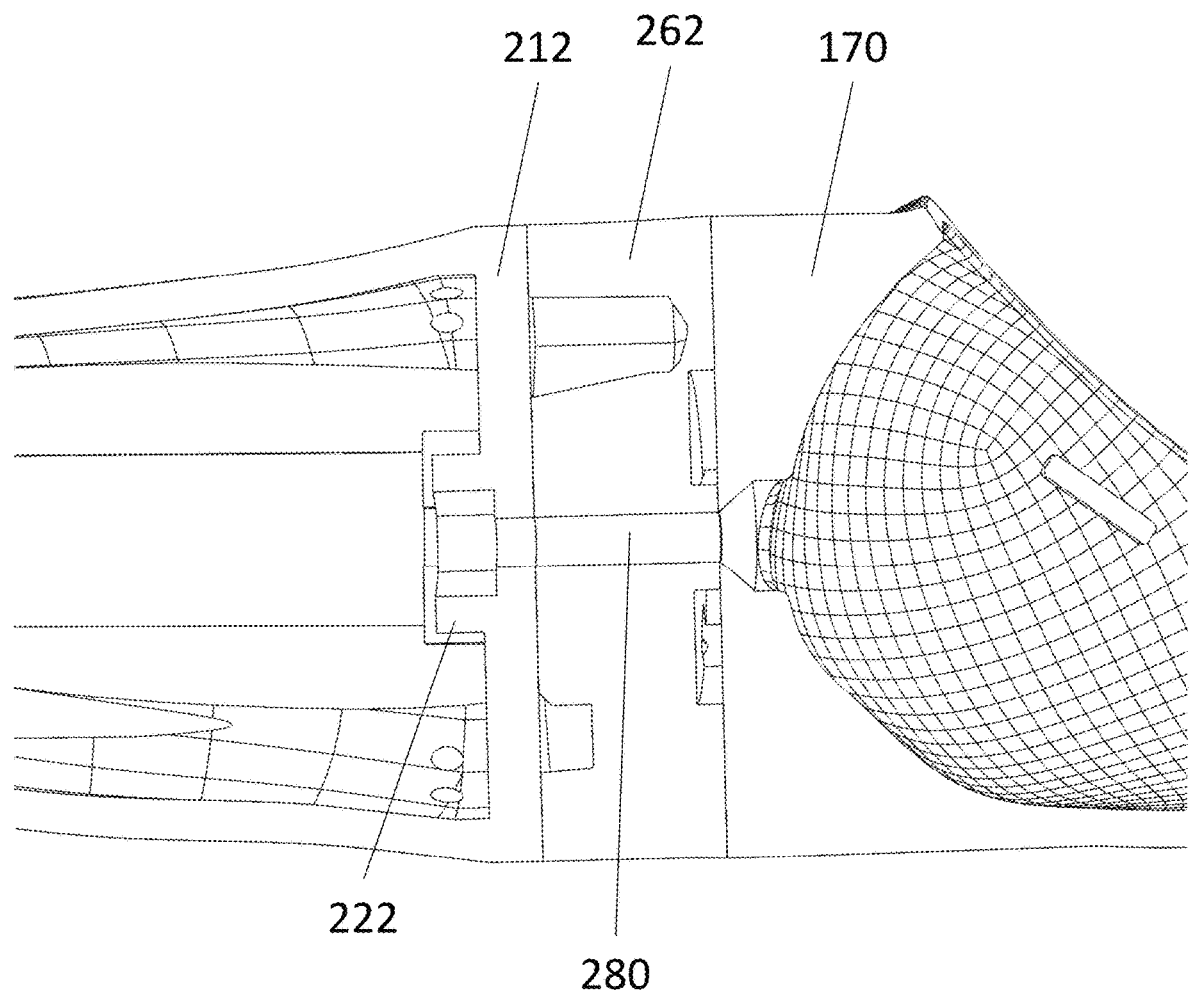
FIG. 9 is a cross-section showing the connection between the socket of FIGS. 2A-C and the prosthetic forearm of FIGS. 6A-E.

The coupling of distal socket 150, cover 260, and main forearm 210 is illustrated in FIG. 9. In the illustrated embodiment the components may be coupled by inserting a threaded bolt through the aperture 172 in the linking portion 170 of the distal socket 150, further through the aperture 268 in the base 262 of the cover 260, and finally through the aperture 216 in the base 212 of the main forearm 210. As described above, a threaded nut may be positioned within nut housing 222. The bolt 280 may be rotated to draw the nut and secure the distal socket 150 to the assembled prosthetic forearm 200. The bolt 280 may be tightened to secure the components together, while also allowing for manual rotation of the prosthetic forearm 200 with respect to the distal socket 150 as described above.

Figure 10A:
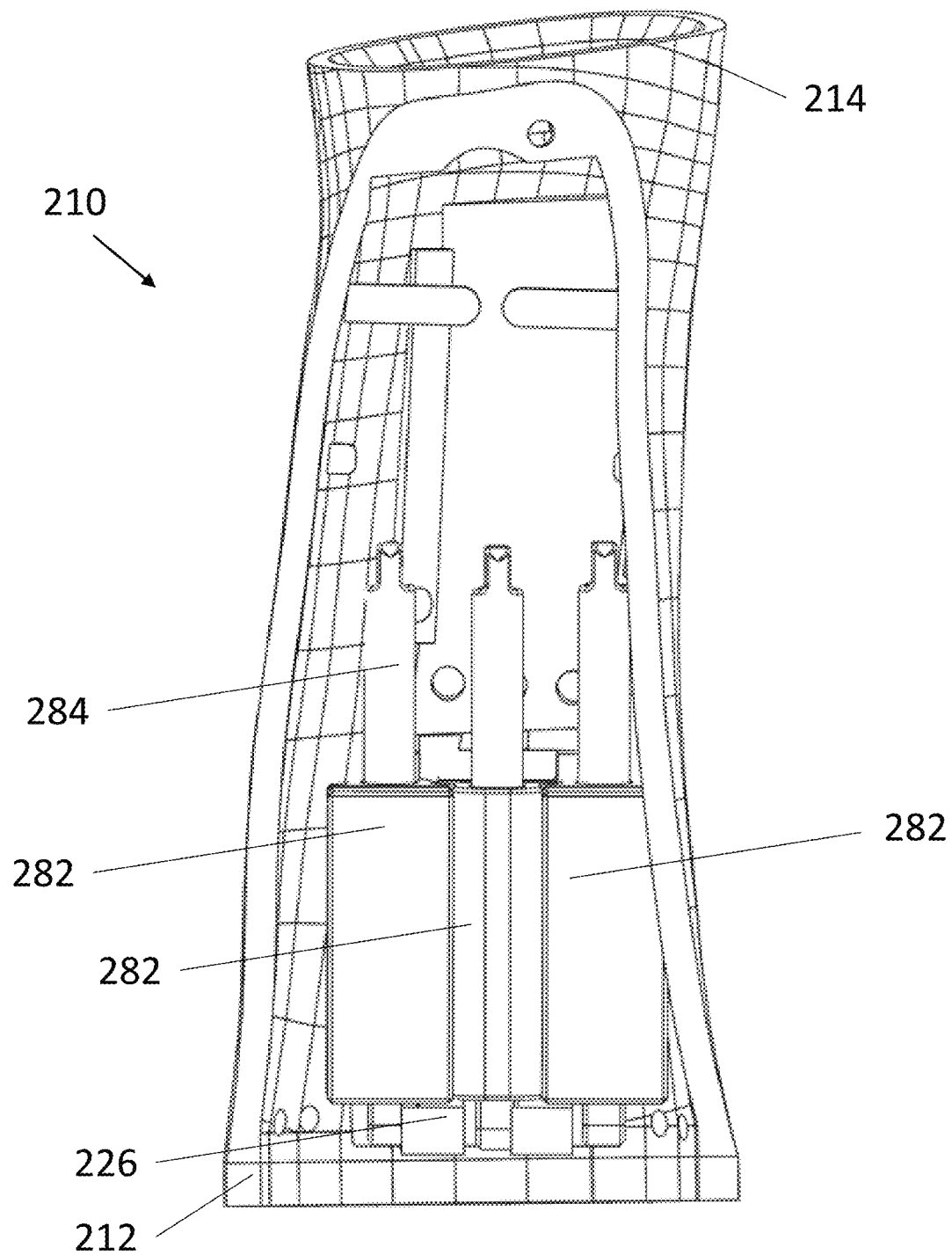
FIG. 10A is a view of the main forearm component of FIGS. 7A-E with actuator components positioned therein.
Figure 10B:
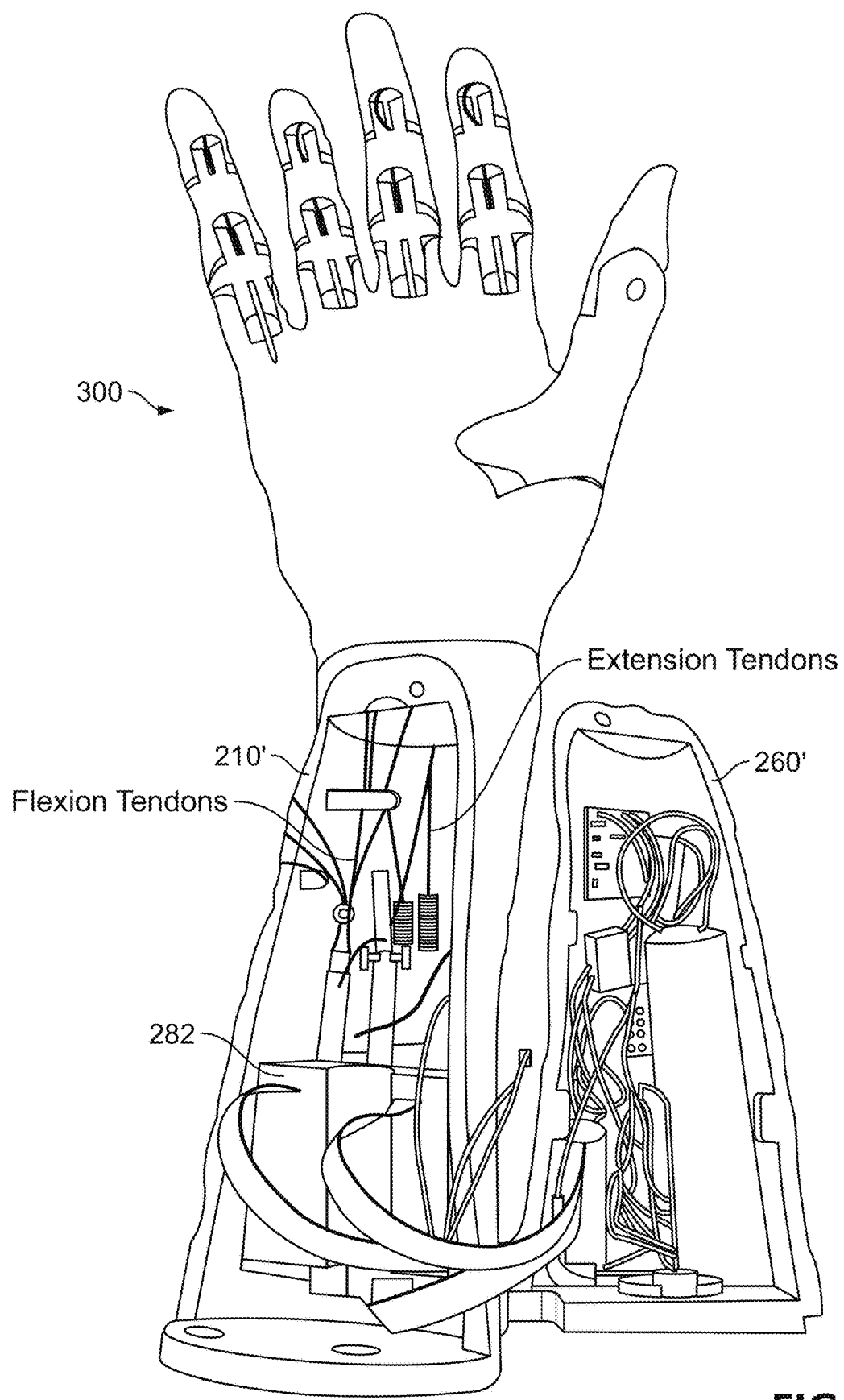
FIG. 10B is a picture of a prosthetic forearm similar to that shown in FIGS. 6A-E with mechanical and electronic components housed therein.

FIG. 10A illustrates main forearm 210 with three linear actuators 282 positioned therein secured to support member 226. Each linear actuator 282 may include a distal portion 284 attached to one or more prosthetic tendons. The distal portion 284 of each linear actuator 282 may be coupled to one or more prosthetic tendons, for example in the form of a cable such as high strength fishing line. In the illustrated embodiment, one linear actuator 282 is coupled to a prosthetic tendon routed to the prosthetic thumb, one linear actuator 282 is coupled to a prosthetic tendon routed to the prosthetic index finger, and one linear actuator 282 is coupled to three prosthetic tendons coupled to the prosthetic middle, ring, and pinky fingers. With this configuration, one linear actuator 282 causes flexion of the prosthetic thumb, one linear actuator 282 causes flexion of the prosthetic index finger, and the remaining linear actuator 282 causes flexion of the remaining three fingers substantially in unison. Thus, these prosthetic tendons may be referred to herein as flexion tendons. FIG. 10B is a picture of a main forearm 210' and cover 260' with mechanical and electronic components coupled thereto. Main forearm 210' and cover 260' are substantially identical to main forearm 210 and cover 260, with the exception that the bases of the two components are substantially reversed so that the base of the cover 260' is positioned distal to the base of the main forearm 210' in an assembled condition. As illustrated, main forearm 210' may include all or substantially all of the mechanical components for moving prosthetic hand 300, while cover 260' may include all or substantially all of the electronic components for moving prosthetic hand 300. These components are described in greater detail below after the remainder of the structure of prosthetic hand 300 is described.

In the illustrated embodiment, each linear actuator 282 includes a geared DC motor, spur gears, a lead screw, a slide potentiometer, and a shaft that is actuated. Such an actuator 282 may work by the DC motor driving a lead screw which pushes a rod that is anchored to a nut that is threaded onto the lead screw. The slide potentiometer may be attached to the enclosure and the push rod of the actuator 282 to be able to track the linear position of the rod. The rod may be the distal portion labeled as 284 in FIG. 10A. The stroke of the linear actuator 282 may vary, but typically the stroke may be around 20 mm, which may allow for precise control over the position of the actuator 282.

Although the function and routing of the prosthetic tendons is described in greater detail below, the connection of the prosthetic tendons within prosthetic forearm 200 is described here. There may be small mounting hole at that the end of the rod 284 of the linear actuator 282. The prosthetic flexion tendons may be attached to this portion of the linear actuator 282. The prosthetic flexion tendons can attach to the rod end in various suitable ways. For example, the end of the prosthetic flexion tendon may be tied directly to the mounting hole of the rod. In another example, a bracket may be provided so there is a hole that runs substantially parallel to the prosthetic flexion tendon path that allows for a hollow threaded rod to sit inside of this hole and is secured and adjusted by a nut sitting inside of the bracket. The prosthetic flexion tendon may be tied off on the hollow threaded rod so that the tension of the prosthetic flexion tendon can be adjusted by rotating the nut on the hollow threaded rod. In a further embodiment, the prosthetic flexion tendon may be run through the hole of the linear actuator rod and an additional part that clamps the tendon to itself may be provided. This may be accomplished by making a loop of the prosthetic flexion tendon, pulling it tight and adding a clamp that attaches to the loop ends so there are two parts of the tendon running through the clamp. The clamp may tightened by turning a fastener which compresses the prosthetic flexion tendon to a flat surface. All of the tendons, both flexion and extension, may be high-end fishing line. Either a monofilament or a braided fishing line may be used depending on the size of the prosthesis 10. Preferably, a line with a break strength between about 20 lbs and about 100 lbs is used, although it should be understood that other types of wires or cables having the same or other break strengths may be suitable. The prosthetic tendons preferably include coatings to minimize friction on surfaces such as the tunnels 311 through which they are routed.

As noted above and explained in greater detail below, similar or identical tendons may be coupled to springs within the forearm to serve as extension tendons to put the fingers 360a-d and thumb 330 in extension in the absence of applied forces. The prosthetic extension tendons may be formed of any of the materials described above for the flexion tendons, and the extension tendons may be coupled to the springs in substantially the same ways as the flexion tendons are coupled to the actuators 282.

Figure 11A:
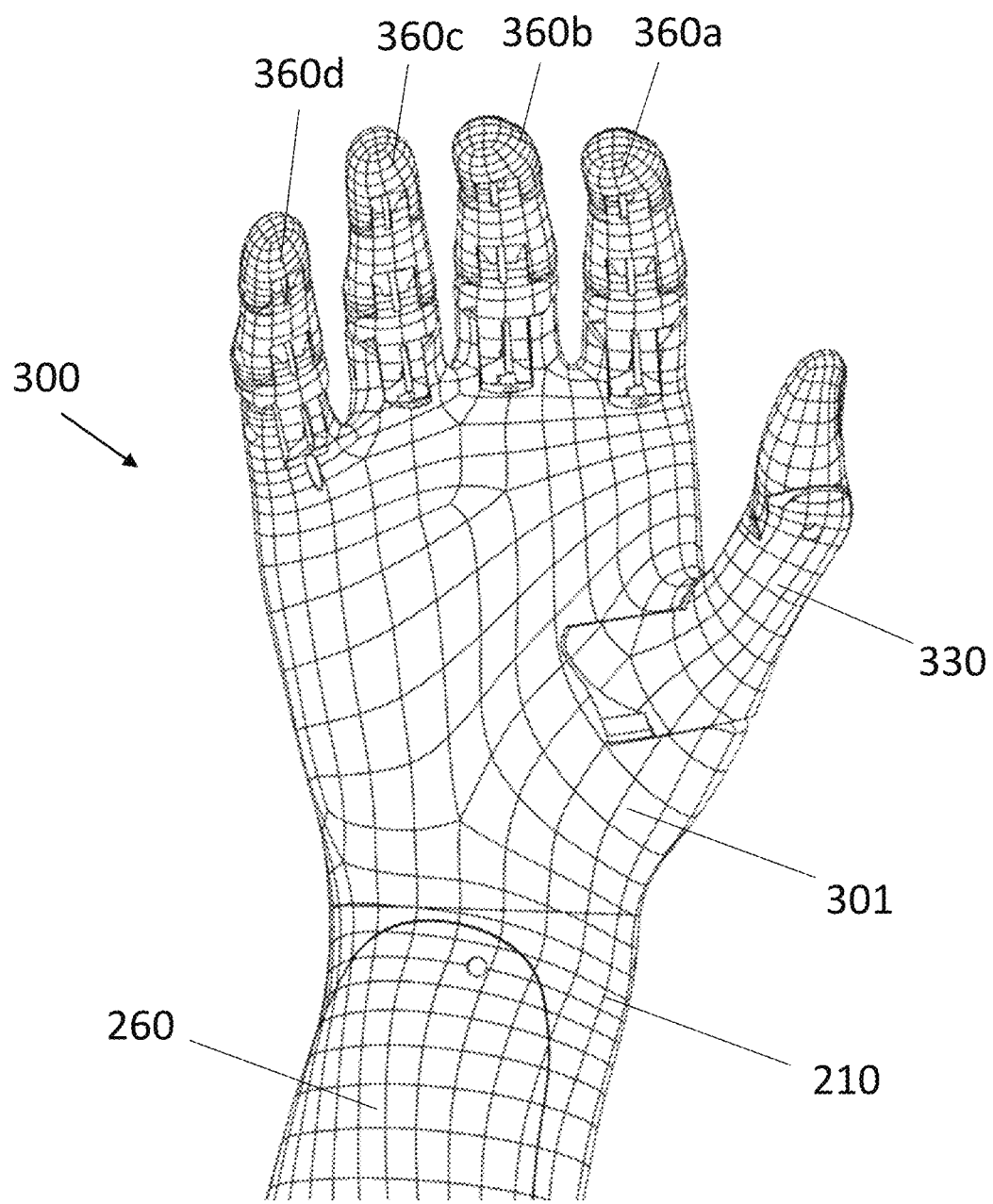
FIGS. 11A-C are views of a prosthetic hand of the prosthetic extremity of FIGS. 1A-C.
Figure 11B:
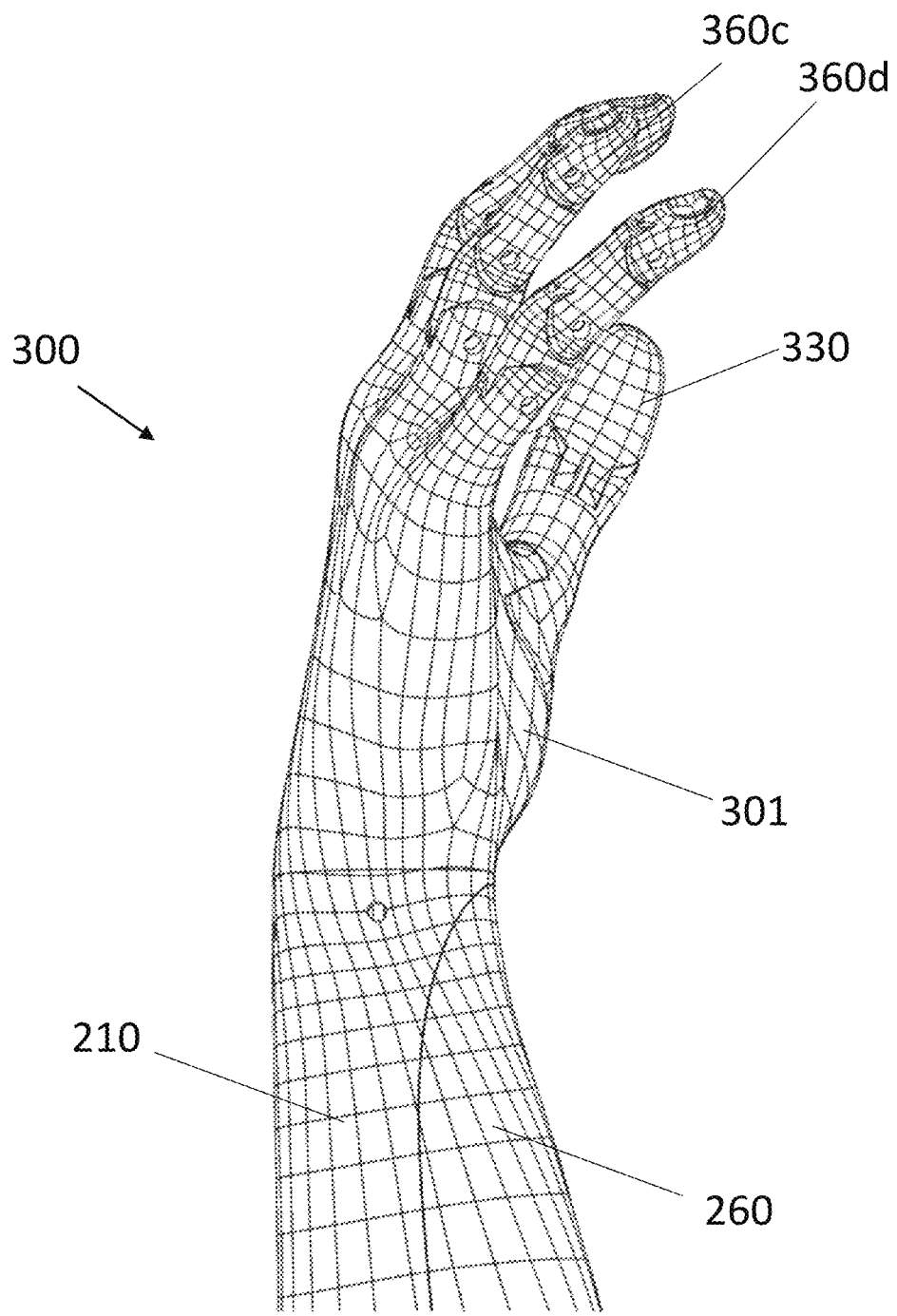
Figure 11C:
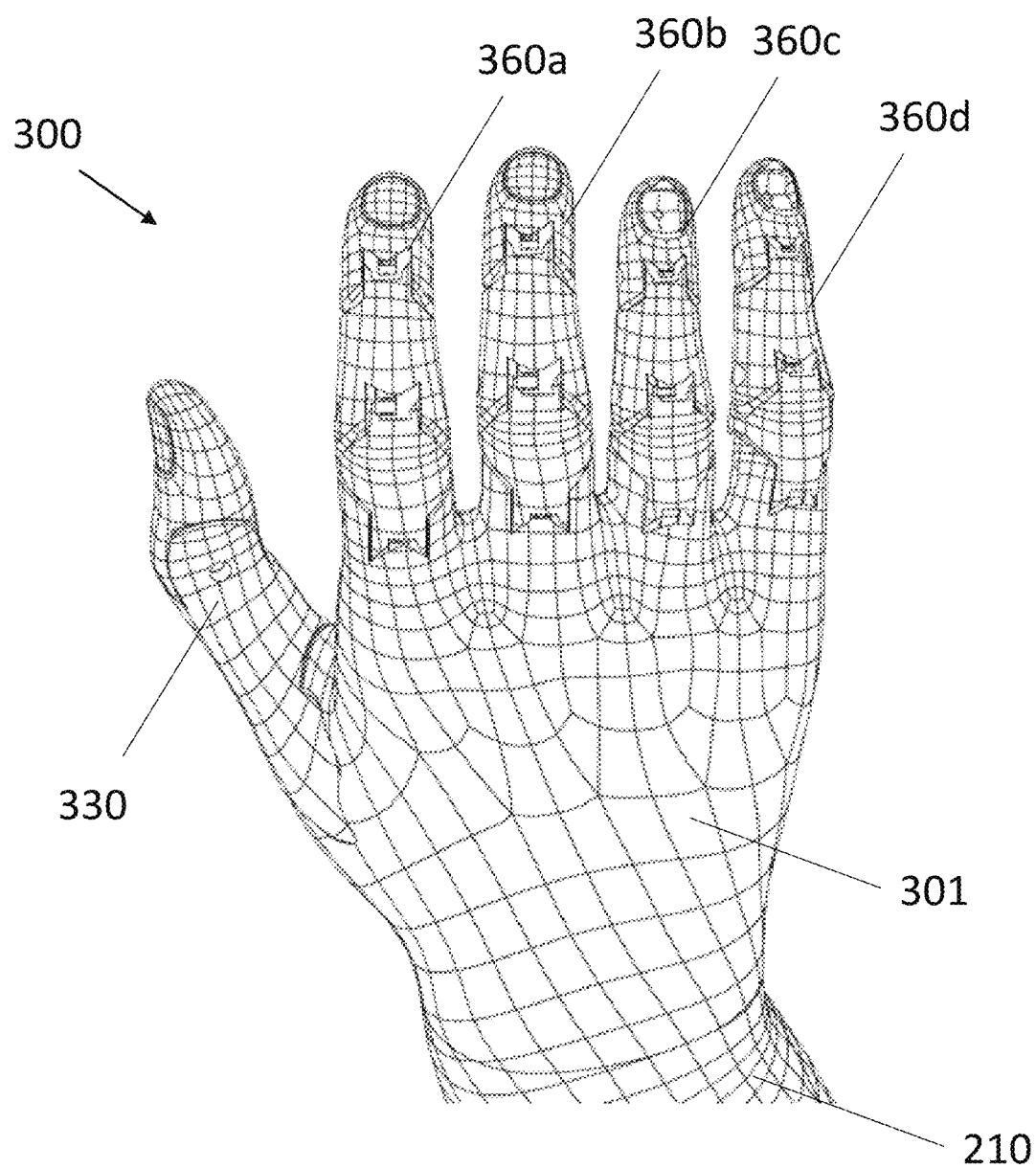
Figure 12A:
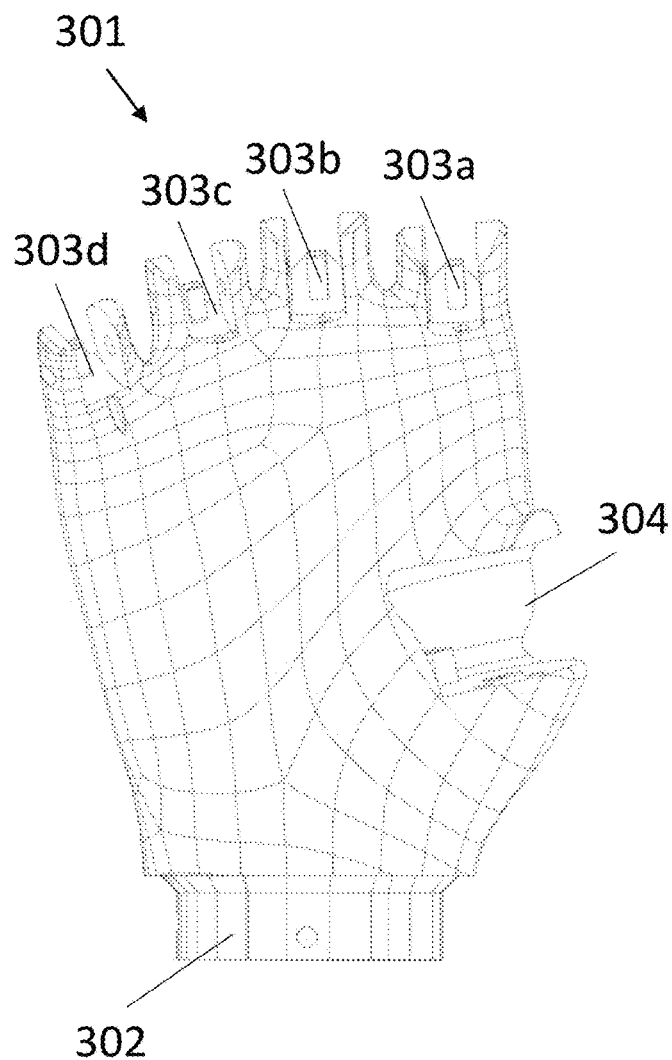
FIGS. 12A-D are views of a palm of the prosthetic hand of FIGS. 11A-C.
Figure 12B:
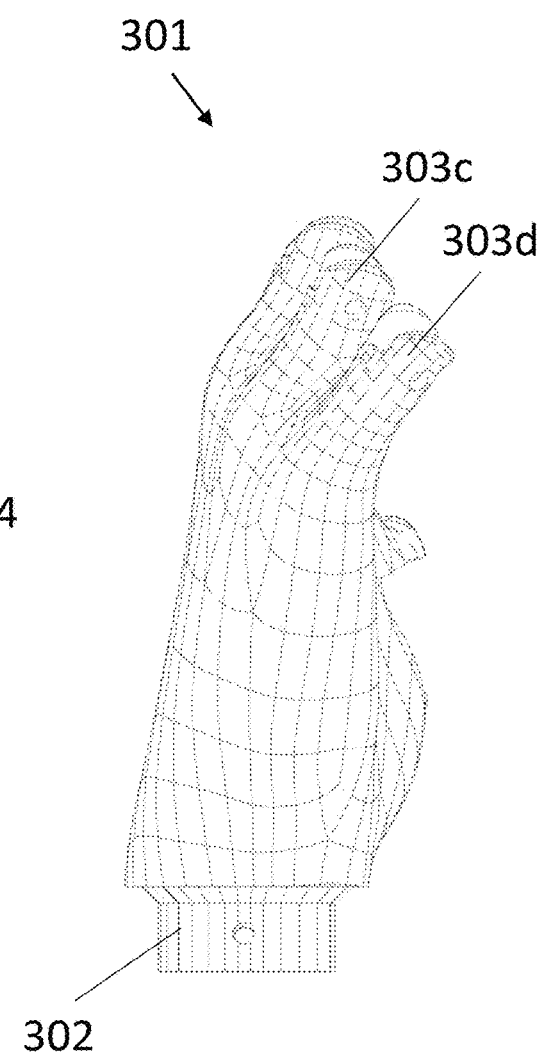
Figure 12C:
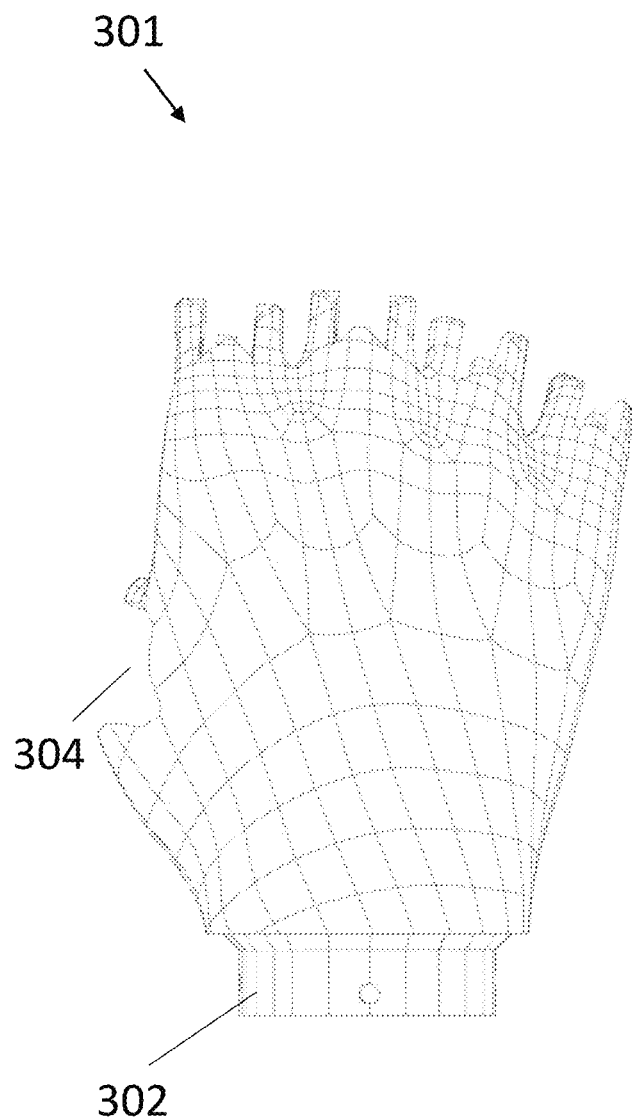
Figure 12D:
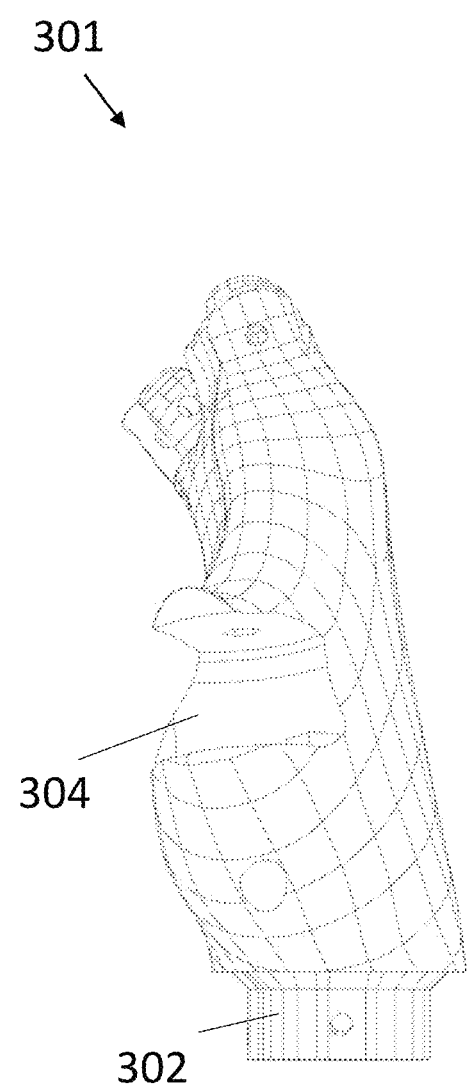

FIGS. 11A-C illustrate various views of prosthetic hand 300 coupled to main forearm 210 of prosthetic forearm 200. Generally, prosthetic hand may include a palm 301, thumb 330, and four fingers 360a-d, including an index finger 360a, middle finger 360b, ring finger 360c, and pinky finger 360d.

As should be clear from the description below, fingers 360a-d may be substantially identical to one another in structure, and thus only the structure of a single finger 360 is described in detail below. However, the various fingers 360a-d and/or components thereof may be slightly differently sized or contoured in order to more closely mimic either an average hand or a remaining hand of a user. Similarly, the palm 301 (described in greater detail below), wrist 214, and prosthetic forearm 200, as well as components of each, may have different sizes and/or contours than are shown in the drawings and different sizes and/or contours relative to each other or relative to other components of the system than are shown in the drawings in order to provide a desired size and contour for a particular user.

FIGS. 12A-D illustrate various views of palm 301 disassembled from thumb 330 and fingers 360a-d. It should be understood that, as used herein, the term "palm" generally refers to the portion of the hand between the wrist and fingers, including both the front surface that may be frequently called a palm, and the back of the hand as well. Generally, palm 301 may include a proximal coupling portion 302 for coupling palm 301 to the main forearm 210 of prosthetic forearm 200, although in some embodiments palm 301 may be formed integrally with main forearm 210. Palm 301 may also include four finger couplings 303a-d and a thumb coupling 304 to facilitate attachment of the fingers 360a-d and the thumb 330 to the palm 301.

Figure 13A:
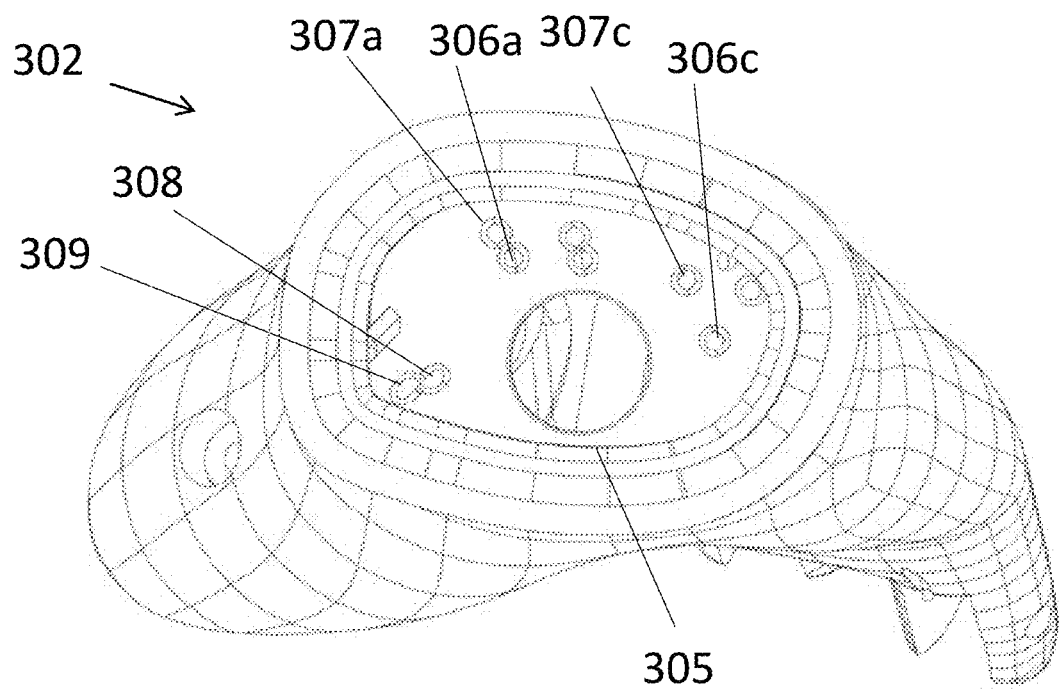
FIGS. 13A-B are views of a proximal coupling portion of the palm of FIGS. 12A-D.
Figure 13B:
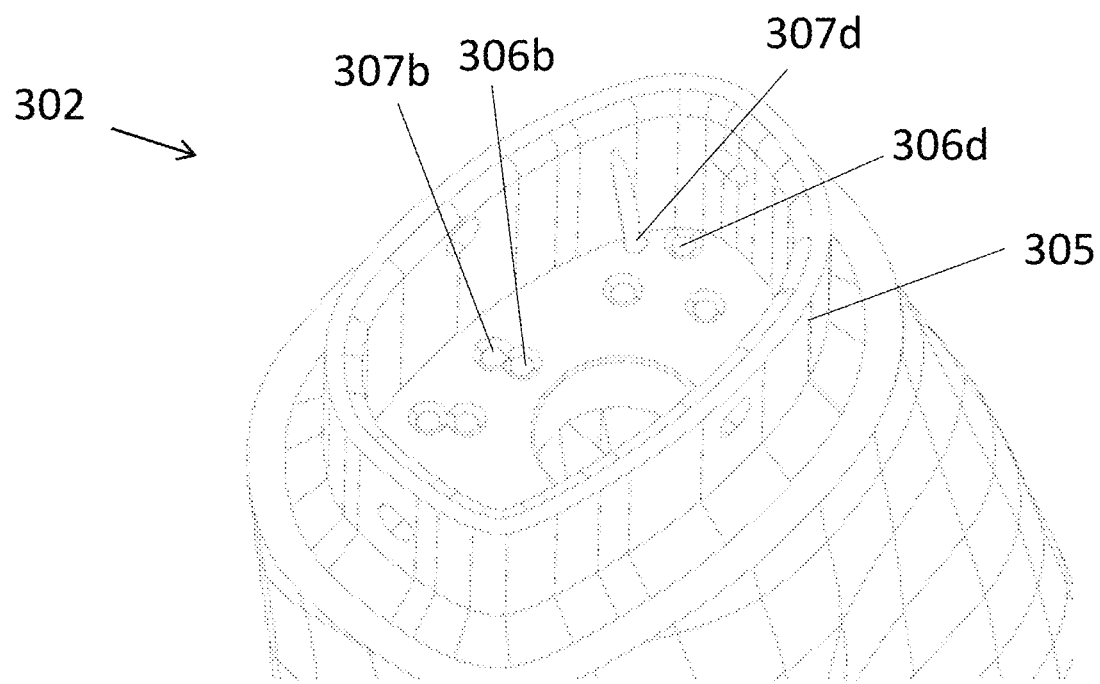

FIGS. 13A-B illustrate aspects of the proximal coupling portion 302 of palm 301. Proximal coupling portion 302 may include a lip 305 extending to the proximal end of palm 301. Lip 305 may be sized and shaped to fit within distal wrist 214 of main forearm 210 in only one or substantially only one configuration, and may include apertures or other coupling features that align or correspond to apertures or coupling features in distal wrist 214. For example, in the illustrated embodiment distal writs 214 and lip 305 include corresponding apertures that are aligned when palm 301 is assembled to forearm component 210. Pins may be inserted through the aligned apertures to secure the palm 301 relative to the main forearm 210. Preferably, the shape of lip 305 and the interior surface of distal wrist 214 are such that, upon assembly, the palm 301 is capable of no or substantially no rotation or other movement. However, as described in greater detail below, in other embodiments the palm 301 may be coupled to main forearm 210 via a joint or other mechanism that allows for movement of the palm 301 relative to the assembled forearm 200. Further, when palm 301 is coupled to assembled forearm 200, the transition between outer surfaces of the assembled forearm 200 and the palm 301 are preferably substantially smooth and continuous.

Still referring to FIGS. 13A-B, proximal coupling portion 302 may include a plurality of apertures to allow for prosthetic tendons, described in greater detail below, to pass from main forearm 210 to the thumb 330 and fingers 360a-d via palm 301. In the illustrated embodiment, proximal coupling portion 302 includes a pair of apertures for each finger 360a-d and a pair of apertures for thumb 330, such that one prosthetic tendon controlling flexion and one prosthetic tendon controlling extension may pass into palm 301 for each finger 360a-d and thumb 330. In the illustrated embodiment, apertures 306a-d correspond to the apertures through which a prosthetic tendon for flexion will pass into fingers 360a-d, respectively, while apertures 307a-d correspond to the apertures through which a prosthetic tendon for extension will pass into fingers 360a-d, respectively. Similarly, as illustrated, aperture 308 is configured to receive a prosthetic tendon for flexion of thumb 330, while aperture 309 is configured to receive a prosthetic tendon for extension of thumb 330. However, it should be understood that the particular positioning of the apertures need not be identical to the positions illustrated. A central hole in may be provided in proximal coupling portion 302, as best seen in FIG. 13A, for manufacturability purposes, for example so the palm 301 can be 3D printed with a hollow interior.

Figure 14A:
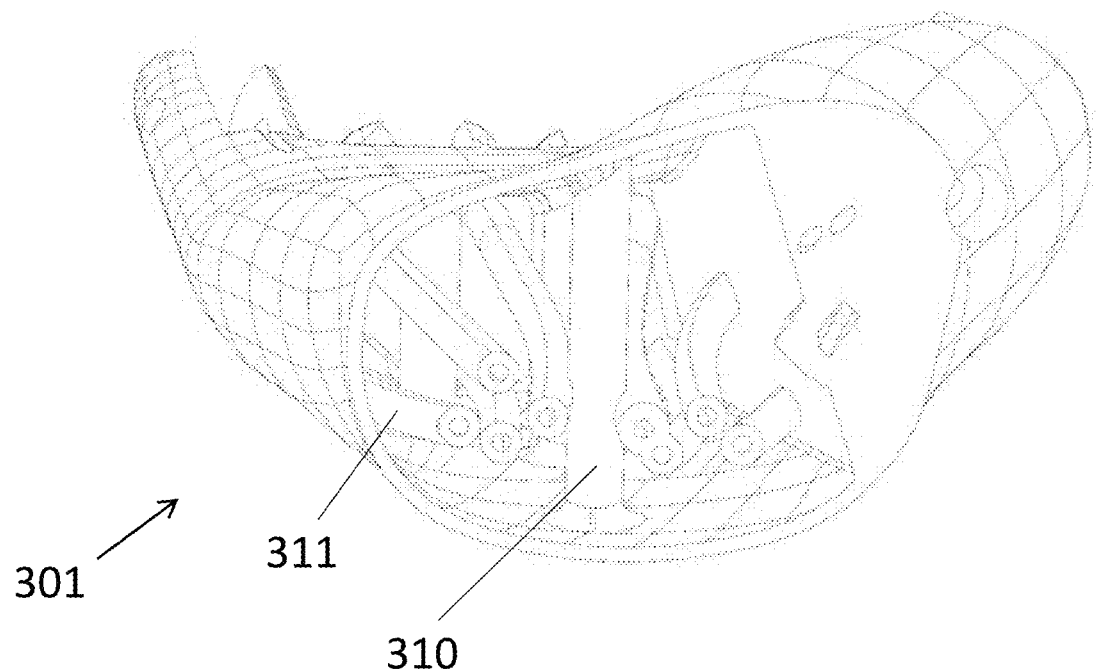
FIGS. 14A-F are various cross-sections of the palm of FIGS. 12A-D to illustrate internal components.
Figure 14B:
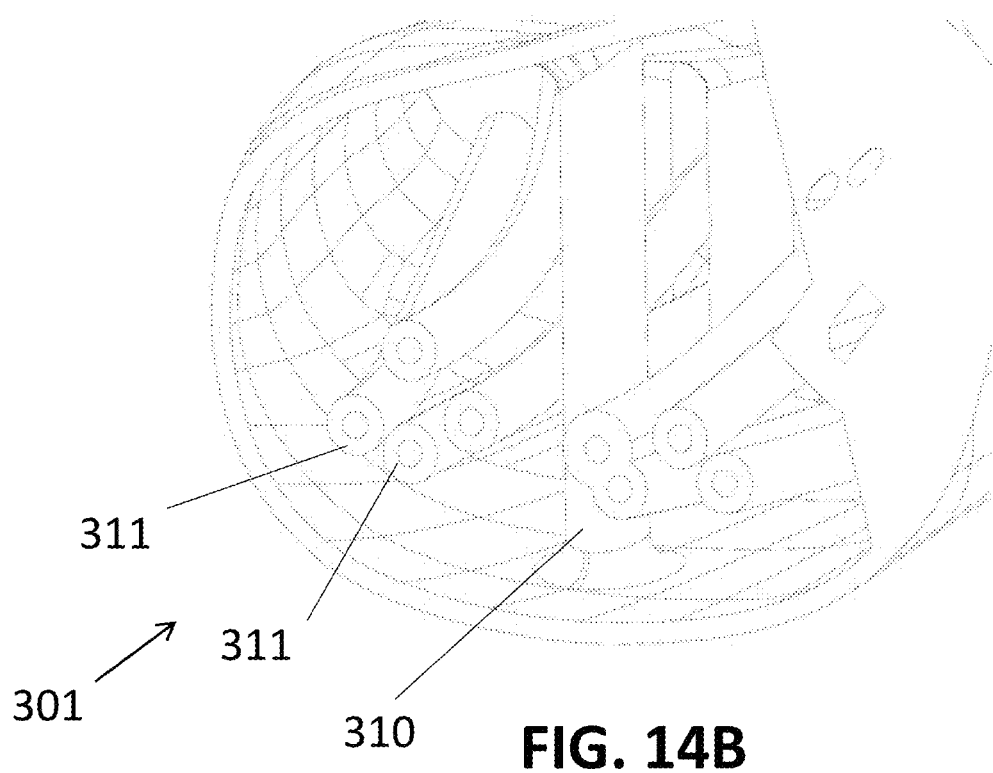
Figure 14C:
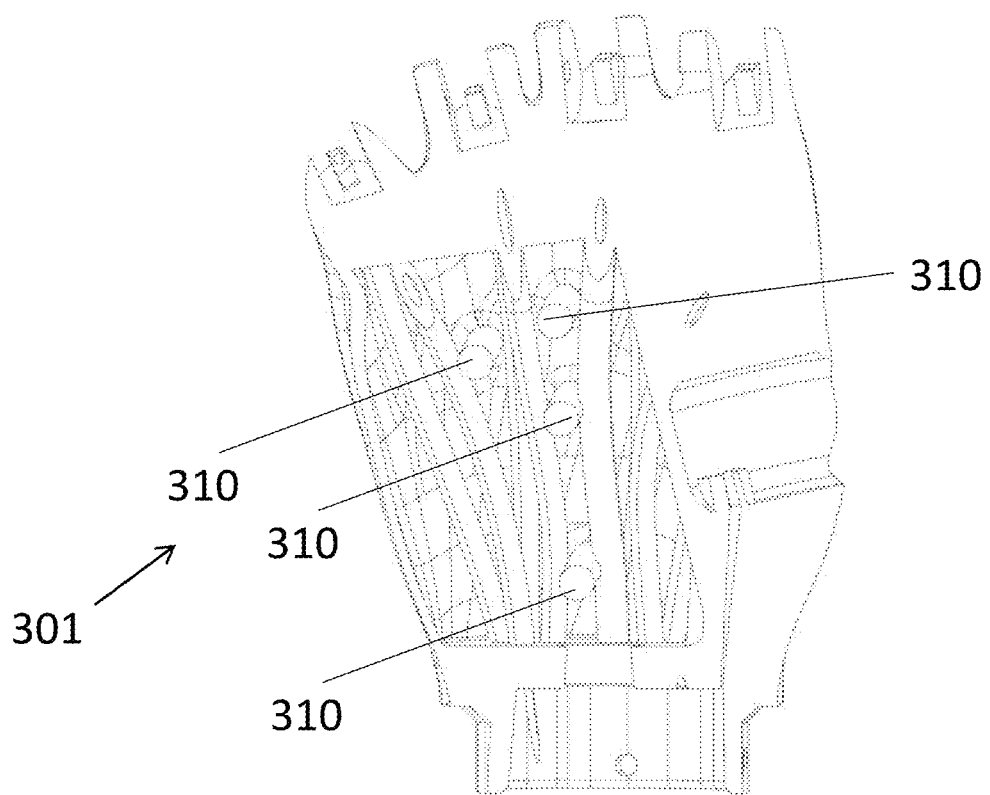
Figure 14D:
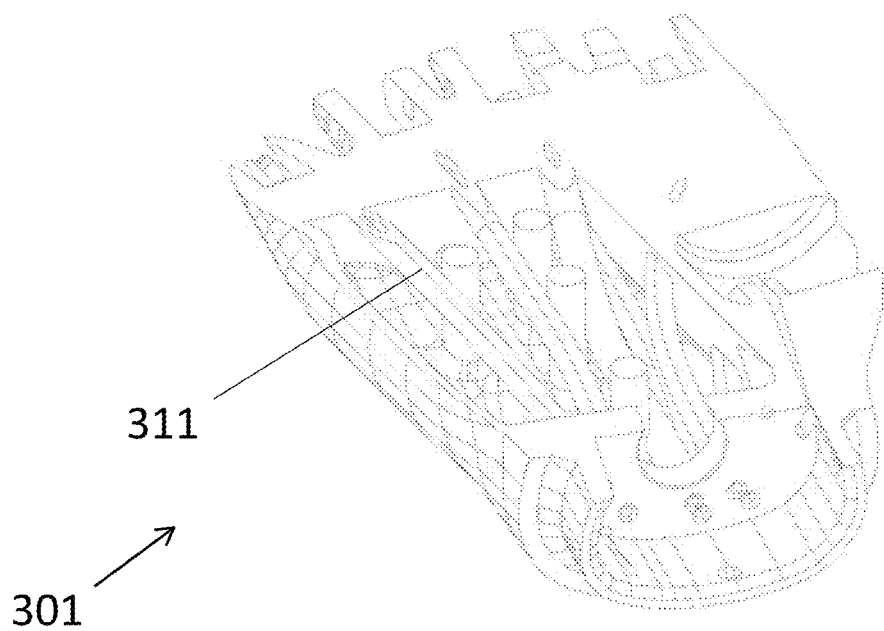
Figure 14E:
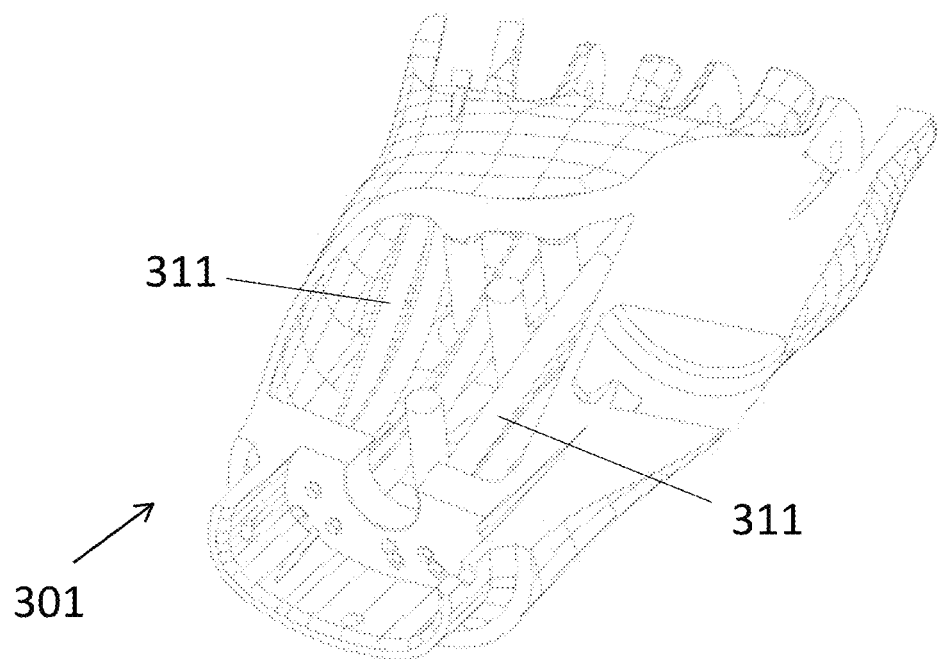
Figure 14F:
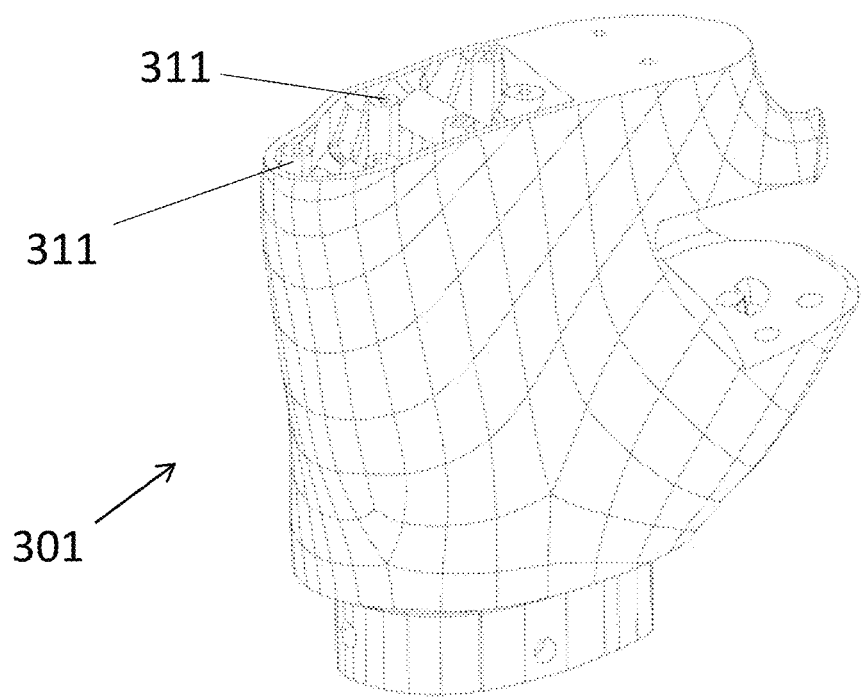

FIGS. 14A-F show various cross-sections of palm 301 to illustrate internal components of palm 301. It should be noted that most of palm 301 is hollow in order to reduce the amount of material required to form palm 301. However, at least because palm 301 is expected to experience various applied forces, particularly when prosthetic hand 300 is in the process of gripping an object by applying force to that object, a variety of support posts 310 are provided within palm 301. For example, as shown in FIGS. 14A-C, a first support post 310 may extend from a front surface to a rear surface of palm 301 near proximal coupling 302. A second support post 310 may extend from the front to the rear of palm 301 near a center of palm 301. A third support post 310 may extend from the front to the rear of palm 301 proximal to the space between the middle finger 360b and ring finger 360c. A fourth support post 310 may extend from the front to the rear of palm 301 proximal to the space between the ring finger 360c and the pinky finger 360d. It should be understood that the position and number of posts 310 may be varied in order to provide support to any hollow areas of palm 301 expected to experience forces that could otherwise compromise the structural integrity of palm 301, particularly when prosthetic hand 300 is gripping or applying force to an object. Further, as best shown in FIGS. 14C-D, the knuckle areas may be made solid since a large amount of mechanical stress is expected in those positions when the fingers 360a-d and thumb 330 come in contact with an object. Other mechanisms for supporting likely stresses while minimizing material use, such as using internal lattice patterns, may also be utilized.

Still referring to FIGS. 14A-F, a plurality of tendon tunnels 311 may be positioned interior to palm 301 in order to help guide prosthetic tendons from the apertures 306a-d, 307a-d, 308, 309 in proximal coupling portion 302 to the corresponding aperture in finger coupling 303a-d or thumb coupling 304. Although the tunnels 311 may not be required, the tunnels 311 may assist in helping ensure that the tendons do not entangle one another and do not experience significant damage, for example by ensuring that as the tendons move, they remain in contact with a substantially smooth inner surface of the tunnels 311 without experience sharp turns. Although every tunnel 311 is not separately labeled in FIGS. 14A-F, it should be understood that, as illustrated, ten tunnels 311 are provided, each tunnel 311 having an inlet defining one of the apertures 306a-d, 307a-d, 308, or 309. Each tunnel 311 also has a corresponding outlet in a finger coupling 303a-d or thumb coupling 304, at which point the prosthetic tendons extend to the front of a fingertip 390 or thumb tip for providing flexion, or to a rear of a fingertip 390 or thumb tip for providing extension. The apertures at the tunnel 311 outlets are described in greater detail below.

Figure 15:
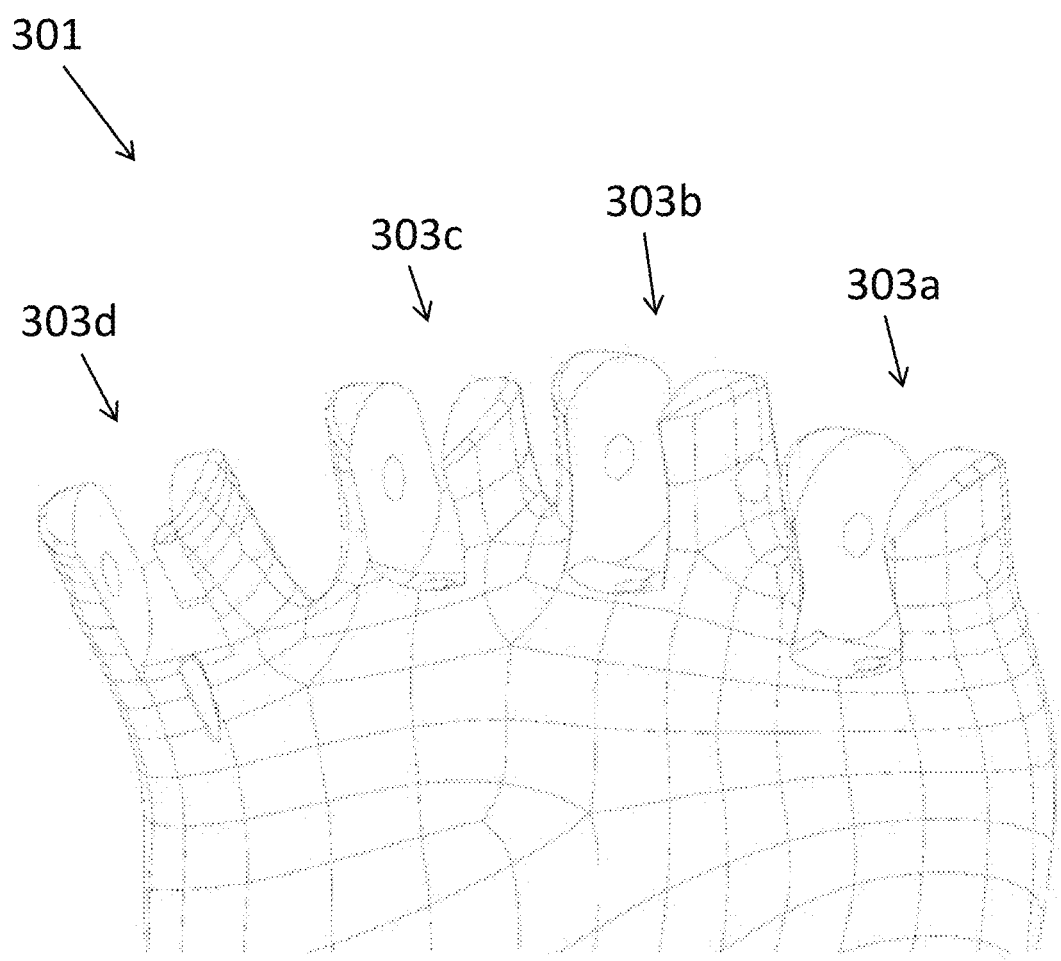
FIG. 15 is an enlarged view of a distal end of the palm of FIGS. 12A-D.
Figure 16C:
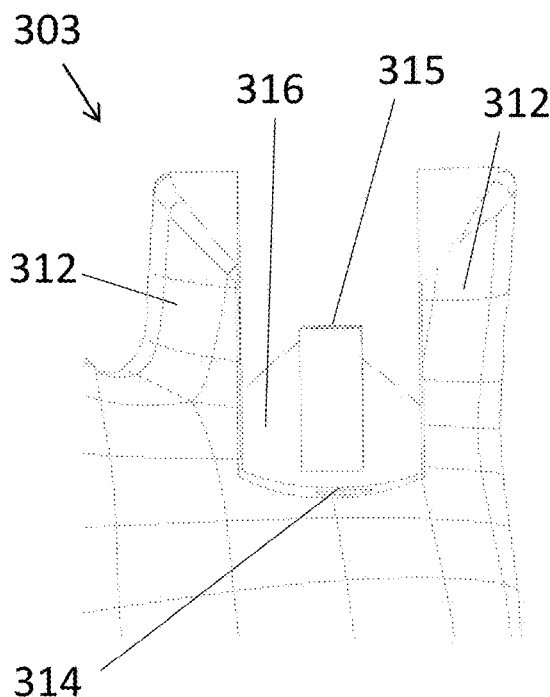
Figure 16C:
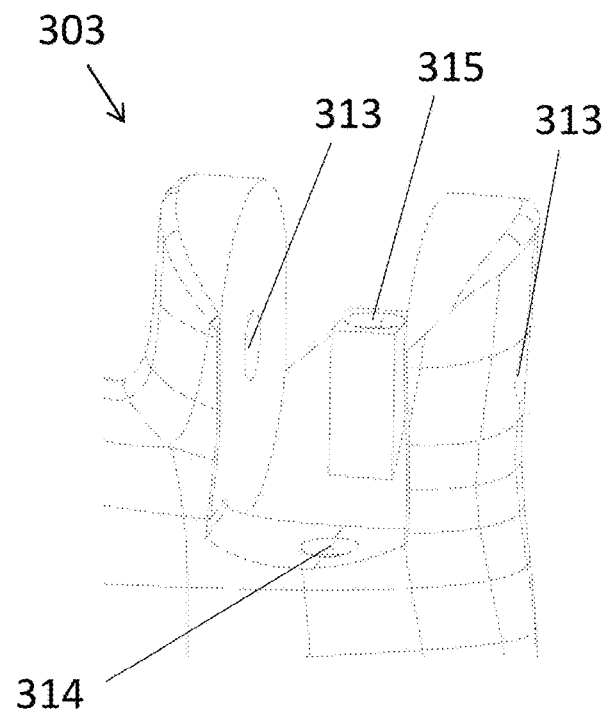
Figure 16C:
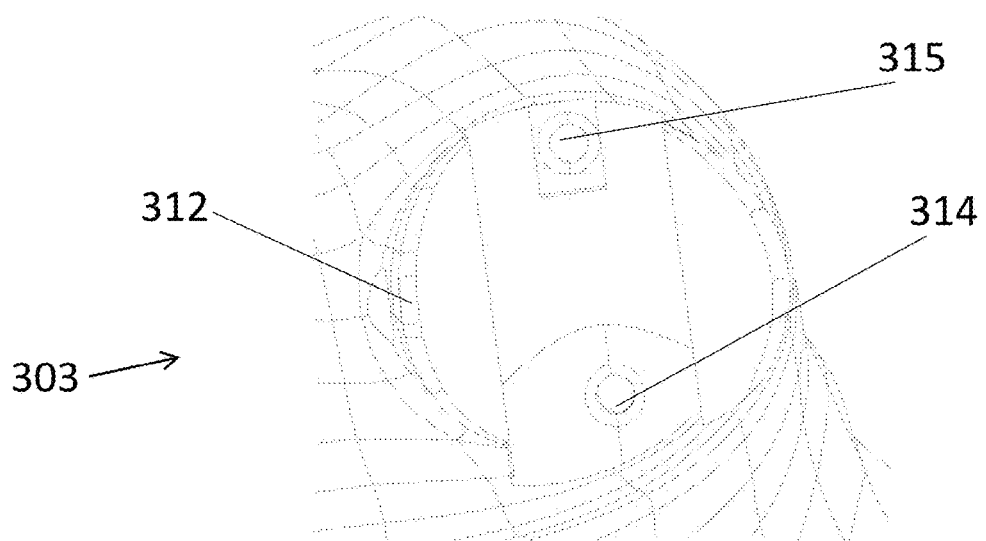
Figure 17A:
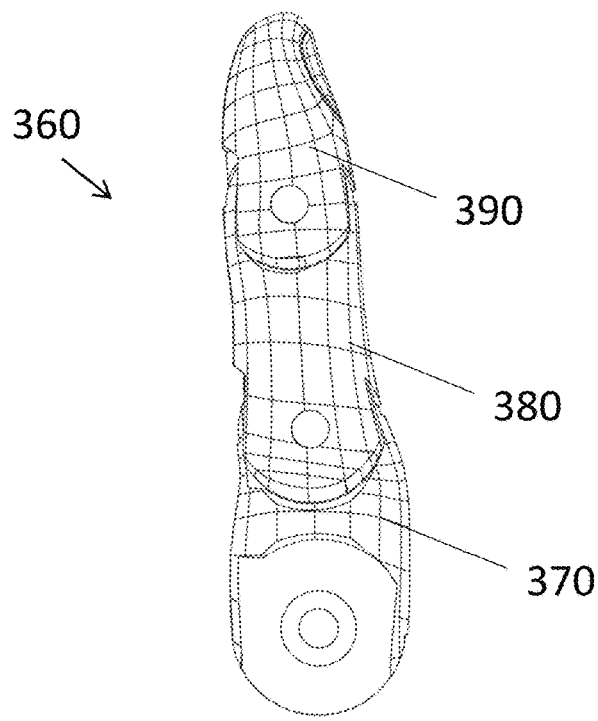
FIGS. 17A-D are views of a representative finger of the prosthetic hand of FIGS. 11A-C.
Figure 17B:
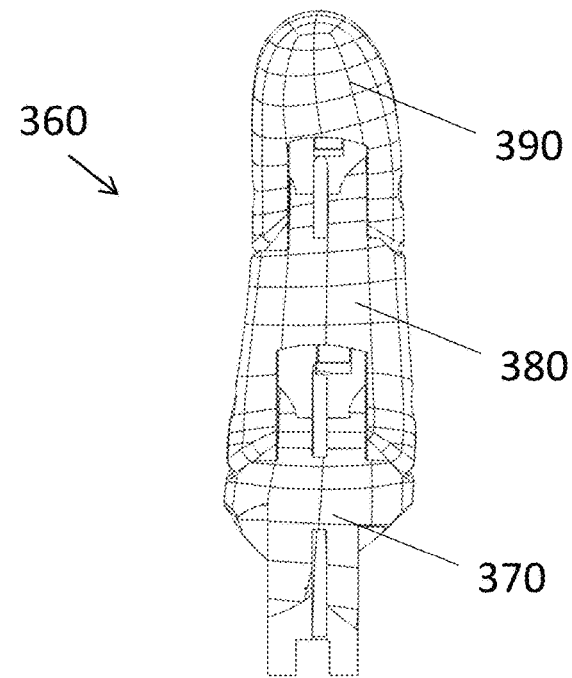
Figure 17C:
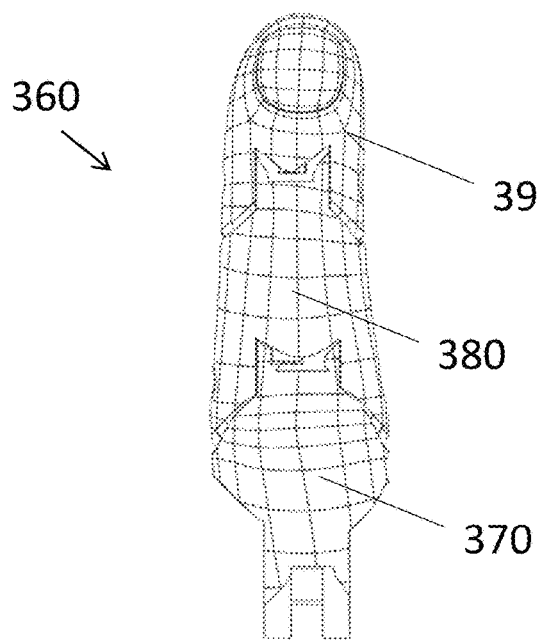
Figure 17D:
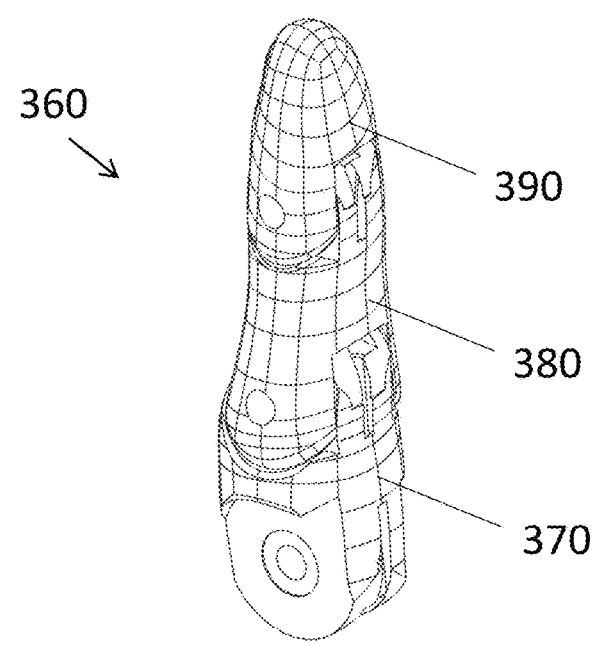

FIG. 15 illustrates a distal end of palm 301 to better show the finger couplings 303a-d. Each finger coupling 303a-d functions to couple a corresponding prosthetic finger 360a-d to the palm 301. FIGS. 16A-C illustrate enlarged views of a representative finger coupling 303. It should be understood that finger couplings 303a-d may be substantially identical to one another, although sizes and shapes may vary slightly in order to better mimic the user's remaining hand. However, because of the similarity of the structure of each finger coupling 303a-d, representative finger coupling 303 of FIGS. 16A-C is described and that description generally applies to each of the individual finger couplings 303a-d.

Referring now to FIGS. 16A-C, finger coupling 303 may include two lateral extensions 312. Each lateral extension 312 may include an aperture 313 therein, as best shown in FIG. 16B. The two lateral extensions 312 may function to receive a finger base 370 therebetween, with a pin or other fastener extending through the apertures 313 and corresponding apertures 371 in the finger base 370 so that the finger base 370 is capable or substantially freely rotating about an axis passing through apertures 313. In addition, each finger coupling 303 may include a flexion tendon aperture 314 and an extension tendon aperture 315. Flexion tendon aperture 314 may be the outlet of a corresponding flexion tendon tunnel 311, while extension tendon aperture 315 may be the outlet of a corresponding extension tendon tunnel 311. In the illustrated embodiment, the lateral extensions 312 form a general "U"-shape with the distal portion of palm 310. As described below, fingers 360a-d may include a finger base 370 that has a complementary shape for insertion between the lateral extensions 312. Further, in the illustrated embodiment, extension tendon aperture 315 is provided within a rear generally "V"-shaped or generally "U"-shaped extension portion that extends farther distally than a front portion of finger coupling 303.

A representative prosthetic finger 360 is illustrated in FIGS. 17A-D. As noted above, each prosthetic finger 360a-d may be substantially identical in structure, although the shape and size of each finger 360a-d may vary slightly to better mimic the user's remaining hand or otherwise an average natural hand. As such, a single representative finger 360 is described and it should be understood that the description generally applies to each prosthetic finger 360a-d. Generally, prosthetic finger 360 may include a base portion 370, a middle portion 380, and a tip portion 390. The individual portions of representative prosthetic finger 360 are described in detail below.

Figure 18E:
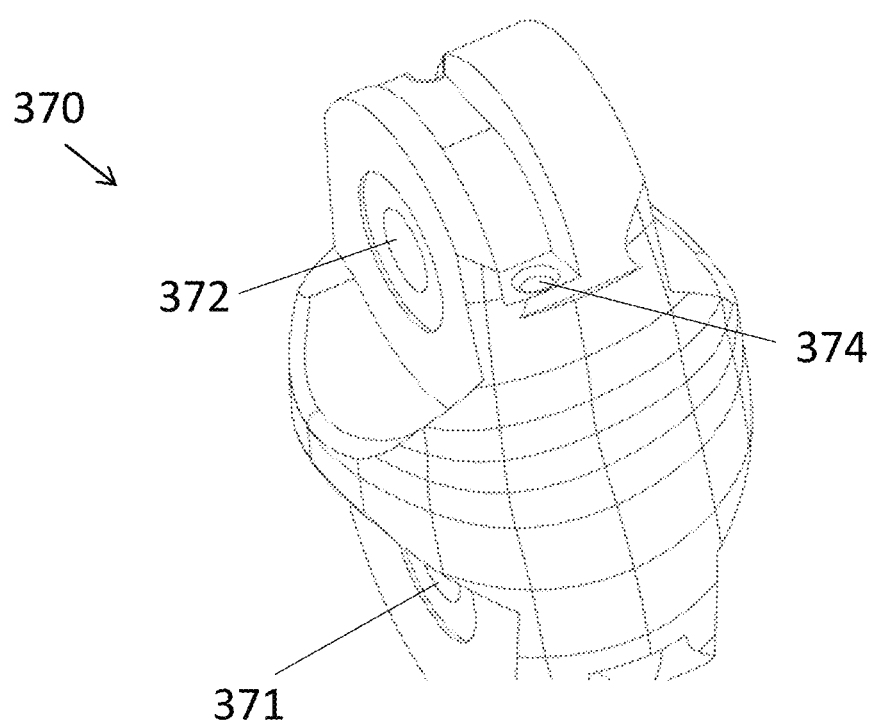

FIGS. 18A-F illustrate various views of finger base 370. Finger base 370 may include a rounded proximal portion with an aperture 371 extending therethrough. As best shown in FIG. 18B, the proximal portion may be substantially "U"-shaped. When coupled to finger coupling 303, a pin or other fastener may pass through both aperture 371 and apertures 313 so that finger base 370 is rotatable about aperture 371. This proximal portion of finger base 370 and finger coupling 303 may substantially mimic the function of the metacarpophalangeal joint. Finger base 370 may similarly include a distal portion with an aperture 372 extending therethrough, the distal portion shaped and configured to jointedly couple to middle portion 380, described in greater detail below.

Figure 18F:
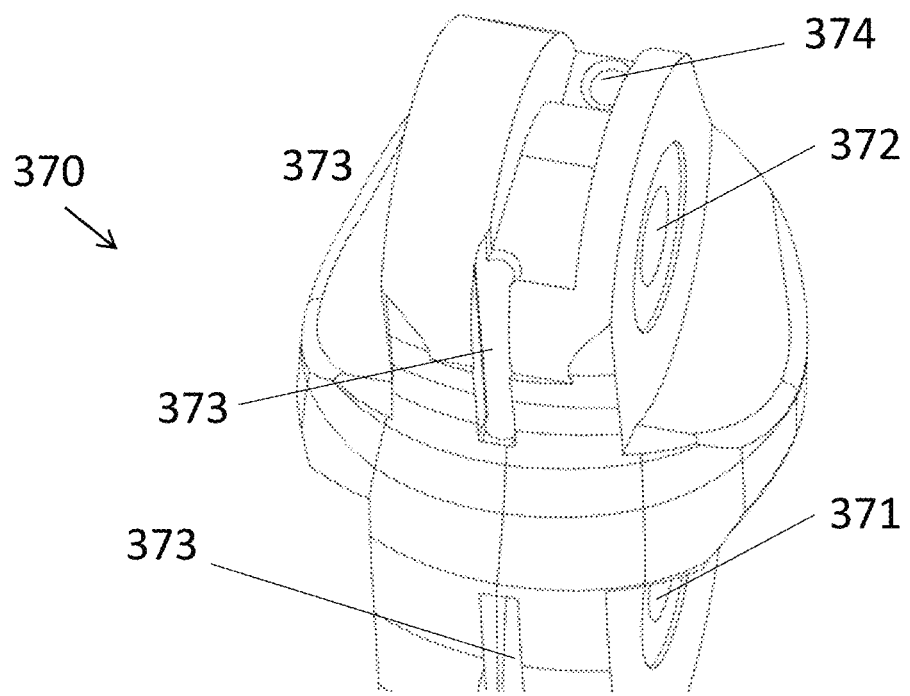

Referring now to the bottom view of finger base 370 of FIG. 18D, an anterior tunnel 373 and posterior tunnel 374 may be provided. When finger base 370 is coupled to finger coupling 303, anterior tunnel 373 may substantially align with flexion tendon aperture 314 and posterior tunnel 374 may substantially align with extension tendon aperture 315. The prosthetic flexion tendon exiting flexion tendon aperture 314 may pass through anterior tunnel 373. As best shown in FIGS. 18A, 18C, and 18E, anterior tunnel 373 may be open at the anterior-most portion, with a middle portion of the anterior tunnel 373 being fully closed between the proximal and distal portions of finger base 370. In this context, "anterior" refers to the front face of the palm, while the "posterior" direction refers to the back face of the hand. As sill become clear by the additional descriptions below, as the prosthetic flexion tendon passing into finger 360 is flexed, the finger base 370 begins to flex with respect to the finger coupling 303. The open anterior portions of anterior tunnel 373 helps to facilitate rotation of the joints in the finger 360 in a desired fashion without binding or otherwise damaging the prosthetic flexion tendon of the finger 360. This may be particularly true if the prosthetic flexion tendon has a substantially fixed length and is rigidly coupled at its first end to the fingertip 390 and at its other end to a linear actuator 282. Posterior tunnel 374, on the other hand, may be fully enclosed, as best shown in FIGS. 18E-F. A prosthetic extension finger tendon passing through extension tendon aperture 315 in finger coupling 303 may pass through posterior tunnel 374 and toward a rear of fingertip 390. As described in greater detail below, one end of prosthetic extension finger tendon may be coupled to a spring fixed within main forearm 210, with the other end fixedly coupled to a rear portion of fingertip 390, so that in the absence of other applied forces, finger base 370 tends to be in the extended condition as opposed to the flexed condition.

FIGS. 19A-E illustrate various views of the middle portion 380 of finger 360. Middle portion 380 may include a proximal portion with two lateral extensions 381, and each lateral extension 381 may include an aperture 382 extending therethrough. Lateral extensions 381 may be sized and shaped to fit over the distal portion of finger base 370 so that apertures 372 align with apertures 382. A pin or other fastener may pass through apertures 382 and 372 to hingedly couple middle portion 380 to finger base 370. Lateral extensions 381 may be substantially rounded at their proximal ends to fit within or adjacent correspondingly rounded portions of the middle section of finger base 370. The coupling between the proximal portion of middle portion 380 and the distal portion of finger base 370 may substantially mimic the function of the proximal interphalangeal joint. Middle portion 380 may similarly include a distal portion with an aperture 383 extending therethrough, the distal portion shaped and configured to jointedly couple to fingertip 390, described in greater detail below.

Figure 19A:
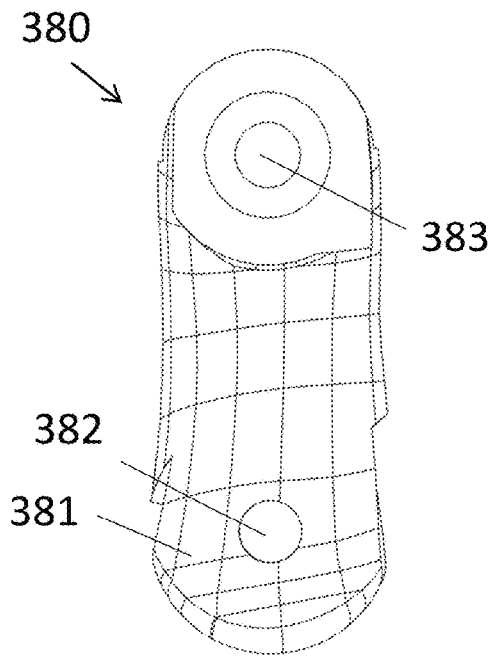
FIGS. 19A-E are views of a middle portion of the finger of FIGS. 17A-D.
Figure 19B:
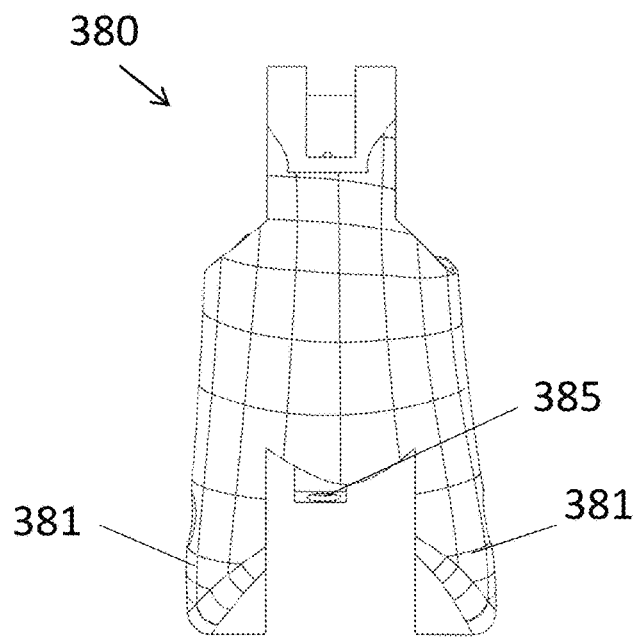
Figure 19C:
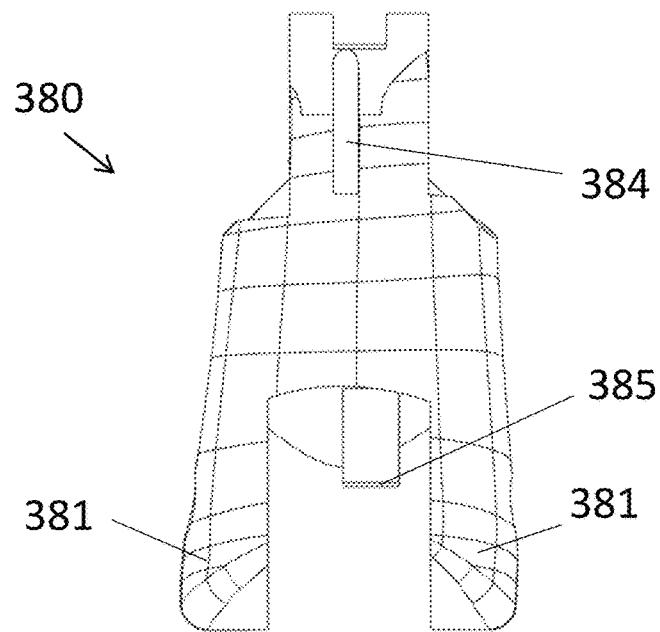
Figure 19D:
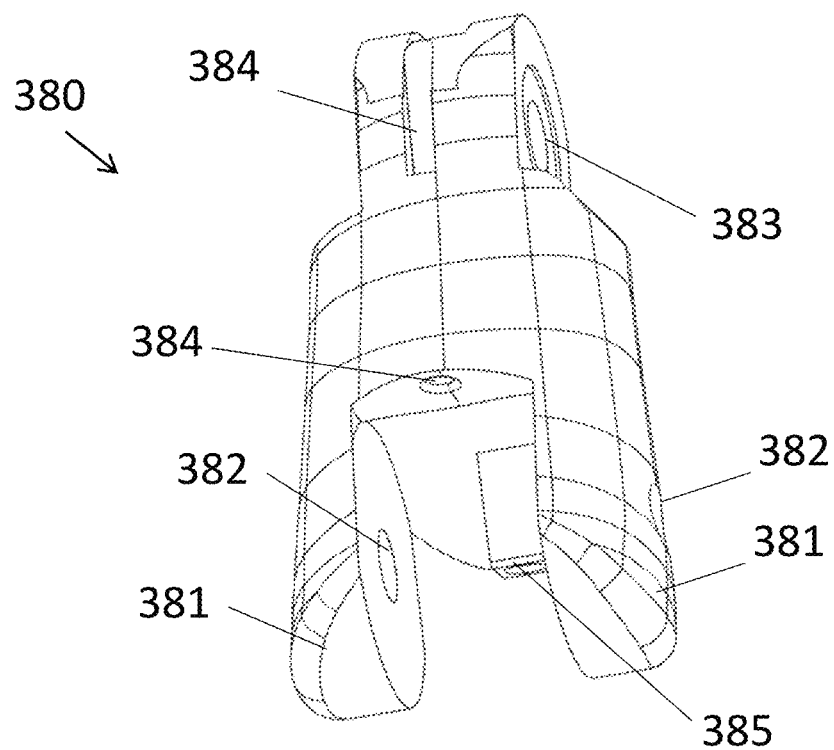
Figure 19E:
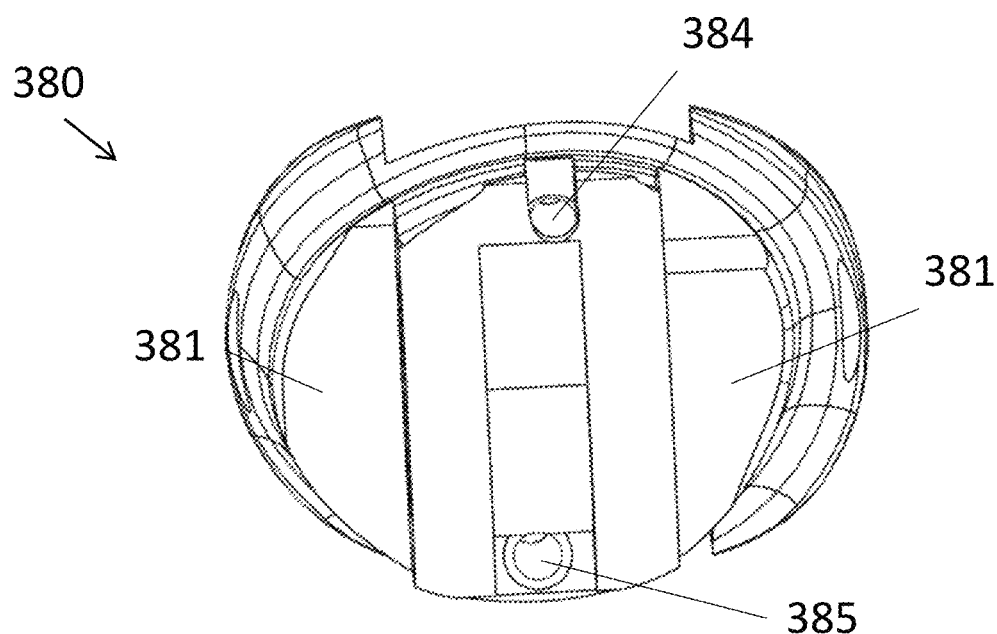
Figure 20E:
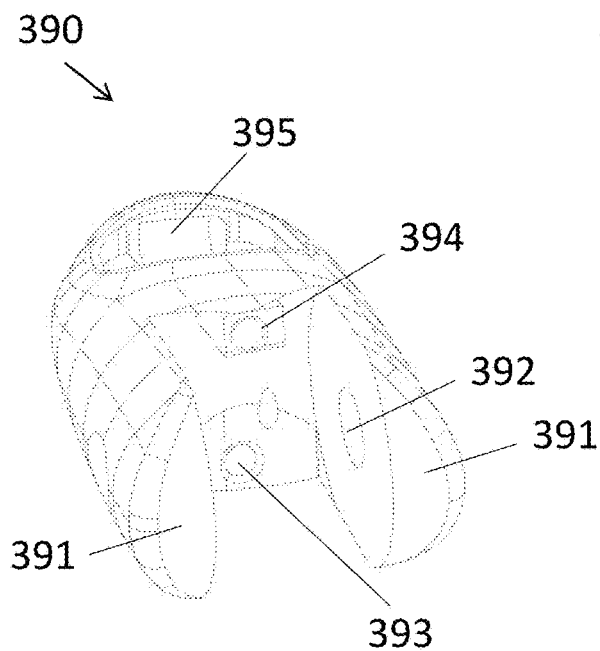
Figure 20F:
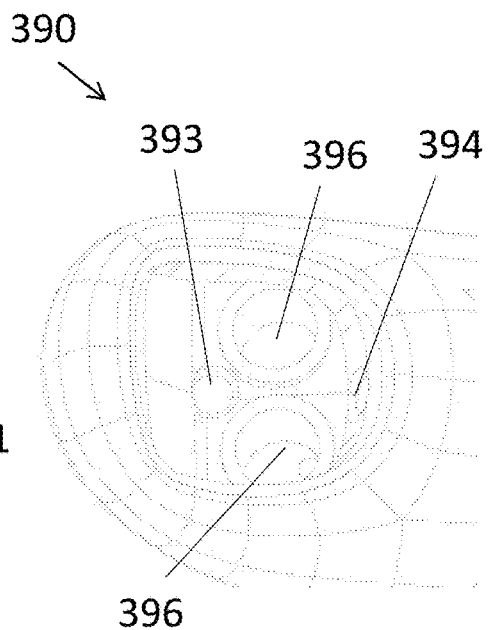
Figure 20G:
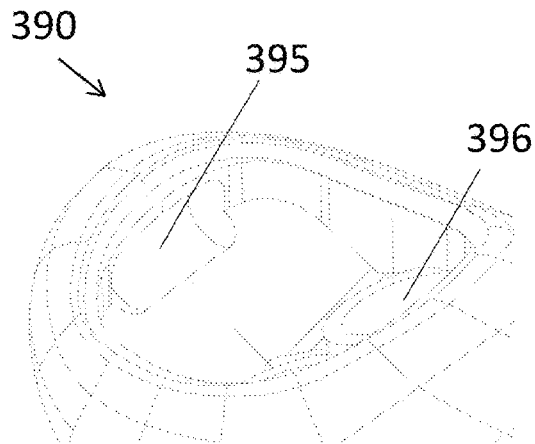
Figure 20H:
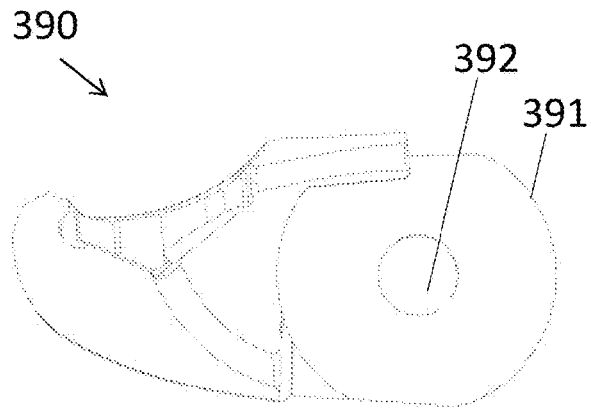
Figure 21A:
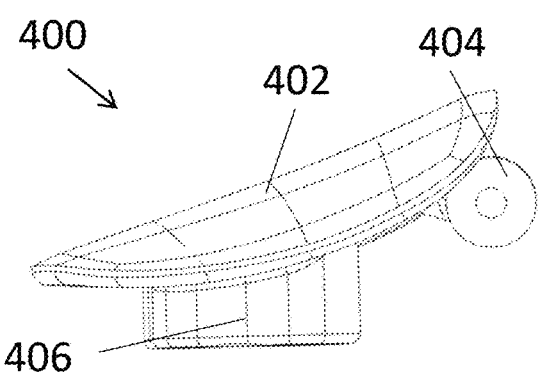
FIGS. 21A-E are views of a nail for use with the fingertip of FIGS. 20A-H.
Figure 21B:
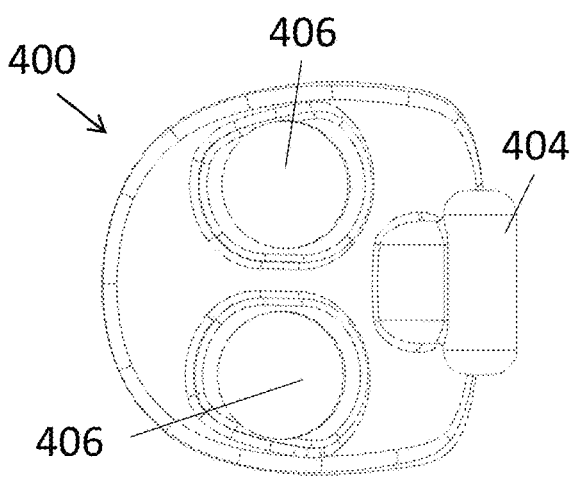
Figure 21C:
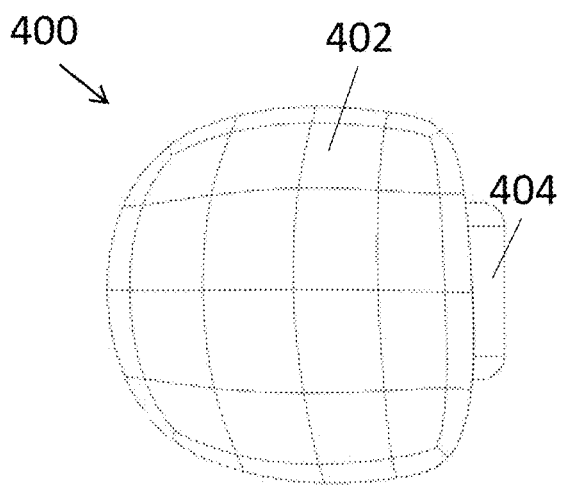
Figure 21D:
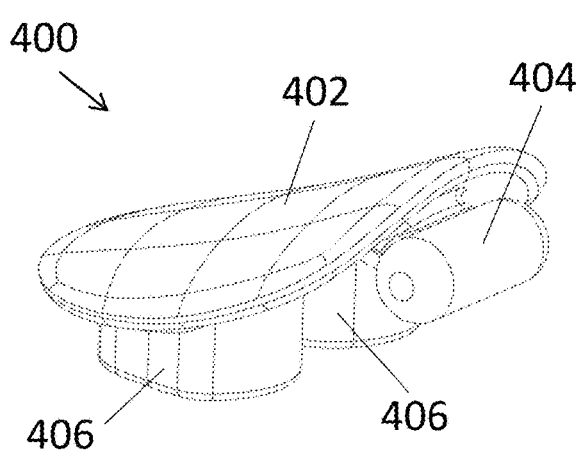
Figure 21E:
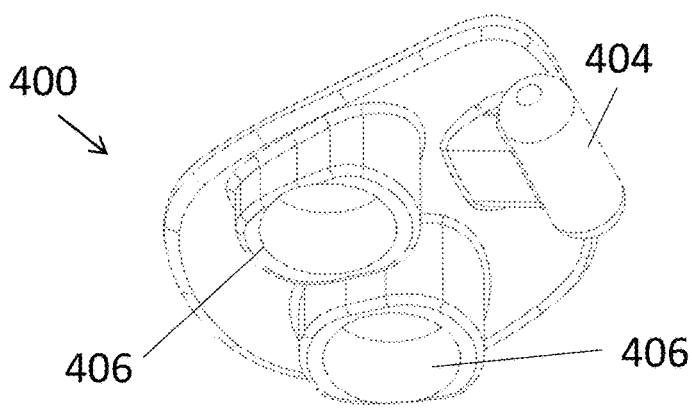

Referring now to the bottom view of middle portion 380 of FIG. 19E, an anterior tunnel 384 and posterior tunnel 385 may be provided. When middle portion 380 is coupled to finger base 370, anterior tunnel 384 may substantially align with the anterior tunnel 373 of finger base 370, while posterior tunnel 385 substantially aligns with the posterior tunnel 374 of finger base 370. As best shown in FIGS. 19C and 19D, anterior tunnel 384 may be open at the anteriormost portion near the distal end of middle portion 380. Posterior tunnel 385, on the other hand, may be substantially closed between the inlet and outlet ends of the posterior tunnel 385. The prosthetic finger flexion tendon may pass from anterior tunnel 373 through anterior tunnel 384, while the prosthetic finger extension tendon may pass from posterior tunnel 374 through posterior tunnel 385.

FIGS. 20A-H illustrate various views of the fingertip 390 of finger 360. Fingertip 390 may include a proximal portion with two lateral extensions 391, and each lateral extension 391 may include an aperture 392 extending therethrough. Lateral extensions 391 may be sized and shaped to fit over the distal portion of middle portion 380 so that apertures 392 align with apertures 383. A pin or other fastener may pass through apertures 392 and 383 to hingedly couple middle portion 380 to fingertip 390. Lateral extensions 391 may be substantially rounded at their proximal ends to fit within or adjacent correspondingly rounded portions of the middle section of middle portion 380. The coupling between the proximal portion of fingertip 390 and the distal portion of middle portion 380 may substantially mimic the function of the distal interphalangeal joint.

The distal portion of fingertip 390 may be include a hollow compartment and may be open in order to allow access to the compartment. Fingertip 390 may include an anterior tunnel 393 and posterior tunnel 394. Anterior and posterior tunnels 393, 394 may have an outlet that opens into the compartment within fingertip 390. When middle portion 380 is coupled to fingertip 390, the inlet of anterior tunnel 393 may substantially align with the outlet of anterior tunnel 384, and the inlet of posterior tunnel 394 may substantially align with the outlet of posterior tunnel 385. With this configuration, a prosthetic finger flexion tendon extending from the prosthetic forearm 200 through the various anterior tunnels may exit the outlet of anterior tunnel 393 and be tied off or otherwise secured within the compartment of fingertip 390. Similarly, a prosthetic finger extension tendon extending from the prosthetic forearm 200 through the various posterior tunnels may exit the outlet of posterior tunnel 394 and be tied off or otherwise secured within the compartment of fingertip 390. The opening within the compartment of fingertip 390 may provide easy access to one end of the tendons in case maintenance must be performed. However, a removable fingernail 400 may be provided to close the compartment when access is not needed, as described in greater detail below.

FIGS. 21A-E show various views of a fingernail 400 that be removably coupled to fingertip 390. The superior surface of fingernail 400 may include a nail plate 402 that is exposed when fingernail 400 is coupled to fingertip 390. A variety of coupling features may be attached to the inferior portions of fingernail 400 to help removably couple the fingernail 400 to the fingertip 390. For example, a cylindrical connector 404 may be positioned on a front of the fingernail 400, the connector 404 shaped to fit within a corresponding recess 395 in the compartment of fingertip 390. In order to couple fingernail 400 to fingertip 390, connector 404 may first be inserted into recess 395. Then, fingernail 400 may be rotated downward about connector 404 toward fingertip 390. One or more additional connectors 406 on the underside of the fingernail 400 may then contact corresponding connectors 396 in the compartment of fingertip 390. In embodiment, connectors 406 and 396 include magnets such that fingernail 400 is held in place on fingertip 390 by magnetic forces and/or friction forces. Fingernail 400 may be removed by applying force and pulling fingernail 400 away from fingertip 390 if access to the compartment of fingertip 390 is desired. Further, fingernail 400 may be formed of a material that can be easily painted so that a user may apply nail polish to the fingernails 400 if desired.

Figures 22A, 22B:
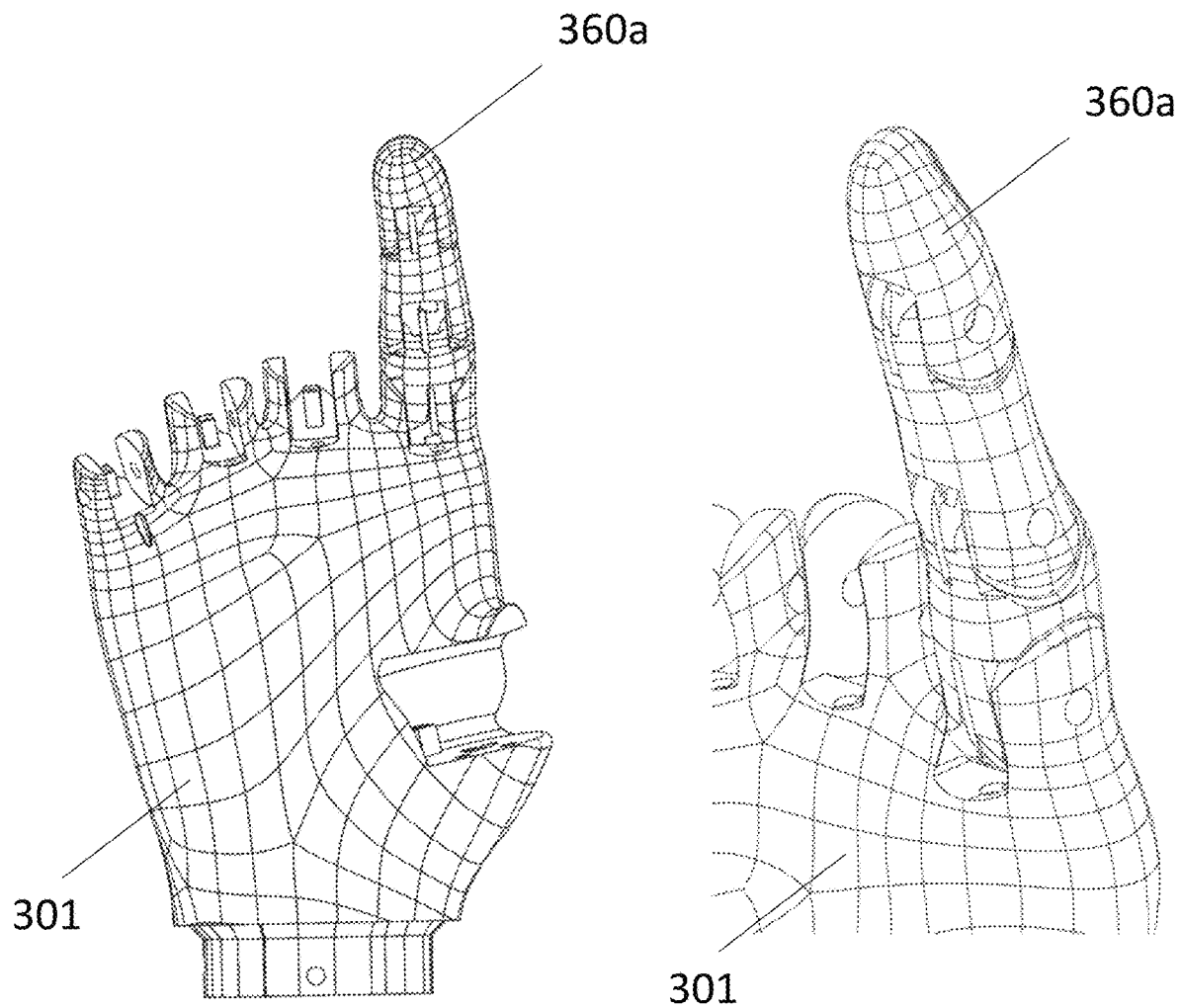
FIGS. 22A-B illustrate a prosthetic finger assembled to the palm in a fully extended condition.
Figure 23A:
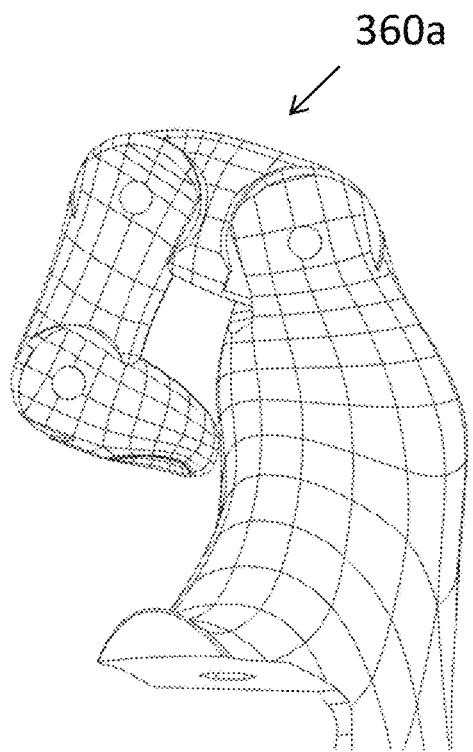
FIGS. 23A-D illustrate the prosthetic finger of FIGS. 22A-B in a fully flexed condition.
Figure 23B:
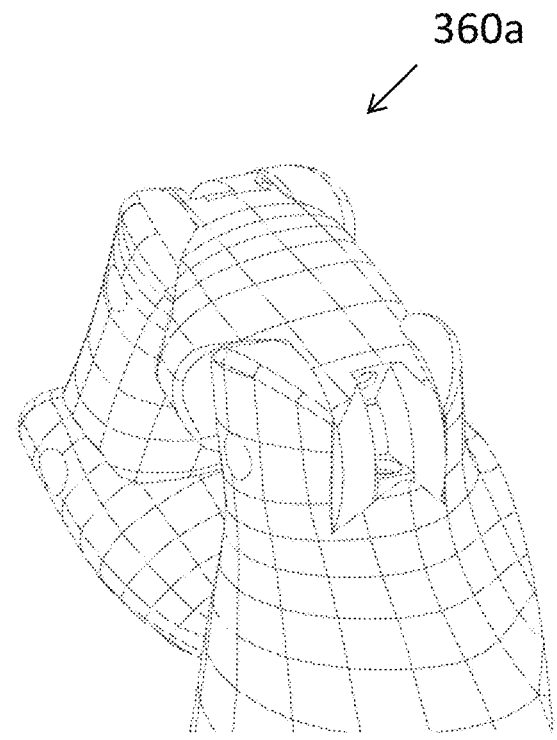
Figure 23C:
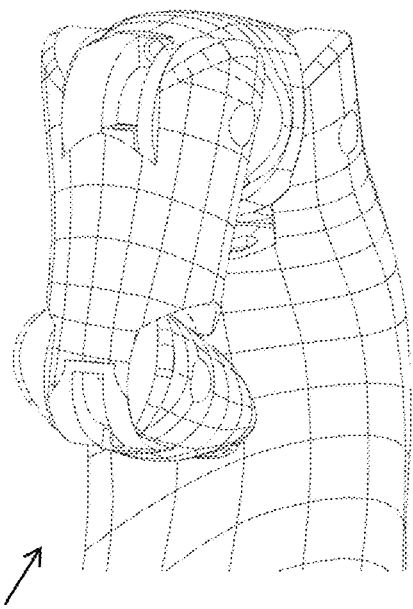
Figure 23D:
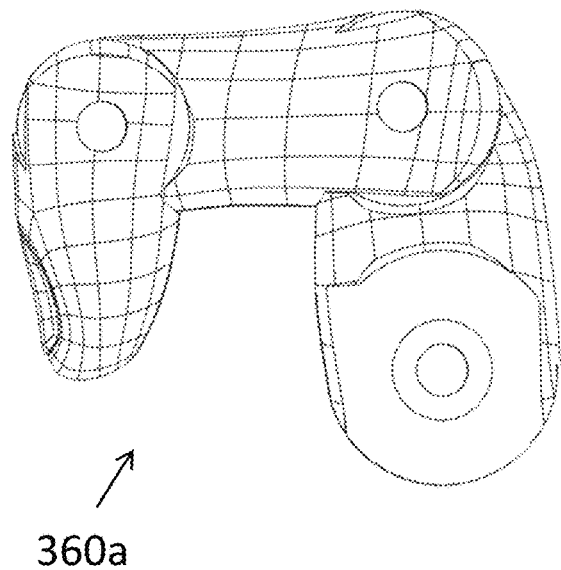

FIGS. 22A-B illustrate the three portions of prosthetic index finger 360a assembled to one another and coupled to palm 301 via finger coupling 303a. In FIGS. 22A-B, index finger 360a is in full extension. As noted above, one prosthetic finger extension tendon may be coupled to a spring that is coupled within forearm 200, with the extension tendon extending through the posterior tunnel 311 within palm 301 corresponding to index finger 360a, and through the various posterior tunnels within finger 360a, the extension tendon terminating and anchored within the fingertip 390. The spring exerts a constant force so that, in the absence of other applied force, index finger 360a tends to be in the full extension position shown in FIGS. 22A-B. FIGS. 23A-D illustrate prosthetic index finger 360a in a condition of full or substantially fully flexion. As noted above, one prosthetic finger flexion tendon may be coupled to an actuator such as linear actuator 282 in forearm 200, with the flexion tendon extending through the anterior tunnel 311 within palm 301 corresponding to index finger 360a, and through the various anterior tunnels within finger 360a, the flexion tendon terminating and anchored within the fingertip 390. The components of finger 360a and the other fingers may be formed to provide certain desired functionality. For example, the shape of the various joints as shown are designed to minimize sharp corners and to maintain a realistic shape when the finger is in the extended condition of FIGS. 22A-B as well as the flexed condition of FIGS. 23A-D. Further, the each finger joint may be structured to allow approximately 90 degrees of flexion relative to the adjacent finger portion (or relative to the palm 301) before a mechanical stop limits further flexion. The order of flexion may also be controlled by controlling mechanical advantage. For example, fingertip 390 may have a smaller diameter than middle portion 380, which in turn may have a smaller diameter than finger base 370. The resulting differential mechanical advantage may result in the finger base 370 flexing relative to palm 301 when linear actuator 282 pulls the prosthetic flexion tendon. As the prosthetic flexion tendon is pulled further, the finger base 370 continues to flex until it hits the mechanical stop at about 90 degrees relative to the palm 301. At that point, if linear actuator 282 continues pulling the prosthetic flexion tendon, the middle portion 380 next begins to flex relative to finger base 370, until middle portion 380 rotates about 90 degrees and hits the mechanical stop. If linear actuator 282 still pulls the prosthetic flexion tendon, the fingertip 390 begins to flex relative to the middle portion 380, until it flexes about 90 degrees relative to the middle portion 380 and hits the mechanical stop, resulting in the full available flexion shown in FIGS. 23A-D. This ordered flexion allows for a more natural gripping motion for a user using the prosthetic extremity 10. It should be noted that, as the three portions of finger 360 flex relative to one another or relative to the palm 301, the open portions of the anterior tunnels allow for the prosthetic flexion tendon to move to facilitate the desired flexing motion. Other components may be provided to facilitate the motion, such as washers or other bearings on the pins that coupled the portions of finger 360 to one another or to the finger coupling 303.

Figure 24A:
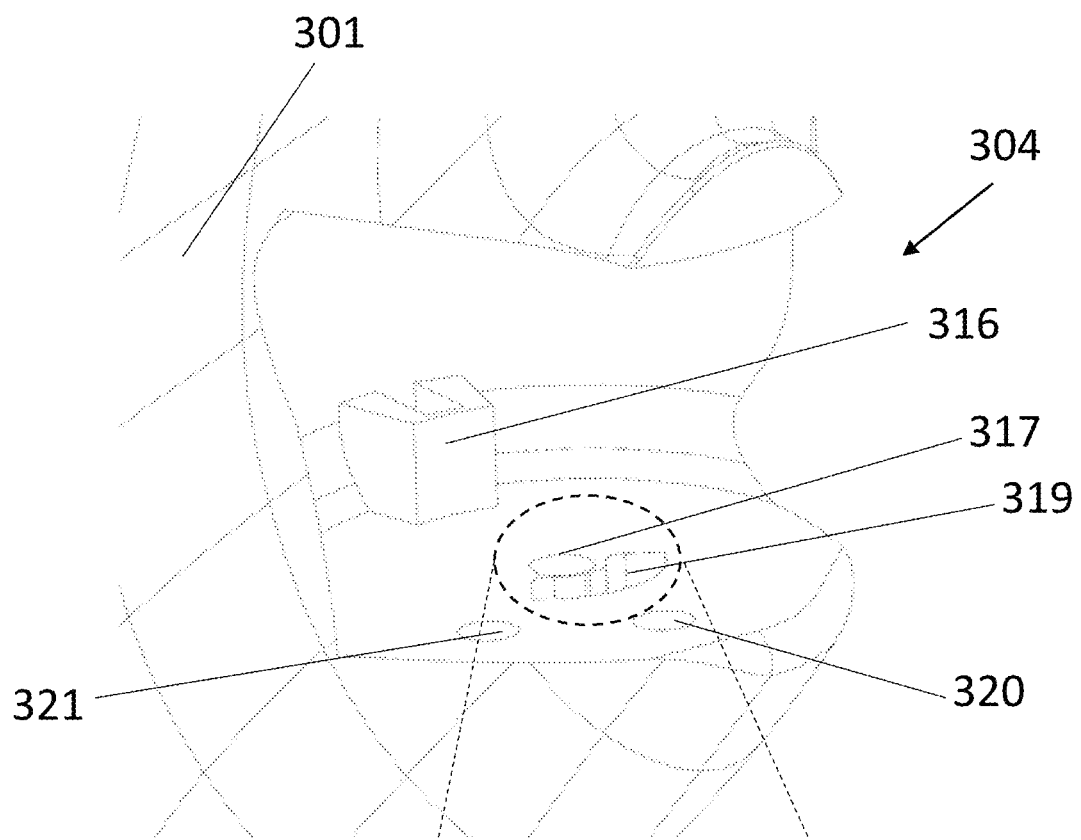
FIGS. 24A-C are views of portions of the thumb coupling of the palm of FIGS. 12A-D.

FIG. 24A is an enlarged view of the thumb coupling 304 of palm 301. Thumb coupling 304 may be substantially in the shape of a recessed cylinder or a portion thereof. The recessed cylindrical shape may include a proximal circular surface shown in FIG. 24A and a distal circular surface shown in FIG. 24C, although it should be understood that these surfaces need not be perfectly circular. Thumb coupling 304 may include a protrusion 316. As is described in greater detail below, protrusion 316 may serve to limit an amount of rotation of thumb 330, and may also house a sensor such as a Hall Effect sensor to sense what rotational position the thumb 330 is in at any moment. The proximal surface may include a central aperture 317 that is aligned with a central aperture 318 in the distal surface of thumb coupling 304. A pin or other fastener may extend through both of these apertures 317, 318 and through a base 340 of the thumb 330 so that the thumb 330 may rotated about that pin.

Figure 24B:
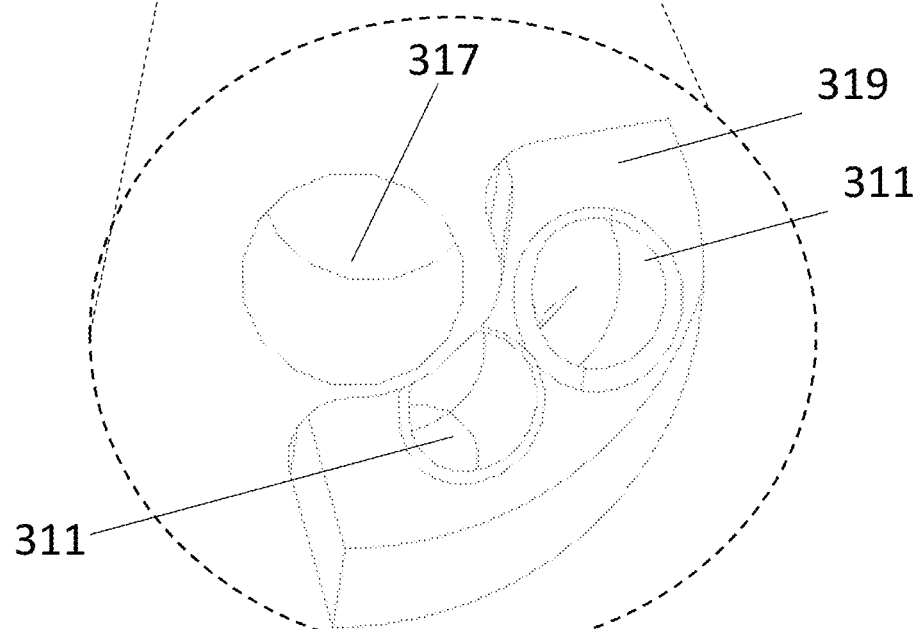
Figure 24C:
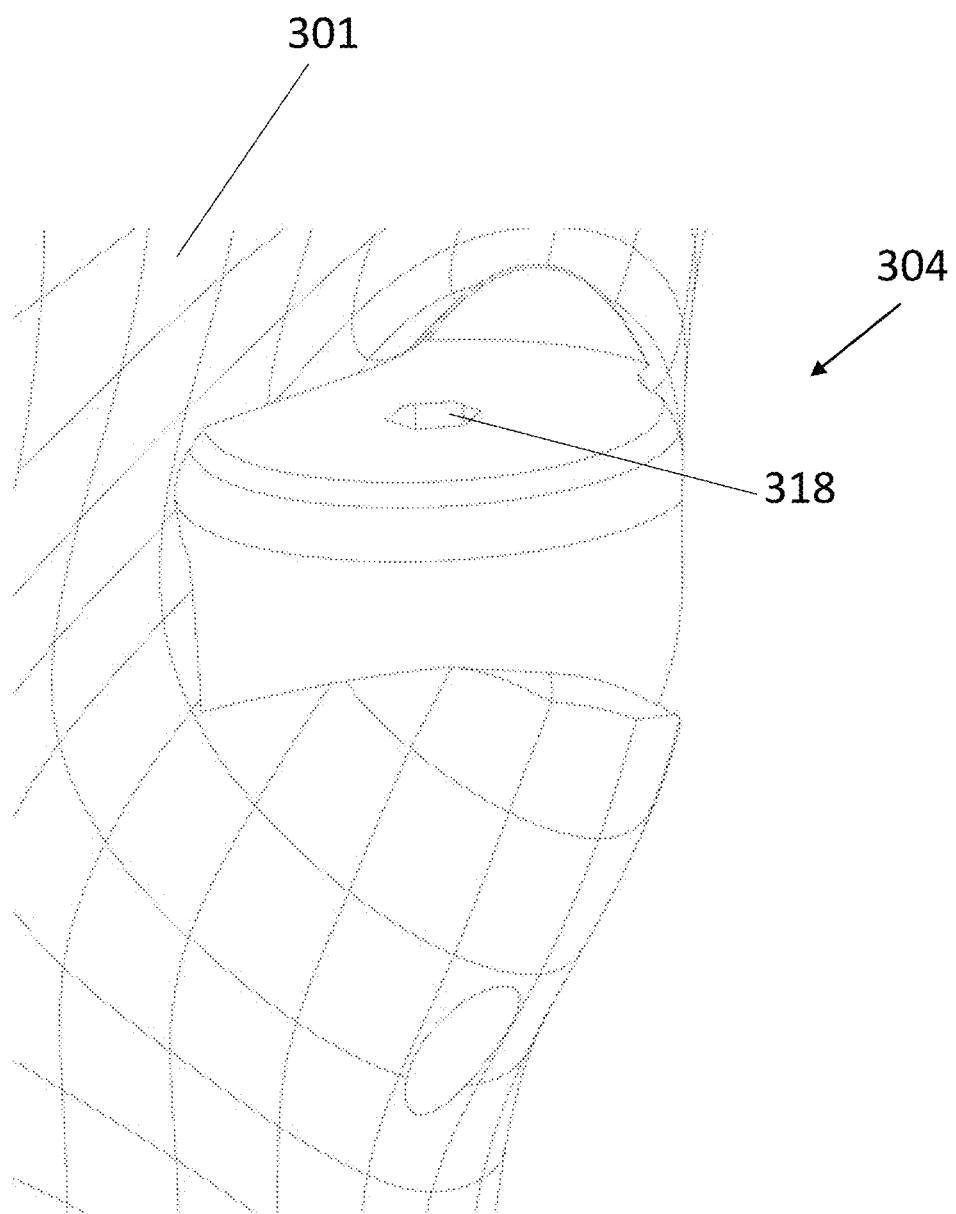

Referring to FIGS. 24A-B, an arcuate recess 319 may be positioned within the proximal surface of thumb coupling 304. Arcuate recess 319 may include therein the outlets of two tendon tunnels 311, corresponding to a prosthetic thumb flexion tendon and a prosthetic thumb extension tendon. As is described in greater detail below, thumb 330 may be capable of rotation in addition to flexion and extension, and the additional space provided by arcuate recess 319 may help ensure that the prosthetic thumb flexion and extension tendons have space to move as the thumb 330 is rotated. The proximal surface of thumb coupling 304 may include two additional apertures 320, 321. As is described in greater detail below, apertures 320, 321 may be sized and positioned two receive a locking pin of thumb 330 so that, when the locking pin of the thumb 330 is received within aperture 320, thumb 330 is locked into one rotational position, while when the locking pin of the thumb 330 is received within aperture 321, thumb 330 is locked into a different rotational position.

Figure 25A:
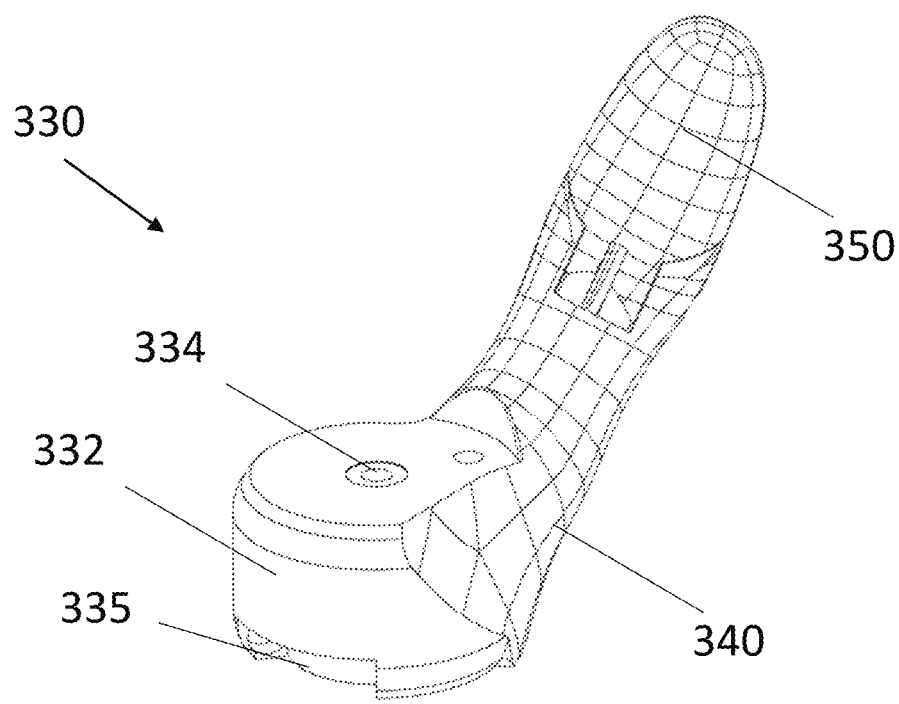
FIGS. 25A-B are views of the prosthetic thumb of the hand of FIGS. 11A-C.
Figure 25B:
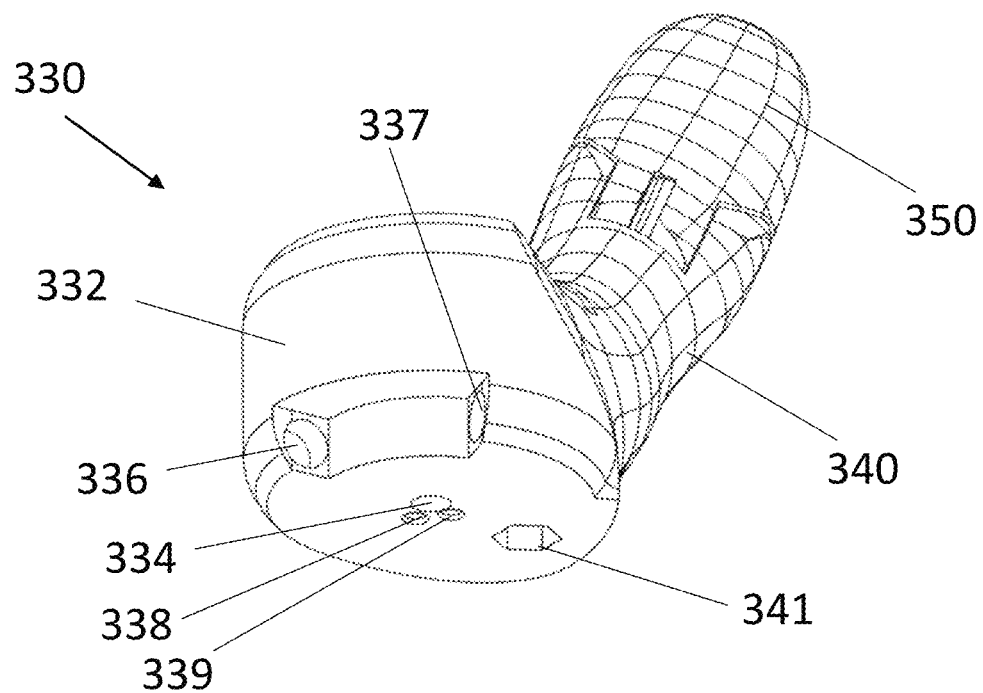

FIGS. 25A-B show two views of prosthetic thumb 330. Generally, thumb 330 may include a thumb base 340 and a thumb tip 350. Base 340 may include a substantially cylindrical member 332 with a central aperture 334 extending therethrough. Base 340 may be coupled to thumb coupling 304 via a pin extending through aperture 334 and into apertures 317, 338 of thumb coupling 304, with the base 340 being rotatable about that pin. Washers or other bearings may be positioned on or adjacent central apertures 334 in order to facilitate rotation of base 340 against thumb coupling 303. A proximal side of cylindrical member 332 may include an arcuate recess 335 into which protrusion 316 is adapted to extend. As thumb 330 is rotated within thumb coupling 304, the two faces 336, 337 of recess 335 may limit the extent to which thumb 330 may rotate in either direction. If a Hall Effect sensor is provided within protrusion 316, the faces 336, 337 of recess 335 may each include a magnet so that the Hall Effect sensor is able to detect the rotation position of thumb 330 within thumb coupling 303.

The proximal face of cylindrical member 332 may include two apertures 338, 339 adapted to receive a prosthetic thumb flexion tendon and a prosthetic thumb extension tendon therethrough, respectively. When thumb 330 is coupled to thumb coupling 304, apertures 338, 339 may generally be located near or adjacent arcuate recess 319, such that even during rotation of thumb 330, the prosthetic thumb tendons are not damaged. Another aperture 341 may be included in the proximal face of cylindrical member 332. Aperture 341 may receive a pin, such as a spring biased pin, therein. The pin within aperture 341 may extend into aperture 320 in a first rotational position of thumb 330, or aperture 321 in a second rotational position of thumb 330. Preferably, the pin is biased such that, upon aligning with either aperture 320 or 321, the pin pops or otherwise moves within the aperture to limit additional rotation of thumb 330. In some embodiments, the biasing force is relatively low so that, although thumb 330 will remain in one of the two rotational positions when the pin is within aperture 320 or 321 in the absence of additional intentionally applied force, applying manual rotational forces to the thumb 330 overcomes the friction force exerted by the pin and the thumb 330 is manually moveable to the other rotational position. In some embodiments, aperture 341 may include a recess such as a hexagonal recess to accept a nut therein, and the pin may be threaded into the nut within apertures 341 in order to adjust the amount of biasing force provided by the pin in aperture 341.

Figure 26A:
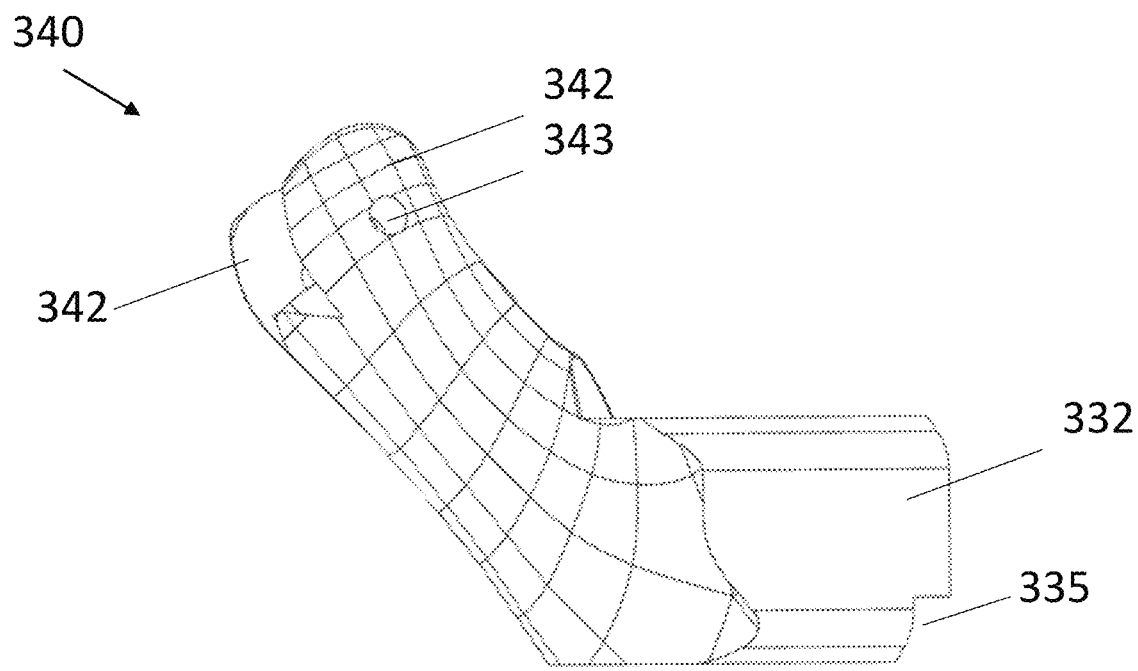
FIGS. 26A-F are various views of the base of the thumb of FIGS. 25A-B.
Figure 26B:
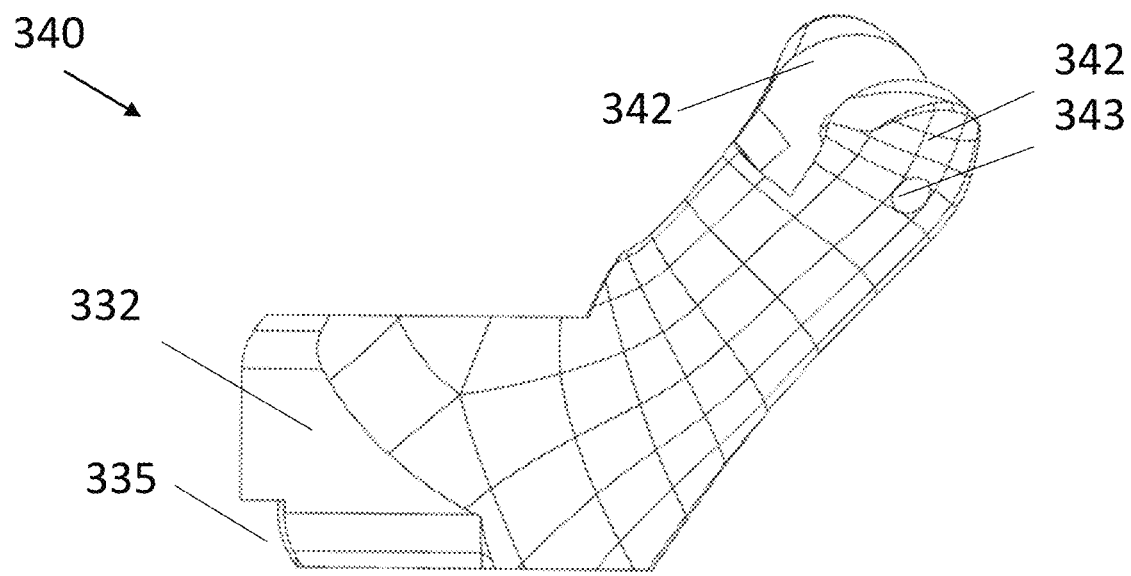
Figure 26C:
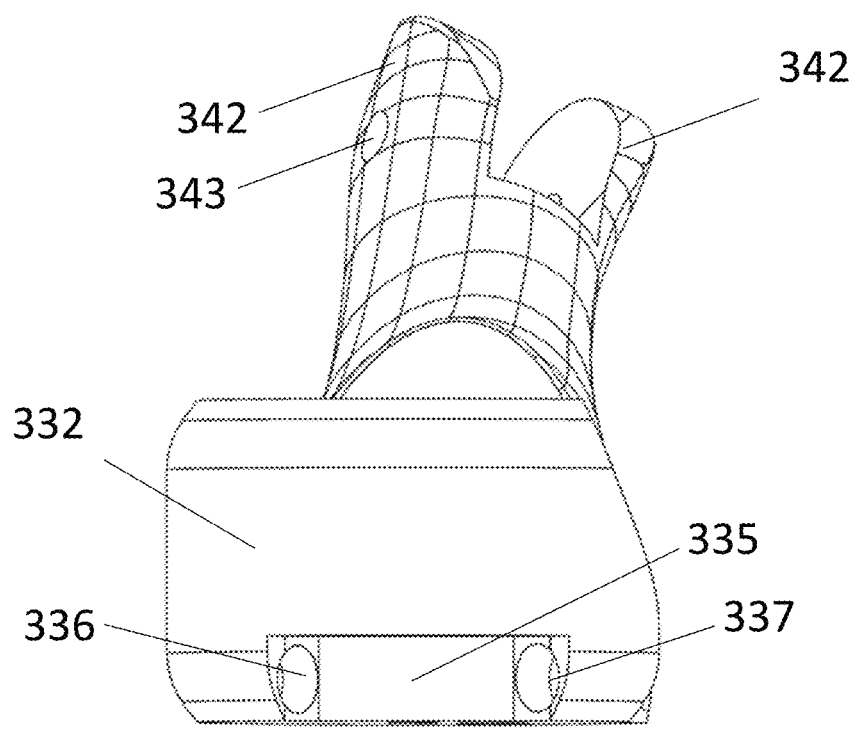
Figure 26D:
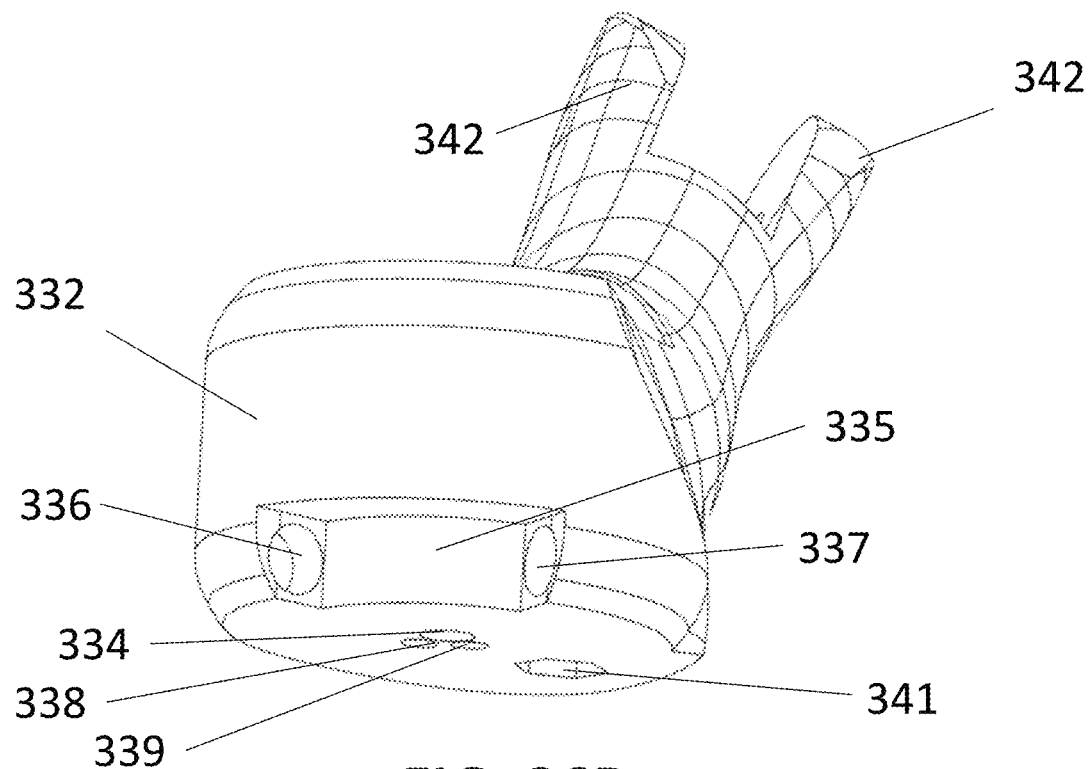
Figure 26E:
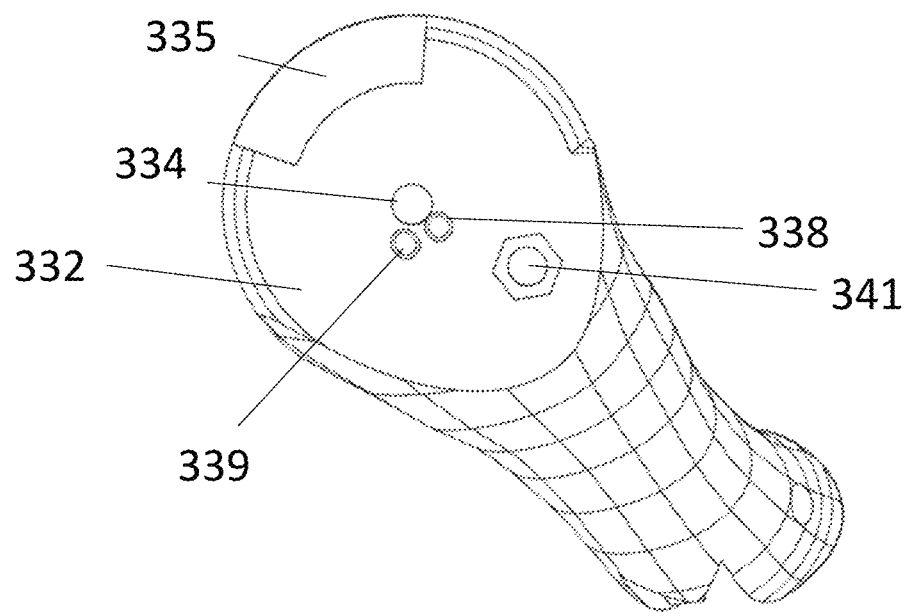
Figure 26F:
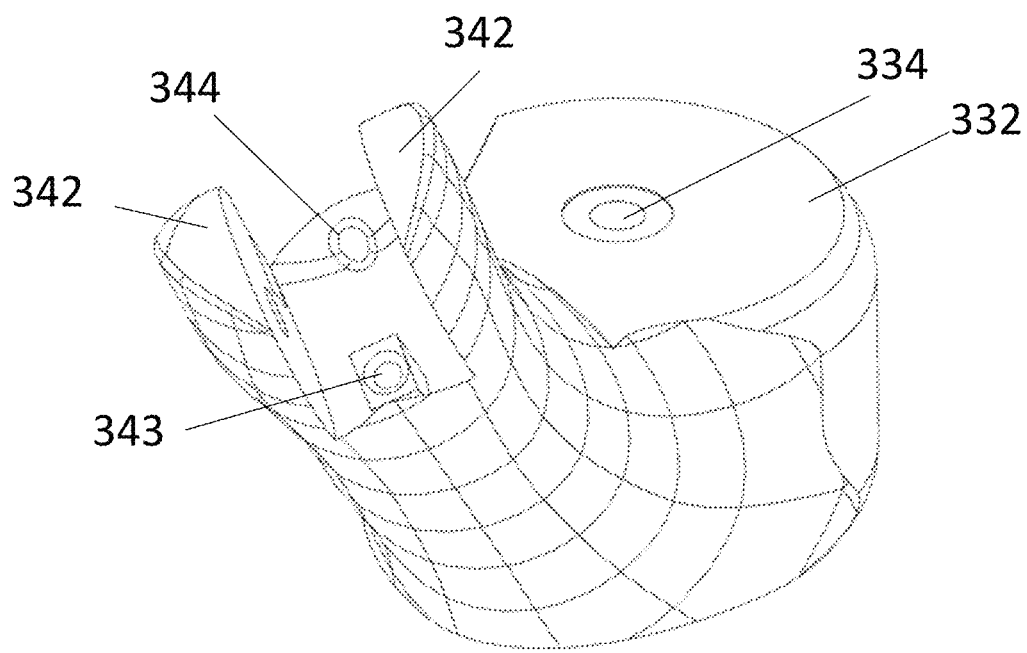

Referring to FIGS. 26A-F, base 340 may include two lateral extensions 342 each having an aperture 343 extending therethrough. Similar to finger base 370, the extensions 342 of thumb base 340 may be shaped and positioned to receive a proximal portion of thumb tip 350 therein, with a pin coupling the thumb base 340 to the thumb tip 350 to allow for flexion or extension of the thumb tip 350 about the pin. Referring to FIG. 26F, thumb base 340 may include a posterior tunnel 343 for receiving a thumb extension tendon therethrough and an anterior tunnel 344 for receiving a thumb flexion tendon therethrough, similar to the corresponding channels described for finger 360.

Figure 27A:
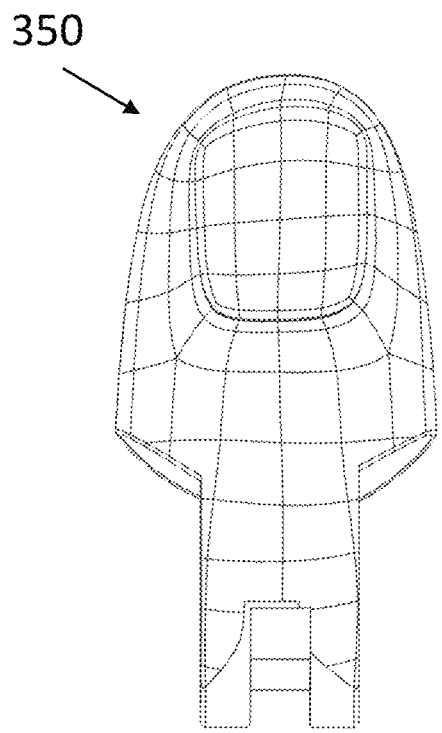
FIGS. 27A-E are various views of the tip of the thumb of FIGS. 25A-B.
Figure 27B:
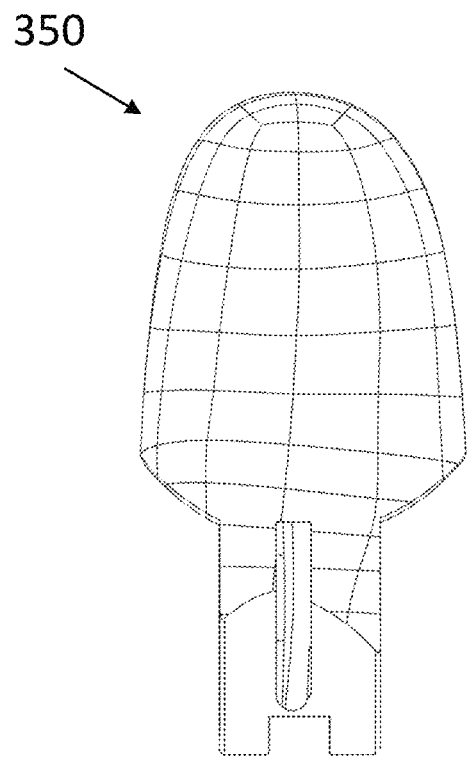
Figure 27C:
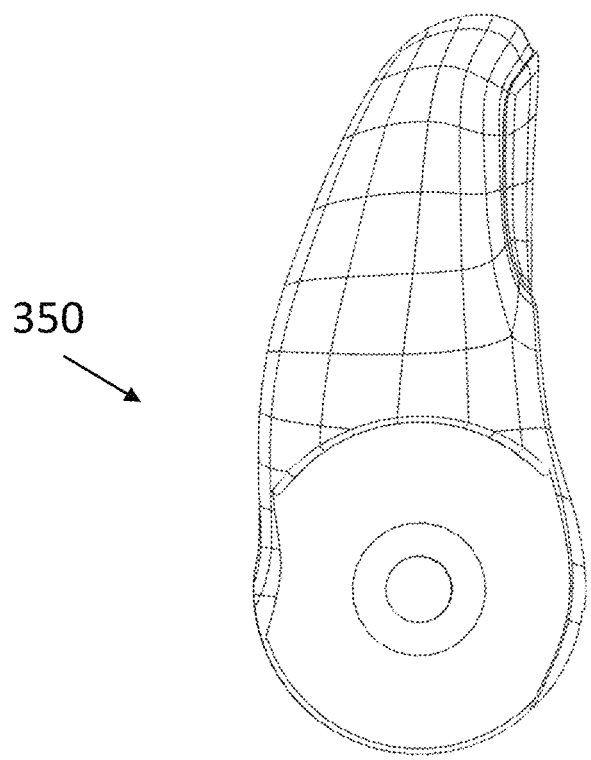
Figure 27D:
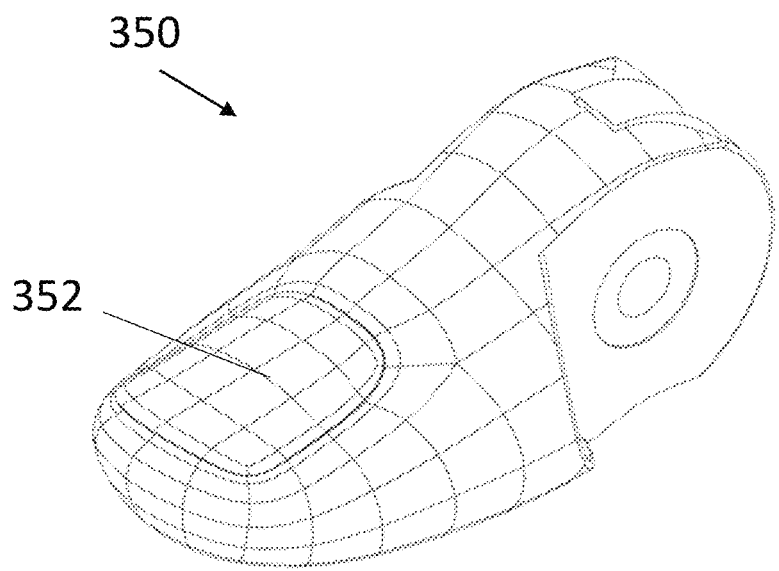
Figure 27E:
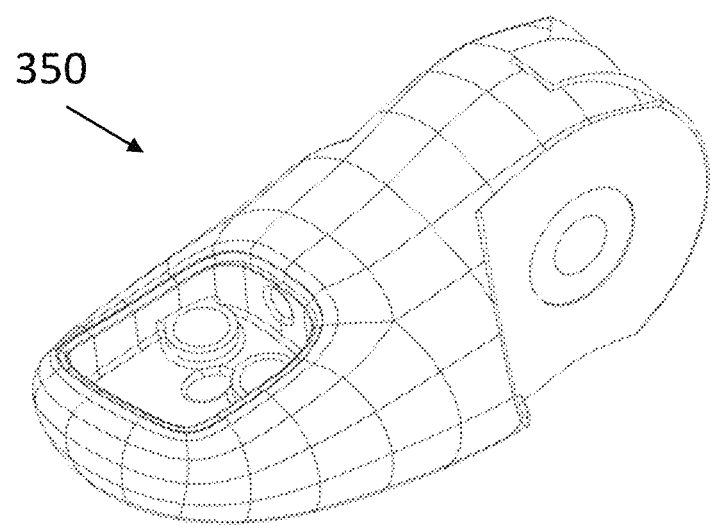

FIGS. 27A-E show various views of thumb tip 350. Thumb tip 350 may include a central aperture for coupling to the a pin extending through extensions 342 to allow for tip 350 to flex or extend relative to base 340. Thumb tip 350 may be substantially similar to fingertip 390 and is thus not described in significant detail herein. However, it should be understood that a thumb flexion tendon and thumb extension tendon may pass through thumb tip 350 into a compartment below thumb nail 352, which may be removable similar to finger nail 400 as shown in FIG. 27E. The thumb flexion and extension tendons may be anchored within the compartment beneath thumb nail 352 to provide for extension or flexion of thumb tip 350 relative to base 340 in a similar fashion as described above for finger 360. Thumb nail 352 may also be substantially similar to fingernail 400 and may couple to thumb tip 350 the same way or substantially the same way which fingernail 400 couples to fingertip 390.

Figure 28A:
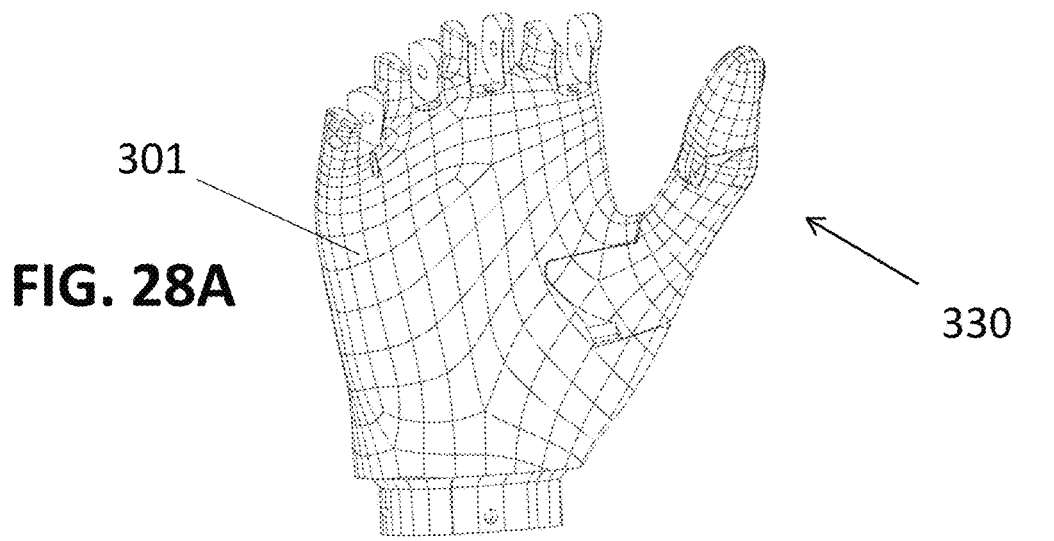
FIGS. 28A-C show the thumb of FIGS. 25A-B coupled to the palm of FIGS. 12A-D in different rotational positions.
Figure 28B:
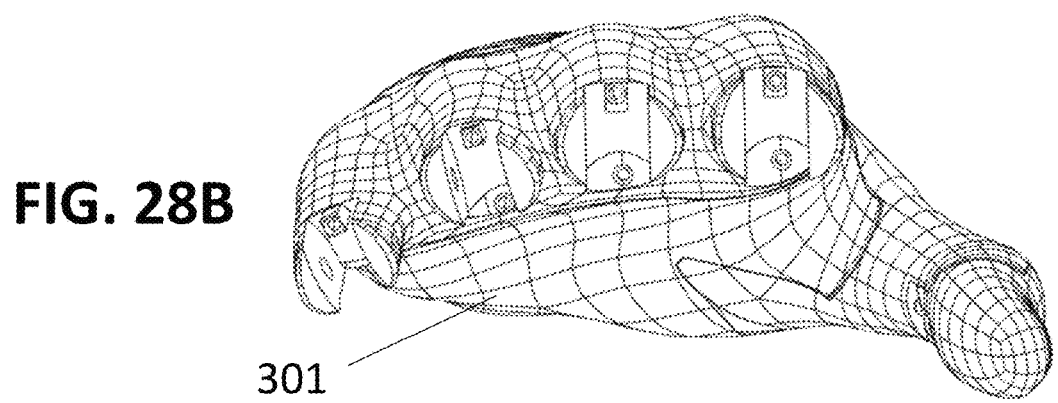
Figure 28C:
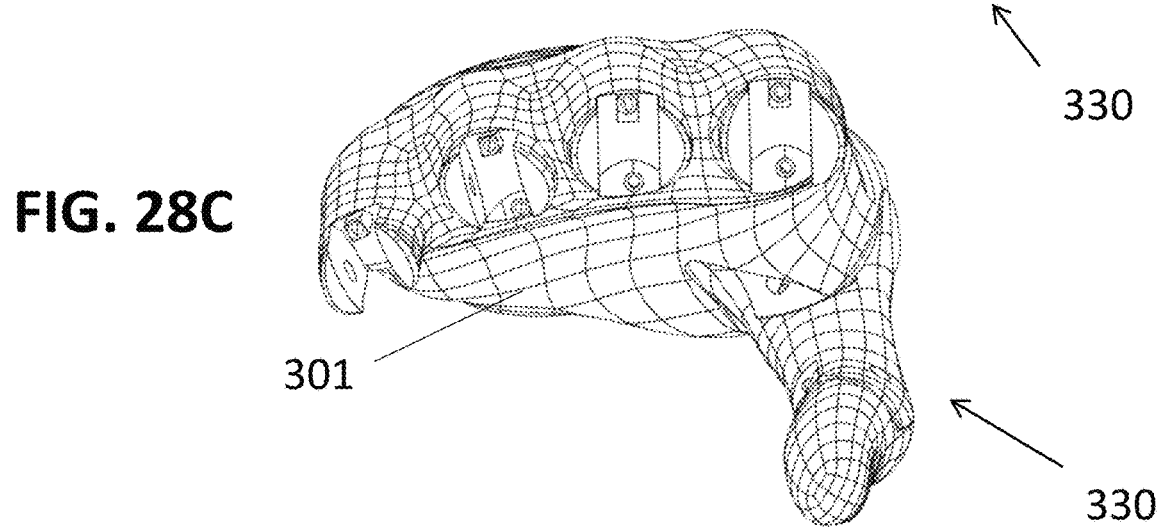
Figure 29A:
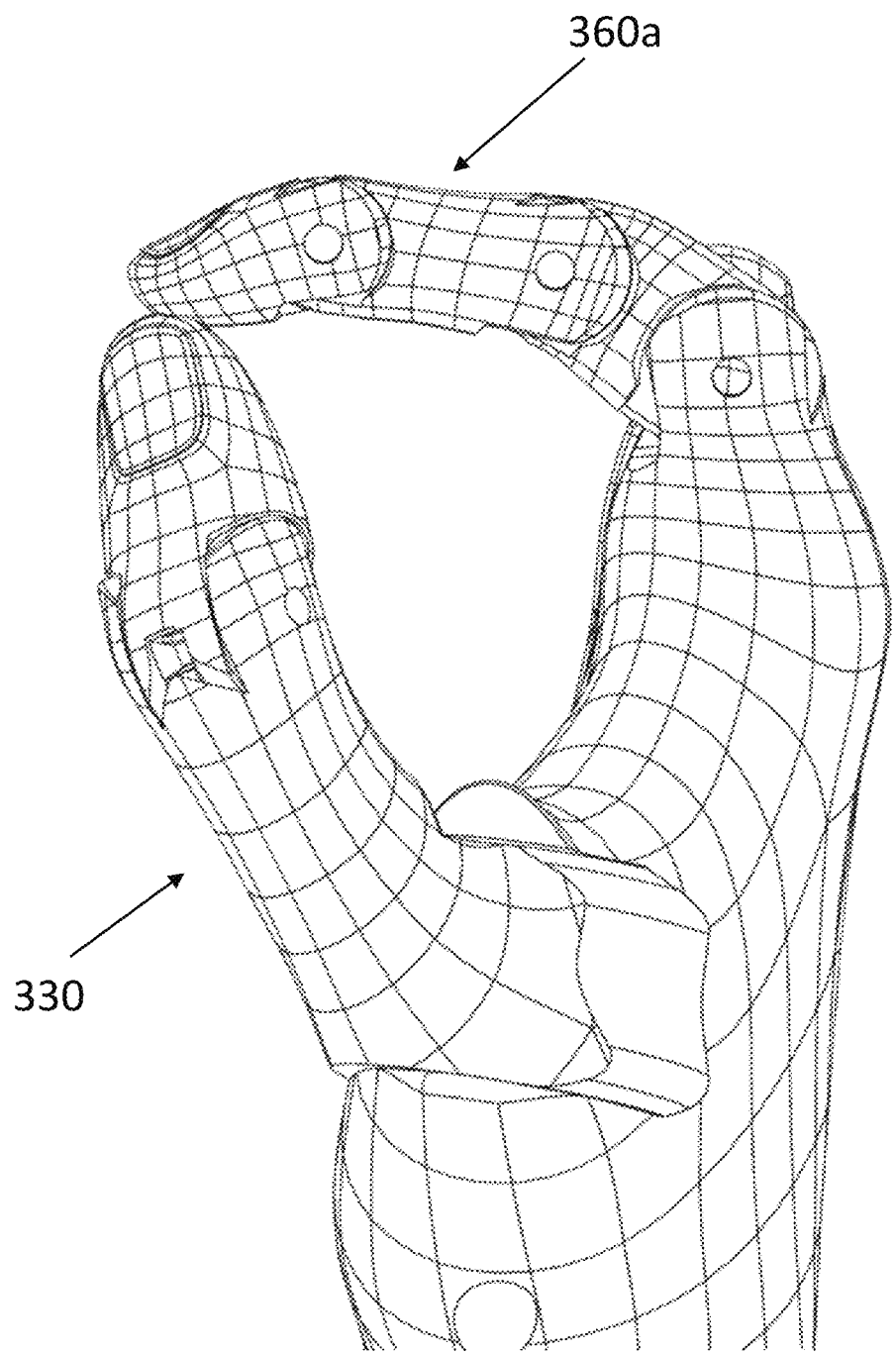
FIGS. 29A-C illustrate possible grips between the prosthetic thumb and prosthetic index finger.
Figure 29B:
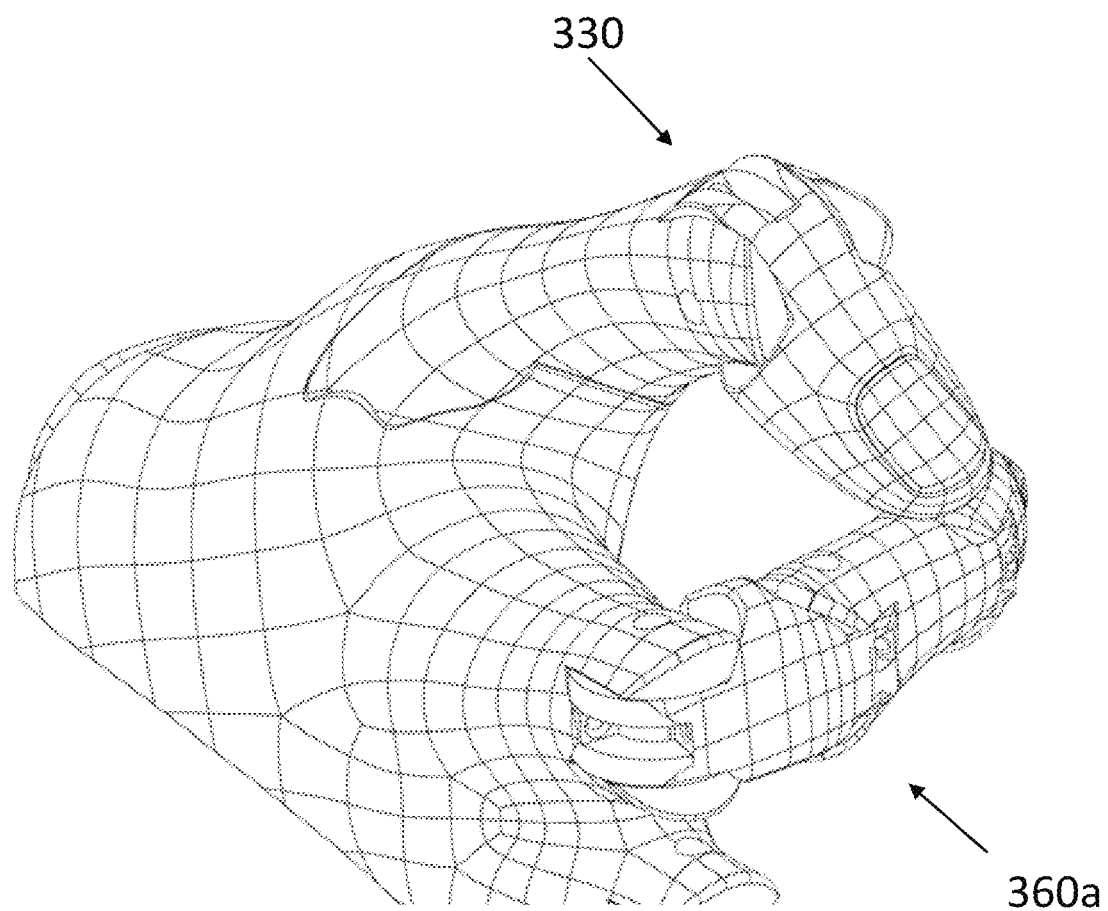
Figure 29C:
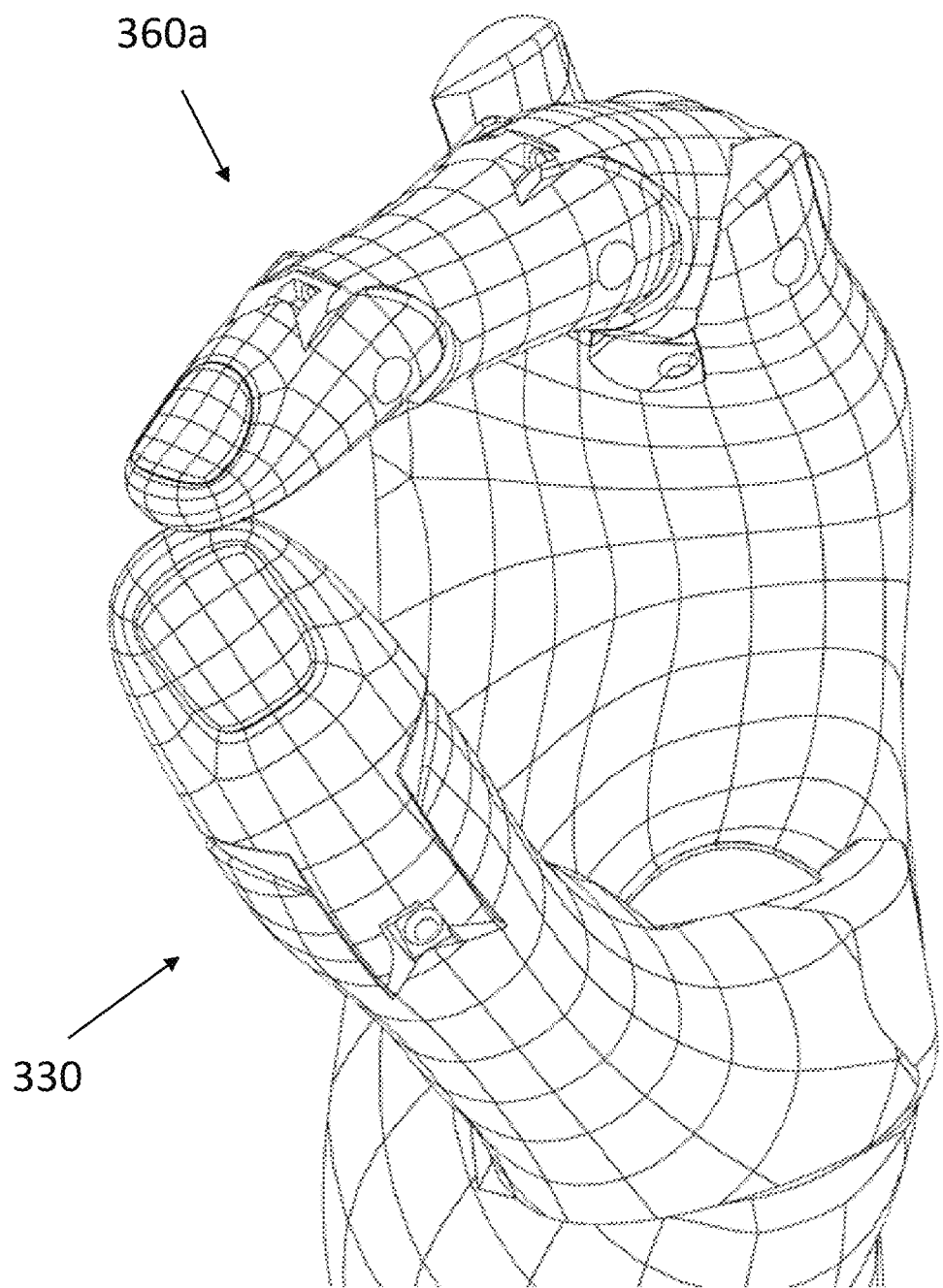

FIGS. 28A-B show thumb 330 assembled to palm 301 in a first rotation position with the locking pin extending from aperture 341 into aperture 320 of thumb coupling 303. As noted above, in this position, the thumb 303 generally remains in this rotational position until an intentional rotational force is applied to the thumb 303 to disengage the pin from aperture 320. After disengaging the pin from aperture 320, thumb 303 may be further rotated until the locking pin is positioned adjacent aperture 321 and springs and locks into aperture 321, locking thumb 330 into the second rotational position shown in FIG. 28C. It should be understood that in either rotational position of thumb 330, pulling the prosthetic thumb flexion tendon, for example via actuating a linear actuator 282, the thumb tip 350 will flex with respect to thumb base 340. Similarly, in the absence of other forces, in either rotation position of the thumb 330, the force applied by a spring to the prosthetic thumb extension tendon will tend to cause the thumb tip 350 to extend relative to the thumb base 340. Similar to the fingers 360a-d described above, thumb 330 may include mechanical stops so that thumb tip 350 is capable of a maximum of about 90 degrees of movement between flexion and extension. FIGS. 29A-C illustrate some grips that are possible between prosthetic thumb 330 and prosthetic index finger 360a.

With much of the structure of prosthetic extremity 10 having been described above, controls for a user to control the movement of fingers 360a-d and thumb 330 are described in additional detail. As noted above, for a user whose arm is amputated distal to the elbow joint, the user may position the prosthesis 10 on the body with the proximal socket 110 attached to the upper arm and the distal socket 150 compressed over the residual forearm, with or without the help of elastic, straps, or additional attachment means.

One or more sensors may be provided on distal socket 150 to be in direct or indirect contact with the user's residual limb in order to assist the user in providing input for controlling prosthetic hand 300. For example, a force sensor may be used to sense the force of a muscle contraction by the user. When the user flexes the muscle, the muscle changes shape and can expand. The force sensor(s) may work when a force is exerted from the user's muscle onto the surface of the force sensor(s), the force being transmitted into layers of a conductive polymer that change resistance based on the amount of force applied. One or more force sensors may be anchored to an elastic band, for example on a surface of distal socket 150 intended to contact the user's residual limb, the elastic band helping to provide consistent pressure of the force sensor to the user's skin. The reading of the force sensor(s) once the elastic band is in the desired position and the user's muscles are in a resting state may be used as a zero point within software to track changes. A small cylindrical shaped foam piece may also be used to concentrate the force from the user's muscle to the force sensing area of the force sensor. By using a smaller diameter piece of foam than the diameter of the sensing area, the reading is amplified and smaller changes may be detected. When a muscle is flexed, the muscle pushes on this piece of foam that pushes on the force sensor. This may also provide proportional data of the amount of muscle activity. In other words, instead of being a binary on/off signal, this above-described sensor configuration may provide data regarding the intensity of the muscle flex, the duration of flexing, and any kind of ramping of the flexing. This data may be used, alone or in combination with other data, to provide information to a controller, such as a controller within the cover 260 of prosthetic forearm 200, and in turn to accurately control the various actuators 282 to accurately flex or extend the fingers 360a-d and thumb 330. It should be understood that any sensors in socket 100 may be coupled to electronics within prosthetic forearm 200, either wirelessly or in a wired fashion as described above.

Another sensor that may be used in order to help a user control the flexion and extension of fingers 360a-d and thumb 330 is an electromyography ("EMG") sensor, which detects the electrical potential generated by muscle cells. In one example, the EMG sensor may include three surface electrodes, including positive, negative, and reference. The positive and negative electrodes may be placed on the desired muscle and the reference electrode may be placed somewhere without muscles, such as the elbow area. The EMG sensor may detect muscle activity and provide information to the electronics within prosthetic forearm 200 in order to control the actuation of actuators 282 and, in turn, control the flexion and extension of fingers 360a-d and thumb 330.

In one embodiment, one or more force sensors may be used along with one or more EMG sensors. In one example, the electrodes of the EMG sensor may be placed on the force sensors so that when a user flexes the muscle, the electrodes make consistent contact and push into the force sensor. This may provide two different types of data to analyze and to translate into desired movement of the prosthetic hand 300. This combination has been found by the inventor to provide better results than using force sensors and EMG sensors independently. It should be understood that for each of the examples above, the linear actuators 282 may be individually controlled, so that the user may individually control the thumb 330, index finger 360a, and the remaining fingers 360b-d.

Additional features may be activated other than through muscle control. For example, as noted above, forearm cover 260 may include a recess 274 for a push button. The push button may provide any desired functionality when pressed. In one example, pressing the push button activates the actuators 282 to cause flexion in the fingers 360a-d and thumb 330, so that the prosthetic hand 300 may be used to grip an object without the user initiating muscle flexing to cause the actuation. The button may be binary in the sense that pressing the button once causes flexion, and pressing it again causes extension. In other embodiments the button may be force sensitive where pressing the button with more force causes the fingers 360a-d and thumb 330 to flex with greater force. Such a button may in some embodiments be coupled with indicators, such as an LED or an array of LEDs to provide visual feedback to the user to communicate a current state of the device, calibration, power level, and/or detected errors.

As noted above, in the illustrated embodiment, most or all of the electronics are coupled to or positioned within the interior of forearm cover 260, similar to the picture shown in FIG. 10B. One or more processors or controllers may be coupled to the various actuators 282 to provide actuation of the prosthetic flexion tendons as described above to flex the fingers 360a-d or the thumb 330. The connection between the processor(s) and the actuators 282 may be any suitable connection such as the ribbons shown in FIG. 10B. Power may be provided to the device by any suitable method. In the illustrated example, a rechargeable battery made from lithium-ion technologies is provided within cover 260. Depending on the size of the user and the prosthetic upper extremity 10, at least a single cell battery may be used. The batteries may be recharged by using an external power source that is connected by a cable to a harness, such as a USB port, a magnetic connector, or other suitable modalities. The batteries can also be charged wirelessly by an inductive charging system including circuitry and transmitting and receiving coils. The receiving coil may be placed on the inside of the forearm cover 260 with the main electronics or in another position, such as within the palm 301. The transmitting coil and circuitry may be in the form of a plate on which the prosthetic forearm 200 may rest. Magnets may be used for alignment to ensure the coils are in a desired alignment. These magnets may be imbedded into the charging plate and placed in the prosthetic forearm 200 below the outer surface so that magnets attract each other.

Haptic feedback systems may be integrated into prosthetic extremity 10 to provide various types of information to the user, including device status, battery level, warnings, errors, selections, triggers, and/or force being encountered by prosthetic hand 300 during gripping. A small vibrating motor, similar to what is used in many cell phones, may be provided within cover 260 or another component of prosthetic device 10 to provide the haptic feedback to the user. In one example, the vibration motor is secured to a flat surface inside of the prosthetic forearm 200 so that the vibrations pass through the forearm 200, to the socket 100, and then to the skin of the user. Certain patterns and intensities of vibrations may be used to communicate different information to the user. For example, the device can calculate force that is being exerted on an object by the prosthetic hand 300, and the amount of force is communicated by a varying intensity of vibration, for example with a lower frequency corresponding to a relatively low amount of force and a high frequency corresponding to a relatively large amount of force. Other examples of haptic feedback may include a particular pattern of vibrations being provided when the prosthesis 10 is powered on to inform the user that the device 10 has adequate battery power and is ready to calibrate.

As noted above, force being exerted by prosthetic hand 300 on an object, for example during gripping, may be calculated for various uses, including to inform the user of the amount of force via haptic feedback as noted above. In one example, this force may be calculated by determining via the processor or other appropriate electronics the amount of current being drawn by the actuators 282 and by determining the position of the actuator compared to time of the actuation. For example, when the fingers 360a-d or thumb 330 meet an object during flexion, the speed of the flexion slows down to a stall, and the measured current draw of the motor can be correlated to the amount of force being exerted. Force can also be calculated by comparing the position of the actuator 282 to the time from the start of movement. When the fingers 360a-d or thumb 330 meet an object during flexion, they slow down the actuator for a small amount of time. By using a combination of both methods described above, an accurate force can be calculated to use for a force limit and to communicate the force being exerted through haptic feedback. Force limiting may be used to ensure the actuators 282 stop before they exert too much force on the object, as well as to protect components in the prosthesis 10. An alternative or additional way to sense the force from the fingers 360a-d or thumb 330 is to provide force sensors on the fingers 360a-d, thumb 330, and/or the front of palm 301.

One additional benefit of the control systems and methods described above is the creation of a feedback loop, which can result when the user has proportional control of the movement of hand 300, as well as feedback, such as visual or haptic feedback, regarding the force. For example, when the user starts to flex the muscle, the user can typically see a response of the prosthetic hand 300 starting to close. This creates a closed loop that allows the user to control the position of the fingers 360a-d and thumb 330 with more precision. When the fingers 360a-d and thumb 330 meet an object, the user may feel vibrations based on the amount of force from the fingers 360a-d and thumb 330. The inclusion of both visual and haptic feedback regarding this force may provide even further precision in control of the prosthetic hand 300.

As noted above, it is preferable that the portions of prosthetic device 10 that are in contact with a residual limb of the user are user-specific in the sense that they closely complement the contours and shape of the residual limb, and also in the sense that the other components such as the forearm 200 and hand 300 substantially match or mirror the user's other limb if it is intact. Exemplary methods of creating components of prosthetic device 10 are described below.

In one embodiment, to begin creating prosthesis 10, three-dimensional scans of the user's residual limb are performed, as well as three-dimensional scans of the opposite full arm if the arm is available for scanning. These 3D scans may be generated from any suitable 3D scanner, preferably a mobile 3D scanner. The 3D scans preferably also include color data which can be used to 3D-print the components of the prosthesis 10 in a matching color. If the 3D scanner is a mobile scanner, the user can create these scans remotely, with or without the assistance of another person. A mobile application may be used to interface with the 3D scanner, which may allow for live monitoring, starting/stopping a scan, reviewing the scan, and/or submitting a scan. The 3D scan(s) of the user's limbs may be used to generate a custom prosthetic hand 300, forearm 200, and socket 100.

A 3D scan of the residual limb may be used to create a socket 100, and in particular distal socket 150, that is complementary to the shape and contours of the residual limb. As noted above, an offset may be built into distal socket 150 to provide an interface layer for foam or another layer, which may not only increase comfort for the user, but help reduce the effect of any inaccuracies in the scanning process. During the design process, it is preferably to have as much surface area from the distal socket 150 in contact with the user's residual limb, as it must support the weight of the remaining components of prosthetic device 10 and any objects the prosthesis may be lifting.

In one embodiment, a test socket may be produced initially to confirm a desired fit with the user prior to producing a final socket. For example, if the user scans his or her residual limb remotely, that data may be sent to a facility to rapidly print a 3D test socket that may be shipped to the user to confirm fit. In one example, the test socket is 3D printed based on the scan data using a FDM 3D printer with a large nozzle to rapidly print the test socket. Because the initial socket is a test socket, it may be produced more quickly than the final socket. The test socket may be printed the same day the 3D scans are received and it may be shipped to the user to confirm fit. The user may contract the manufacturer to determine if any alterations to the design are required or desired, and a final socket may be 3D printed with higher quality, which may take a longer time, with or without modifications from the shape of the test socket. The final 3D-printed socket may be rigid and may be 3D-printed on FDM 3D printer using clear plastic, which may be preferred or aesthetics compared to, for example, carbon fiber. In other embodiments, flexible plastics or other flexible materials may be used to construct the socket, or a combination of rigid and flexible materials may be used to construct the socket, which may make the socket more universal and have a better fit and relieve points of pressure.

While 3D scan data of the user's residual limb may be used to design the socket 100 (or portions thereof), the 3D scan of the user's opposite limb may be used to design the shape, contours, and dimensions of the prosthetic forearm 200 and hand 300. For example, from the 3D scan data of the opposite limb, specific dimensions may extracted and used to create a proportional forearm 200 and hand 300. These dimensions may include finger length, finger height, finger width, palm length, palm thickness, palm width, wrist circumference, forearm length and various circumferences of the opposite limb.

The measurements extracted from the 3D scans may be input into a master CAD model that has all of the mechanical and robotic features described above already designed in. Measurements may be automatically imported or manually entered into this CAD model to create a new user specific model using the user's specific measurements. For example, the finger length may be entered and the master CAD model would update to match the user's finger length. This methodology allows for rapid creation of custom devices without having to design a custom model for each user.

Once a custom model is generated from the user's measurements from the master CAD model, the individual parts are ready to be made physically by using a 3D printer. A high-end 3D printer is preferably used to provide high levels of accuracy that ensure the mechanisms within the prosthesis 10 are able to function properly. Such a 3D printer may use a secondary support material which may reduce the design constraints of a model. As a result, it is possible to print parts assembled. For example, instead of joining the finger joints together using a pin, an interlocking structure can be printed utilizing the support material, so the parts do not fuse together.

It should be noted that, when printing the prosthetic forearm 200 and hand 30, it may be preferably that the weight of those devices, including components positioned therein, are as close as possible to the weight of the user's residual limb to help avoid creating a lever effect, which may make the device feel heavier to the user. As a result, it should be understood that certain internal components may be positioned in uniquely for each prosthesis 10 to provide desired weights and weight distribution.

It may be preferable to utilize a 3D printer that is capable of printing in full color which allows the outer surface of the prosthesis 10 to match the skin color of the user. In one example, all of the components of prosthesis 10 may be printed in a single color that is extracted from the 3D scan color data. In another example, a texture map may be created from the 3D scan, and the texture map can wrap the CAD model so that a 3D picture is printed on the exterior surfaces of the 3D printed components. This method may provide extreme realism, for example as the user's arm hair, wrinkles, blemishes, freckles, variations in color, veins, etc. may all visually show on the prosthesis 10. Further, by changing the texture of the outer surfaces of the printed components from a smooth surface to a textured surface, a feel can be provided that matches that of skin. For example, small dimples can be added to provide a touch that feels like rough skin or small ridges for finger print ridges. This latter feature may also help with gripping onto objects as well as improving the aesthetics of prosthesis 10. Physical wrinkles and veins can be added too in combination with the coloring/texturing described above to increase the realistic appearance of the prosthesis 10.

The printed prosthesis components may also be coated using a sealant and/or a clear coat to increase the strength and durability of the parts and to make the parts scratch resistance. The clear coat may also be used to match the gloss of skin.

Once the components of prosthetic device 10 are finalized and printed or otherwise manufactured, they may be provided to the user. When the user receives prosthesis 10, the user may go through an initial calibration to ensure the sensors, such as the combined force/EMG sensors, are reading the user's muscle activity correctly. The muscle sensors, described above, are mounted to the inside of the distal socket 150 so that when the user puts the prosthesis on, the sensor is in a consistent position relative to the residual limb and makes contact with the muscle. An application such as a smartphone app may provide live data from the sensor to the user, which may allow the user to place the sensor on the muscle and to test the sensor before mounting the prosthetic forearm 2000 to the socket 100. Once the data meets the requirements the sensor may be mounted, and the prosthesis 10 may be ready to use. Once the device is in position on the user and powered on, the user may be prompted on the mobile application to train a gesture profile. This process may display a gesture on the screen and record the raw data from the sensors that correspond to that gesture. Haptic feedback may be used to communicate to the user when the arm in powered on, when the data is recording for a grip, and/or when the recording has stopped. For example, the user may be prompted make a closed hand gesture for five seconds and the raw data may be recorded from the sensors for that time. The data resulting for all the hand grips may be loaded into a neural network that utilize machine learning to look for patterns and to watch the raw data and trigger a particular grip in response to a recognized pattern. This process can be repeated many times to improve accuracy.

Additional electronics and/or software may be provided to enhance functionality. For example, onboard accelerometers, gyroscopes, and/or magnetometers may be used to measure the orientation and movement of the prosthesis. This monitoring may allow software to analyze this data and recognize patterns to trigger events or to conserve battery. For example, these components may be able to detect that the user is walking. In response, the prosthesis 10 may be put into a low power mode as it is unlikely that gripping motions will be used while walking. In another example, the monitoring may result in recognition that the walking is being performed during a particular event, such as carrying groceries, and the grip of the prosthetic hand 300 may be locked to help ensure the groceries remain firmly secure within the prosthetic hand 300. In another example, if the sensors detect a hand shake, the prosthetic hand 300 may close to make an intelligent selection based on movement. Recognizing these types of patterns throughout the day and week can help the prosthesis 10 become easier to use and to conserve battery. For example, if a certain grip is used more than others, the software can change the sensor input needed to trigger this grip making it easier to control.

The mobile application may also be used to configure the different grips and how those are triggered. For example, a user may be able to select the "pointer" grip to be triggered by the muscle being held for one second and the full hand close being triggered by a muscle burst. This allows the user to customize the device to function in a desired way.

It should be understood that the particular embodiment of prosthesis 10 illustrated in the figures and described above may be for a user with a forearm that has been amputated distal to the elbow joint. In other words, prosthesis 10 is suited for a user with an intact elbow joint. However, it should be understood that the concepts described herein can be applied to similar prosthetic devices for user's with various conditions of residual limbs, including a completely missing upper extremity.

For example, if the user is missing the elbow joint, the socket could include a lower and upper structure that attaches to the bicep area and shoulder area, instead of the bicep area and the residual forearm. In such a circumstance, a robotic elbow joint may be provided to replicate the motion of the elbow. For that circumstance, the electronics and mechanical parts may be located in a compartment within a prosthetic upper arm, rather than the prosthetic forearm.

In still another example, if the user has a large amount of the forearm remaining, there may be limited space within the prosthetic forearm to house the mechanical and/or electronic components. In that circumstance, the components may be positioned within the hollow space of the prosthetic hand 300. In this situation, the tunnels 311 may be unnecessary since the prosthetic tendons could be routed directly from the actuators within the hand to the fingers 360*a-d* and the thumb 330, freeing up more space for electronic components. The actuators in this scenario may be mounted in a staggered pattern to fit in the relatively small space. These may start near the knuckles and end near the wrist. The electronics and batteries could also be mounted in the palm cavity, for example either on top of or below the actuators.

Although in the embodiment described above, the prosthetic forearm 200 is substantially fixed relative to the palm 301, a mechanical joint may be provided to join the prosthetic forearm to the palm that allows for an amount of rotation. This rotation can be manual, for example similar to how the thumb rotates relative to the palm, or via an actuator. Such a wrist joint may instead be a powered wrist joint, which could provide one, two, or more degrees of freedom of motion, which could be controlled manually, via an actuator and electronics, or both. For example, one of the degrees of freedom may be flexion and extension. Another of the degrees of freedom may be pronation and supination. And another of the degrees of freedom may be radial deviation and ulnar deviation. It should be understood that any one or combination of the above movements may be provided in a wrist joint. These wrist joint movements may be driven through ha direct drive or tendon-based mechanism coupled to an actuator on the joint or within the prosthetic forearm 200 or palm 301.

Still further, the illustrated embodiment of device 10 includes three linear actuators 282 coupled to five prosthetic flexion tendons, with three attached to one of the linear actuators, and the other two linear actuators being coupled to a single flexion tendon, either for flexing the index finger or the thumb. However, the use of three actuators 282 may be particularly suited to smaller prostheses 10 in which there is limited space within prosthetic forearm 200. If there is space, at least five actuators may be provided so that each finger (and the thumb) has independent flexion control.

If the user is a candidate for a socket that requires a mechanical joint at the elbow or shoulder, mechanical springs may be used to assist with lifting the prosthesis. For example, torsion springs can be integrated into the mechanical joint to provide rotational force, so that the prosthesis feels lighter during elbow flexion. This may be achieved by mounting the legs of the spring to the upper and lower part of the socket so that the center of the spring is in line with the socket's axis of rotation. The default position of the spring may be when the elbow is bent to its maximum amount of flexion. This will then provide increasing resistance from the spring as the socket starts to straighten. The spring tension may be balanced so that the weight of the prosthetic device will overcome the spring tension, so the prosthetic device can be in a straight position. When a small amount of flexion force is added by the user, the springs assist, making the device easier to move. Further, one or more actuators may be used to assist with prosthetic elbow flexion and extension when a mechanical elbow joint is included in the upper extremity prosthesis. Such an actuator may be mounted on the socket and positioned to exert rotational force on an axis of rotation of the socket. One or more sensors may be incorporated into the system to determine if the user is extending or flexing the arm so that the motor powers the joint in the desired direction of movement. This may allow for less physical exertion and easier use for the user in flexing or extending the elbow. These actuators may be located on the axis of rotation, elsewhere on the socket, and/or within the prosthetic forearm and may transmit rotation or linear force to the axis of rotation of the socket.

The prosthetic device 10 described above may be designed to be modular so that the socket can be replaced with an electro-mechanical powered joint. This joint could be a prosthetic elbow joint that fastens to the forearm in the same or a similar way as the socket attaches. This prosthetic elbow joint may have an actuator and sensory feedback for accurate control. The prosthetic elbow joint may be able to lift the prosthetic forearm and hand and may be controlled using muscle sensors. Additional modular joints may be added to create a powered bicep and shoulder to achieve pronation, supination, abduction, adduction, flexion and extension of the shoulder and bicep. A universal bolt pattern may be used to fasten the joints together similar to how the socket attaches to the forearm as shown in FIG. 9. Wires for power and control may be routed to the forearm where they connect to the main control electronics. A secondary control board may be integrated into the module joints to control the motor and read position and current sensors. This may allow for easy integration, fewer wires being routed and smaller main control electronics. This may also allow the main control electronics to send desired position data to the modular joints where the secondary control electronics compute and control the joint.

Figure 30:
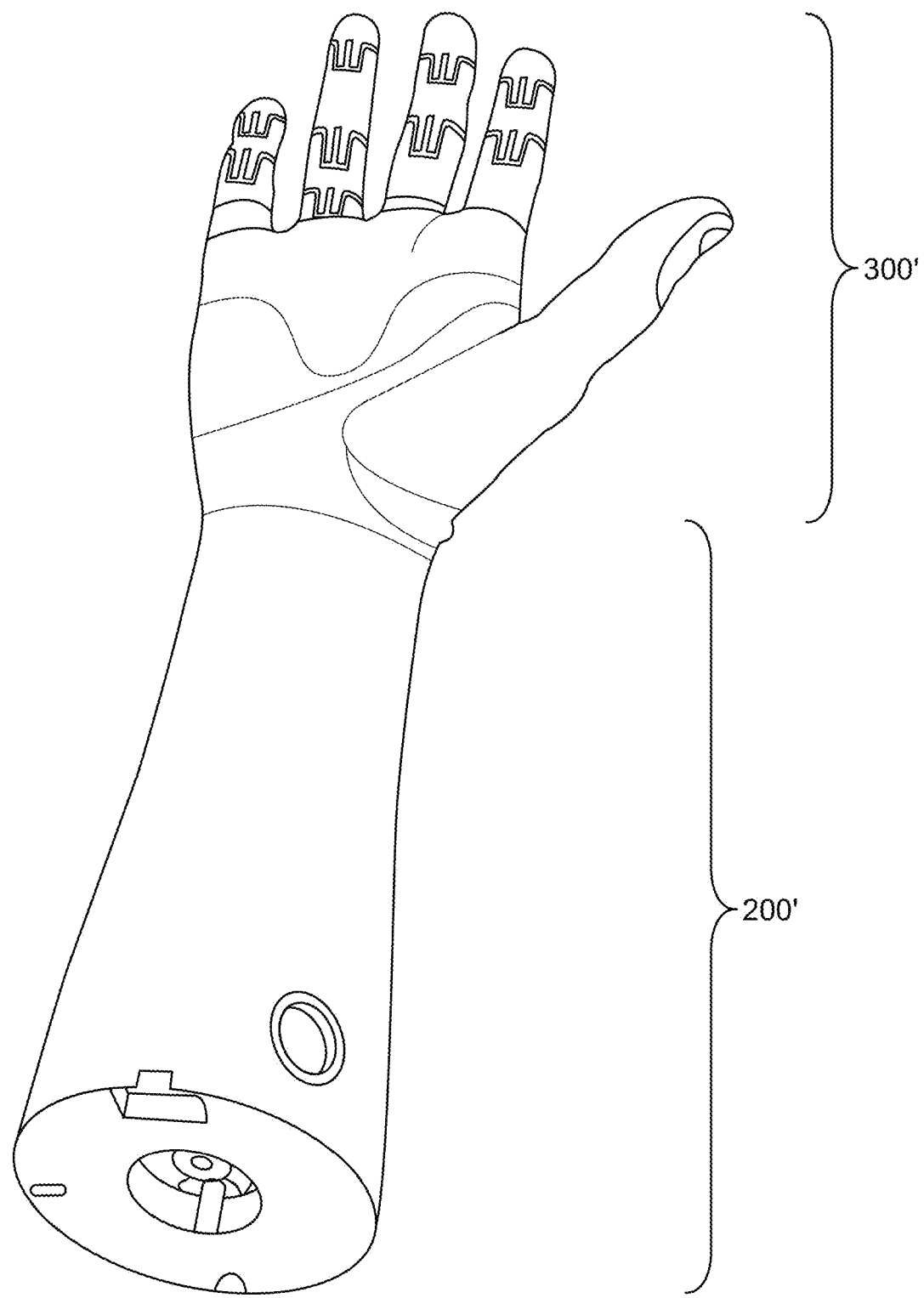
FIG. 30 is a perspective view of a prosthetic forearm assembled to a prosthetic hand according to another aspect of the disclosure.

As noted above, although in some embodiments most or all of the mechanical and electrical components of prosthetic upper extremity 10 may be housed within prosthetic forearm 200, in other embodiments, most or all of the mechanical and electrical components may be housed within prosthetic hand 300. On example of such an embodiment is shown in FIG. 30, which illustrates prosthetic forearm 200' and prosthetic hand 300'. It should be understood that many of the components of upper extremity 10 may otherwise be identical when using the embodiment of prosthetic forearm 200' and prosthetic hand 300', so much of the above description applies with equal force to prosthetic forearm 200' and prosthetic hand 300'.

Figure 31:
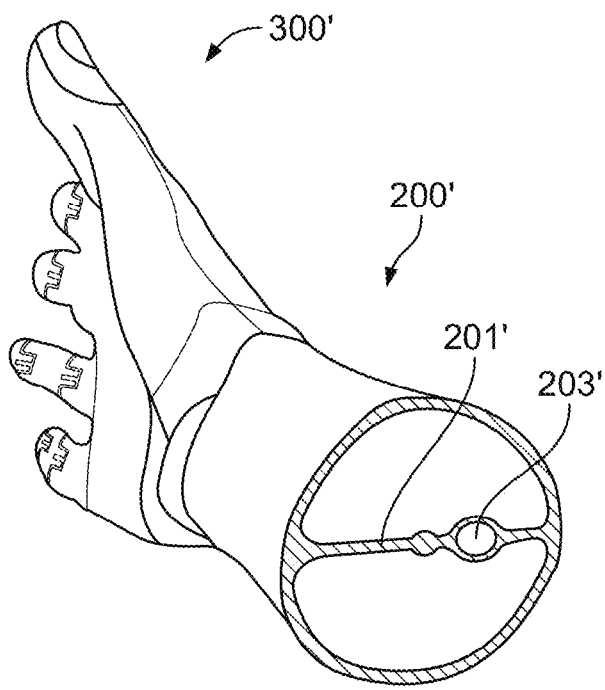
FIG. 31 is a transverse cross-section of the prosthetic forearm of FIG. 30.

Still referring to FIG. 30, prosthetic forearm 200' may be formed as a single integral member, as opposed to prosthetic forearm 200. For example, since prosthetic forearm 200' may not need to be accessed or need to house a significant amount of electrical and/or mechanical components therein, there may be no need to form prosthetic forearm 200' from multiple pieces, although it may be formed of multiple pieces if desired. The proximal end of prosthetic forearm 200' may include a feature(s) to couple to a prosthetic socket, such as prosthetic socket 100, that may the same or similar to those described above in connection with prosthetic upper extremity 10. In some embodiments, a mechanical attachment may be provided between prosthetic forearm 200' and socket 100 (or a socket similar to socket 100). As an example, a bolt or other fastener may be used to fasten prosthetic forearm 200' to socket 100, and may also act as a rotational pivot to rotate the prosthetic forearm 200' manually relative to the socket 100. This bolt or fastener may be tensioned to an appropriate degree so that the components are substantially fixed relative to each other, but still capable of manual rotation. The proximal end of prosthetic forearm 200' may also include a slot or other feature to allow for wires to pass between socket 100 and the interior of prosthetic forearm 200'. Prosthetic forearm 200' may include a recess 274' to receive a button, switch, or similar item therein, in the same or similar manner as described above in connection with recess 274 of prosthetic forearm 200. Prosthetic forearm 200' may be mostly hollow in order to reduce the weight of the prosthetic forearm 200' and to ease manufacturing. As shown in FIG. 31, prosthetic forearm 200' may include one or more supports 201, which may be in the form of ribs, flanges, etc. that assist in maintaining structural integrity of the prosthetic forearm 200' despite being substantially hollow. In addition, prosthetic forearm 200' may include one or more lumens, conduits, or passageways 203' that may assist in passing cables, such as electrical wires, through the prosthetic forearm 200', for example to connect sensors in a prosthetic socket to components within prosthetic hand 300'. Passageway 203' is shown in FIG. 31 as being formed as part of support 201', and extends from a proximal end to a distal end of prosthetic forearm 200'.

Figure 32:
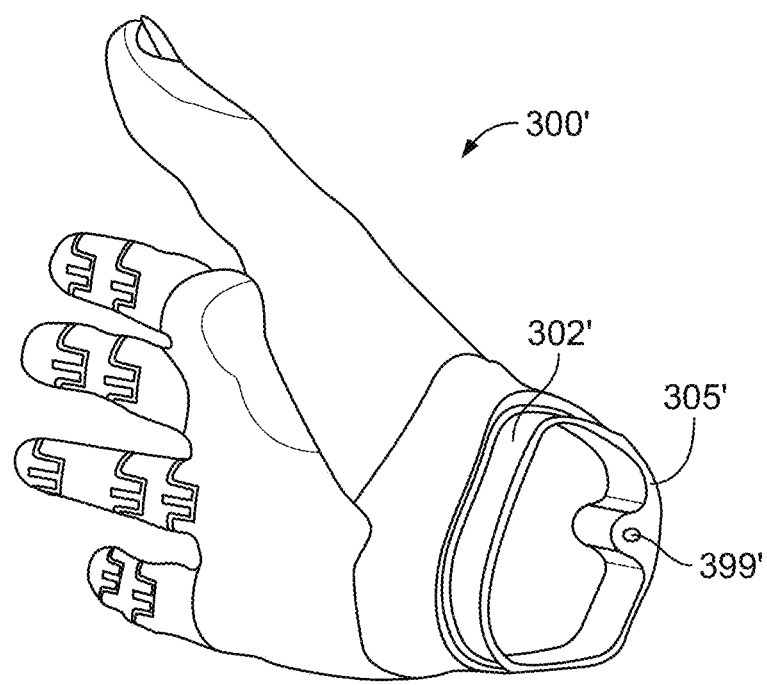
FIG. 32 is a perspective view of the prosthetic hand of FIG. 30.

Prosthetic hand 300' is illustrated isolated from the prosthetic forearm 200' in FIG. 32. Prosthetic hand may include a proximal coupling portion 302' that includes a lip 305' that is generally similar to proximal coupling portion 302 and corresponding lip 305 of prosthetic hand 300. Proximal coupling portion 302' may also include an aperture 399' that may align with a distal opening in passageway 203' to allow cables, wires, or other components that extend through prosthetic forearm 200' to enter the interior of prosthetic hand 300'.

Figure 33:
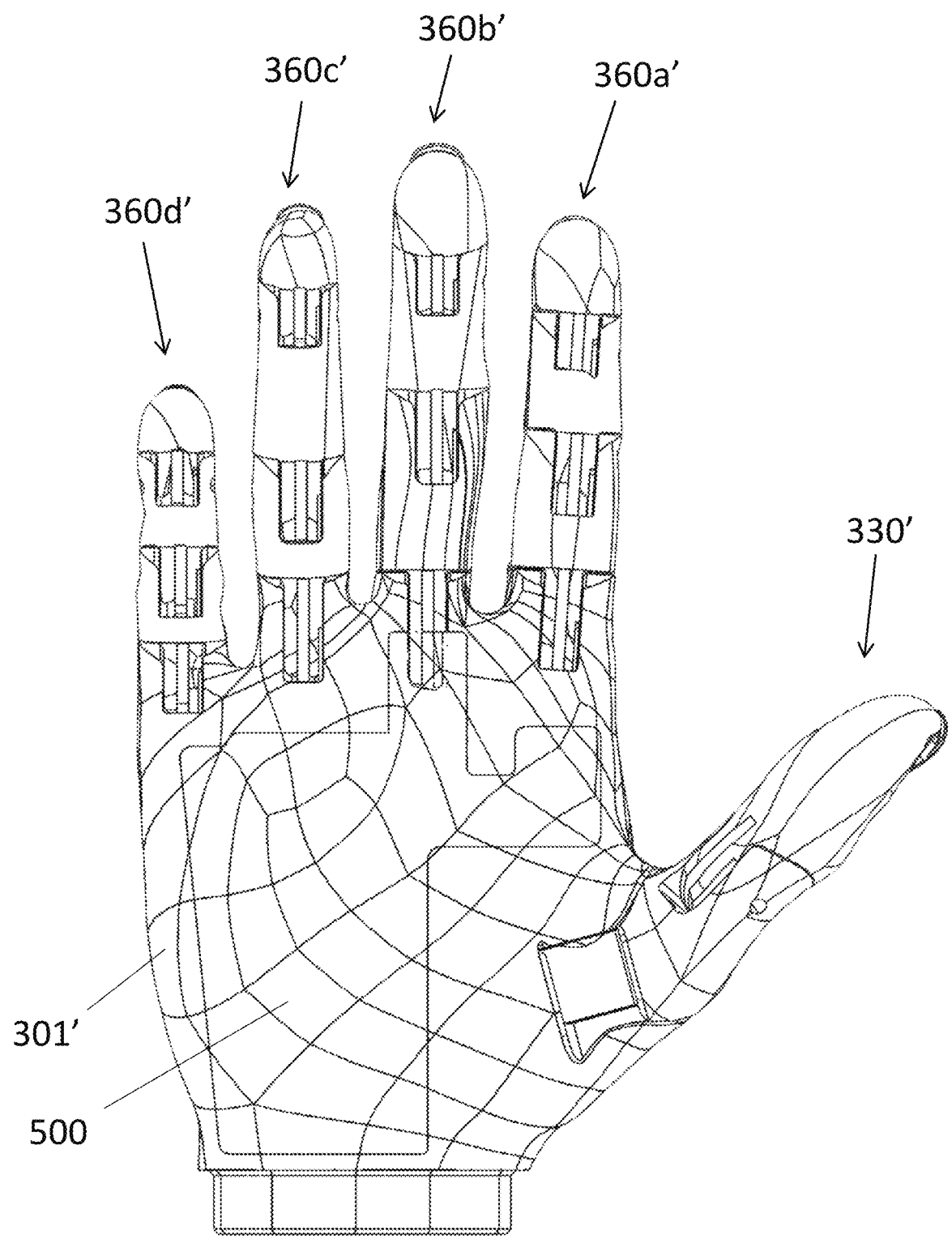
FIG. 33 is a front view of the prosthetic hand of FIG. 30.

FIG. 33 illustrates a front view of the palm 301' of prosthetic hand 300'. Generally, prosthetic hand 300' may be substantially identical to prosthetic hand 300 described above, with certain exceptions described below. In other words, unless a difference is pointed out between prosthetic hand 300 and prosthetic hand 300', or unless a difference is otherwise clearly present, the description of the corresponding portions of prosthetic hand 300 apply with equal force to prosthetic hand 300'. Generally, these exceptions include the fact that palm 301' includes an access panel 500 to access an interior volume of the palm 301' that may house electrical and/or mechanical components. Further, while the movement of fingers 360a'-360d' and thumb 330' may be generally similar or identical to those described in connection with hand 300, prosthetic hand 300' may utilize biasing members in the form of springs at each joint instead of extension tendons. And, as will be understood, internal components and structure of prosthetic hand 300' may be different than those of prosthetic hand 300.

Figure 34:
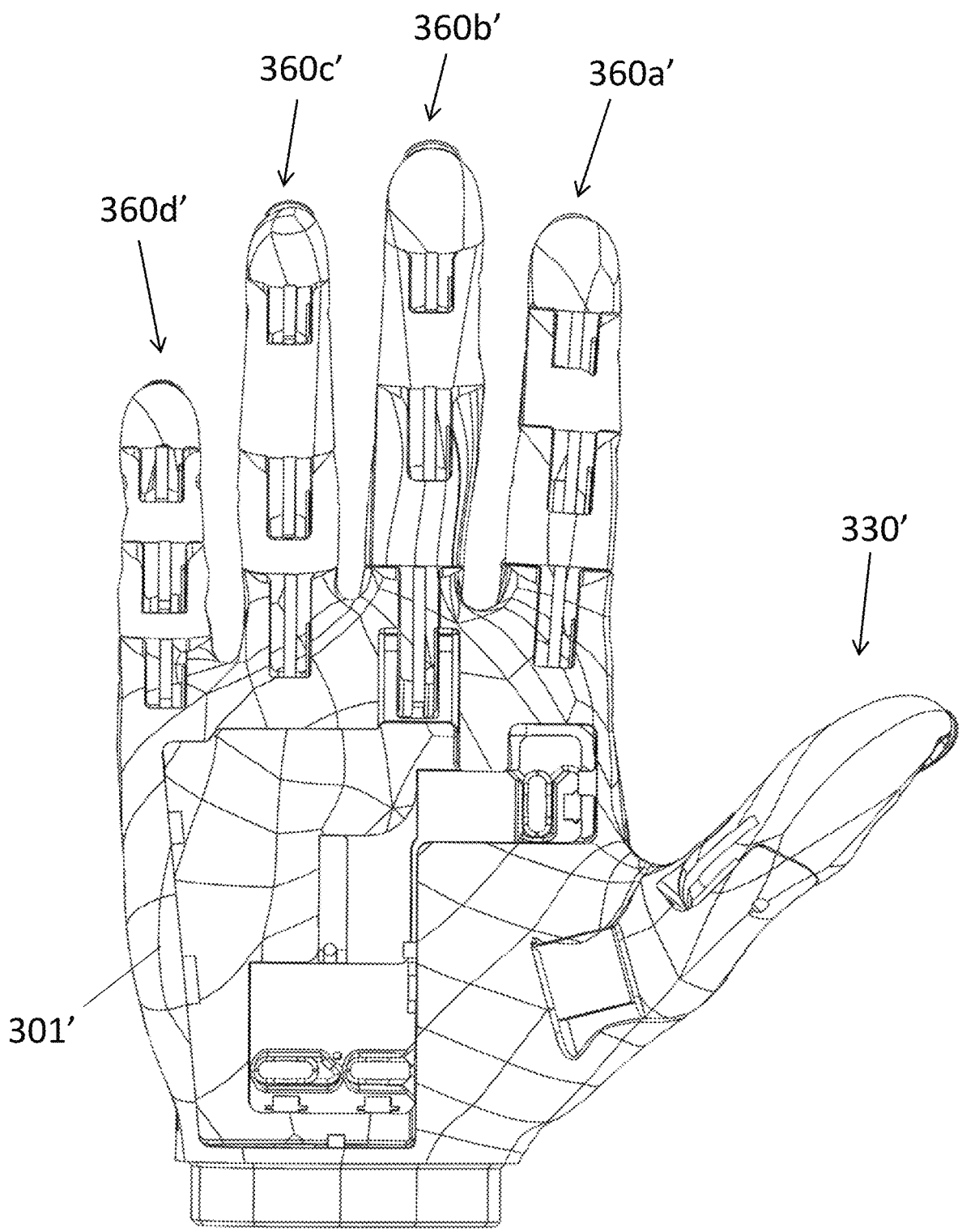
FIG. 34 is a front view of the prosthetic hand of FIG. 30 with an access panel removed.
Figure 35:
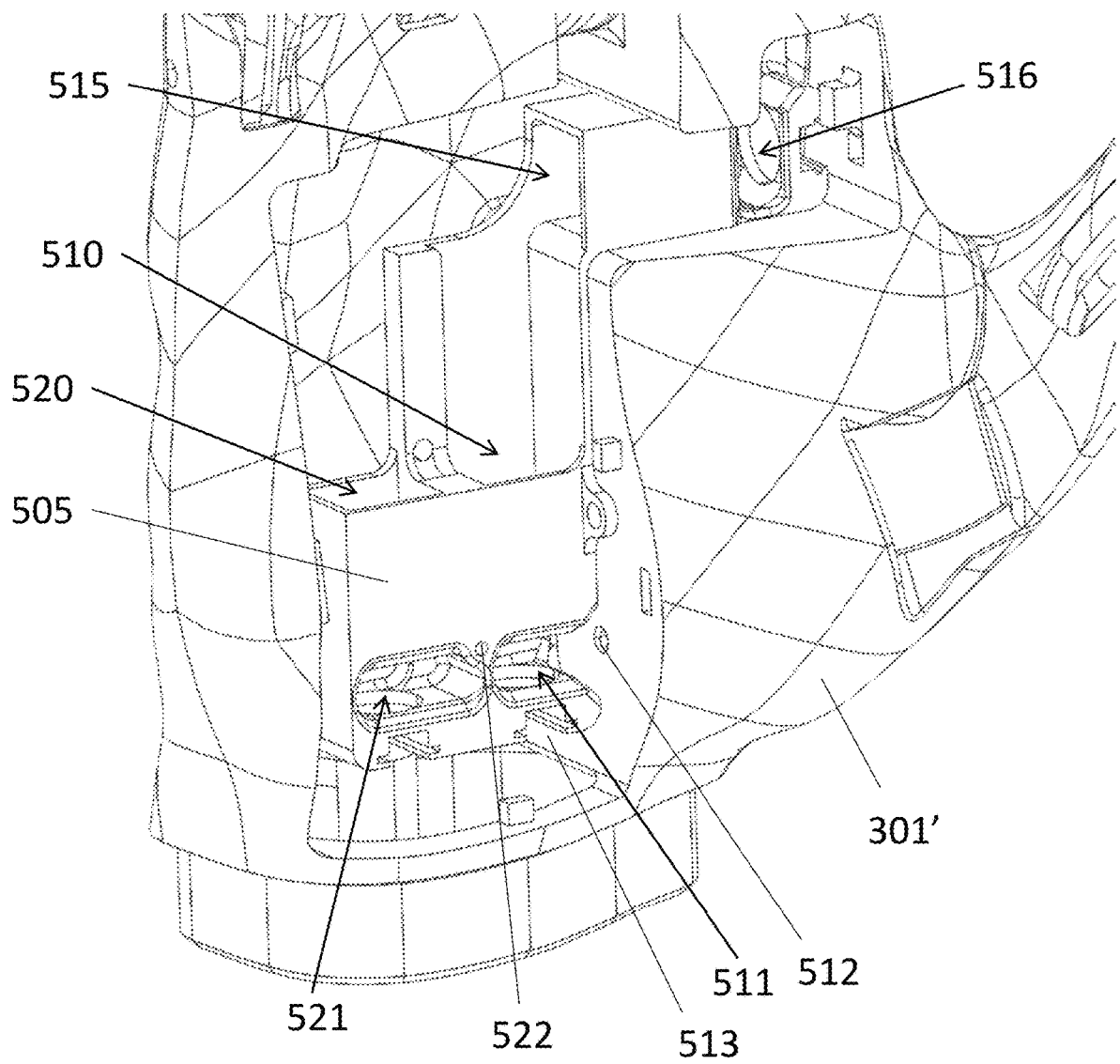
FIGS. 35-36 are enlarged perspective views of the prosthetic hand of FIG. 30 with the access panel removed.
Figure 36:
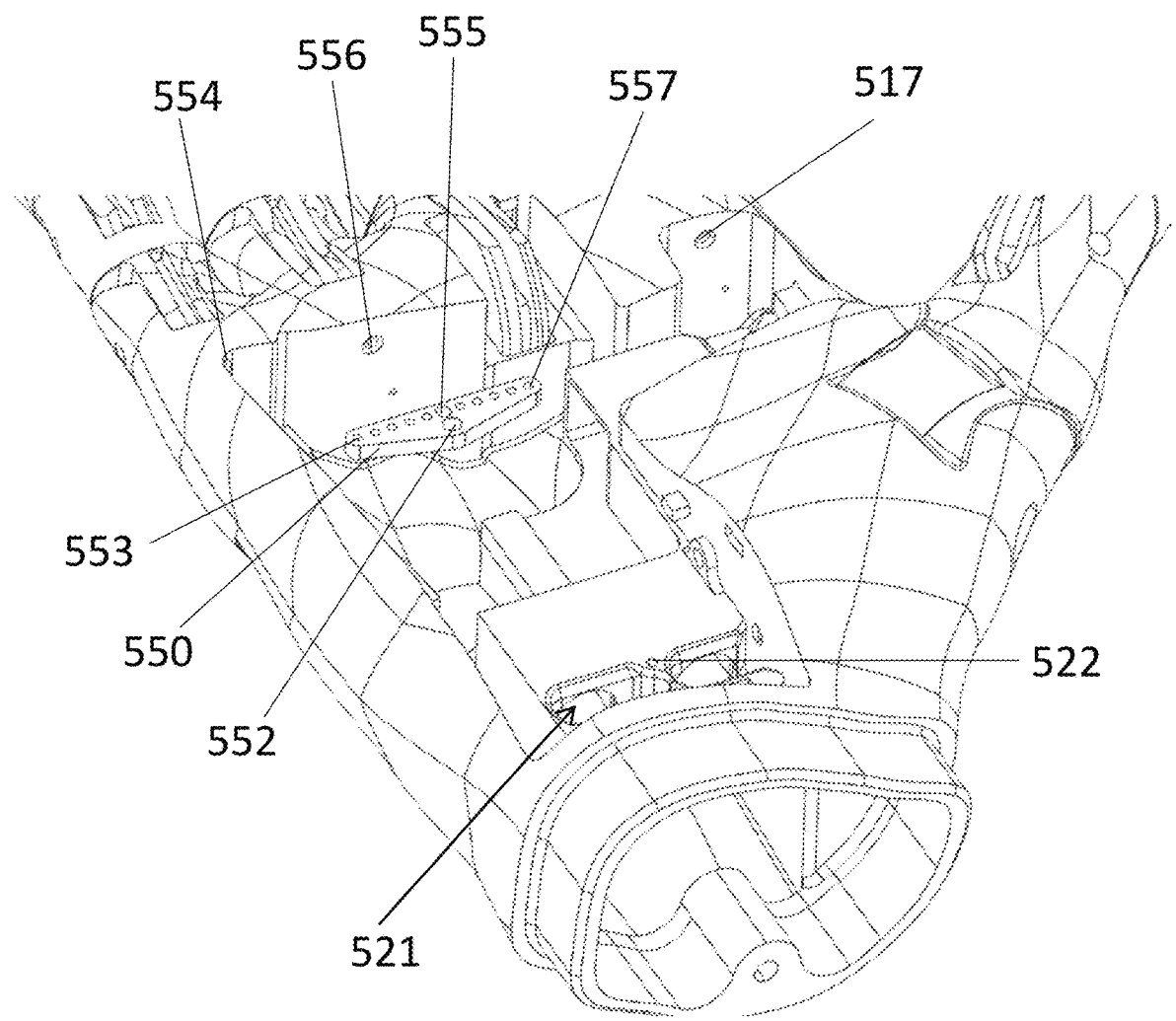

FIGS. 34-36 illustrate different views of prosthetic hand 300' with access panel 500 removed. It should be understood that FIGS. 34-36 do not illustrate motors, tendons, or other electrical components, which are instead shown in FIG. 36. Referring in particular to FIG. 35, the interior of palm 301' may include one or more receiving blocks or mounting members 505. In the illustrated embodiment, palm 301' includes a single mounting member 505 with three separate receiver cavities 510, 515, 520. Each receiver cavity 510, 515, 520 may function to receive and secure therein an actuator. However, it should be understood that multiple mounting members may be provided, each with a single (or more) receiver cavity, and more or fewer than three receiver cavities may be provided depending on the number of actuators that will be used with prosthetic hand 300'.

Figure 38:
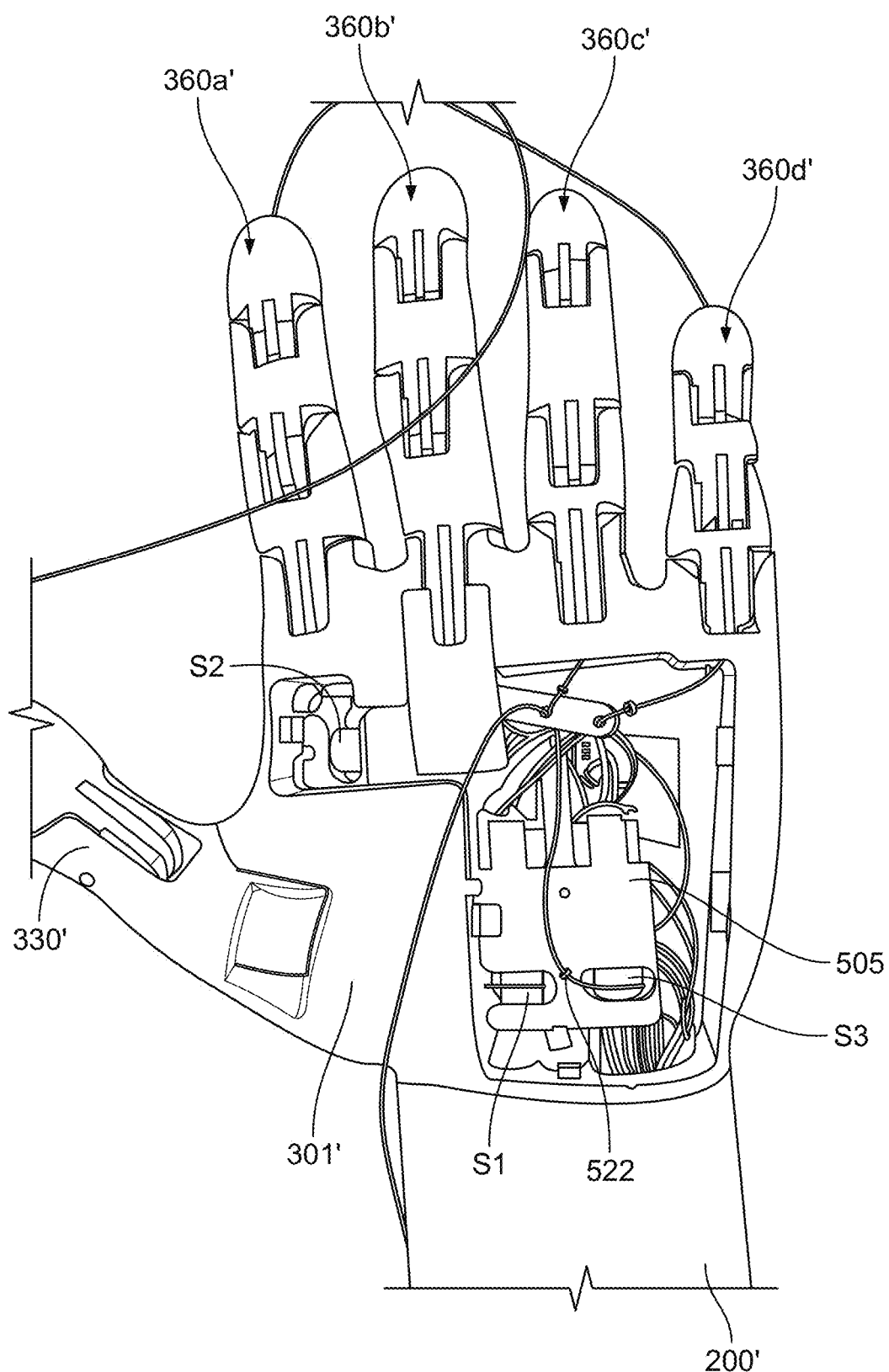
FIGS. 38-39 are pictures of a prosthetic hand similar to that shown in FIG. 30 with certain mechanical and electrical components in an assembled state.
Figure 39:
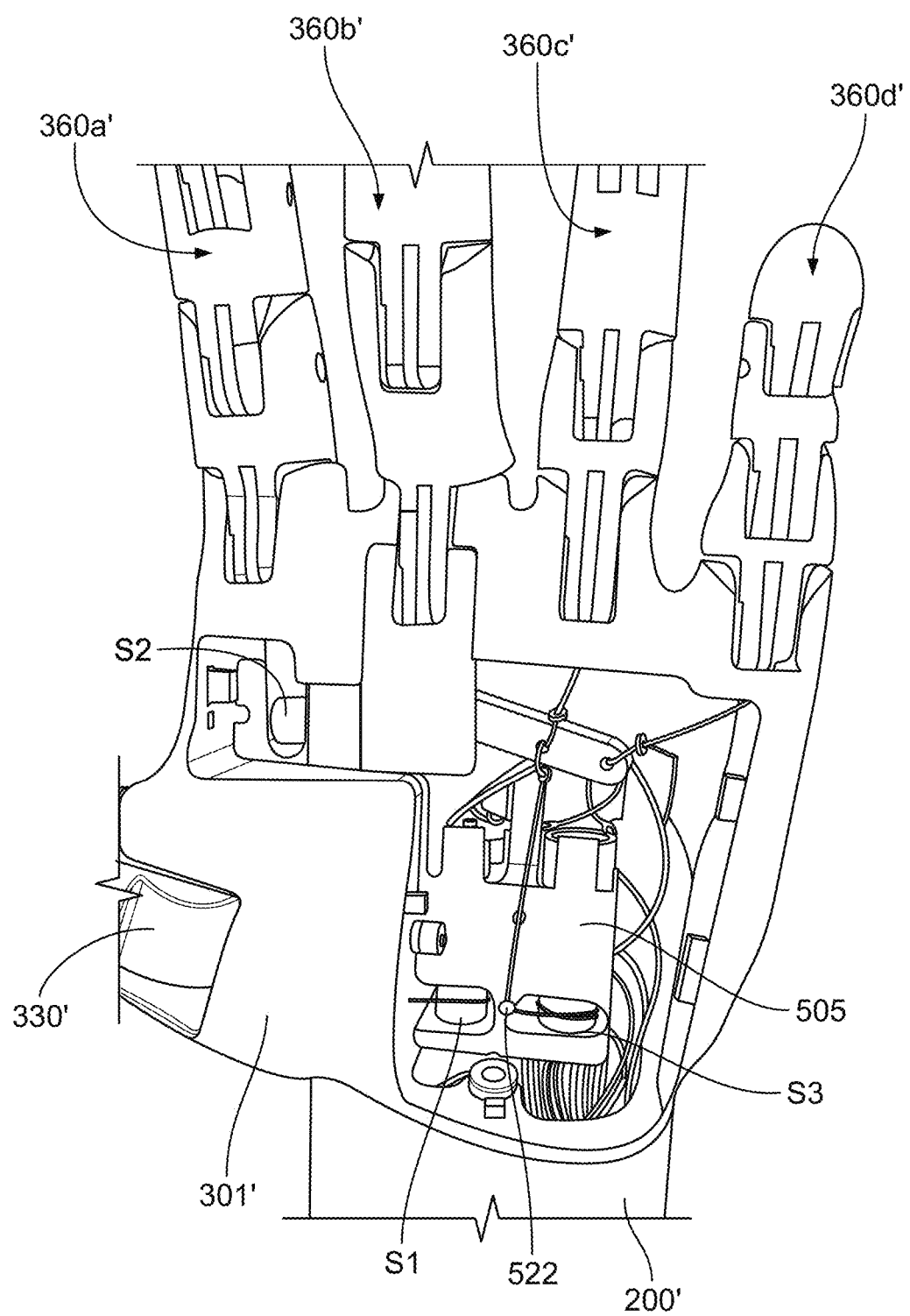

Receiver cavity 510 may receive an actuator for controlling the flexion of prosthetic thumb 330'. For example, a portion of the actuator may be received within cavity 510, with a portion of the actuator exposed via opening 511. A flexion tendon, which may take any suitable form, including the materials described in connection with the tendons above, may be spooled around a spindle portion of the actuator that is exposed via opening 511, with the actuator controlling the rotation of the spindle, and thus controlling flexion of the tendon. For example, the spindle may be positioned within opening 511 so that the tendon extends substantially tangentially to the spindle into an aperture 512. From there, the tendon may be routed through the joints of, and connected to the tip of, prosthetic thumb 330' in substantially the same way as described above for the flexion tendon of prosthetic thumb 330. As the actuator within receiver cavity 510 actuates, the spindle about which the tendon is wrapped may rotate, causing flexion of the prosthetic thumb 330' in substantially the same way as described for prosthetic thumb 300. The actuator may be any suitable type for precisely controlling flexion of the prosthetic thumb 330', including any of the actuators described above. For example, the actuators may be geared DC motors that utilize Hall Effect position feedback sensors. Further, it should be understood that, although upper extremity 10 was generally described to include linear actuators, other actuators that provide the desired flexion movement could be used for any of the embodiments described herein, whether or not considered "linear" actuators. Mounting member 505 and/or receiver cavity 510 may also include a slot 513 or other cavity to receive therein electronic components for use with the actuator. FIGS. 38-39 illustrate an example of prosthetic hand 300' (although it should be understood that FIGS. 38-39 illustrate a left hand, whereas FIGS. 33-36 illustrate a right hand) with spindle S1 positioned within opening 511 and a flexion tendon extending into the aperture 512 of prosthetic thumb 330'.

Referring again to FIG. 35, another actuator may be received within receiver cavity 515 to control flexion of prosthetic index finger 360a'. That actuator may be similar or identical to the actuator described above for prosthetic thumb 330'. One notable difference is that the actuator may be positioned within receiver cavity 515 in an orientation substantially orthogonal compared to the actuator received within receiver cavity 510. With this configuration, a spindle of the actuator may be exposed at opening 516 so that the flexion tendon extends substantially tangentially from the spindle and directly into an aperture 517, as best illustrated in FIG. 36, at the base of prosthetic index finger 360a'. The flexion tendon may be routed through the joints of, and connected to the tip of, prosthetic index finger 360a' in substantially the same way as described above for prosthetic index finger 360a, so that actuation of the actuator within receiver cavity 515 causes flexion of the prosthetic index finger 360a'. An example of a spindle S2 of an actuator within receiver cavity 515 is illustrated in FIGS. 38-39, which also illustrate the flexion tendon extending directly from the spindle into the aperture 517 at the base of prosthetic index finger 360a'. Receiver cavity 515 may also include a slot similar to slot 513 for receiving an electronic board or other electronic components.

Referring once again to FIG. 35, a third actuator may be received in receiver cavity 520 to control flexion of prosthetic middle finger 360b', prosthetic ring finger 360c', and prosthetic pinky finger 360d'. As with prosthetic hand 300, the flexion of these three fingers may all be controlled with a single actuator, although in other embodiments, if space allows, the flexion of each finger may be controlled by a dedicated actuator. Similar to receiver cavity 510, receiver cavity 520 may include an opening 521 through which a spindle of the actuator may be exposed. However, a number of differences may also be present with respect to this actuator. For example, whereas the spindles of the actuators that control the prosthetic thumb 330' and prosthetic index finger 360a' are generally positioned close to and in line with the flexion tendon on the spindle, opening 521 is positioned farther away from the three fingers it controls and may be offset from the point of connection of the flexion tendon. A loop or other guide member 522 may be provided near opening 521 so that the flexion tendon may extend from the spindle of the actuator within opening 521, and then in a direct line to its point of connection. This is best illustrated in FIGS. 38-39. Further, while prosthetic hand 300 was described as including three flexion tendons for the prosthetic fingers 360b-360d that were each coupled to a piston of a linear actuator, prosthetic hand 300' may instead include an adaptive grip bar 550. However, it should be understood that the adaptive grip bar 550, described in more detail, may be used with prosthetic hand 300, or in other embodiments, a system similar to the control of prosthetic fingers 360b-d in prosthetic hand 300 may be used with prosthetic hand 300'.

Adaptive grip bar 550 is best illustrated in FIGS. 36 and 38-39. Referring to FIG. 36, adaptive grip bar 550 is illustrated as suspended, although it will be understood that the suspension of the adaptive grip bar 550 is provided by its connection to various tendons. Referring to FIG. 36, adaptive grip bar may be wider than it is tall, and have a plurality of apertures to which tendons may be connected, for example by knotting ends of the tendons to the apertures. Preferably, the adaptive grip bar 550 includes a base aperture 552 near its bottom at a left-to-right center of the bar. The tendon that runs from the spindle of the actuator positioned within opening 521, for example spindle S3 of FIGS. 38-39, may first pass to guide member 522, and then connect to base aperture 552. Preferably, the tendon is substantially vertically positioned between guide member 522 and aperture 552. Thus, as the actuator within receiver cavity 520 actuates, it pulls the tendon and thus pulls adaptive grip bar 550 downwards toward the proximal end of prosthetic hand 300'. Three separate flexion tendons may be coupled to the other apertures in adaptive grip bar 550. For example, a flexion tendon may have one end coupled to aperture 553 of adaptive grip bar 550, which may be positioned in vertical alignment with an aperture 554 in the base of prosthetic pinky finger 360d'. Similarly, another flexion tendon may have one end coupled to aperture 555 of adaptive grip bar 550, which may be positioned in vertical alignment with an aperture 556 of prosthetic ring finger 360c'. A third flexion tendon may have one end couple to aperture 557 of adaptive grip bar 550, which may be positioned in vertical alignment with a base of prosthetic middle finger 360b'. An aperture similar to apertures 554, 556 is not shown in connection with prosthetic middle finger 360b'. In some embodiments, such an aperture may be included in a similar fashion as shown with respect to prosthetic pinky finger 360d' and prosthetic ring finger 360c'. In other embodiments, such an aperture may be provided within access panel 500 at or near its points of coupling to prosthetic middle finger 360b'. Each of these three flexion tendons may be routed through the joints of, and coupled to the tips of, their respective prosthetic fingers 360b'-360d' in substantially the same way described above for the prosthetic flexion tendons of prosthetic fingers 360b-360d.

As the actuator received within receiver cavity 520 actuates, the tendon coupled to base aperture 552 pulls, causing the adaptive grip bar 550 to move toward the proximal end of prosthetic hand 300', which in turn pulls each of the three flexion tendons coupled to the adaptive grip bar 550, causing flexion of each of the three prosthetic fingers 360b'-360d'. However, during flexion of those three prosthetic fingers, for example when gripping an object, there may come a point at which one finger, such as the prosthetic middle finger 360b', has essentially fully gripped the object, but another finger, such as the prosthetic pinky finger 360d', has not fully gripped the object. At this point, as the tendon coupled to base aperture 552 continues to pull on adaptive grip bar 550, the relative forces will cause the adaptive grip bar 550 to begin to pivot about base aperture 552, allowing the flexion tendon connected to the prosthetic pinky finger 360d' to continue to pull, while the flexion tendon connected to prosthetic middle finger 360b' does not pull or only minimally pulls. In other words, the adaptive grip bar 550 allows for the prosthetic middle finger 360b', the prosthetic ring finger 360c', and the prosthetic pinky finger 360d', to flex to different levels depending on the object gripped by the prosthetic hand 300', despite the fact that a single actuator is used to cause flexion in all three prosthetic fingers. As should be understood, the adaptive grip bar 550 acts as a "teeter totter" of sorts, pivoting based on the amount of, and relative positioning of, forces applied on the adaptive grip bar 550 by the three flexion tendons and the tendon connecting the adaptive grip bar 550 to the actuator.

The above description provides an explanation of how each of the prosthetic fingers 360a'-360d' and the prosthetic thumb 330' flex when actuated. Regarding extension, as noted above, a different embodiment may be used in prosthetic hand 300' than compared with prosthetic hand 300, although it should be understood that either method may be used in either prosthetic hand, depending on the particular desire. Typically, if prosthetic hand 300' includes most or all of the mechanical components of the prosthetic upper extremity 10, the amount of available space is reduced compared to if the mechanical components are provided within the larger prosthetic forearm 200'. Thus, while prosthetic forearm 200 includes biasing members in the form of various extension tendons coupled to compression springs to bias the fingers to the extended position, prosthetic hand 300' may use different biasing members that may require less space.

Figure 37:
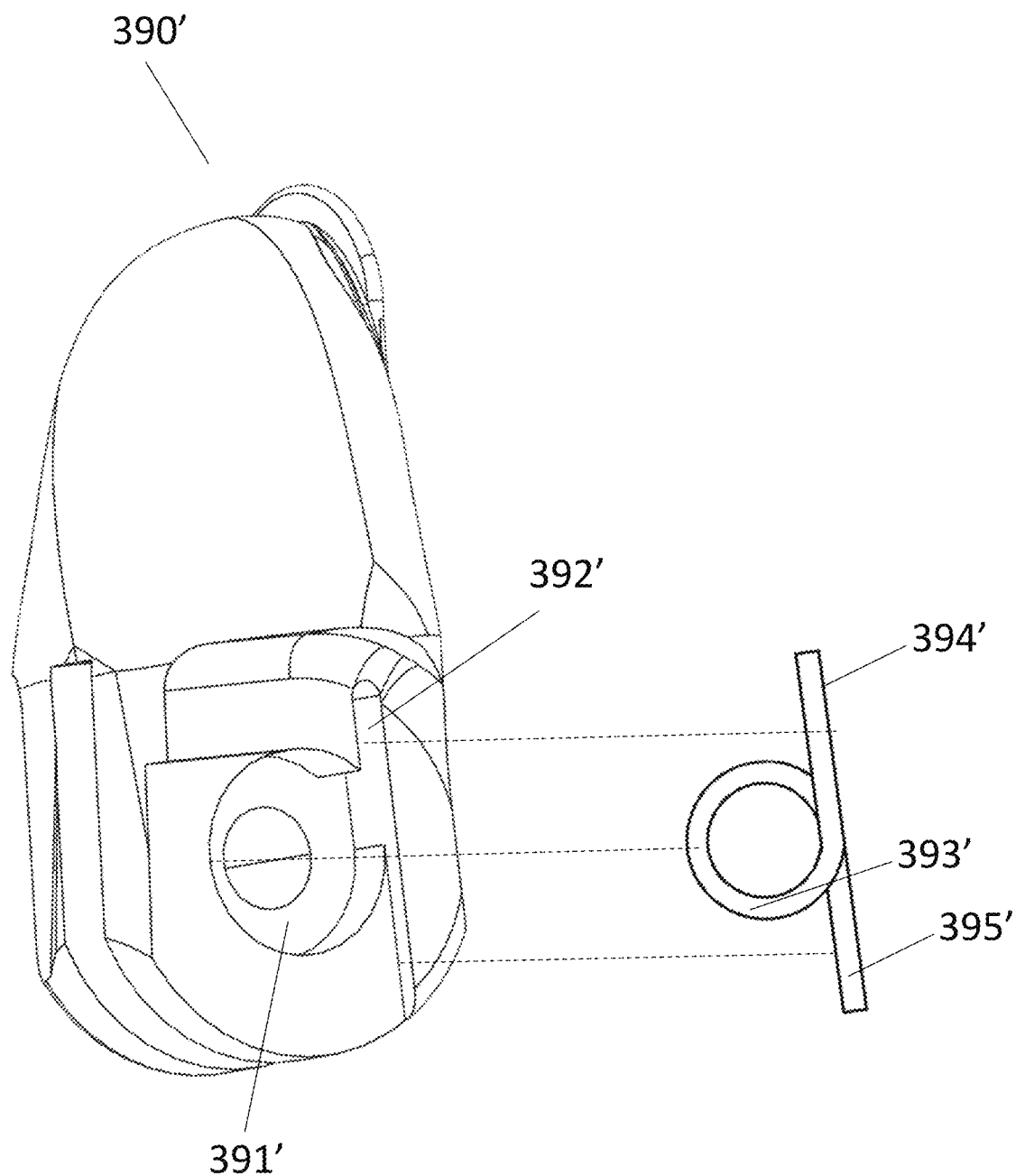
FIG. 37 illustrates a fingertip of one of the prosthetic fingers of the prosthetic hand of FIGS. 32-34.

FIG. 37 illustrates a fingertip 390' of one of the prosthetic fingers of prosthetic hand 300'. It should be understood that fingertip 390' is representative of the tip of each prosthetic finger, including prosthetic thumb 330'. Fingertip 390' may be similar or identical to fingertip 390 described above in all ways, with at least one exception. Finger 390' may include a recess 391' that is generally circular, and which opens to a substantially straight recess 392'. These recesses 391', 392' may be sized and shaped to receive a biasing member, for example a spring such as a torsion spring. Torsion springs are generally known, and an example torsion spring having a center portion 393' and two legs 394', 395' at about a 180 degree angle is illustrated. The center portion 393' of the torsion spring may be received within recess 391', and the legs 394', 395' of the torsion spring may be received in recess 392'. With this configuration, the legs 394', 395' of the torsion spring are at about 180 degrees with the relevant finger is fully extended. As the finger begins to flex, leg 395' of the torsion spring may be in contact with the adjacent joint, causing the angle between legs 394' and 395' to reduce as the finger flexes. The torsion spring thus will provide a counter biasing force that tends to extend the particular joint as the flexion forces from the flexion tendons are released. It should be understood that although only a single torsion spring for a single finger joint is illustrated, a similar torsion spring may be provided for each of the three joints in the prosthetic fingers 360a'-360d', as well as the flexion joint of the prosthetic thumb 330'. And it should be understood that each portion of each prosthetic finger may include a similar structure to receive or otherwise house a torsion spring, such that each joint is independently biased toward the extended condition in the absence of other applied forces. In FIG. 37, a single torsion spring is illustrated on one side of the fingertip 390'. It should be understood that a single torsion spring may be provided on either side of the fingertip 390', or in comes cases, it may be desirable to provide a torsion spring (or other similar biasing member) on each side of the fingertip 390. The same applies to each of the other portions of the fingers and the thumb.

Although sensors and related electric components described in connection with the first embodiment of prosthetic upper extremity 10 have not been described in great detail with respect to prosthetic forearm 200' and prosthetic hand 300', it should be understand that many or all of the same electric components (including batteries) and/or sensors may be used. For example, sensors in the socket (whether the socket is adapted for an above the elbow or below the elbow amputee) may be coupled to appropriate electronic controls within prosthetic hand 300', for example via cables or other wires extending through prosthetic forearm 200'. The mounting member 505 may also serve as a mount for all of the electronics and the batteries within palm 301'. For the sake of brevity, these components are not described here again.

Although an upper prosthetic extremity 10 that includes prosthetic arm 200 and prosthetic hand 300 may be effective for many uses, an upper prosthetic extremity 10 that includes prosthetic hand 300' may have particular benefits. For example, for an amputee missing a hand and an entire forearm, the desired prosthesis may be relatively large as an entire prosthetic forearm may be required. However, in other situations, space may be at more of a premium. For example, for an individual that has a significant amount of the native forearm remaining, a prosthesis would have a correspondingly smaller forearm portion. Thus, an upper extremity prosthesis that includes the entire prosthetic forearm 200 described above may not be possible or practical, and thus a relatively smaller prosthetic forearm may have less space to house mechanical and/or electrical components. Thus, housing these components in prosthetic hand 300' may allow for more versatility. In fact, by having the prosthetic hand 300' act as essentially a self-contained prosthesis, the remaining portions of the upper extremity prosthesis could be designed to fit essentially any patient. For example, for an amputee who has portions of the native forearm, a socket could be created in essentially the same manner described above for the forearm, and only the missing portion of the patient's forearm needs to be replicated, for example via additive manufacturing, and the prosthetic hand 300' would be coupled to that prosthetic forearm. Regardless of the particularities of the missing extremity, because all or mostly all of the functional components are positioned within prosthetic hand 300', the remainder of the prosthesis could easily be designed for the particular patient without significant concerns about how and where to house the functional components of the prosthesis.

Figure 40:
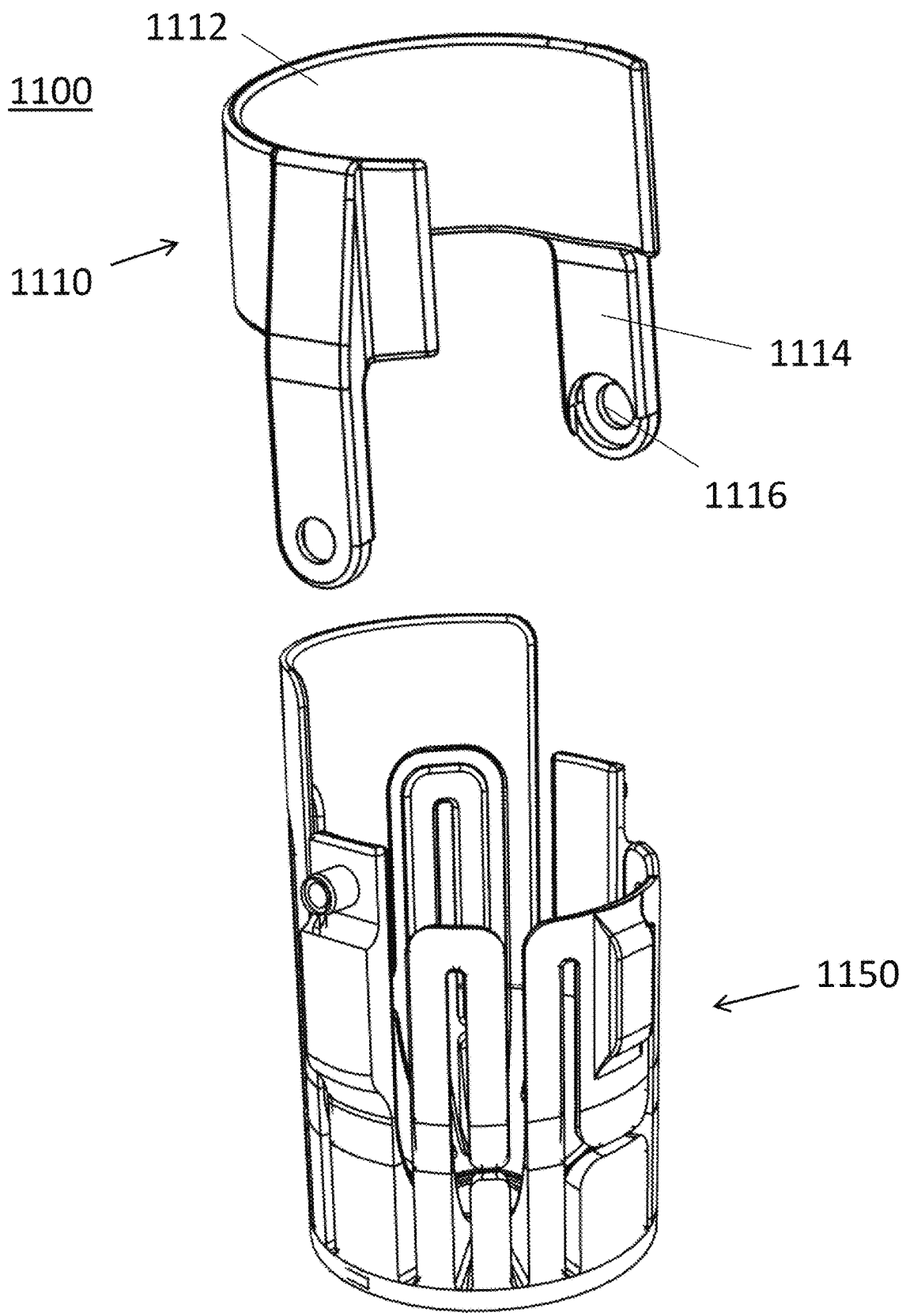
FIG. 40 is a perspective exploded view of a generic model of a socket according to another aspect of the disclosure.
Figure 41:
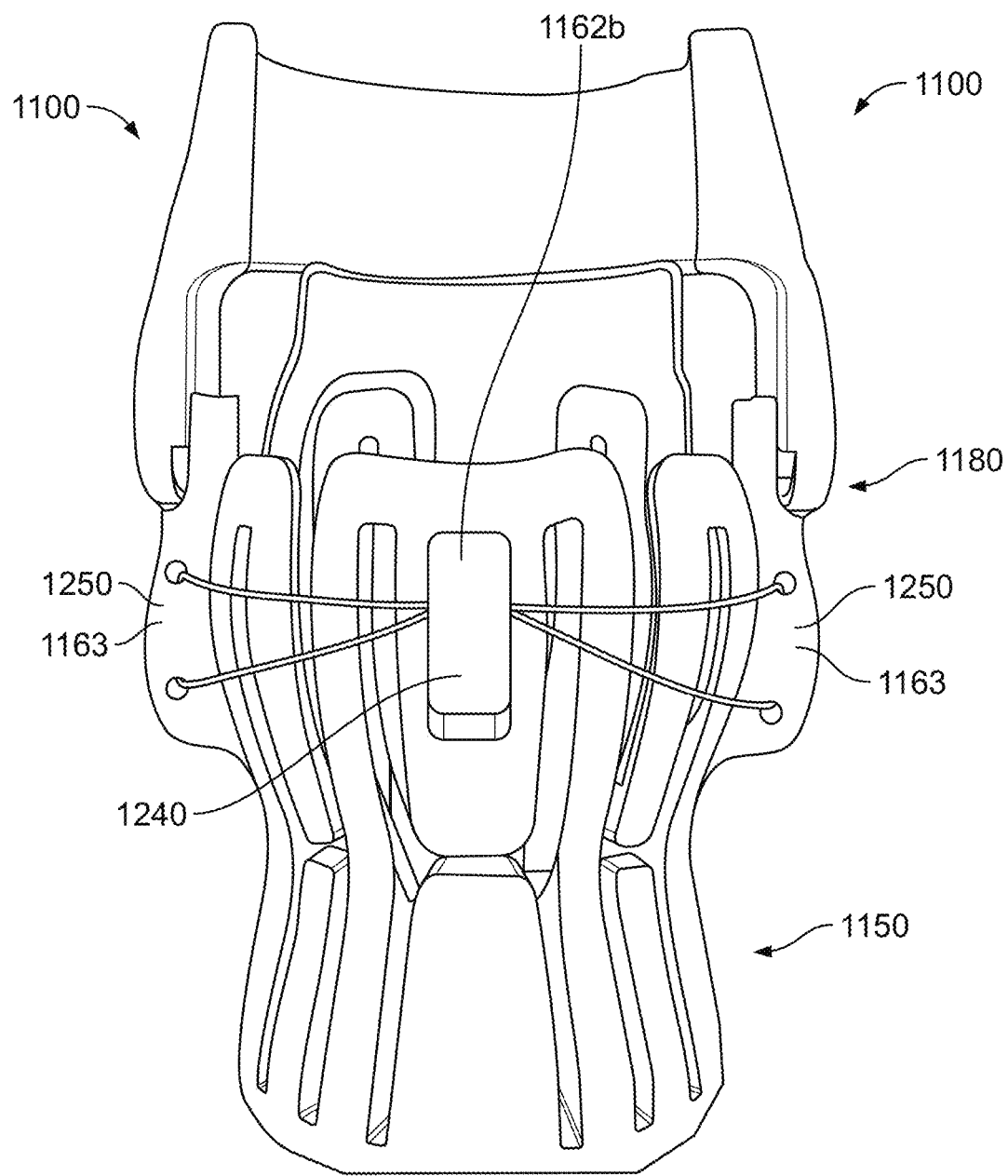
FIG. 41 is a perspective view of the assembled socket of FIG. 40 after the generic model is conformed to a particular user.

Although certain examples of sockets for connecting an upper extremity prosthesis to a user have been described above, still further examples of sockets may be appropriate for use with any of the prosthetic extremities described herein, as well as other type prosthetic extremities. For example, FIG. 40 illustrates an exploded view of another embodiment of a generic socket 1100, which may generally function to couple the user's residual upper extremity. The term "generic," as used in connection with socket 1100, refers to the fact that one or more portions of socket 1100 may be fit to a user's specific anatomy and/or prosthesis-specific dimensions from a generic model. In other words a generic model of socket 1100 may be morphed, conformed, or otherwise modified so that the portions in contact with the user's residual limb are specifically shaped and sized to correspond to the shape and size of the user's residual limb, and so that portions of the socket 1100 configured to couple to the remainder of the upper extremity prosthesis (e.g. a prosthetic forearm) are specifically sized and shaped to correspond to the size and shape of the remainder of the upper extremity prosthesis. FIG. 41 illustrates socket 1100 after the generic model of FIG. 40 has been morphed into, or conformed to, a patient- and prosthesis-specific device, manufactured (for example via additive manufacturing or 3D printing) and assembled. While FIG. 40 illustrates the generic model, it should be understood that FIGS. 41-51 illustrate the morphed or contoured version of the generic model. Similar to socket 100, socket 1100 includes a proximal socket 1110 and a distal socket 1150, the proximal socket 1110 and distal socket 1150 being coupled by one or more joints 1180.

Figure 42:
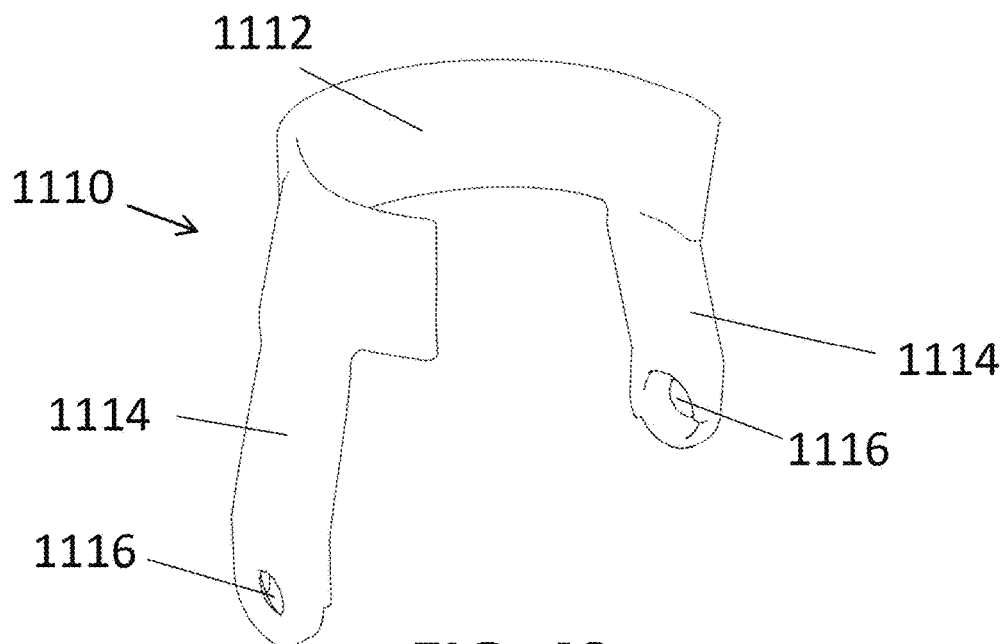
FIG. 42 is a perspective isolated view of a proximal portion of the socket of FIG. 41.

Now referring to FIG. 42, proximal socket 1110 is shown in isolation. It should be understood that FIGS. 42-45 illustrate components of socket 1000 after the generic model has been morphed or conformed to a patient- and/or prosthesis-specific model, but prior to physically manufacturing the device according to the model. Proximal socket 1110 is preferably formed of a single integral member. Proximal socket 1110 may be intended to fit over or otherwise couple to a user's upper arm. To this end, proximal socket 1110 may include a support member 1112 intended to fit onto a user's residual limb, such as the triceps area of a residual upper arm. In the illustrated embodiment, the support member 1112 is generally "C"- or "U"-shaped in transverse cross-section. Preferably, proximal socket 1110 is formed of a material that has an amount of rigidity to provide the necessary support, but enough flexibility to be able to compress an amount over the user's residual limb. In one example, proximal socket 1110 is formed of nylon via additive manufacturing. The support member 1112 may be formed with dimensions specific to the user's residual limb so that the support member 1112 may fit onto, including via a compressive fit, the user's residual limb. In some embodiments, the compressive fit of proximal socket 1110 is enough so that no additional support is needed. In other embodiments, a strap or other support may be used to help maintain proximal socket 1110 in the desired position on the user's limb.

Proximal socket 1110 may also include two extension members 1114 that each form part of a corresponding joint 1180. The extension members 1114 may extend from substantially opposite ends of the support member 1112, and may each include an opening or aperture 1116 at or near a distal end thereof. As is described in greater detail below, the apertures 1116 may assist in coupling the proximal socket 1110 to the distal socket 1150, and may include features that assist in biasing the joints 1180 to a particular desired position.

As with proximal socket 110, proximal socket 1110 may include an interior surface adapted to directly or indirectly couple to the user's upper arm. As noted above, the interior surface may be user-specific in the sense that it is shaped and contoured to match the shape of the portions of the user's upper arm that will contact the interior surface of the proximal socket 1110. A pre-determined offset may be introduced into proximal socket 1110. In other words, rather than produce proximal socket 1110 to include an interior surface that exactly matches the contours of the user's upper arm, the surface may be offset a fixed distance to allow for foam or other compressible or moldable material to be positioned as an interface between the user's upper arm and the interior surface of the proximal socket 1110. The thickness of the foam or other interference material may be equal or substantially equal to the amount of fixed distance offset.

Figure 43:
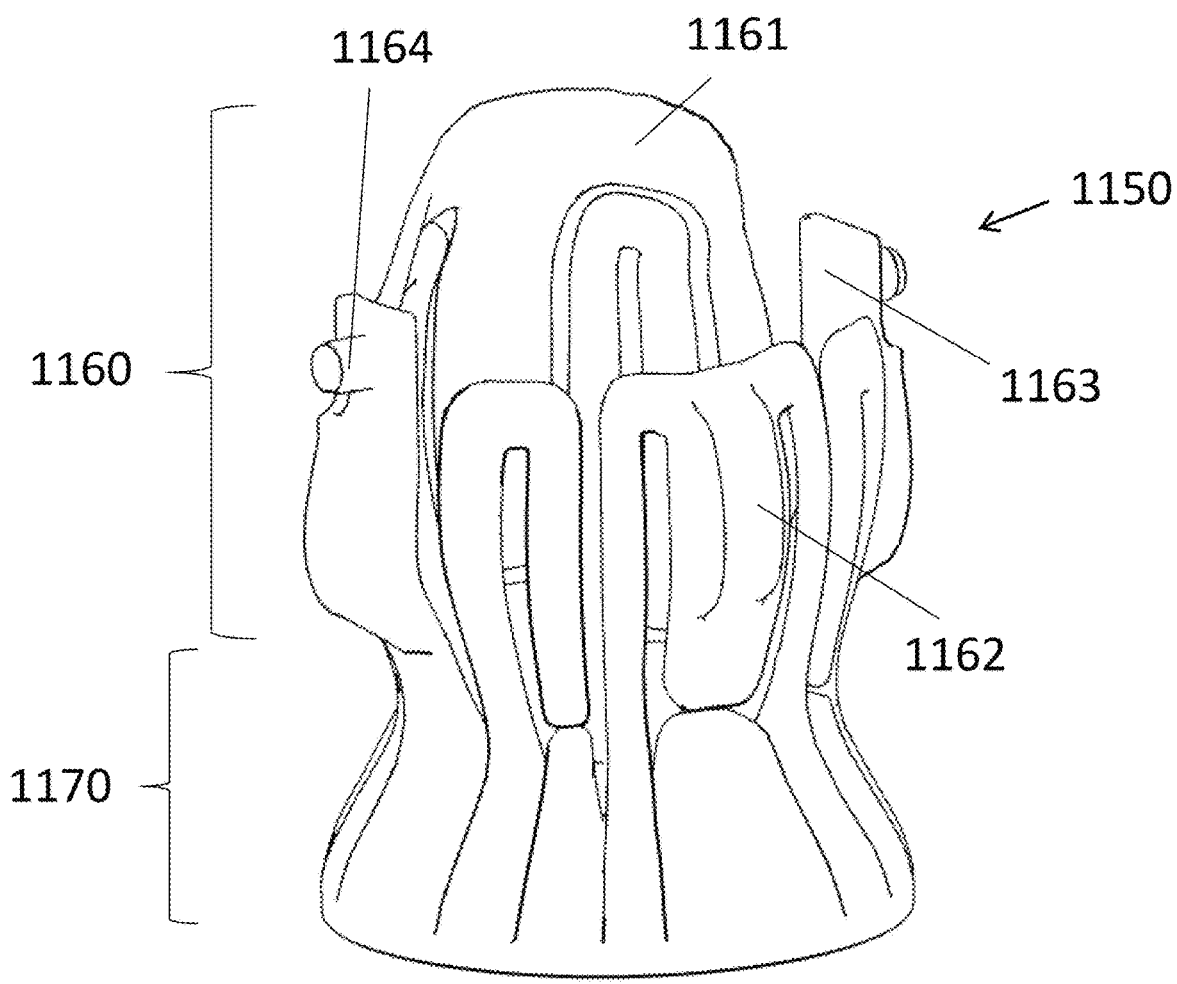
FIG. 43 is a perspective isolated view of a distal portion of the socket of FIG. 41.

Now referring to FIG. 43, distal socket 1150 is shown in isolation. Distal socket 1150 is preferably formed of a single integral member. Distal socket 1150 may generally include a coupling portion 1160 for directly or indirectly attaching to the residual limb of a user (such as the distal-most end of the residual limb), and a linking portion 1170 for coupling to the remainder of the prosthetic upper extremity, such as any of the prosthetic forearms described above. As noted above, while FIG. 40 illustrates a generic model of the socket 1100, FIG. 43 illustrates the distal socket 1150 after being morphed or conformed from the generic model to a patient-specific and/or prosthesis-specific version. In other words, the morphed or conformed geometry of coupling portion 1160 is sized and shaped to receive the distal end of a particular user's limb therein, while linking portion 1170 is sized and shaped to provide a smooth transition between the distal socket 1150 and the prosthesis coupled thereto. However, similar to proximal socket 1110, an offset may be introduced into the contact surface of the coupling portion 1160 in order to account for one or more additional interface layers, such as foam or another compressible or moldable material, which may be positioned between the user's residual limb and the interior surface of coupling portion 1160.

Referring now to FIGS. 41 and 43, coupling portion 1160 may broadly be thought of as including four sides, including a posterior side 1161, an anterior side 1162, and two lateral portions 1163 on opposite sides of each other. In the particular illustrated embodiment, the coupling portion 1160 is shaped to receive a distal residual limb of a user that is relatively short. In this context, relatively short may correspond to an amputation in which the arm is amputated about two to three inches distal to the elbow joint, although this is just an example of length and the invention should not be restricted solely to use for these dimensions. In use, posterior side 1161 may be adapted to contact the posterior side of the user's arm, such as the area where the triceps transitions into the forearm. Similarly, anterior side 1162 may be adapted to contact the anterior side of the user's arm, such as the anterior forearm distal to the elbow joint. To achieve this relative positioning, posterior side 1161 may extend a greater distance from linking portion 1170 that does anterior side 1162. Further, posterior side 1161 and anterior side 1162 may both be generally U- or C-shaped in transverse cross-section to help cup or cradle the anterior and posterior sides of the user's limb. Lateral portions 1163, on the other hand, may each be positioned on a periphery of the distal socket 1150 between the posterior side 1161 and the anterior side 1162. Each lateral portion 1163 may include a projection, such as a pin 1164, extending radially away from the lateral portion 1163 near a free end thereof. Each pin 1164 is sized and shaped to be received within a corresponding aperture 1116 of proximal socket 1100, as shown in FIG. 41, to form joint 1180. When the socket 1100 is assembled and coupled to a user, the joints 1180 may be configured to be positioned generally in alignment with the residual elbow joint.

Figure 44:
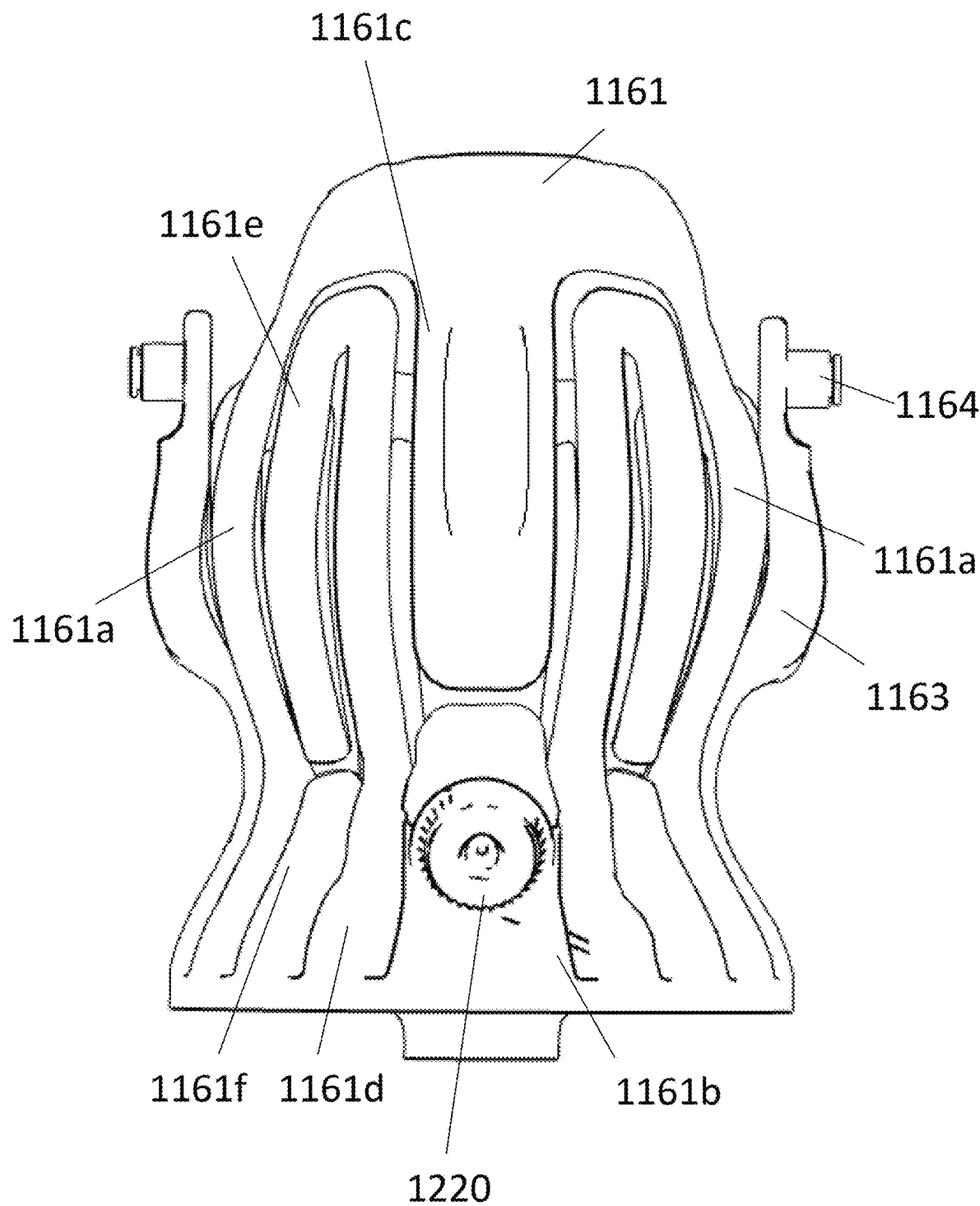
FIGS. 44 and 45 are rear and front views, respectively, of the distal socket of FIG. 43.

The various sides of distal socket 1150 are described in greater detail below with particular reference to FIGS. 41, 43, and 44. Referring to FIG. 44, which illustrates the rear or posterior side 1161 of distal socket 1150, the posterior side 1161 may include a plurality of axially extending ribs, fins, or bars. Generally, the axially extending ribs are spaced apart from adjacent ribs to allow for various degrees of flexibility of the individual rib members. In the particular illustrated embodiment, posterior side 1161 includes two lateral ribs 1161a that extend between bottom and top terminal ends of posterior side 1161 forming an overall outline of the posterior side 1161. A medial rib centered between the two lateral ribs 1161a may be split and include a distal medial rib 1161b, and a proximal medial rib 1161c. The distal medial rib 1161b may include a structure 1220 to assist in tensioning the distal socket 1150, while the proximal medial rib 1161c may include a thickened portion to receive therethrough a component of a tensioning system, both described in greater detail below. A window may be defined between each lateral rib 1161a and the medial rib portions 1161b, 1161c. Each window may include further axially extending ribs nested therein. For example, one of the windows may include an axially extending rib 1161d extending from the distal end toward the proximal end of the distal socket 1150. The axially extending rib 1161d may hook back toward the distal end of the distal socket 1150 to form a partial rib 1161e. Partial rib 1161e may be spaced apart from another partial rib 1161f that extends from the distal end of distal socket 1150 toward the terminal end of partial rib 1161e, with a gap being positioned therebetween. The other window may include a substantially identical rib structure, although the rib structure in the second window may be a mirror version of rib 1161d and partial ribs 1161e, 1161f.

Generally, the various axially extending ribs, including the gaps or separations between rib portions, may assist in allowing the coupling portion 1160 of the distal socket 1150 to be tensioned while the user's limb is positioned therein to better conform the coupling portion 1160 of the distal socket 1150 to the user's limb. To that end, distal socket 1150 may formed of a material that has an amount of rigidity to provide the necessary support, but enough flexibility to be able to compress an amount over the user's residual limb. In one example, distal socket 1150 is formed of nylon via additive manufacturing.

Figure 45:
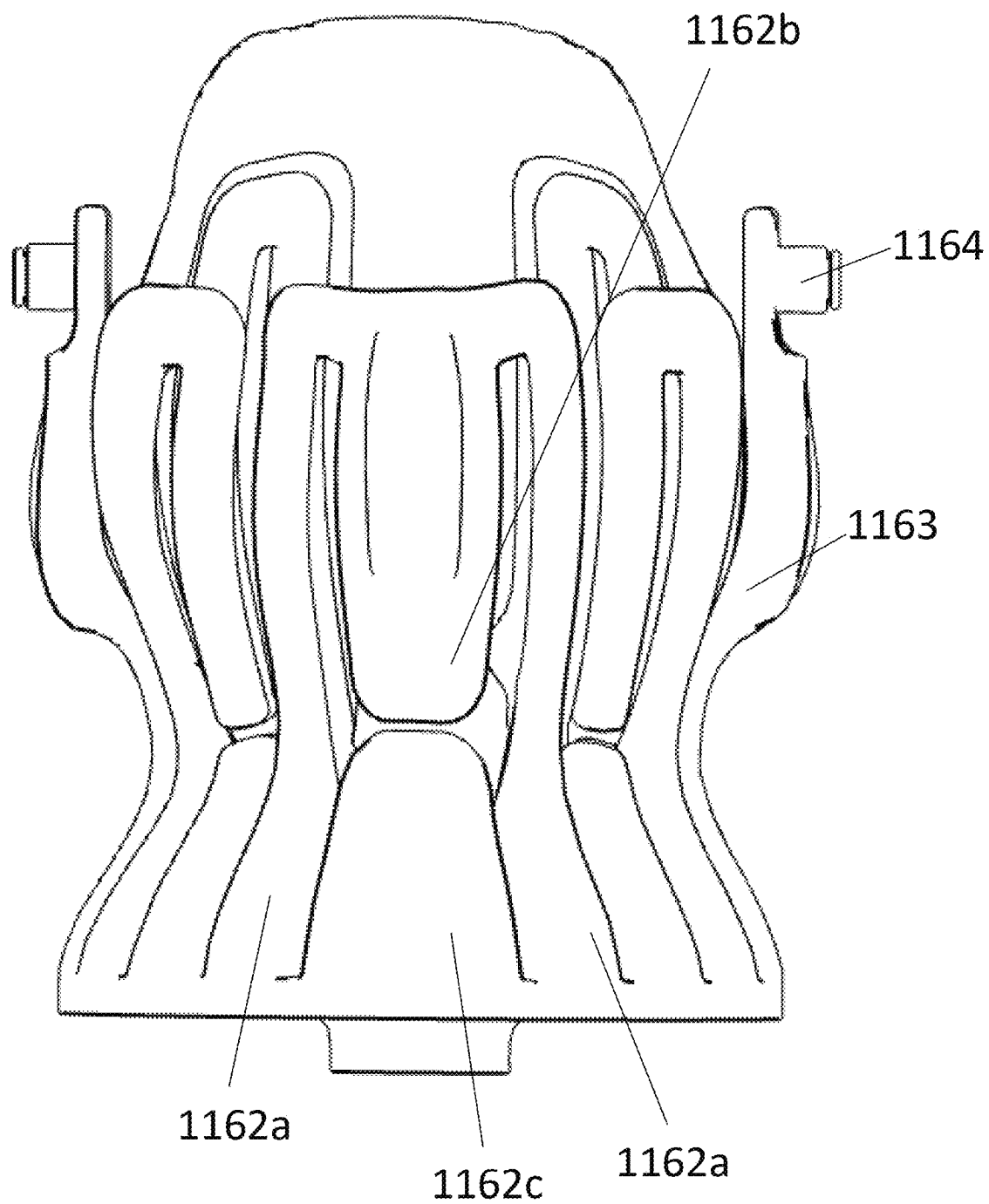

FIG. 45 illustrates the anterior side 1162 of distal socket 1150. Anterior side 1162 may include two lateral rib portions and a medial rib portion. The medial rib portion may include two axially extending ribs 1162a that extend from the distal end of distal socket 1150 toward the proximal end of the distal socket. Each rib 1162 may join to a proximal medial rib portion 1162b, which may be wider than ribs 1162a. Proximal medial rib portion 1162b may thus be positioned between ribs 1162a, and may extend distally. A distal medial rib portion 1162c may extend from the distal end of the distal socket 1150 toward the proximal medial rib portion 1162b, with a gap formed therebetween. Proximal medial rib portion 1162b may include a thickened portion to receive therethrough a component of a tensioning system, described in greater detail below. Anterior side 1162 may include two additional groups of lateral ribs between which ribs 1162a are positioned. The two groups of lateral ribs may have similar or identical configurations as ribs 1161d and partial ribs 1161e, 1161f described above. As with posterior side 1161, the general configuration of anterior side 1162 that includes a plurality of thin, flexible elements or ribs may assist in allowing the coupling portion 1160 of the distal socket 1150 to be tensioned while the user's limb is positioned therein to better conform the coupling portion 1160 of the distal socket 1150 to the user's limb.

Referring to FIGS. 43-45, each lateral portion 1163 may include a single rib extending from the distal end of the distal socket 1150 toward a free end at the proximal end of the distal socket 1150, the pin 1164 extending radially outward from the free end. As will be described in greater detail below, each rib of each lateral portion 1163 may include a thickened portion to receive therethrough a component of a tensioning system.

Figure 46:
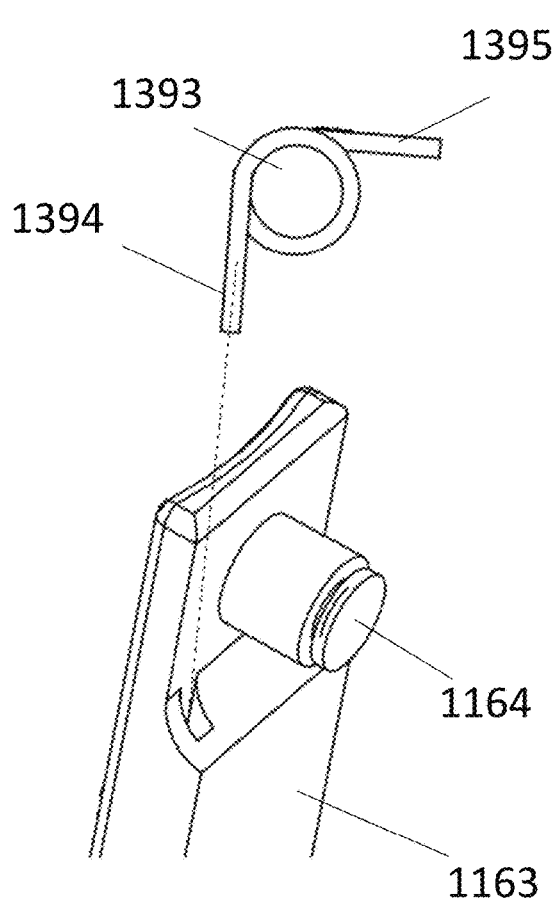
FIGS. 46 and 47 are perspective exploded views of joint portions of the socket of FIG. 41.
Figure 47:
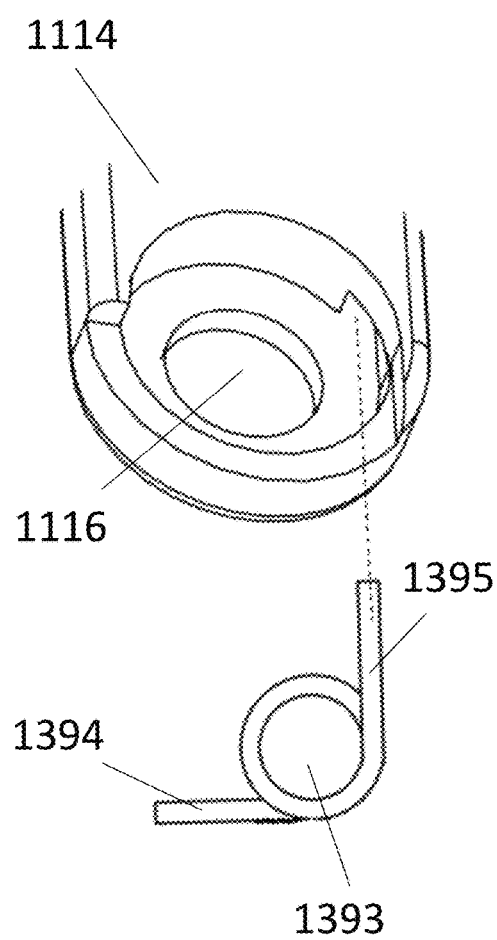

FIGS. 46-47 illustrate enlarged views of the free end of a lateral portion 1163 of distal socket 1150 and the free end of an extension member 1114 of a proximal socket 1110. As noted above, the pin 1164 may be sized and shaped to pass through aperture 1116 in order to form joint 1180. A biasing element such as a torsion spring may be provided with joint 1180 to bias the proximal socket 1110 into a flexed condition with respect to the distal socket 1150. The torsion spring may include a center portion 1393 and two legs 1394, 1395 that are positioned about ninety degrees with respect to one another in the absence of applied forces. As shown in FIG. 46, one of the legs 1394 may be positioned within a corresponding passage in lateral portion 1163 (FIG. 46) and the other leg 1395 may be positioned within a corresponding passage in extension member 1114. In the assembled condition, the pin 1164 may pass through the center 1393 of the torsion spring. With this configuration, the torsion spring tends to flex the distal socket 1150 with respect to the proximal socket 1110. The torsion spring may be provided with a biasing force such that, when the proximal socket 1110 is coupled to the distal socket 1150, and the socket 1100 is coupled to a prosthesis such as prosthetic forearm 200, the weight of the prosthesis will keep the distal socket 1150 in an extended condition relative to the proximal socket 1110. If the user applies force to flex the prosthetic forearm (and thus the distal socket 1150) relative to the proximal socket 1110, the biasing force of the torsion spring will assist in the flexing motion. In use, joint 1180 may align with the elbow joint of the user so that, as the user rotates his or her residual forearm relative to the upper arm via the elbow, the proximal socket 1110 correspondingly rotates relative to the distal socket 1150. As should be understood, the biasing element(s) may provide assistance in the user flexing the prosthetic forearm relative to the residual upper arm about the residual elbow.

Figure 48A:
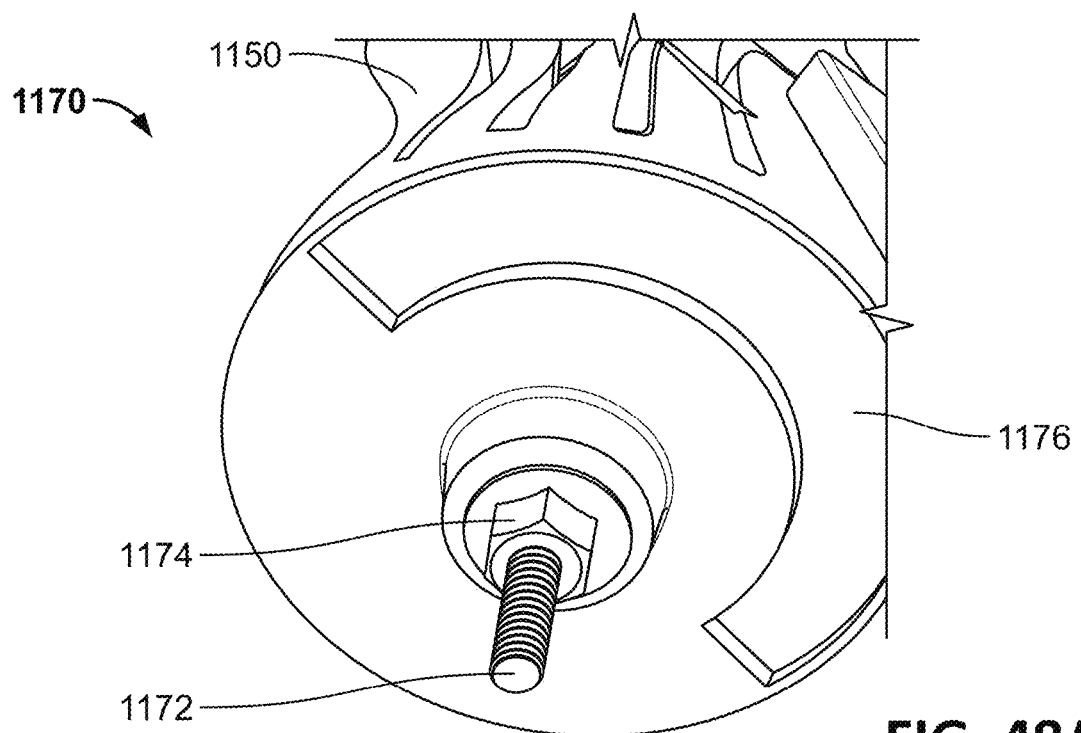
FIG. 48A is a bottom perspective view of the distal socket of FIG. 43.
Figure 48B:
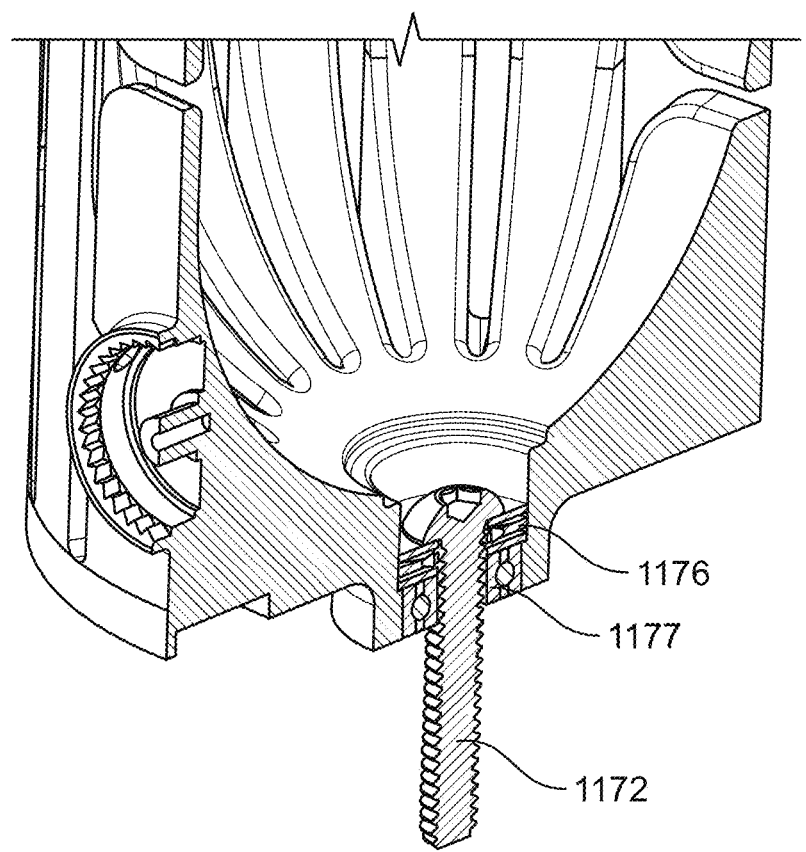
FIG. 48B is a cross-section of the distal socket illustrating a bolt and bearing accessories.

Referring to FIG. 48A, a distal end of the linking portion 1170 of distal socket 1150 is illustrated. As noted above, linking portion 1170 may be configured to couple to a prosthetic upper extremity member, such as prosthetic forearm 200, or a similar component. The attachment between linking portion 1170 and a prosthetic forearm may be generally similar to the attachment between linking portion 170 and prosthetic forearm 200 described above in connection with FIGS. 4C-4D, 6D and 9. For example, the distal face of linking portion 1170 may include a central aperture for receiving a screw or bolt 1172 therethrough. Bolt 1172 may extend into a corresponding aperture in a prosthetic forearm, and a nut 1174 may be used to couple the prosthetic forearm to the linking portion 1170. Further, the distal face of linking portion 1170 may include a recess or track 1176, which in the illustrated embodiment is provided as a semi-circular or arcuate track extending about 180 degrees. The track 1176 may be adapted to receive a corresponding protrusion or other member of the prosthetic forearm. When the prosthetic forearm is assembled to the linking portion 1170, the prosthetic forearm may be manually rotated up to about 180 degrees, with the protrusion on the prosthetic forearm moving along the arc of track 1176. This may be generally similar to the configuration described above in connection with linking portion 170 and prosthetic forearm 200, although the track and the protrusion are generally reversed compared to linking portion 170 and prosthetic forearm 200. FIG. 48B illustrates a first bearing 1176 that may be used with bolt 1172. For example, in the illustrated embodiment, first bearing 1176 is a thrust bearing, for example a thrust needle roller bearing, which may be positioned within or on a lip of distal linking portion 1170. A second bearing 1177 may also be used with bolt 1172. For example, in the illustrated embodiment, second bearing 1177 is a radial bearing, for example a ball bearing. The radial bearing 1177 may allow for free axial rotation and resists lateral forces. The thrust bearing 1176 may allow for reliable reaction against axial forces while not disturbing axial rotation. Axial forces, in this case, may come both from prosthetic arm weight/movement/held objects and the tension of the screw or bolt 1172 tightened into the prosthetic arm to hold the assembly together. Although not illustrated in FIG. 48B, thrust bearing 1176 may be used with washers on either side of thrust bearing. In the illustrated embodiment, the radial bearing 1177 and thrust bearing 1176 are stacked on one another, with the thrust bearing 1176 being proximal to the radial bearing 1177, although other stacked configurations may be suitable. As best shown in FIG. 48B, the bearings 1176, 1177 may be positioned within a lip of the linking portion 1170.

Figure 49:
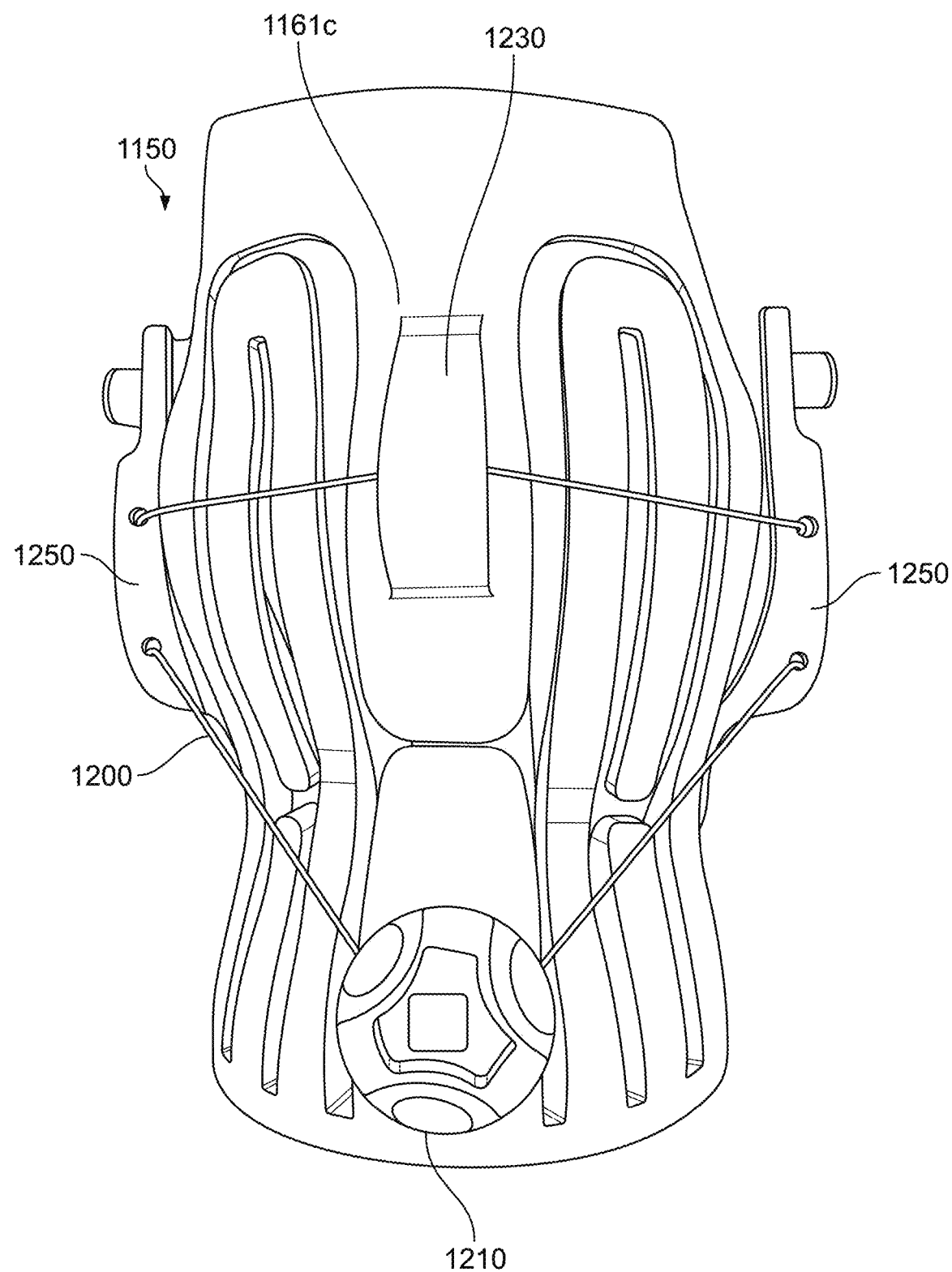
FIG. 49 is a rear view of the distal socket of FIG. 41.

As noted above, distal socket 1150 may include a tensioning system to assist in securely coupling the distal socket 1150 to the user's residual limb. One example of a tensioning system that may be used with distal socket 1150 is a lace system, where the lace may be tightened to compress the distal socket 1150. The lacing system is best illustrated in FIGS. 41 and 49. Referring to FIG. 49, the lacing system may be formed of at least two components, including a lace 1200 and a tensioner 1210. Lace 1200 may be formed of a single thread, wire, or lace that has two ends, each end being coupled to the tensioner 1210, although it is possible to use more than a single lace in the tensioning system.

As described above, certain portions of the coupling portion 1160 of distal socket 1150 may include an additional thickness. In the illustrated embodiment, the posterior side 1161, anterior side 1162, and the two lateral portions 1163 each include a portion with increased thickness, one or more apertures being formed in the portions with increased thickness to allow the lace to be laced therethrough. In particular, posterior side 1161 may include an area of increased thickness 1230 on proximal medial rib 1161*c*. In the illustrated embodiment, area of increased thickness 1230 includes a single passage for a single portion of lace 1200 to pass therethrough (best shown in FIGS. 49-51). Anterior side 1162 may include an area of increased thickness 1240 on proximal medial rib portion 1162*b*. In the illustrated embodiment, area of increased thickness 1240 includes a single passage for two portion of lace 1200 to pass therethrough (best shown in FIGS. 41 and 50-51). Each lateral portion 1163 may include an area of increased thickness 1250. In the illustrated embodiment, areas of increased thickness 1250 each include two passages, each passage adapted to allow a single portion of lace 1200 to pass therethrough (best shown in FIGS. 41 and 49).

Referring now to FIG. 44, the distal socket 1150 may include a mating structure 1220 that receives tensioner 1210 thereon. In some embodiments, mating structure 1220 may be formed integrally with the distal socket 1150, although in other embodiments the mating structure 1220 may be provided separately and attached to the distal socket 1150, or otherwise provided as part of tensioner 1210, with the combined tensioner 1210 and mating structure 1220 being attached to distal socket 1150. Whether the mating structure 1220 is formed integrally with distal socket 1150, or otherwise, the tensioner 1210 may be received in or on the mating structure 1220 so that the tensioner 1210 can be rotated about the mating structure 1220. As the tensioner 1210 rotates, it may wind the portions of lace 1200 connected to the tensioner 1210 to tension the lace 1200 on the distal socket 1150. The tensioner 1210 and/or mating structure 1220 may include a ratchet-type structure so that the tensioner 1210 is normally rotatable only in one direction to tension the lace 1200, and upon releasing the tensioner 1210, the tensioner 1210 is prevented from unintentionally rotating in the opposite direction to relax the tension on the lace 1200. In some embodiments, the tensioner 1210 may include an engagement mechanism that may be disengaged to release the tension on lace 1200, and engaged so that rotating the tensioner 1210 tensions the lace 1200.

Figure 50:
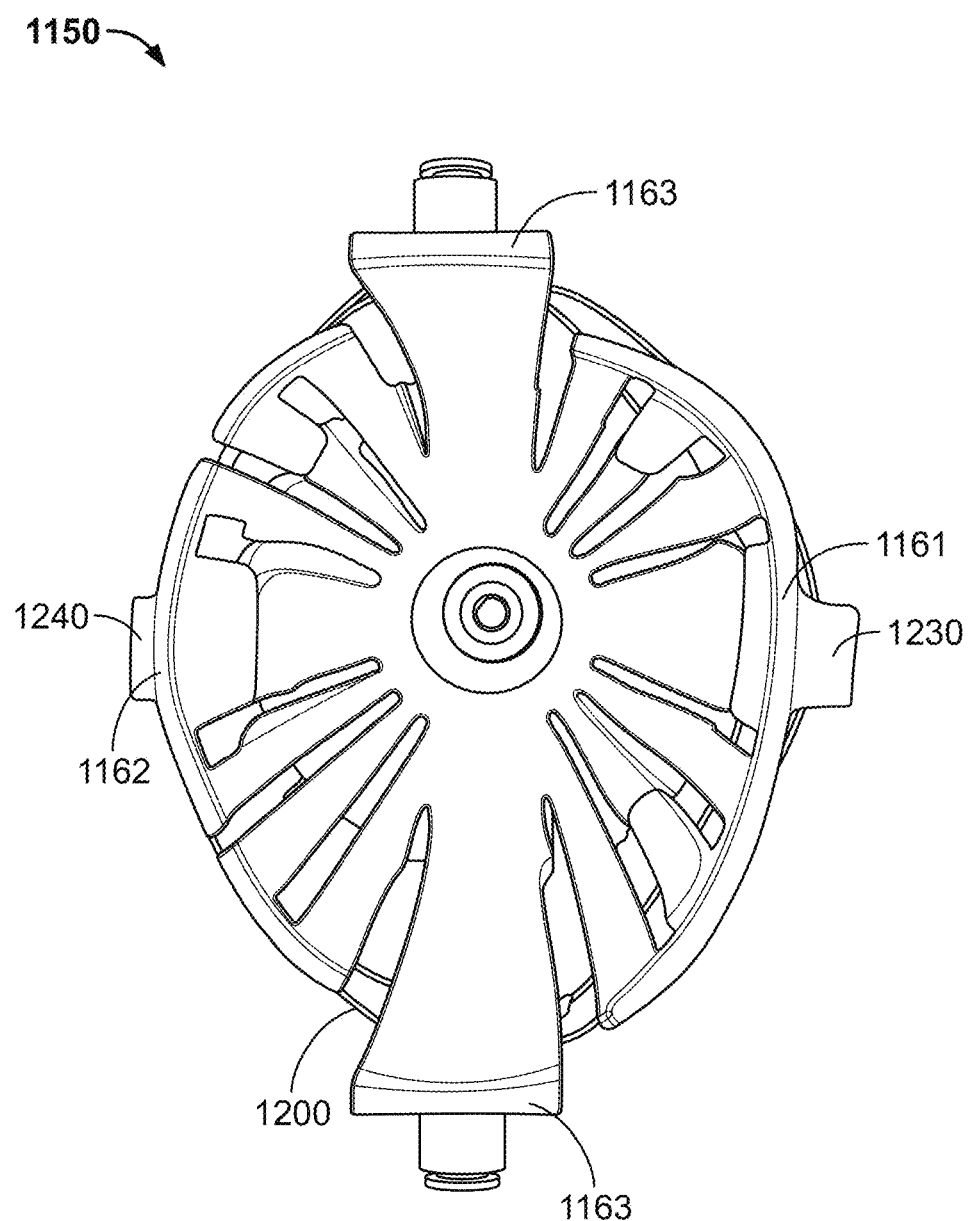
FIG. 50 is a top view of the distal socket of FIG. 41 in an un-tensioned state.
Figure 51:
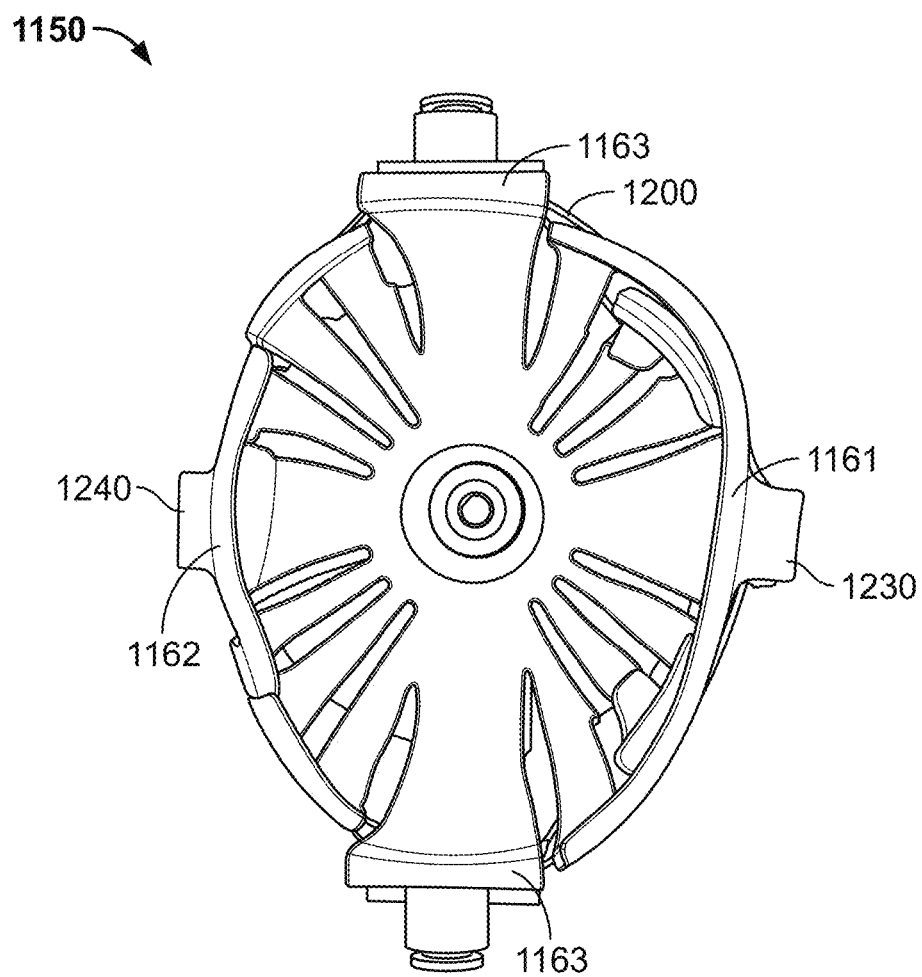
FIG. 51 is a top view of the distal socket of FIG. 41 in a tensioned state.

Referring now to FIGS. 50-51, FIG. 50 shows the distal socket 1150 where the tensioning system is in an untensioned state, while FIG. 51 shows the distal socket 1150 in a tensioned state, for example after rotating tensioner 1210 to cause the lace 1200 surrounding the distal socket 1150 to tension by being drawn into tensioner 1210. In some embodiments, the posterior side 1161, anterior side 1162, and lateral portions 1163 may all have substantially similar rigidities so that tensioning the lace 1200 draws each of the components radially inward similar amounts. However, in the preferred embodiment, lateral portions 1163 have a greater rigidity than posterior side 1161 and anterior side 1162, which may have substantially similar rigidities. The difference in rigidities may be achieved via the particular dimensions of the various sides of the distal socket 1150. With this configuration, as the tensioner 1210 is rotated to tension the lace 1200, the posterior side 1161 and the anterior side 1162 both tend to draw radially inwardly to a greater degree than the lateral portions 1163. This may be desirable because the main contact between the coupling portion 1160 of the distal socket 1150 and the residual limb of the user is between the limb and the posterior side 1161 and anterior side 1162. Further, because the lateral portions 1163 include pins 1164 that form the joints 1180 with the proximal socket 1110, it may be preferable that the lateral portions 1163 do not shift significantly during tensioning of lace 1200 to maintain the joints 1180 in their positions. As can be seen by comparing FIGS. 50 and 51, upon tensioning the lace 1200, the posterior side 1161 of distal socket 1150 and anterior side 1162 draw radially inward toward each other to help clamp or compress over a user's residual limb positioned within the distal socket 1150. The tension may be maintained via the connection between the tensioner 1210 and the corresponding mating structure 1220 so that the user's limb may be comfortably maintained secured within the distal socket 1150. In other embodiments, however, the tensioning system may be omitted. For example, the distal socket 1150, and particularly the coupling portion 1160, may be formed in a pre-compressed fashion so that, although the distal socket 1150 is sized and shaped to match the contours of the specific user, the distal socket 1150 may be undersized so that, when worn by a user, the distal socket 1150 effectively automatically compresses onto the user's residual limb.

It should be further understood that socket 1100 may be provided with any number of desired sensors, such as muscle sensors. Various types of sensors, including muscle sensors, have been described in detail above. It should be understood that any of the previously described sensors, including muscle sensors, may be provided with socket 1100 to help the user control movement of the prosthetic arm attached to the socket 1100.

Figure 52:
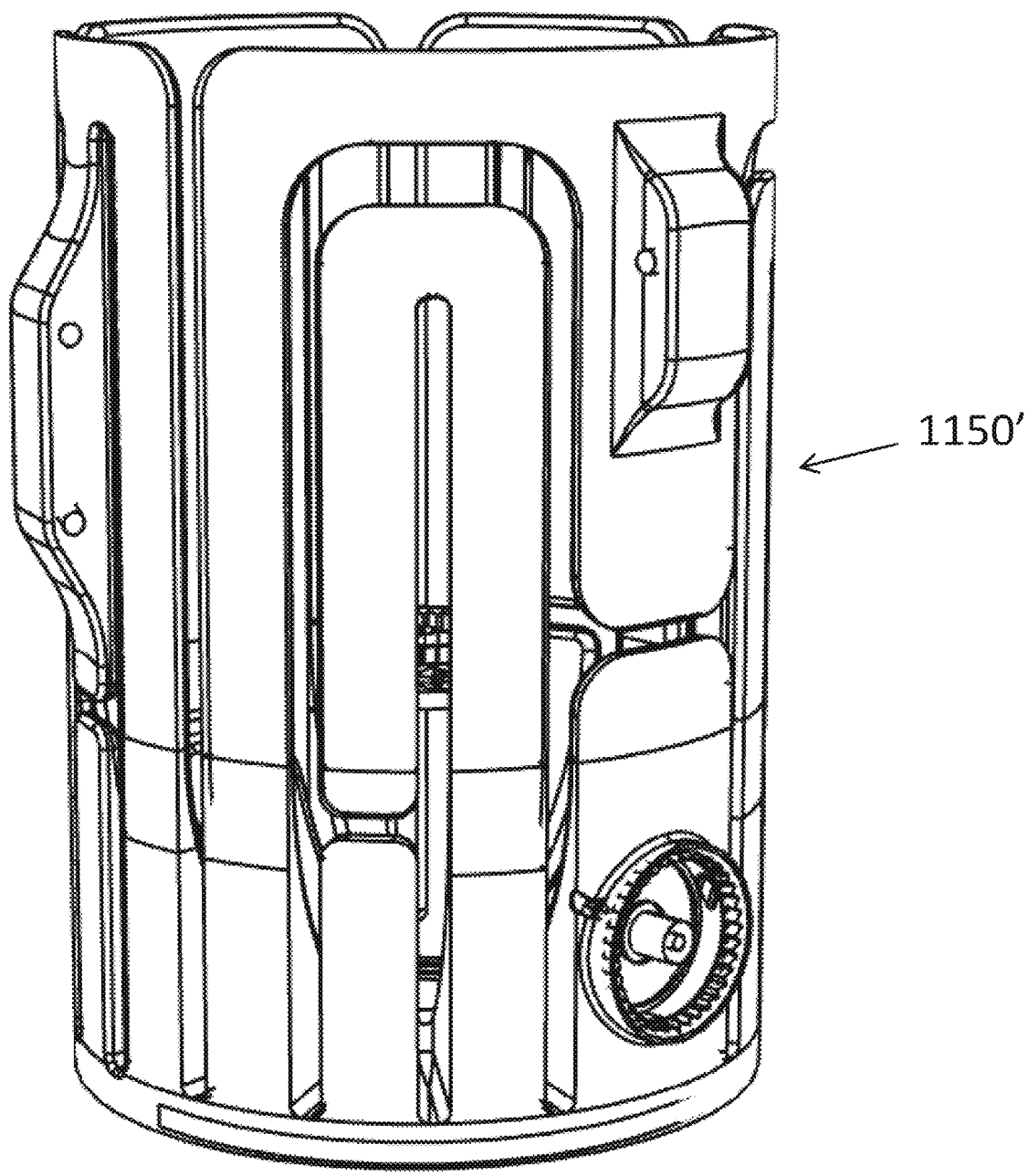
FIGS. 52-53 are perspective views of a generic model of a socket according to a further aspect of the disclosure.
Figure 53:
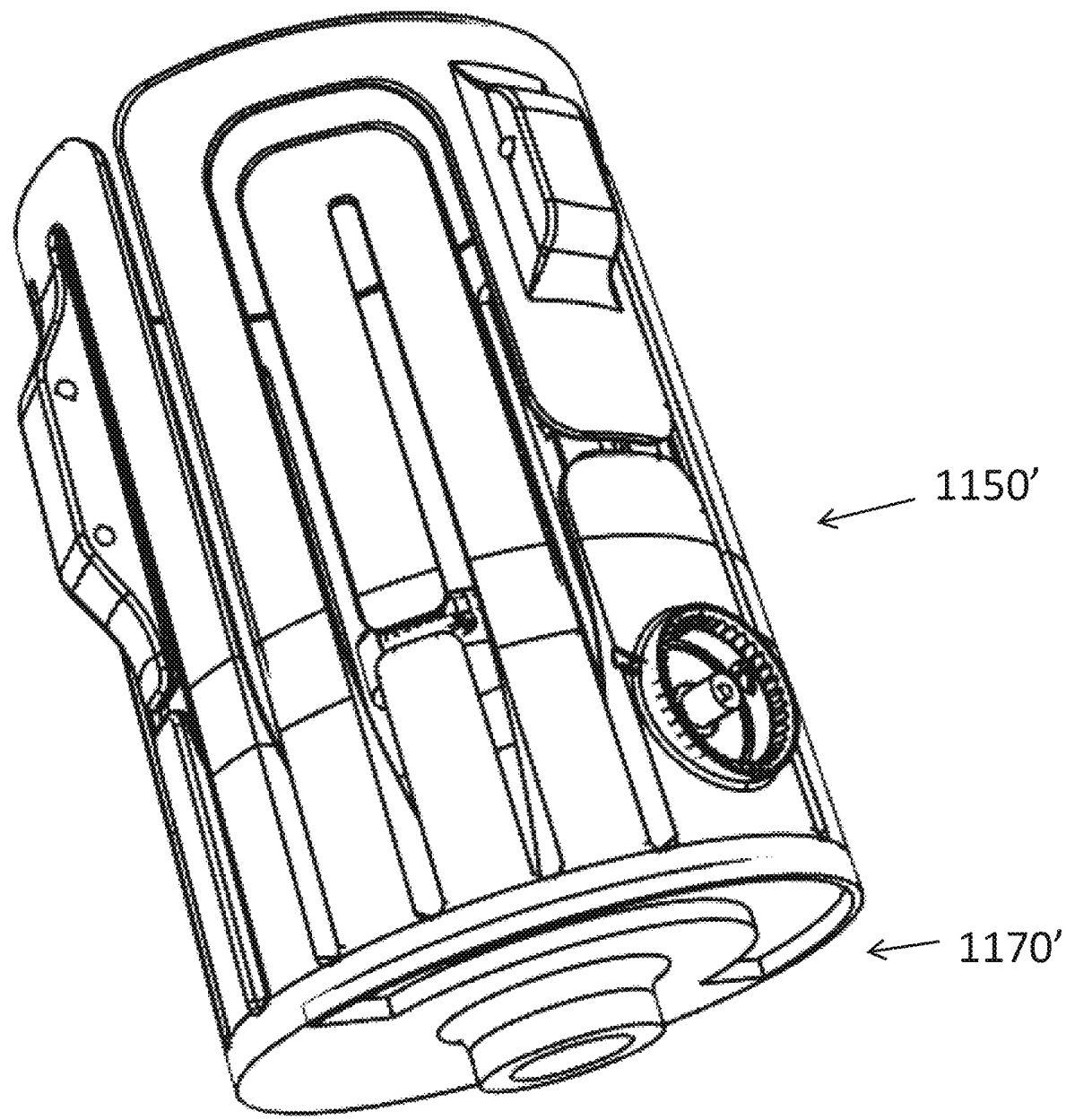

Although socket 1100 is illustrated in a version generally adapted for use in an amputee with a short trans-radial amputation (i.e. a relatively short length of the radius remains in the residual limb) or a trans-humeral amputation (i.e. an amputation across the humerus), the same or similar concepts may be applied to accommodate amputees having a long trans-radial amputation (i.e. a relatively large length of the radius remains in the residual limb). The main difference for a socket designed for a long trans-radial amputee is that a jointed socket need not be supplied, as the residual forearm has enough length to fully support the socket. For example, FIGS. 52 and 53 illustrate top and bottom perspective views, respectively, of a socket 1100' that has many of the same design principles of socket 1100, but which is specifically designed for a long trans-radial amputee. As with FIG. 40, FIGS. 52-53 illustrate a generic model of the socket 1100', prior to the model of the socket being conformed or morphed to the patient's specific anatomy. Because socket 1100' does not need the additional upper arm support provided by proximal socket 1110 of socket 1100, socket 1100' only includes a distal socket 1150'. However, the term distal socket 1150' is used for convenience and comparison to distal socket 1150, since distal socket 1150' is the sole socket, and there is no corresponding proximal socket in socket 1100'. In addition, whereas distal socket 1100 may include an extended posterior side 1161, the proximal end of distal socket 1150' may omit any extended sides because of the intended use with a long trans-radial amputee.

Distal socket 1150' may be substantially similar to distal socket 1150 in most respects, including the general design of relatively thin axially extending support members that may be conformed or morphed to the patient's anatomy to support the residual limb therein. Although not separately labeled, distal socket 1150' may include a lacing system similar or identical to the lacing system described in connection with distal socket 1150. For example, a plurality (e.g. two, three, four, or more) of thickened sections (not separately labeled) may be provided on the axially extending support members of distal socket 1150' to receive a lace (not shown) therethrough. The lace may be similarly operably connected to a tensioner (not shown) that is operably coupled to a mating structure (shown but not separately labeled) so that, as the tensioner is rotated, the lacing system compresses portions of the distal socket 1150' over the user's residual forearm. As best shown in FIG. 53, the distal socket 1150' may include a linking portion 1170' that is identical or substantially similar to the linking portion 1170 described in connection with distal socket 1150. For example, the linking portion 1170' may include a central lip and aperture for receiving a bolt (with or without bearings, such as thrust and/or radial bearings) that may be used to tighten a prosthetic forearm component to the distal socket 1150'. Similarly, linking portion 1170' may include a recessed (or protruding) arcuate track that is configured to engage a corresponding protrusion (or recess) of a prosthetic forearm to allow for guided rotation of the prosthetic forearm relative to the distal socket 1150'.

Figure 54A:
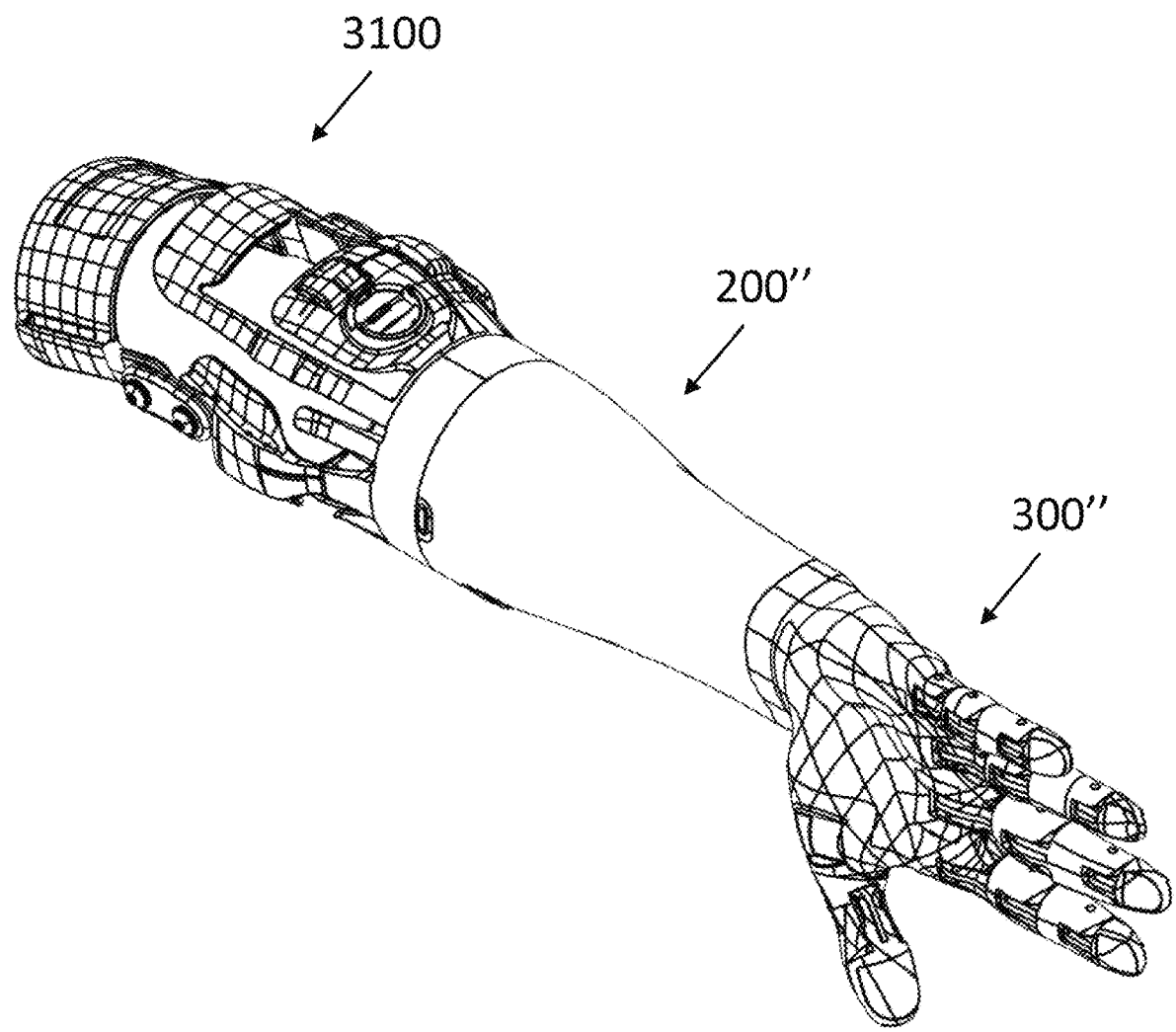
FIGS. 54A-P are various views of another embodiment of a socket and/or prosthetic forearm for use with the socket.

FIG. 54A is a perspective view of an upper extremity prosthesis system 3000 according to an aspect of the disclosure. Briefly, the upper extremity prosthesis system 3000 includes a prosthetic socket 3100, prosthetic forearm 200", and prosthetic hand 300". It should be understood that the prosthetic forearm 200" and prosthetic hand 300" may be similar or identical to any of the related component described above, including prosthetic forearms 200, 200', and prosthetic hands 300, 300', although some differences are described below. Socket 3100 may have an overall similar design to other sockets described herein, but with various differences noted below. And, as with other sockets described herein, a generic (or "unconformed") model of the socket may be "morphed," "conformed," or otherwise altered to fit a particular user based on measurements of the user uploaded to a system. Unless noted otherwise, the figures of socket 3100 provided below are of one example of a "morphed" version of the socket, as opposed to the generic version.

Figure 54B:
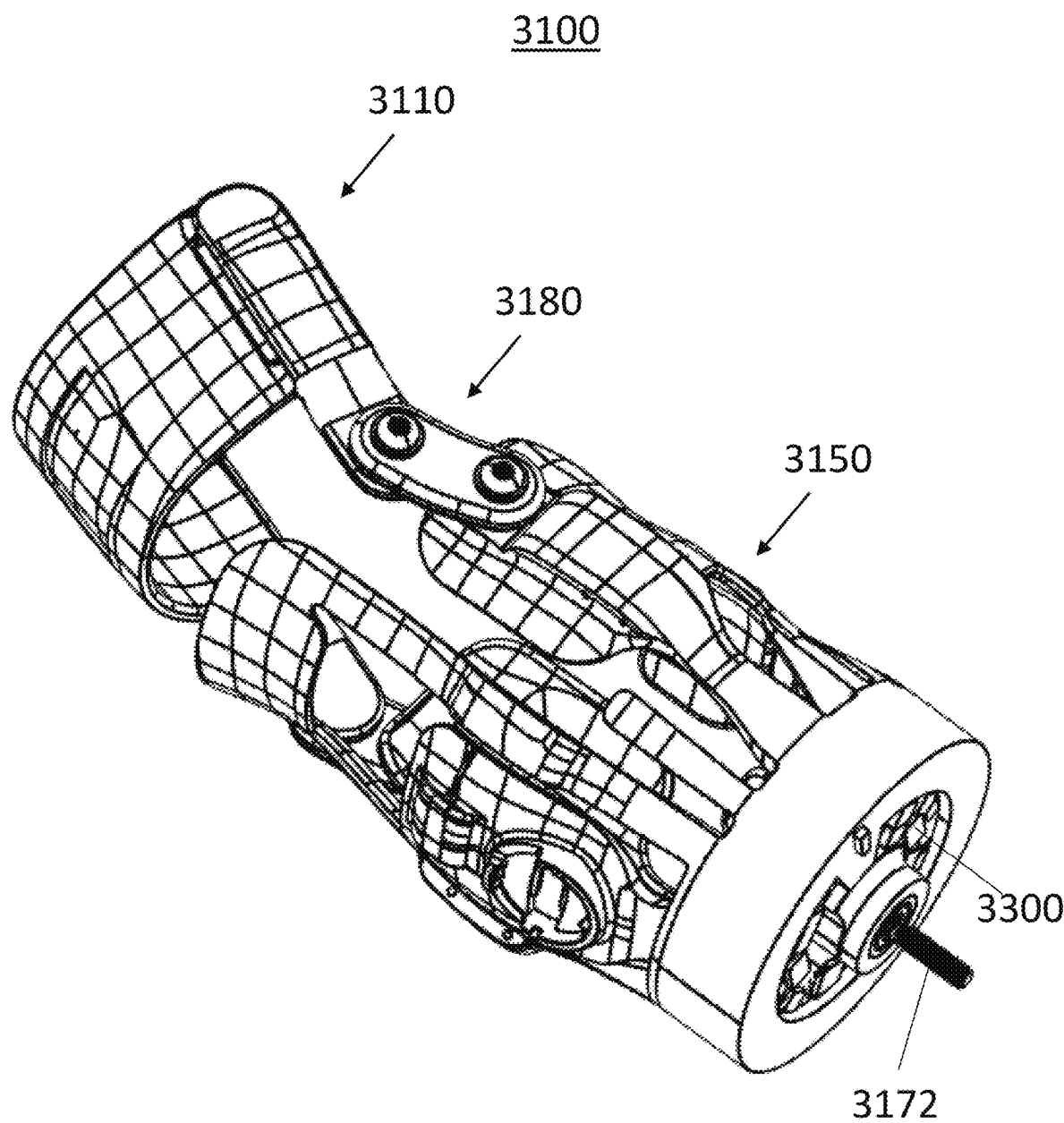

FIG. 54B is a perspective view of socket 3100 in isolation. Compared to socket 1100, socket 3100 may have certain main differences, each of which is described in greater detail below. A first difference is that socket 3100 may include a double or polycentric hinge coupling the proximal socket 3110 to the distal socket 3150. A second difference may include that the proximal socket 3110 is provided with a strap or strap system to help secure the proximal socket to the user's upper extremity. A third difference may include the particular type and/or style of tensioning system that is used. A fourth difference may include the inclusion of an electronic control board in the socket 3100, including structures within the socket for receiving the control board.

Figure 54C:
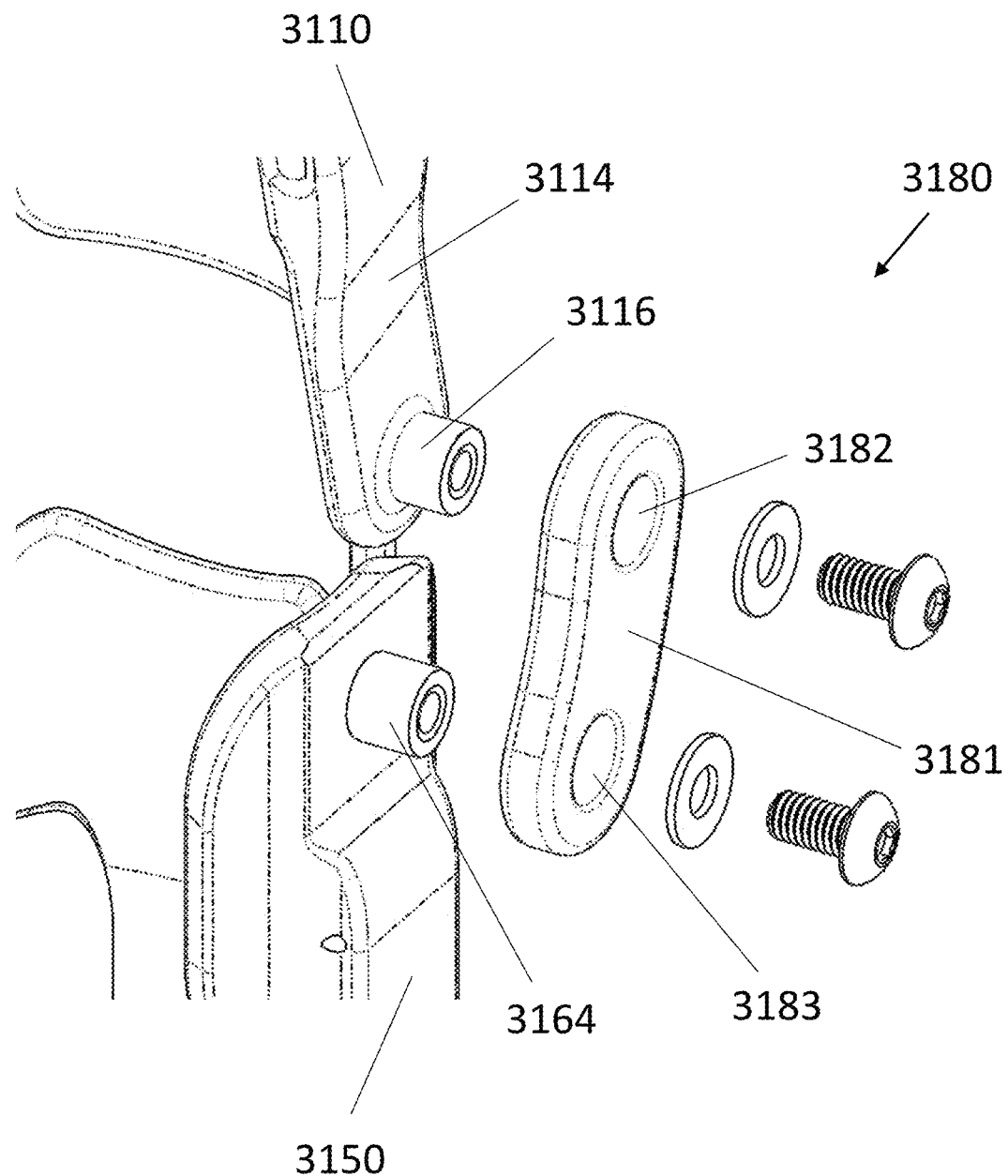

Regarding the first difference, joint 3180 is shown in an exploded view in FIG. 54C. In particular, proximal socket 3100 may include a pair of extensions 3114, each extension including a pin 3116. Distal socket 3164 may also include a corresponding pair of pins 3164 (only one visible in FIG. 54C). Joint 3180 may include a plate 3181 or linkage with two apertures 3182, 3183 extending through opposite ends thereof. The pins 3116 and 3164 may extend through apertures 3182, 3183, respectively, and fasteners (such as screws or bolts) may couple the plate 3183 to the pins 3116, 3164. With this configuration, as the distal socket 3150 rotates relative to the proximal socket 3110, the rotation may occur about two pivot axes extending through the center of the two pints 3116, 3164. This is in comparison to socket 1100, which includes hinged motion about a single pivot axis. In other words, joint 3180 may actually comprise two joints. Anatomic motion at the elbow joint may be more complex than rotation about a single, fixed axis. Thus, the polycentric joint 3180 may allow for easier rotation of the socket 3100 as the user flexes or extends the user's elbow. In other words, if the user flexes or extends the natural elbow joint in a manner that is not hinging about a single static pivot axis, the polycentric joint 3180 may allow the socket 3100 to move in a fashion that substantially replicates the natural elbow joint motion. Although only one polycentric joint 3180 is illustrated in FIG. 54C, it should be understood that one joint may be provided on each side of the socket 3100. Also, due to the increased complexity of polycentric joint 3180 compared to joint 1180, the torsion spring described in connection with joint 1180 may be omitted from polycentric joint 3180.

Figure 54D:
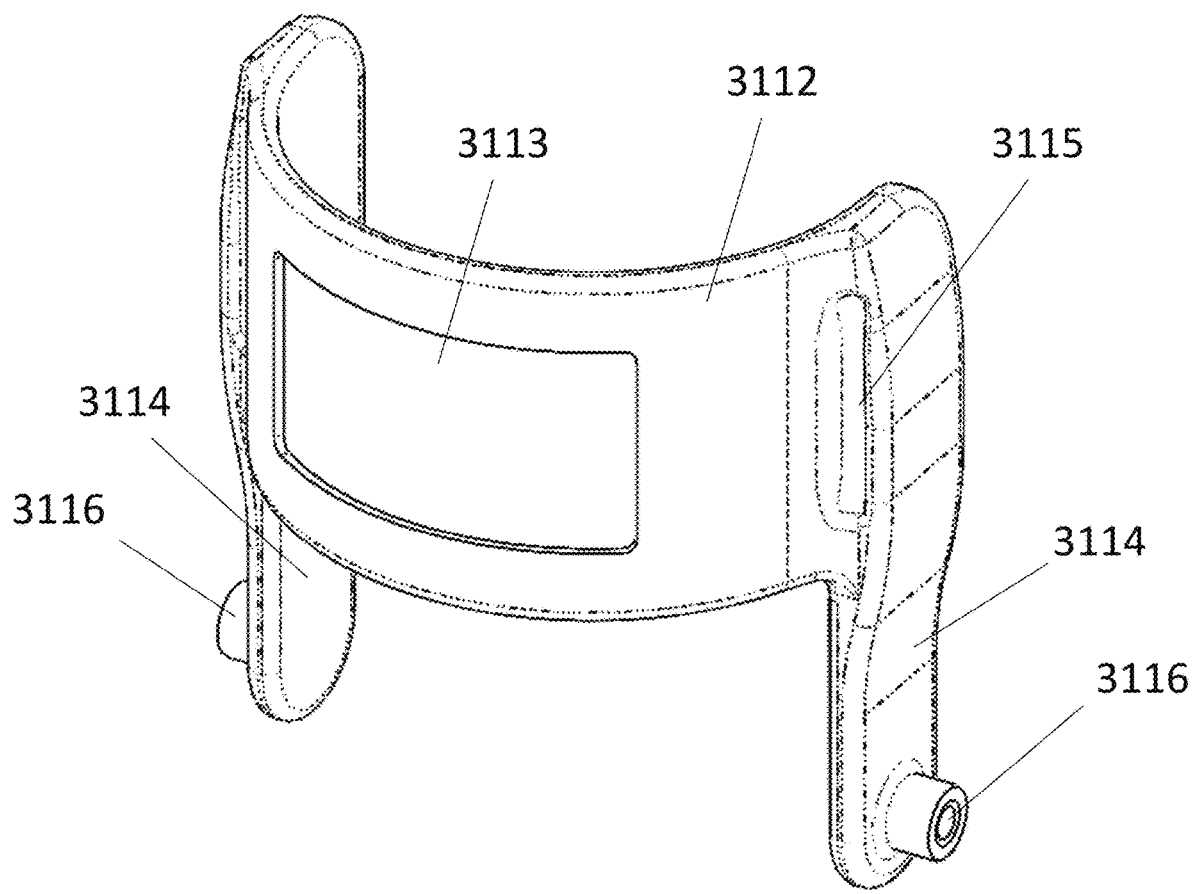
Figure 54E:
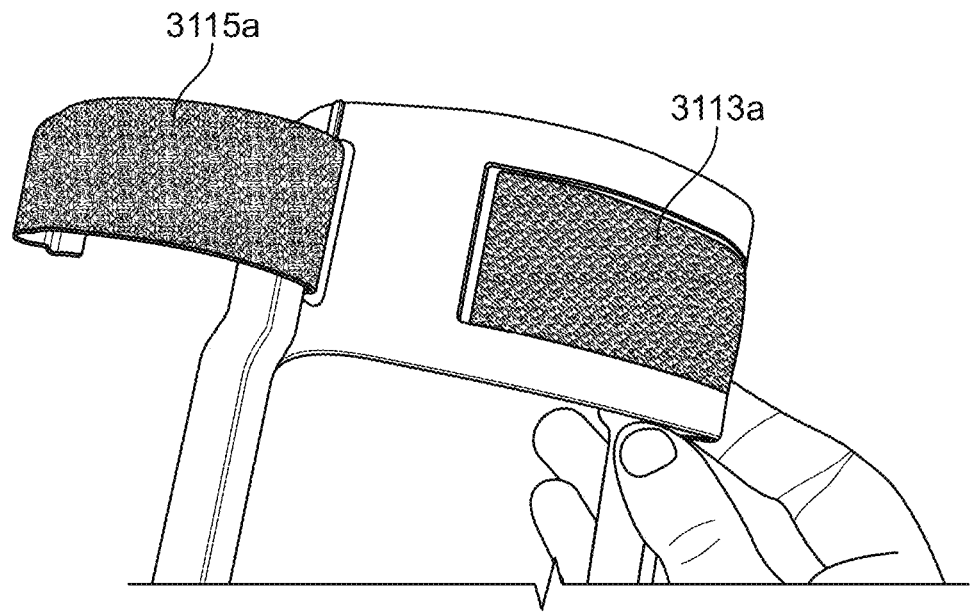
Figure 54F:
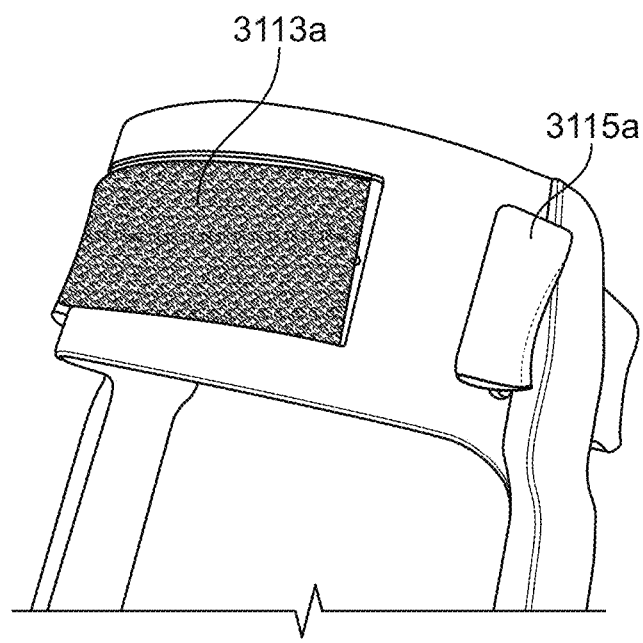

Regarding the second difference, while proximal socket 1110 is described above as being configured to couple to a user's upper arm via a compressive fit, proximal socket 3110 may include a strap system to assist with securing the proximal socket 3110 to the user's upper arm, either in addition to or instead of a compressive fit. FIG. 54D illustrates a rear perspective view of proximal socket 3110, including a generally "C" or "U"-shaped support member 3112 extending between adjacent extensions 3114. As with proximal socket 1110, proximal socket 3110 may be adapted to be positioned over the biceps and/or triceps region of the user's upper extremity. A rear portion of the support member 3112 may include a recessed area 3113 in which a portion of the strap system may be located. In one example, if the strap system has a hook-and-loop connection, a portion of the strap system with hooks or loops may be positioned on or within recessed area 3113. That portion 3113a is illustrated in FIGS. 54E-F. It should be understood that portion 3113a may be a separate member of the strap system (as illustrated), but in other embodiments, the strap system may be formed of single member. Referring back to FIG. 54D, near the areas where the support member 3112 meets the extensions 3114, a slot 3115 or other recess may be formed. Although only one slot 3115 is visible in FIG. 54D, it should be understood that a second slot is preferably included opposite to the location of the illustrated slot. As shown in FIGS. 54E-F, a strap 3115a of the strap system may pass through both of the slots 3115, so that the strap traverses the open portion of the "C"-shaped support 3112. In the particular illustrated embodiment, strap 3115a has a first end (illustrated in FIG. 54F) that is too large to pass through one of the slots 3115, with the other free end (illustrated in FIG.

54E) passing through the other slot. With this configuration, when the support member 3112 of proximal socket 3110 is positioned on a user's biceps and/or triceps area, the strap 3115a can be pulled to tighten the strap over the user's biceps and/or triceps, with the strap 3115a coupled to portion 3113a to maintain the desired level of tension. Although illustrated as a hook-and-loop configuration (for example of the type known under the VELCRO trade name), it should be understood that other mechanisms for maintaining the tension on the strap system may be suitable, including buttons, a ratcheting mechanism, etc. And, as noted above, although the strap system is shown has having two individual components 3113a and 3115a, the strap system could be a single member or more than two members.

Figure 54G:
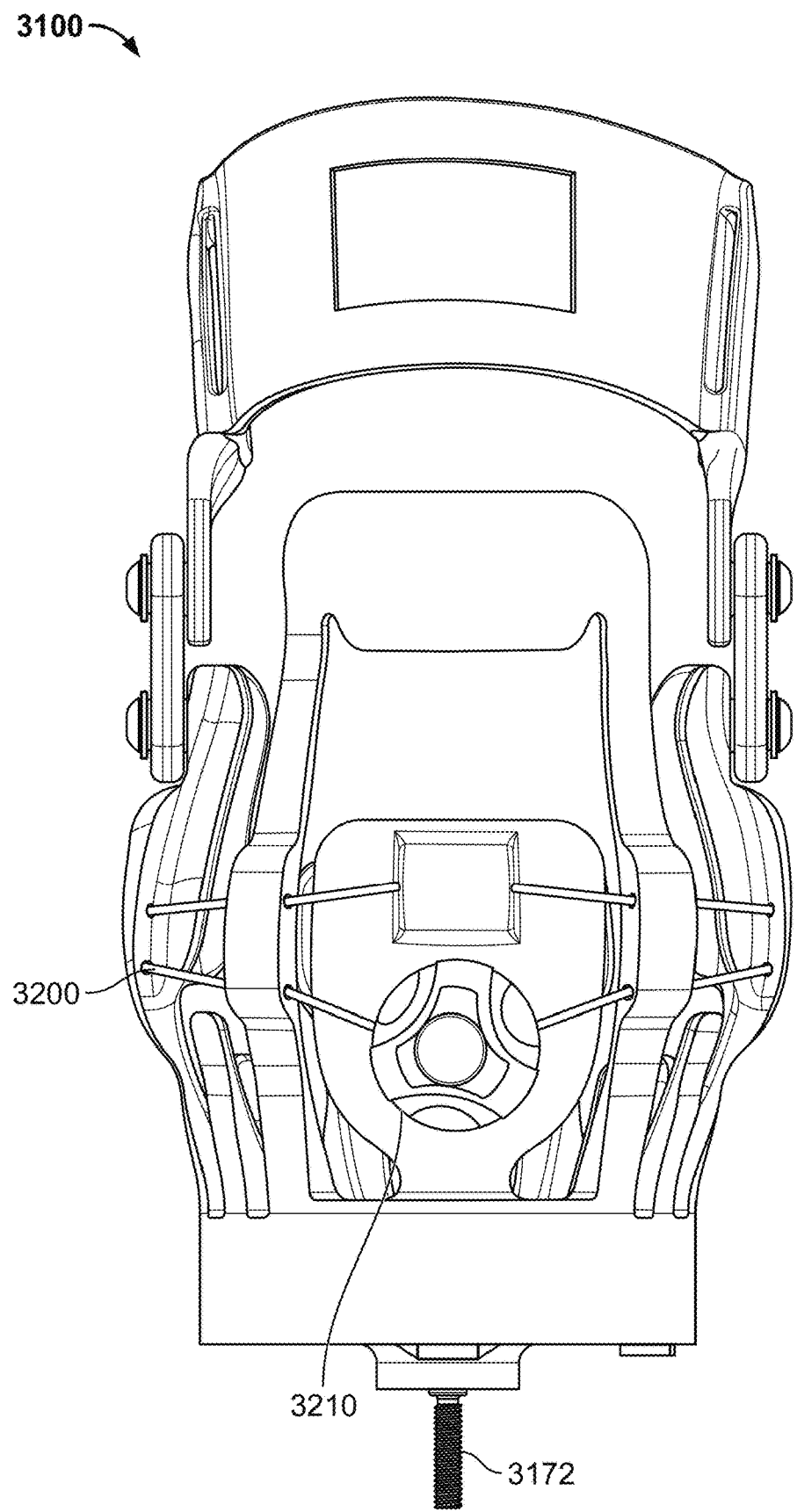
Figure 54H:
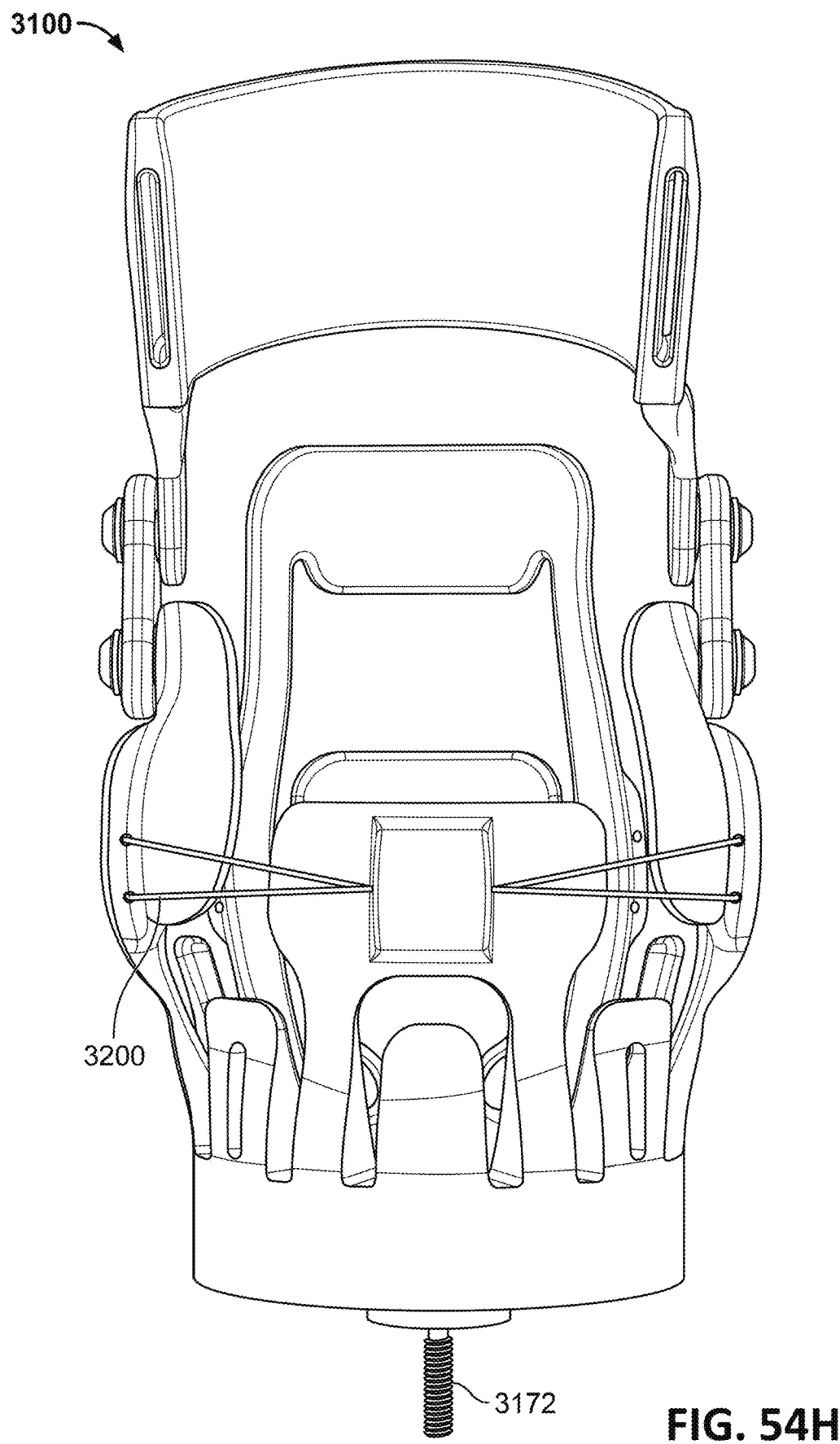
Figure 54I:
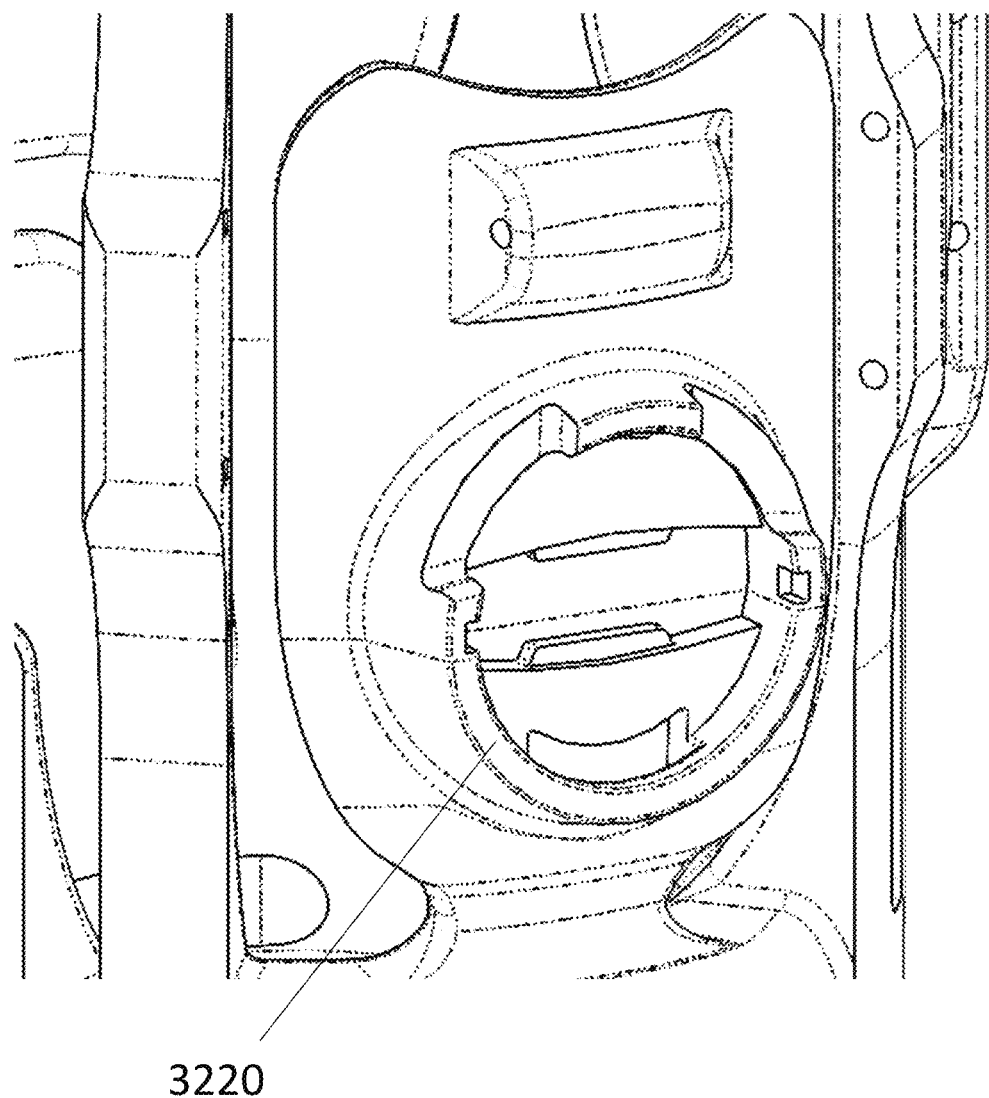

Regarding the third difference, the particular 3210 tensioner incorporated into socket 3100 may have a different configuration than the tensioner 1210 of socket 1100. Referring to FIGS. 54G-I, posterior and anterior views of socket 3100 are illustrated, respectively, with a tensioning system that includes a tensioner 3210 and a lace 3200. The tensioner 3210 and lace 3200 may be generally similar in structure and function to tensioner 1310 and lace 1200, with some differences, where the tensioner 3210 may be rotated in one direction to draw the lace 3200 into the tensioner to increase tension, or rotated in the opposite direction to allow the lace to exit the tensioner to decrease tension in the lace. One difference between tensioner 3210 and tensioner 1210 is how the tensioner 3210 interacts with a mating structure 3220 on the socket 3100. FIG. 54I is an enlarged perspective view of the mating structure 3220 onto which the tensioner 3210 is received, with the tensioner and lace 3200 omitted from the view of FIG. 54I. As described in connection with socket 1100, mating structure 1220 may be formed integrally with the distal socket 1150 and include a ratchet-type structure to interact with a corresponding ratchet-type structure in or on tensioner 1210. However, tensioner 3210 may instead include all of the ratchet-type structures within the tensioner, eliminating any need to form a corresponding ratchet-type structure in the mating structure 3220. Thus, mating structure 3220 may be sized and shaped so that tensioner 3210 may be snapped or otherwise coupled to the distal socket 3150 via the mating structure, but the working mechanisms of the tensioner may be mostly or fully included within the tensioner itself.

Figure 54J:
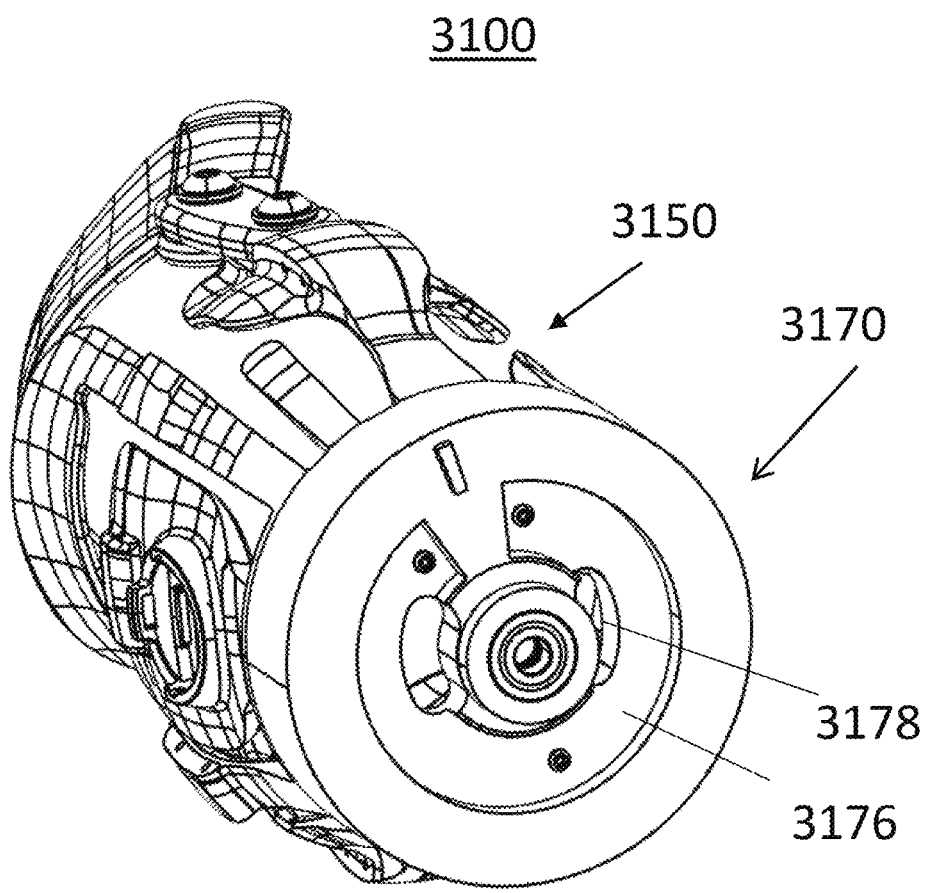
Figure 54K:
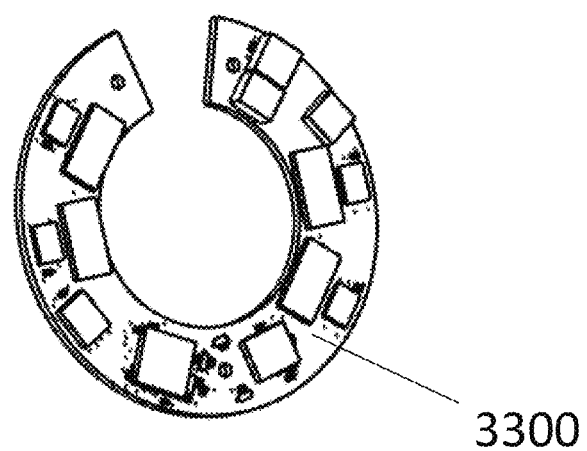

Regarding the fourth difference, FIG. 54J illustrates a linking portion 3170 at a distal end of the distal socket 3150, and FIG. 54K illustrate an exemplary electronics control board 3300 that may be received within the linking portion 3170. Similar to linking portion 1170, linking portion 3170 may be configured to couple to a prosthetic upper extremity member, such as prosthetic forearm 200", or a similar component. The distal face of linking portion 3170 may include a central aperture for receiving a screw or bolt 3172 therethrough (shown in FIG. 54B). Bolt 3172 and related structures may be substantially similar or identical to those described in connection with bolt 1172, for example including associated thrust and radial bearings, and connection to a prosthetic forearm via a nut. However, whereas distal socket 1150 is described as having a recess or track 1176 to guide and/or limit rotation of the distal socket 1150 relative to the prosthetic forearm 200, distal socket 3150 instead includes an electronics board recess 3176. Electronics board recess 3176 may be substantially "C"-shaped, with the bolt 1372 configured to extend through a center of the electronics board recess and through the electronics control board 3300. As noted above in connection with socket 1100, any one or more of various sensors and sensor types may be provided within socket 3100, including for example various muscle sensors (including electromyography or "EMG" sensors) within distal socket 3150 that may read information from the user's residual limb, including muscle contractions. Specific structures and configurations of such sensors are described in greater detail in U.S. Provisional Patent Application No. 62/912,117 filed Oct. 8, 2019 and titled "Biometric Sensor Array," the disclosure of which is hereby incorporated by reference herein. Information from the sensors within socket 3100 may be used, at least in part, to control motion of prosthetic hand 300. Information from the sensors within socket 3100 may be passed to electronic control board 3300, for example via cables extending between the sensors to components on electronic control board 3300. Referring to FIG. 54J, the distal face of linking portion 3170 may also include one or more apertures 3178, the apertures providing a pathway between the interior of socket 3100 and the electronics board recess 3176. In the illustrated embodiment, two apertures 3178 are provided on opposite sides of the recess that receives the bolt 3172. With this configuration, when the electronics control board 3300 is received within the electronics board recess 3176, part of the apertures 3178 remain uncovered so that cables (e.g. ribbon cables) can connect sensors within the socket 3100 to components on the electronics control board 3300. The electronics control board 3300 may include any suitable electronic components, for example including one or more microcontrollers that receive signals from EMG sensors within socket 3100, process those signals, and send signals to the prosthetic hand 300 to cause components of the prosthetic hand to move in a particular fashion based on the signals from the user's muscles. It should be understood that, although electronics board recess 3176 of distal socket 3150 and track 1176 of distal socket 1150 have generally similar shapes, the electronics board recess 3176 does not serve a similar function as track 1176. In other words, the electronics board recess 3176 functions to receive the electronics control board 3300, and to allow for cables to pass through the distal face of the distal socket 3150, but the electronics board recess 3176 is not intended to limit rotation of the socket 3100 relative to the prosthetic forearm 200".

Figure 54L:
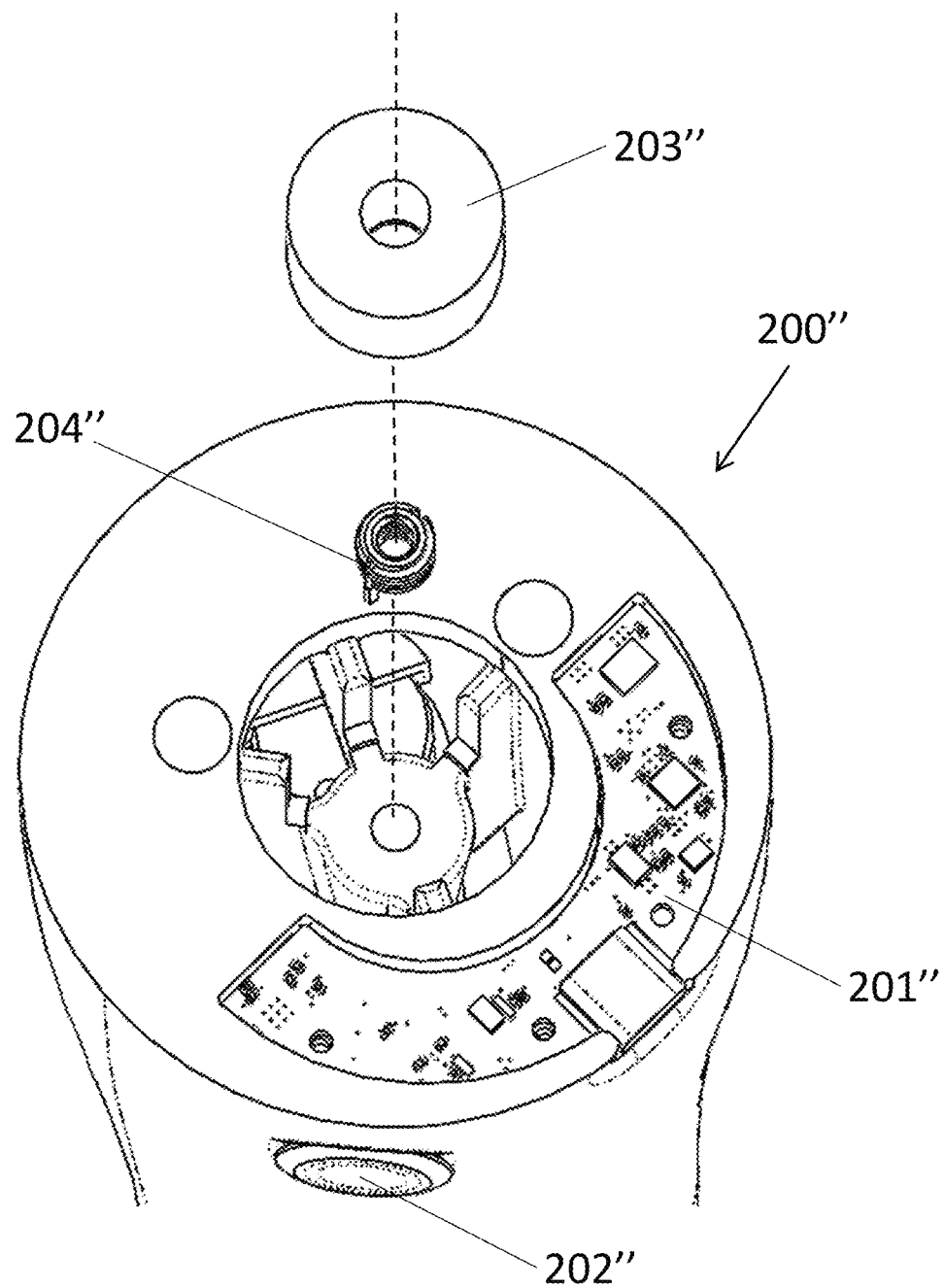
Figure 54M:
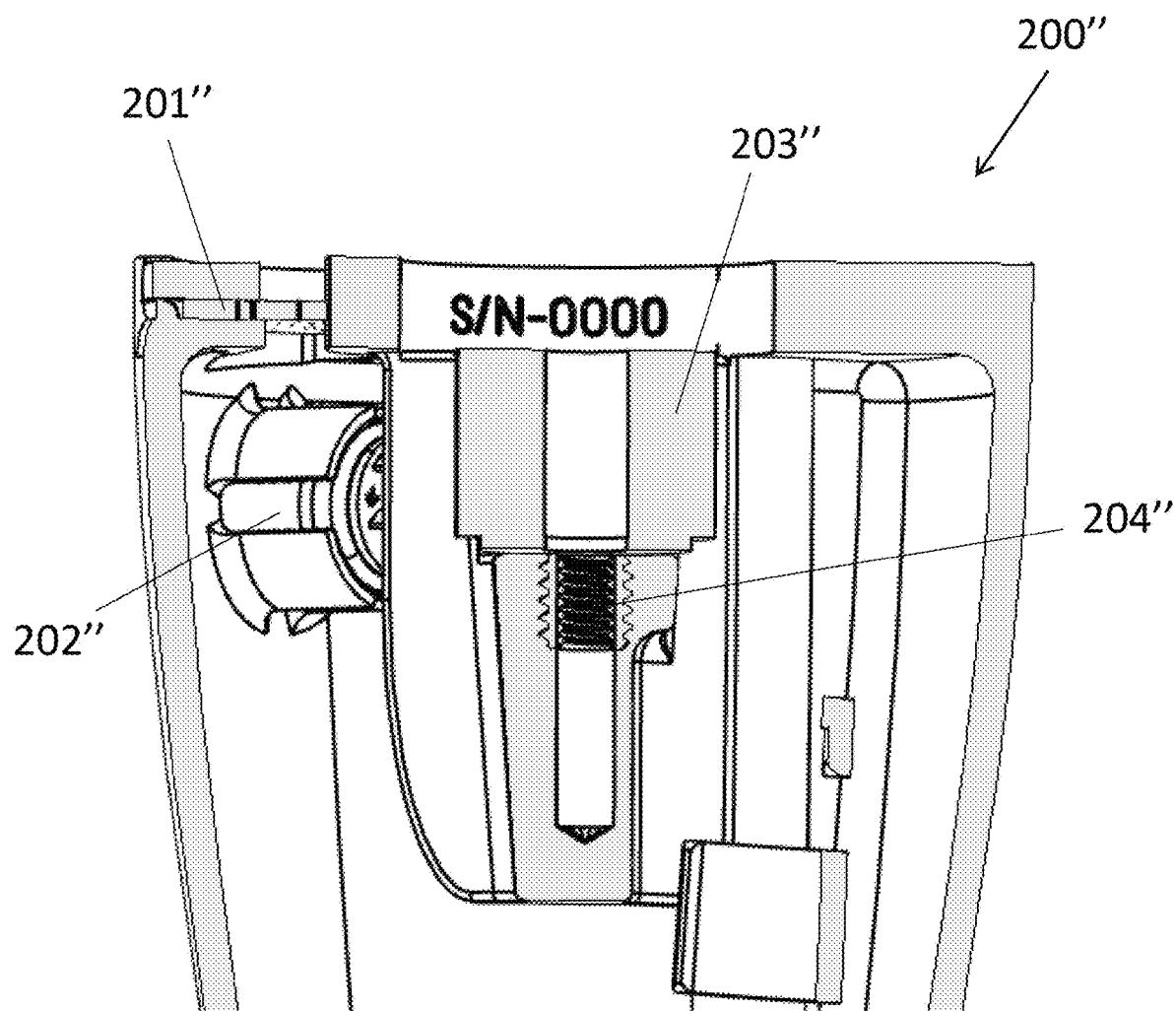

As noted above, the specific configuration of socket 3100 does not include a rotation limiting feature between the socket and prosthetic forearm 200", a potential problem is that any cables extending from socket 3100 to the prosthetic forearm 200" and/or prosthetic hand 300" may be at risk from damage if over-rotation occurs, because the cables may twist and become strained. In order to overcome this issues, a slip ring system may be provided in prosthetic forearm 200". FIG. 54L is a perspective view of a proximal portion of prosthetic forearm 200" with certain components illustrated in an exploded view. FIG. 54M is a cross-section of the proximal portion of prosthetic forearm 200". In addition to an electronic control board 201" and a power button 202", a slip ring 203" and threaded insert 204" are also illustrated in an exploded view. Slip ring 203" may generally an outer housing positioned coaxially around an inner housing. The slip ring 203" may be an intermediate junction between the socket 3100 and the ultimate end point of the cables, either in the prosthetic forearm (if a forearm similar to prosthetic forearm 200 is used) or the prosthetic hand (if a hand similar to prosthetic hand 300' is used). In other words, a first set of cables may extend from the electronic control board 3300 of the socket 3100 and connect to and terminate at the outer (or inner) housing of slip ring 203". Then another set of cables may extend from the inner (or outer) housing of slip ring 203" and connect to the desired location within the prosthetic forearm 200" or prosthetic hand 300". The inner and outer housings of slip ring 203" are electrically coupled, so that as the socket 3100 rotates relative to the prosthetic forearm 200", the inner and outer housings of slip ring 203" may rotate relative to one another to reduce or eliminate strain on the two sets of cables, allowing for the prosthetic forearm 200" to rotate without limit relative to the socket 3100 while still passing signals between the socket 3100 and the prosthetic forearm 200" or prosthetic hand 300".

As shown in FIG. 54M, the slip ring 203" may be coupled to prosthetic forearm 200' near a central proximal recess thereof, and the slip ring 203" may define a central bore therethrough. When the prosthetic forearm 200" is coupled to the socket 3100, the bolt 3172 may extend through the central bore of the slip ring 203". As shown in FIG. 54M, a central support with a central bore may extend distally to the point where the slip ring 203" is attached to the prosthetic forearm 200". A threaded insert 204" may be secured within the central bore the central support (for example via outer threads), and the threaded insert 204" may also include inner threads so that the bolt 3172 may be threaded into the threaded insert 204". The threaded insert 204" may serve a generally similar purpose as bolt 1174 shown in FIG. 48A. Thus, with this configuration, the socket 3100 may be screwed into the threaded insert 204" to couple the socket to the prosthetic forearm 200", and afterwards the prosthetic forearm 200" may rotate without limit and without risk of damage to electrical cables passing information between the socket 3100 and the prosthetic forearm 200" or prosthetic hand 300".

Figure 54N:
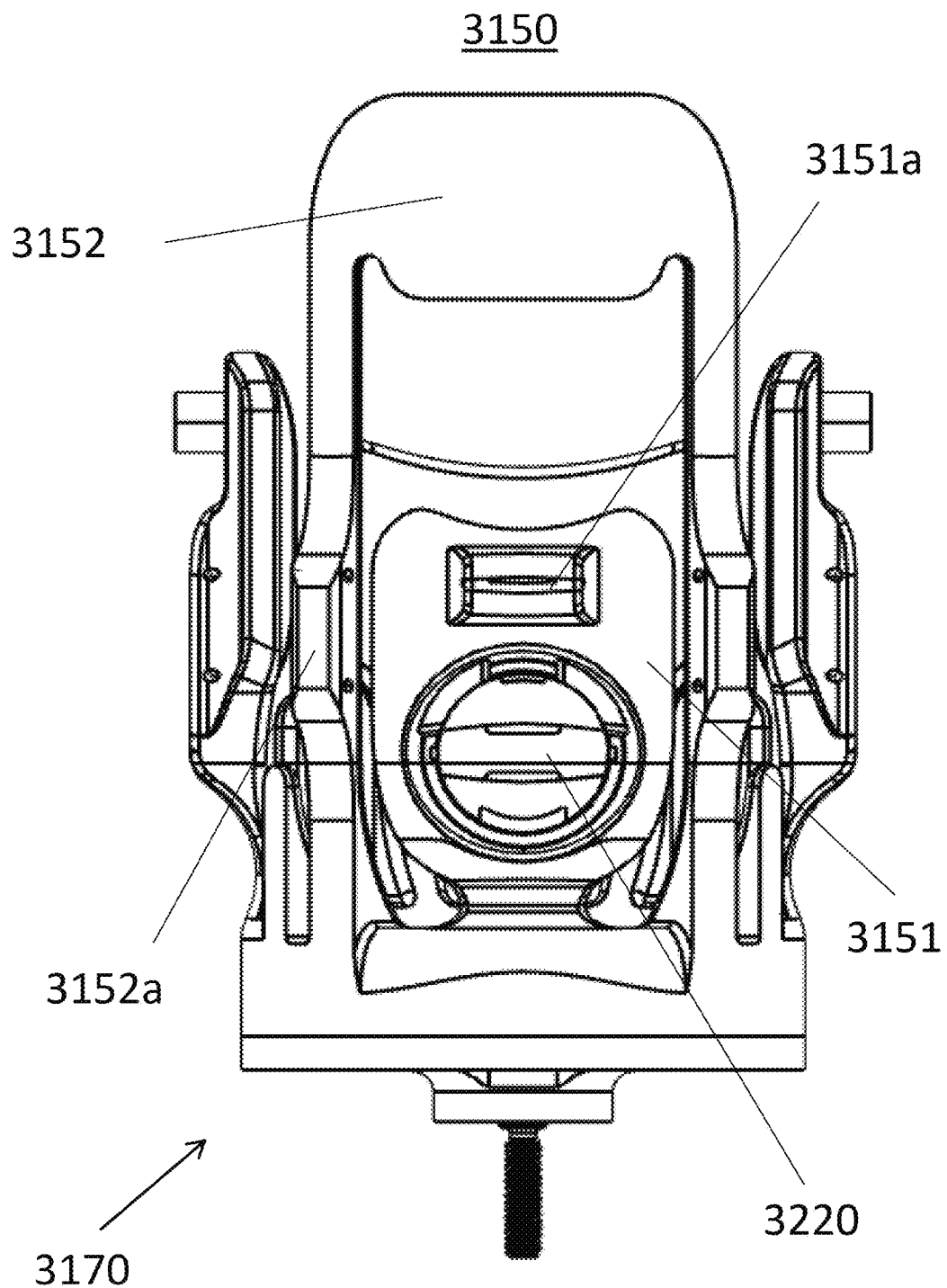
Figure 54O:
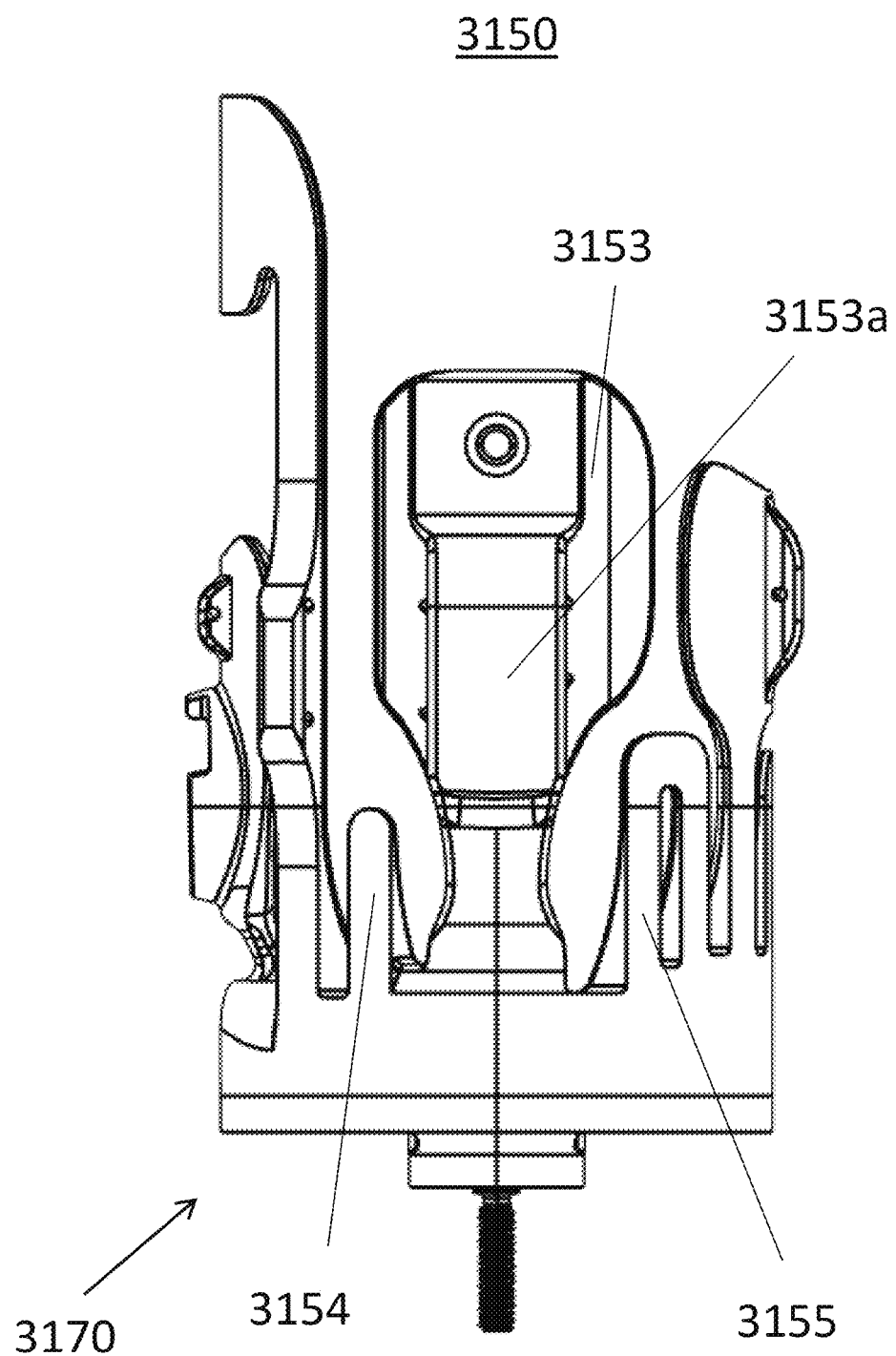
Figure 54P:
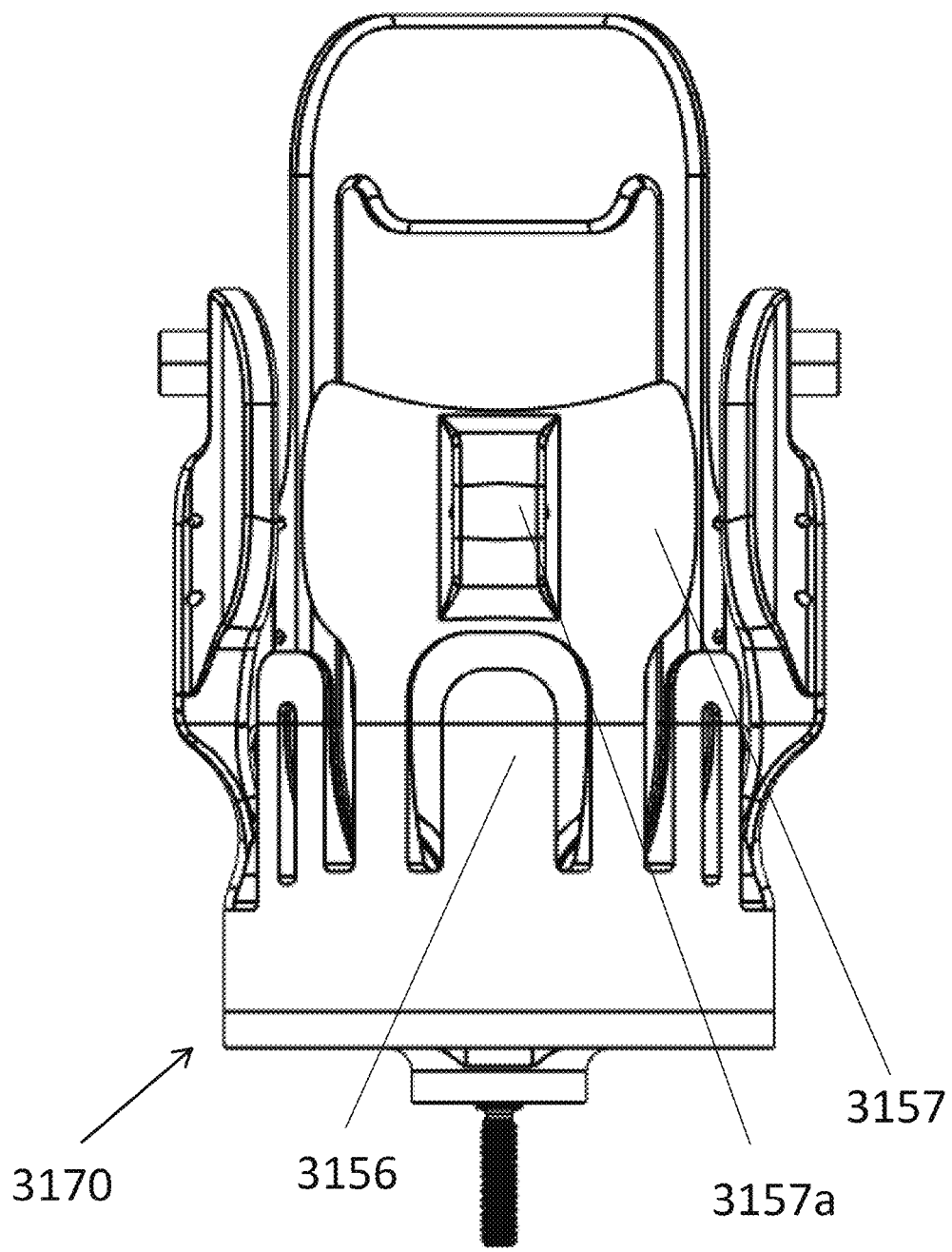

As with socket 1100, socket 3100 may be designed and shaped so as to provide secure fixation of a prosthetic extremity to a residual limb of the user, while also providing for high levels of comfort and airflow/breathability. To better illustrate some of the features that assist achieving this goal, FIGS. 54N-P illustrate posterior, side, and anterior views, respectively, of distal socket 3150 in an unconformed state (e.g. prior to being "morphed" or "conformed" to fit a particular anatomical shape of a user). Referring to FIG. 54N, the posterior side of distal socket 3150 may include a center paddle 3151 which includes the mating structure 3220 to which the tensioner 3210 may be coupled. The center panel 3151 may only attach to the linking portion 3170 at the distal end of the center panel at a narrowed portion of the center panel. The center panel 3151 may also include a thickened or bumped out portion that includes one or more apertures to couple the lace 3200 to the center panel 3151. The center panel 3151 may be adapted to contact a central posterior area of the user's residual limb. The posterior portion of distal socket 3150 may also include an outer panel 3152. Outer panel 3152 may effectively surround the center panel 3151 without any direct contact with the center panel. As illustrated, outer panel 3152 may include two long narrow fingers that flank either side of the center panel 3151, and the two fingers may be the only points of connection between the outer panel 3152 and the linking portion 3170. The two fingers may both converge into the main portion of outer panel 3152 that serves to contact the user's triceps area above (or proximal to) where the center panel 3151 contacts the user's residual limb. Each of the long fingers attaching outer panel 3152 to the linking portion 3170 may also include a bumped out or thickened portions 3152a with one or more apertures therein to connect to the outer panel 3152 to lace 3200. With this configuration, as the tensioner 3210 is rotated to tension the lace 3200, the center panel 3151 and the outer panel 3152 may both pull towards the user's posterior residual limb with the ability to flex and maneuver relatively independent of each other to effectively conform to the user's anatomy. Further, it should be clear from FIG. 54N that there are large gaps and open spaces that remain to provide airflow and breathability to the user while the center panel 3151 and outer panel 3152 help secure the distal socket to user's residual limb. A main gap between the center panel 3151 and the proximal or top of outer panel 3152 may allow for a user's elbow joint to be positioned therein.

FIG. 54O illustrates a side view of distal socket 3150 in an unconformed or unmorphed condition. It should be understood that the two sides of the distal socket 3150 may have substantially identical configurations, so the descriptions in connection with FIG. 54O may apply equally to both sides of the distal socket 3150. Distal socket 3150 may include a side panel 3153 that is generally similar to center panel 3151 in that it is only connected to linking portion 3170 at a relatively narrow portion of the side panel 3153. The side panel 3153 may include a thickened or bumped out portion 3153a which may include one or more passages through which laces 3200 may pass to couple the tensioner 3120 to the side panel 3153. With this configuration, as the tensioner 3210 is rotated to tension the lace 3200, one side panel 3153 will be drawn toward the medial side of the user's residual limb and the other side panel will be drawn toward the lateral side of the user's residual limb. As shown in FIG. 54O, additional relatively short fingers 3154, 3155 may be provided extending from the linking portion 3170 to provide additional contact points with the user's residual limb, although short fingers 3154, 3155 may not be coupled to the lace 3200.

FIG. 54P illustrates an anterior view of distal socket 3150 in the unmorphed or unconformed condition. As shown in FIG. 54P, this portion may include a short finger 3156 extending upwardly and proximally from the linking portion 3170, and a center anterior panel 3157 that surrounds, but is not directly coupled, to the short finger 3156. The center anterior panel 3157 may be coupled to the linking portion 3170 only by two long narrow fingers that flank both sides of the short finger 3156. The center anterior panel 3157 may include a thickened or bumped out portion 3157a with one or more passageways extending therethrough to receive lace 3200. As with the other panels that are connected to lace 3200, upon rotating the tensioner 3210 in one direction, the laces 3200 tensions and draws the center anterior panel 3157 toward the user's anatomy, the center anterior panel 3157 being adapted to contact the user's anterior residual limb (e.g. the residual forearm).

Summarizing the description of FIGS. 54N-P, the distal socket 3150 includes a number of fingers and/or panels that provide for contact and securement of the distal socket 3150 to the user's arm. Some of those panels or fingers can be drawn inwardly toward the user's arm, with a relatively large amount of flexibility that allows the panels to conform to the user's arm while also allowing for significant airflow through the distal socket 3150, providing comfort to the user while ensuring that the distal socket 3150 remains secured to the user. Further, although not explicitly shown or described, the interior distal portion of the distal socket 3150 may have a general cup or concave shape (similar to that shown and described in connection with FIGS. 50-51) to receive the terminal end of the user's residual limb. Finally, it should be understood that certain features not described explicitly in connection with distal socket 3150 may be the same or similar to those for sockets described above, for example including materials and additional or accessory components to be included therewith.

It should be understood that various prosthetic sockets for a prosthetic upper extremity are described herein, as are various embodiments of the prosthetic upper extremity (including a prosthetic forearm and prosthetic hand). Although specific embodiments are described, it should be understood that features from certain embodiments may be combined with features of other embodiments. For example, the different tensioner systems described herein may be substituted for one another, any of the sockets may be modified for use with any of the prosthetic forearms and/or prosthetic hands described herein. This also applies, where appropriate, to additional versions of sockets described below.

Figure 55:
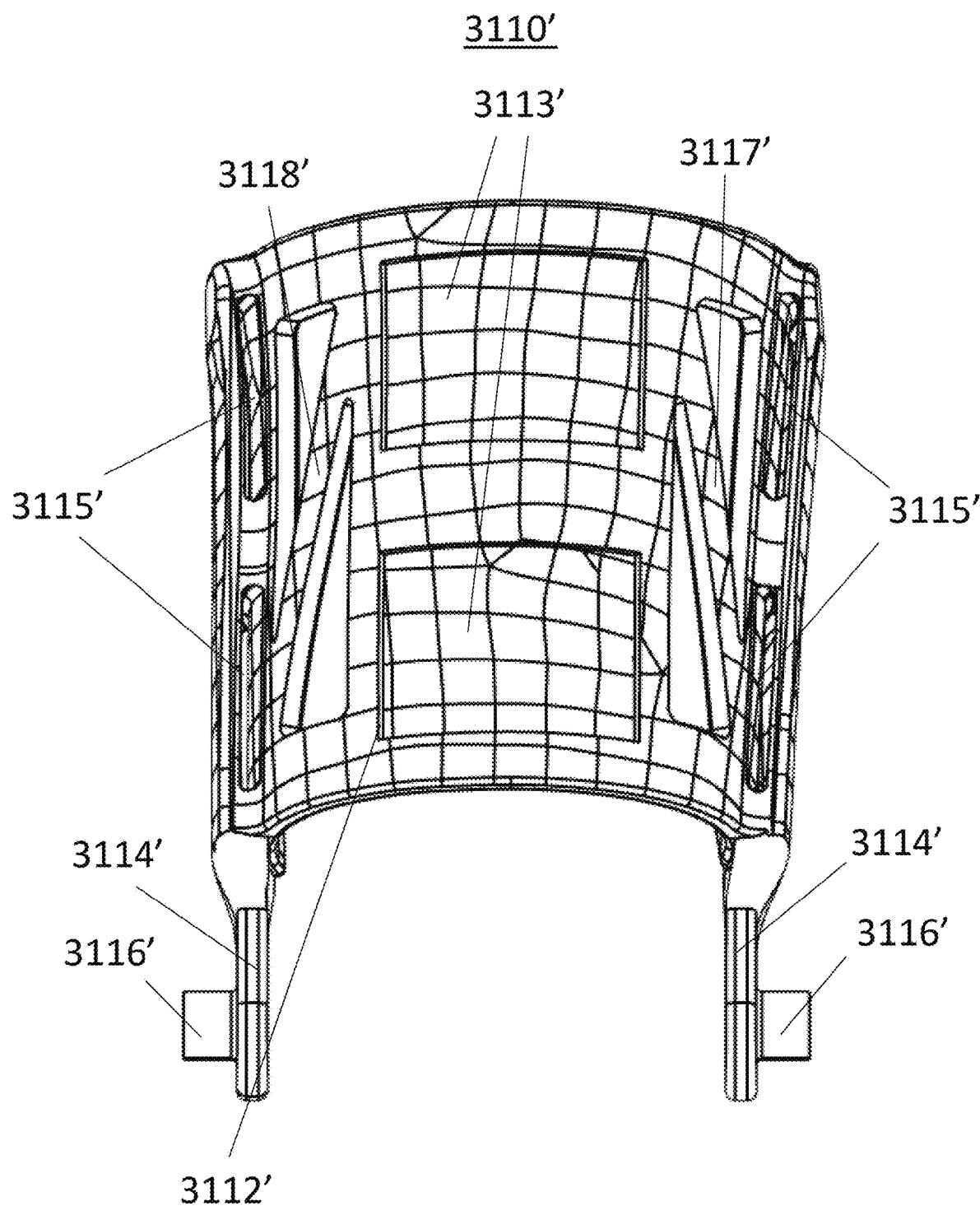
FIG. 55 is a posterior view of an extended version of a proximal socket.

In socket 3100 described above, the support member 3112 of proximal socket 3110 may be about two inches in height, although variations are permissible. This configuration may be suitable for situations in which the residual limb (e.g. the residual forearm) of the user is relatively long. In situation in which the residual limb of the user is very short, the distal socket 3150 may only be able to provide limited securement of the socket 3100 to the user. Thus, in some embodiments, the socket 3100 may be provided with an extended proximal socket 3110', for example as shown in FIG. 55. Extended proximal socket 3110' may be substantially similar to proximal socket 3110 in that it includes pins 3116' for coupling to a joint (such as a polycentric joint), and extensions 3114' coupled to a generally "C"-shaped support member 3112'. However, support member 3112' may be substantially longer than support member 3112, and may be for example between about 2 inches and about 8 inches in height. As shown, instead of a single strap or strap system, proximal socket 3110' may include two or more pairs of slots 3115' and two or more corresponding recessed areas 3113'. Other than the fact that proximal socket 3110' may include two strap systems, the function and structure of the strap systems may be similar or identical. In other words, the strap systems may be used to better secure the proximal socket 3110' to the triceps and/or biceps areas of the user. As should be understood, if the user has a shorter residual limb, the additional securement provided by the extended proximal socket 3110' may compensate for a relatively smaller amount of fixation of the distal socket 3150 to the shorter residual limb. One additional difference between proximal sockets 3110 and 3110' is that openings or voids may be added to support member 3112' to provide for increased airflow. In other words, because support member 3112' is longer than support member 3112, it may be desirable to reduce the overall surface area of the support member 3112' to provide additional breathability. In the illustrated example, voids 3117' may be created on either sides of the recessed areas 3113', with supports 3118' extending across the voids to help provide sufficient structural integrity of the proximal socket 3110' despite the voids 3118'. Otherwise, proximal socket 3110' may interact with distal socket 3150 in substantially the same way as proximal socket 3110. It should be understood that although proximal socket 3110' is illustrated with features for two strap systems, a single large strap system or more than two strap systems could be used with proximal socket 3110' to provide the desired level of securement to the user's biceps and/or triceps area.

Figure 56A:
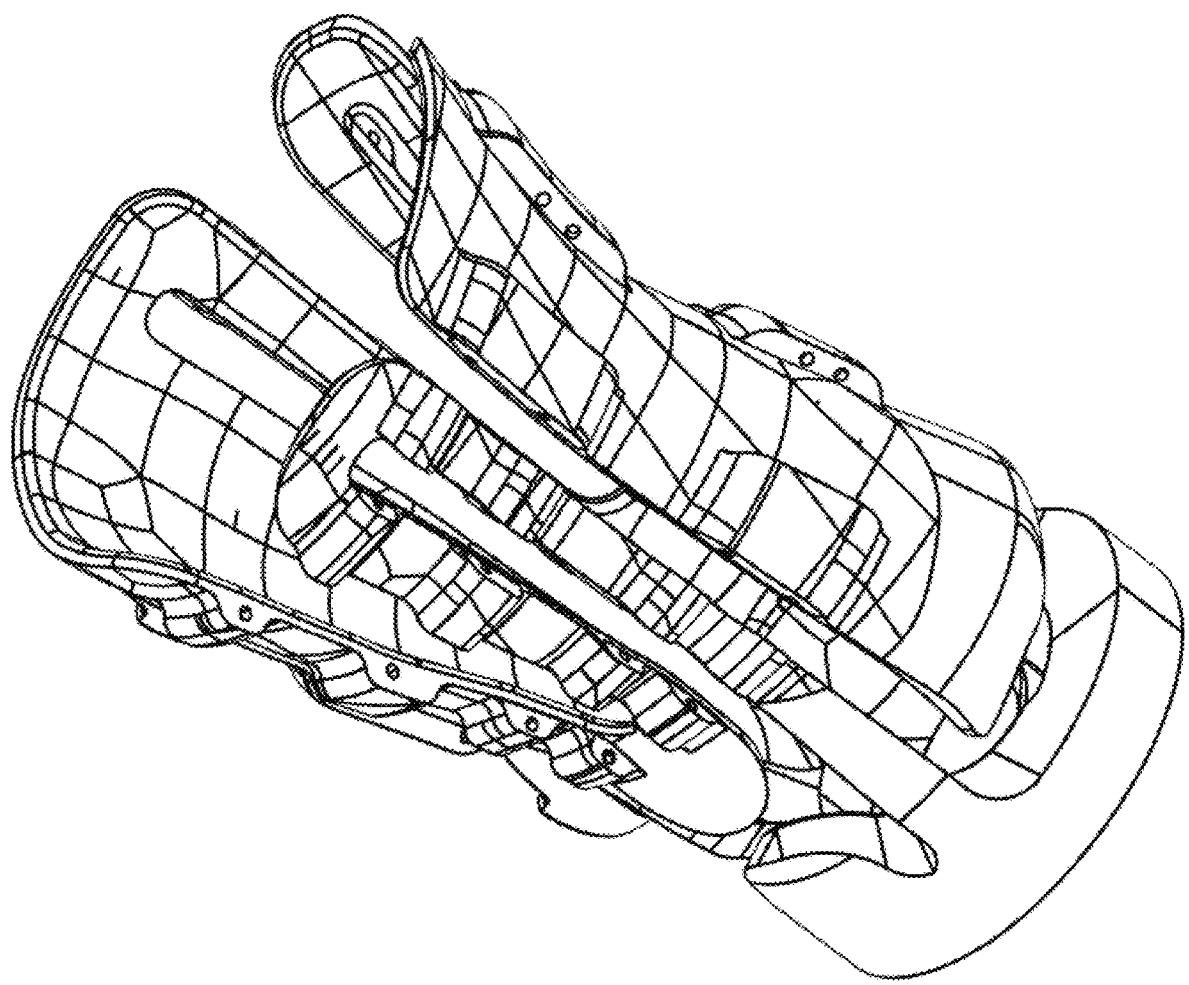
FIGS. 56A-G are various views of a jointless embodiment of a socket.
Figure 56B:
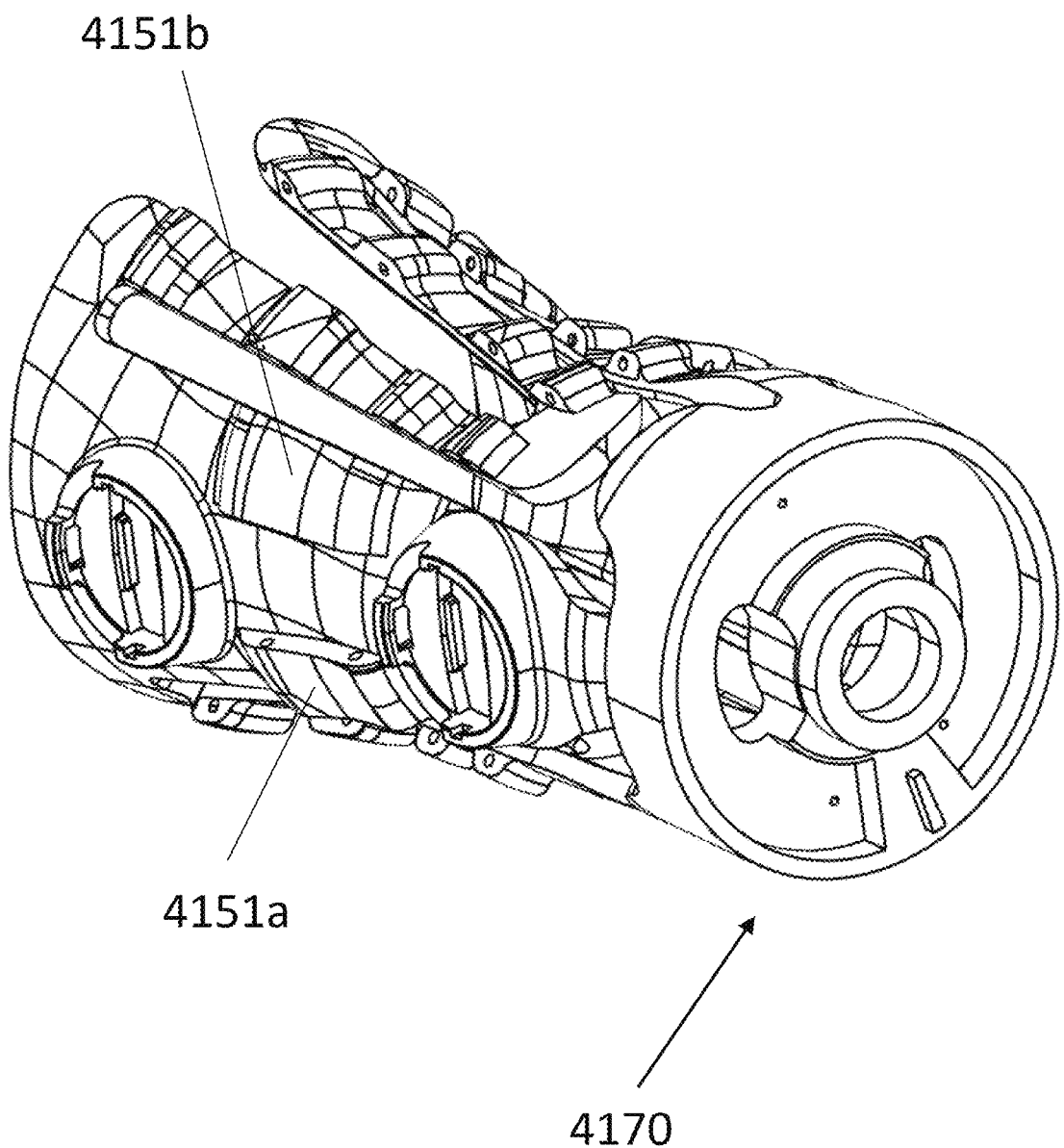

While most or all of the sockets described above may be particularly useful for coupling a prosthetic forearm and/or prosthetic hand to a user's residual limb about the elbow joint, some user's may have residual limbs that are signifi-cantly long, for example residual forearms that are longer than three inches. In certain scenarios where a user has a relatively long residual limb, it may be impractical to use a jointed socket about the elbow. FIGS. 56A-B illustrate a jointless socket 4100 that may be used to couple to a prosthetic forearm 200" and/or a prosthetic hand 300', although it should be understood that jointless socket 4100 may be used to couple to any suitable embodiment of a prosthetic forearm and/or hand. FIGS. 56A-B are both perspective views of the jointless socket 4100 after being conformed or morphed to fit a particular user. As can be seen in FIG. 56B, the linking portion 4170 of the distal end of socket 4100 may have substantially the same configuration as the distal end of the linking portion 3170 of distal socket 3150. Although control boards and bolts are not illustrated in connection with FIGS. 56A-B, it should be understood that those components may interact with socket 4100 in substantially the same was as described in context with socket 3100, and are thus not described in detail again here.

The general features of socket 4100 may have significant similarities in both structure and purpose as to socket 3100 and other sockets described herein, and thus only certain differences are described herein. The major difference, as noted above, is that socket 4100 does not include two portions jointed together, but rather is a singular member, although a floating panel described in greater detail below may technically result in the socket 4100 being a two-piece member.

Figure 56C:
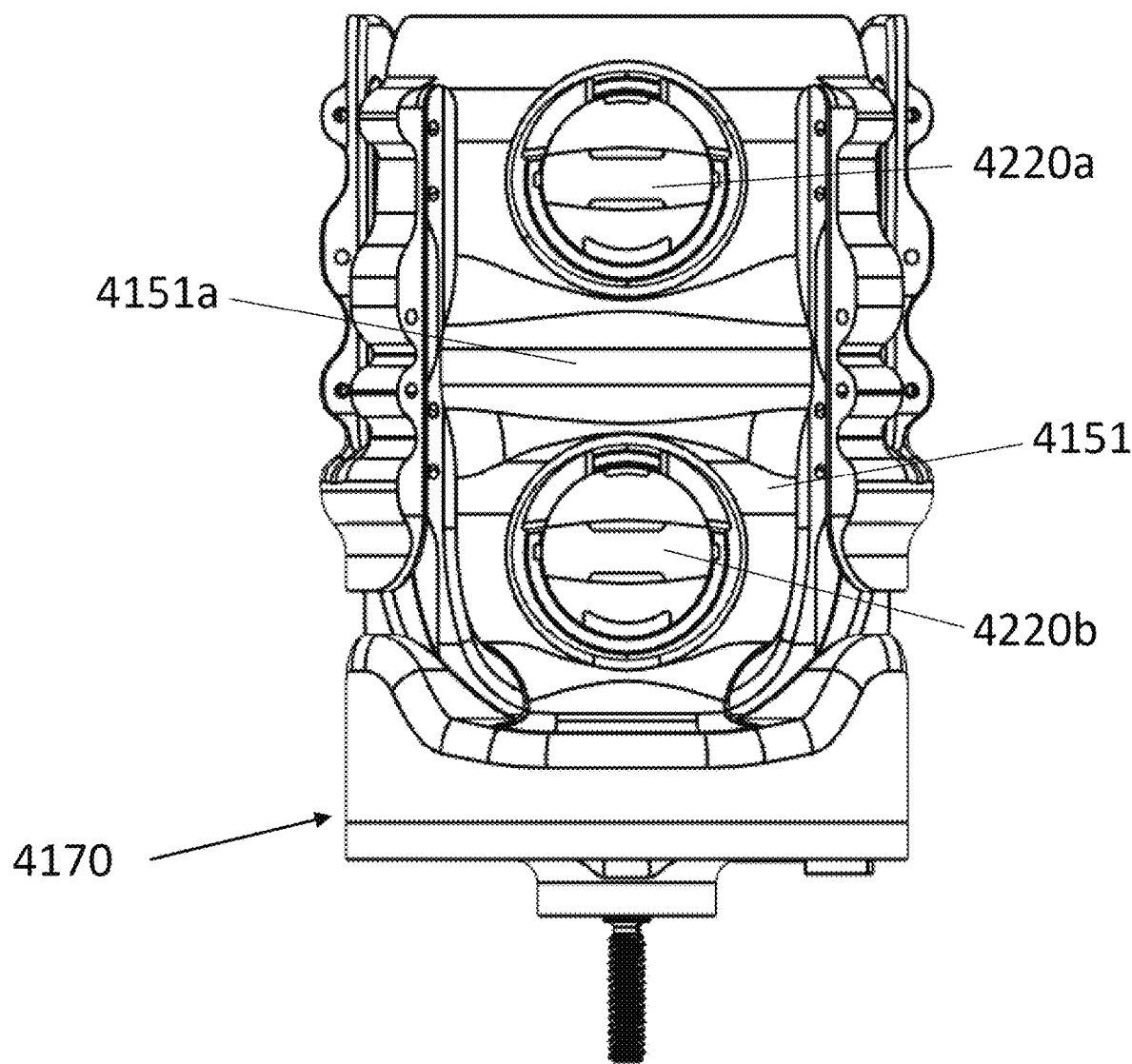
Figure 56D:
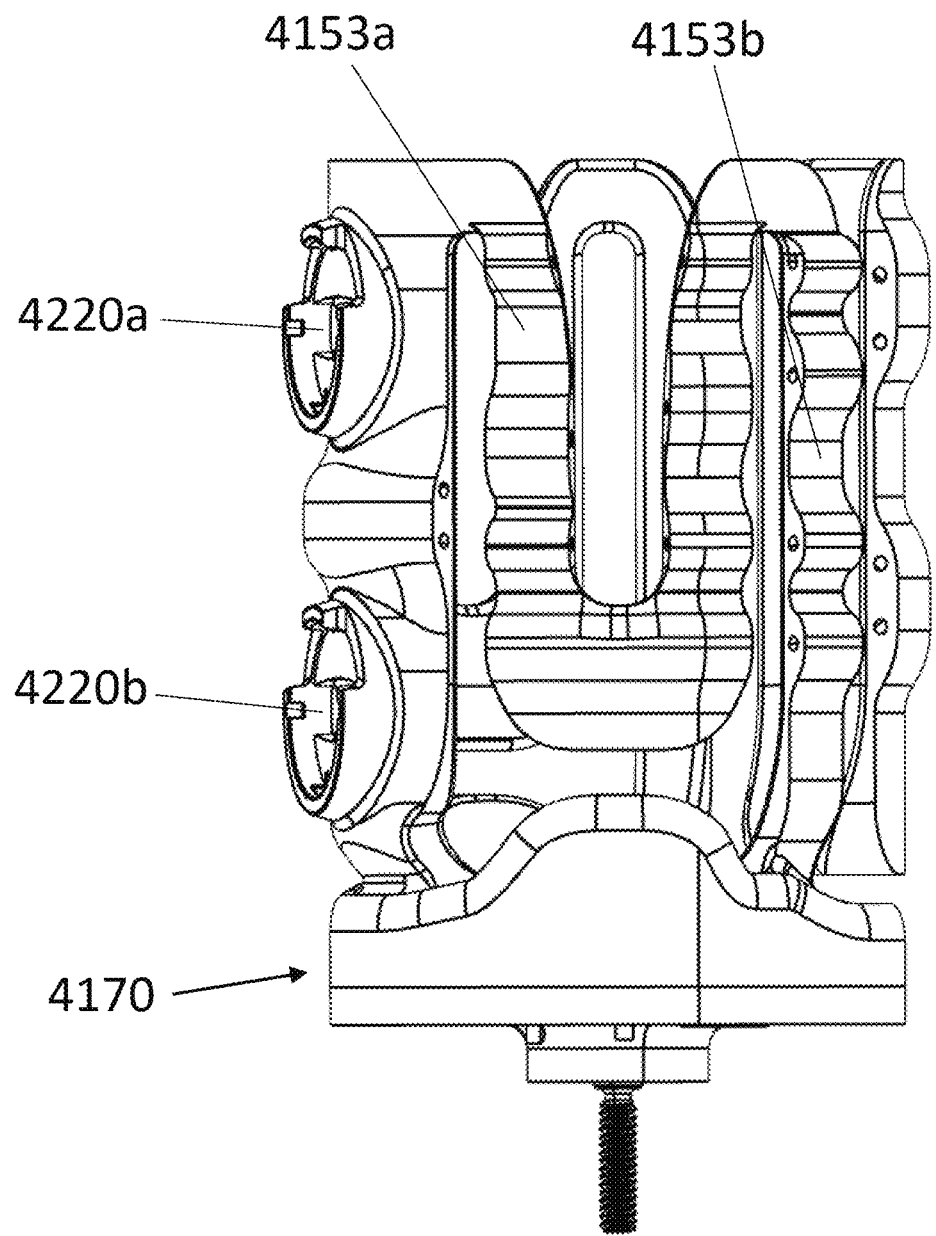
Figure 56E:
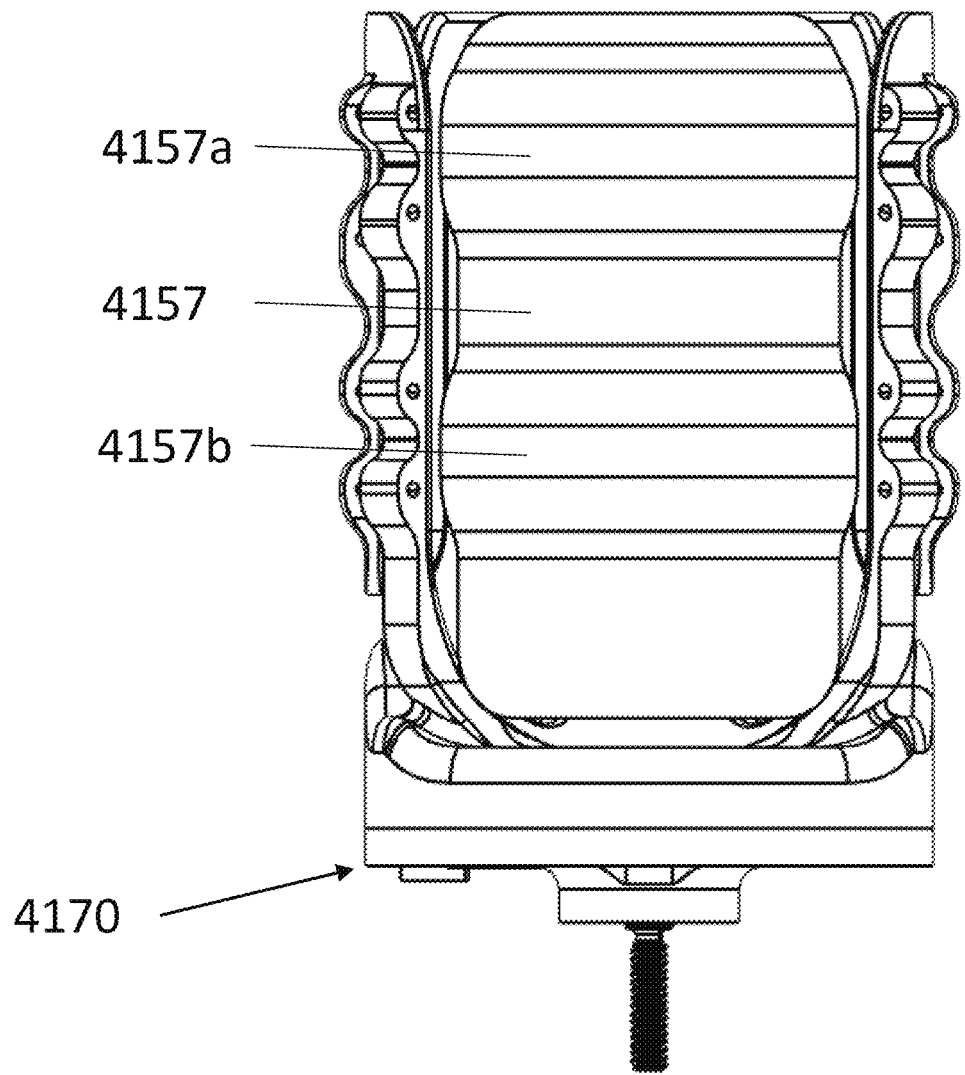
Figure 56F:
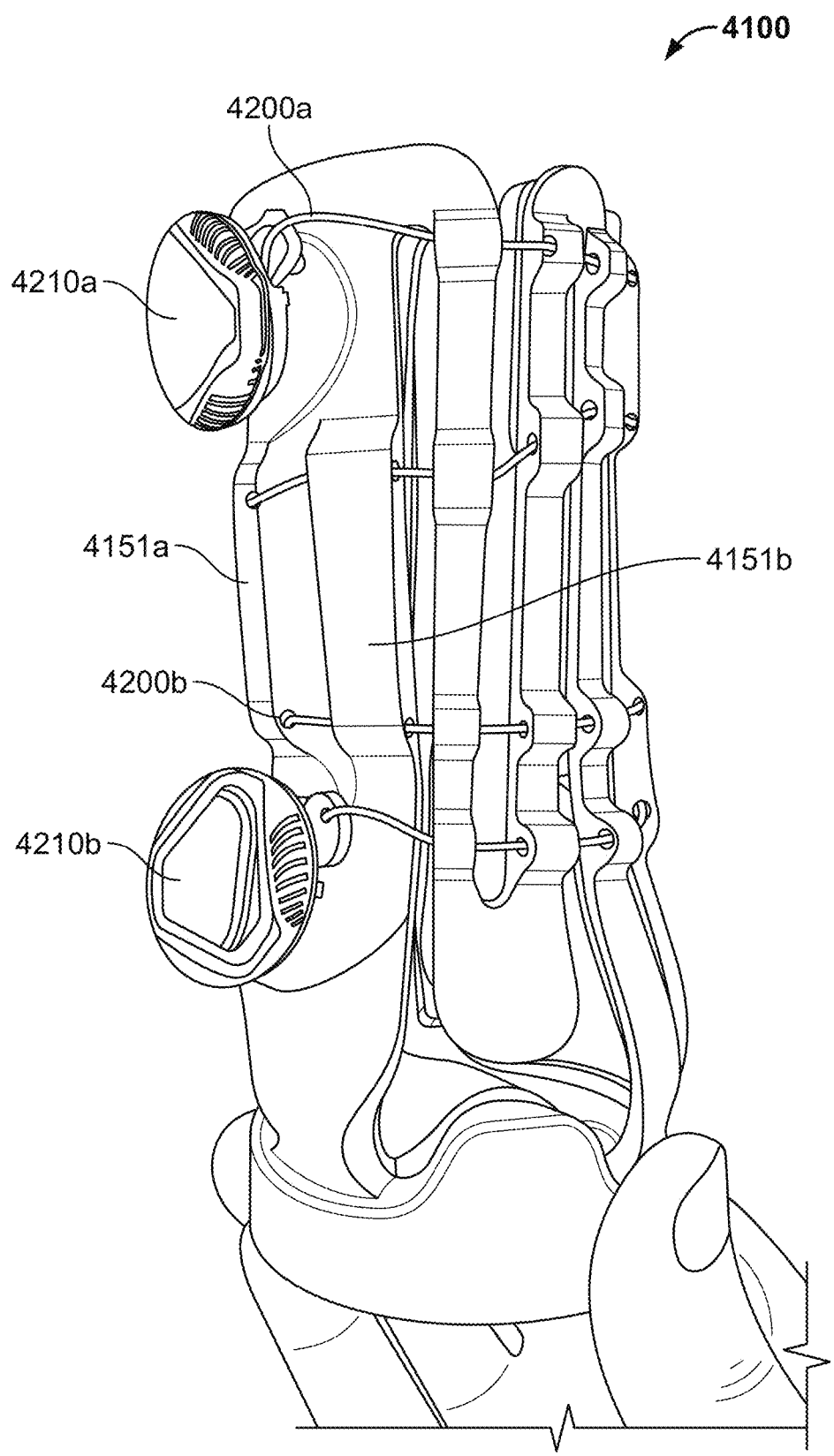

FIGS. 56C-E illustrate posterior, side, and anterior views, respectively, of socket 4100 in an unconformed or unmorphed condition. Referring generally to FIGS. 56A-E, it should be understand that many of the design rationales for socket 4100 are similar to that of socket 3100, for example including the desire to have secured fixation while maintaining breathability and comfort, and thus may not be needed to be repeated in detail below. For example, the posterior portion of socket 4100 may include a center posterior panel 4151 that includes a thickened or bumpout portion 4151a that may include one or more channels therethrough for receiving a lace similar to lace 3200. However, in some embodiments, as shown in FIG. 56B, the bumpout portion 4151a may be split into two separate spaced apart bumpouts 4151a, 4151b. Additionally, the center panel 4151 may include two mating structures 4220a, 4220b. The mating structures 4220a, 4220b may each be substantially similar or identical to mating structure 3220, and may be adapted to receive a tensioner similar or identical to tensioner 3210. The mating structures 4220a, 4220b may be spaced apart in the proximal-to-distal direction so that a tensioning system (including lacing) can be used to independently tension the proximal end of the socket 4100 and the distal end of the socket. FIGS. 54F-G illustrate socket 4100 with two tensioners 4210a, 4210b with two corresponding laces 4200a, 4200b to illustrate how the two independent tensioning systems may be configured. Referring back to FIG. 56C, the center panel 4151 may be attached to linking portion at a relatively narrow portion of the center panel 4151, and the center panel may be attached directly to the side panels at a proximal end thereof, the side panels described directly below.

FIG. 56D illustrates a side view of an unconformed or unmorphed configuration of socket 4100. It should be understood that the socket 4100 include two side portions coupling the anterior portions to the posterior portions, and each side portion may be substantially identical, so only one side portion is described in detail herein. The side portion may include a side panel that may have a general "S" shape. For example, the side panel may include first "U"-shaped side panel portion 4153a and a second generally vertical side panel portion 4153b. The second vertical side panel portion 4153b may be narrow and have a distal end directly coupled to the linking portion 4170, and a proximal end coupled to a proximal end of the first "U"-shaped side panel portion 4153a. The distal end of the first "U"-shaped side panel portion 1453a may be spaced away (e.g. not directly connected) to the linking portion 4170, and the other side of the proximal end of the first "U"-shaped side panel portion 4153a may be directly coupled to the center posterior panel 4151. With this configuration the two side panels (each including the first and second side panel portions 4153a, 4153b) and the posterior center panel 4151 may collectively only have three points of contact with the linking portion 4170, with a substantial amount of open space among and between the panels. With this configuration, including with two independent tensioning systems, the socket 4100 may be easily and securely fixed to the user's residual forearm (without any connection to the user's upper arm), with a large amount of flexibility in how the tensioning of the socket 4100 allows causes the socket 4100 to conform to the user's anatomy, while simultaneously allowing significant breathability and comfort to the user.

Figure 56G:
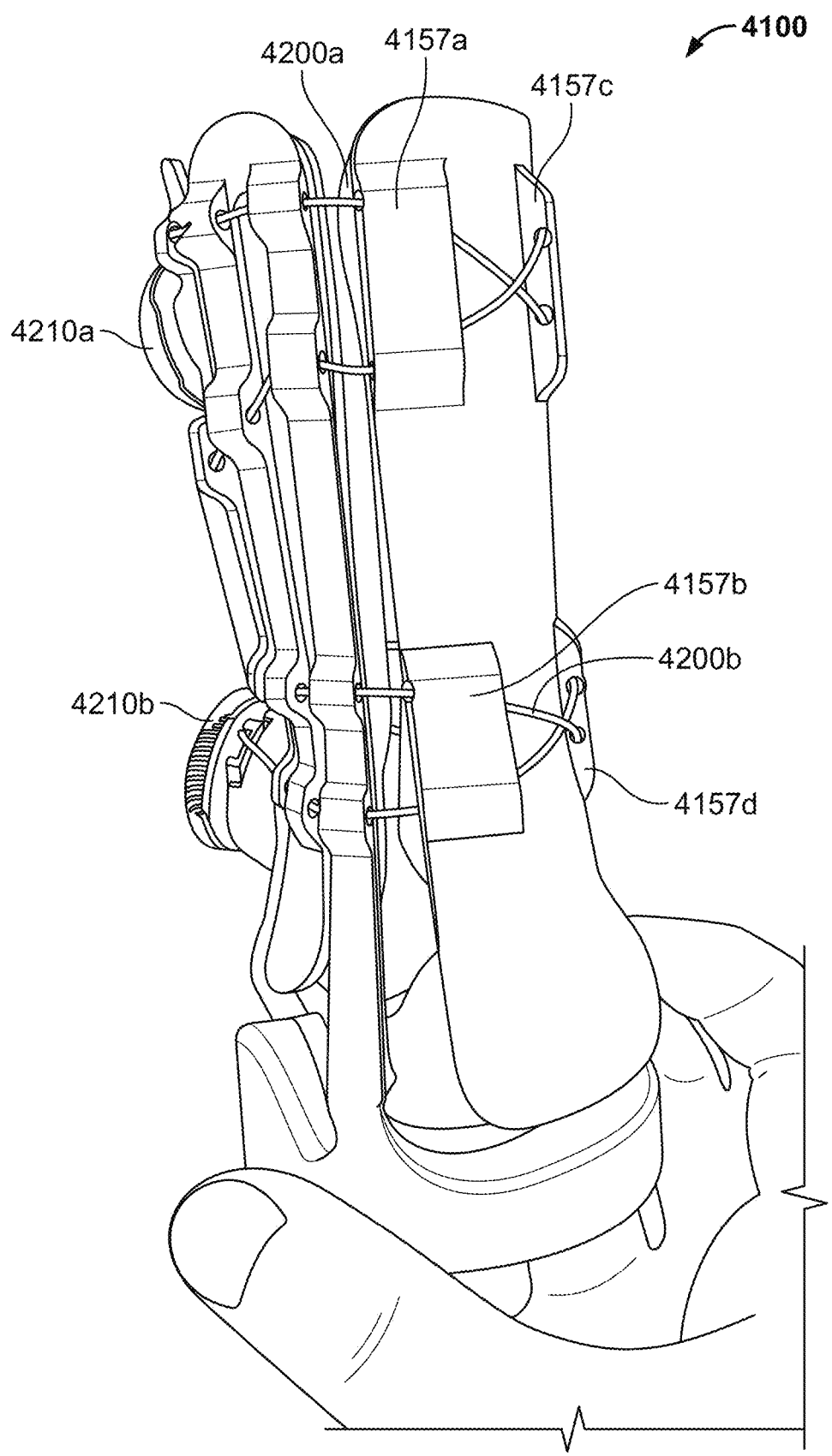

Another main difference between socket 4100 and socket 3100, besides the socket 4100 being jointless, is that socket 4100 may include a "floating" anterior panel 4157, best shown in FIG. 56E. In the anterior view of FIG. 56E, it should be clear that anterior panel 4157 is not directly coupled to any other portion of the socket 4100. Rather, anterior panel 4157 includes two thickened portions or bumpouts 4157a, 4157b that include one or more channels therethrough for receiving laces 4200a, 4200b. Thus, as best illustrated in FIG. 56G, with the tensioning system in place and with the laces 4200a, 4200b coupled to the tensioners 4210a, 4210b and threaded through the various bumpouts, the anterior panel 4157 is suspended via the laces 4200a, 4200b. Although FIG. 56E illustrates two continuous bumpouts 4157a, 4157b, it should be understood that these bumpouts may be split into different portions. For example, as shown in FIG. 46G, bumpout 4157a may be split into a second bumpout 4157c, and bumpout 4157b may be split into a second bumpout 4157d.

With the configuration described above, the floating anterior panel 4157 may be positioned directly between the second vertical side panel portions 4153b of the two side panels. When the user positions his residual forearm into socket 4100, he may tension the proximal and distal portions of the socket 4100 independently. As the tensioners 4210a, 4210b are rotated, the floating anterior panel 4157 is drawn into the anterior portion of the user's residual forearm, with the side and posterior panels being drawn into the side and posterior portions of the user's residual forearm. Other features of socket 4100 not described in detail herein, such as materials that may form the socket, and accessories that may be used with the socket, may be similar or identical to those described above in connection with other embodiments of sockets.

Even though various embodiments of sockets are shown and described above, including sockets 3100 and 4100, it should be understood that these sockets may be tuned specifically to fit a particular user based on the dimensions of that user's residual limb. Such morphing or tuning may be performed by inputting a user's anatomical measurements at and near the residual limb into a computer program, with the computer program morphing one of the generic models to more closely follow the contours of the user's particular anatomy. So, for example, two individuals may both have relatively long residual forearms that are suitable for use with socket 4100, but the actual sizes and dimensions of those sockets may be formed quite differently depending on differences in the dimensions of the user's residual forearm. For example, for one user that has a residual forearm having a length of about three inches from the elbow joint, the jointless socket 4100 may have a configuration very similar to that shown in FIGS. 56C-E, but with additional contouring from the unmorphed or generic model shown. However, there is a level of amputation referred to as wrist disarticulation, in which essentially the entire forearm proximal to the wrist remains. For a user with this level of amputation, the jointless socket 4100 may still be appropriate, but it may look significantly different than that shown in FIGS. 56C-E. For example, the socket 4100 may be relatively long and narrow. In that scenario, there may not be a need for any prosthetic forearm. Thus, the distal end of the socket 4100 may be shaped and configured to mate directly with prosthetic hand 300'. However, with a trans-radial amputation in which 3-4 inches of the forearm remains, the distal end of the socket 4100 may be generally puck or cylinder shaped for mating with a prosthetic forearm, such as prosthetic forearm 200".

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A socket for coupling a prosthetic upper extremity to a residual limb of a user, the socket comprising:
   a proximal socket portion;
   a distal socket portion coupled to the proximal socket portion by a polycentric joint;
   wherein the polycentric joint includes a plate having a first end coupled to the proximal socket portion via a first fastener, and a second end coupled to the distal socket portion via a second fastener, so that the proximal socket portion is rotatable relative to the distal socket portion about a first axis passing through the first fastener and about a second axis passing through the second fastener;
   wherein the distal socket portion includes a proximal coupling portion for receiving the residual limb of the user, and a distal linking portion for coupling to the prosthetic upper extremity;
   wherein the distal linking portion includes a distal-facing recess therein, an electronics control board being received in the distal-facing recess.

2. The socket of claim 1, wherein the polycentric joint includes two polycentric joints.

3. The socket of claim 1, wherein the proximal coupling portion includes a plurality of muscle sensors therein.

4. The socket of claim 3, wherein the plurality of muscle sensors are coupled to the electronics control board via one or more cables.

5. The socket of claim 4, wherein the one or more cables extend through one or more apertures in the distal-facing recess of the distal linking portion.

6. The socket of claim 5, further comprising a first connecting cable that connects the electronics control board to a slip ring.

7. The socket of claim 6, wherein the slip ring includes a second connecting cable connecting the slip ring to another component distal to the slip ring, the slip ring being configured to be received within a prosthetic forearm of the prosthetic upper extremity so that the prosthetic forearm is rotatable relative to the distal linking portion with an unlimited range of rotation.

8. The socket of claim 1, wherein the proximal socket portion includes at least one adjustable strap, the adjustable strap configured to secure the proximal socket portion to a biceps or triceps area of the user.

9. A socket for coupling a prosthetic upper extremity to a residual limb of a user, the socket comprising:
- a first socket portion adapted to receive the residual limb of the user therein, the first socket portion having an anterior panel for contacting an anterior surface of the residual limb, a posterior panel for contacting a posterior surface of the residual limb, and at least two side panels for contacting at least two side surfaces of the residual limb;
- a tensioning system coupled to the first socket portion, the tensioning system including a tensioner and a lace coupled to the tensioner, the lace passing through the anterior panel, the posterior panel, and the at least two side panels, so that upon rotation of the tensioner, the lace is drawn into the tensioner so that the anterior panel, the posterior panel, and the at least two side panels are drawn radially inwardly; and
- a second socket portion, the first socket portion being a distal socket portion, the second socket portion being a proximal socket portion, the proximal socket portion being coupled to the distal socket portion by a polycentric hinge.

10. The socket of claim 9, further comprising an outer panel on a posterior side of the first socket portion, the outer panel surrounding the posterior panel, the outer panel configured to contact both the user's residual limb and a biceps or triceps region of the user.

11. The socket of claim 10, wherein a gap is formed between the outer panel and the posterior panel, the gap configured to align and receive a portion of an elbow joint of the user.

12. The socket of claim 9, wherein the residual limb is a residual forearm, and the first socket portion is configured to receive the residual forearm without any other portion of the socket being supported by a biceps or triceps region of the user.

13. The socket of claim 9, wherein the tensioning system includes a first tensioning system and a second tensioning system, the first tensioning system being coupled to a proximal portion of the first socket portion, the second tensioning system being coupled to a distal portion of the first socket portion, the first and second tensioning systems being independently controllable.

14. The socket of claim 9, wherein the anterior panel includes a thickened area that is thickened relative to a remainder of the anterior panel, the thickened area including a passageway therethrough, the lace received through the passageway.

15. The socket of claim 9, wherein the posterior panel includes a thickened area that is thickened relative to a remainder of the posterior panel, the thickened area including a passageway therethrough, the lace received through the passageway.

16. The socket of claim 15, wherein the posterior panel is not directly coupled to the anterior panel and is not directly coupled to the at least two side panels, so that the posterior panel is suspended via the lace of the tensioning system.

17. The socket of claim 16, wherein the first socket includes a distal linking portion configured to couple to the prosthetic upper extremity, and the anterior panel, the posterior panel, and the at least two side panels are collectively directly coupled to the distal linking portion at no more than three locations.

* * * * *